(12) United States Patent
VanSickler et al.

(10) Patent No.: US 11,181,541 B2
(45) Date of Patent: Nov. 23, 2021

(54) AUTOMATED SAMPLE PREPARATION SYSTEM FOR DIAGNOSTIC TESTING OF SAME

(71) Applicant: BECTON DICKINSON AND COMPANY, Franklin Lakes, NJ (US)

(72) Inventors: Michael T. VanSickler, Columbia, MD (US); Kevin Bailey, Monkton, MD (US); Christopher John Tesluk, Baltimore, MD (US); Dwight Livingston, Fallston, MD (US); Steven C. Rotundo, Baltimore, MD (US); Stephen Robert LaChance, Cockeysville, MD (US); Michael J. Touma, Hudson, NH (US); Brian James McKeen, Bow, NH (US); Gerard Sevigny, Nashua, NH (US)

(73) Assignee: BECTON DICKINSON AND COMPANY, Franklin Lakes, NJ (US)

(*) Notice: Subject to any disclaimer, the term of this patent is extended or adjusted under 35 U.S.C. 154(b) by 403 days.

(21) Appl. No.: 16/077,875

(22) PCT Filed: Feb. 17, 2017

(86) PCT No.: PCT/US2017/018358
§ 371 (c)(1),
(2) Date: Aug. 14, 2018

(87) PCT Pub. No.: WO2017/143182
PCT Pub. Date: Aug. 24, 2017

(65) Prior Publication Data
US 2020/0319219 A1 Oct. 8, 2020

Related U.S. Application Data

(60) Provisional application No. 62/296,349, filed on Feb. 17, 2016, provisional application No. 62/409,013, filed on Oct. 17, 2016.

(51) Int. Cl.
*G01N 35/00* (2006.01)
*G01N 35/02* (2006.01)
(Continued)

(52) U.S. Cl.
CPC ....... *G01N 35/04* (2013.01); *G01N 35/00732* (2013.01); *G16H 10/40* (2018.01);
(Continued)

(58) Field of Classification Search
CPC ............ G01N 35/04; G01N 35/00732; G01N 2035/00801; G01N 2035/00831;
(Continued)

(56) References Cited

U.S. PATENT DOCUMENTS 5,262,049 A   11/1993  Ferkany
5,772,962 A   6/1998   Hiroyasu et al.
(Continued)

FOREIGN PATENT DOCUMENTS

EP   0745855 B1   12/1996
EP   0895088 B1   2/1999
(Continued)

OTHER PUBLICATIONS

Office Action issued in corresponding Japanese Patent Application No. 2018-543609 dated Feb. 25, 2021, 10 pp.
(Continued)

*Primary Examiner* — Matthew D Krcha
*Assistant Examiner* — Sophia Y Lyle
(74) *Attorney, Agent, or Firm* — Botos Churchill IP Law LLP

(57) ABSTRACT

An automated pre-analytical processing method and an apparatus for pre-analytical processing of samples to be forwarded to an adjacent analyzer for analysis. Rack label information is read and communicated to a processor. From the rack label information, the processor determines where
(Continued)

to route the rack. The pre-analytical system has a rack robot that conveys racks to discrete locations depending upon the routing information assigned to the rack by the processor. The pre-analytical system has an automated station that reads the labels of individual sample containers in the rack that are brought to the automated station on instructions from the processor. Depending on the type of sample container and the type of sample disposed therein, the samples are either prepared for analysis by the automated station or the sample containers are directly passed through the automated station. Prepared samples and passed through samples are passed individually to a batching rack.

12 Claims, 64 Drawing Sheets

(51) Int. Cl.
  *G01N 35/10* (2006.01)
  *G16H 10/40* (2018.01)
  *G01N 35/04* (2006.01)
(52) U.S. Cl.
  CPC .............. *G01N 2035/00801* (2013.01); *G01N 2035/00831* (2013.01); *G01N 2035/0465* (2013.01); *G01N 2035/1032* (2013.01)
(58) Field of Classification Search
  CPC ... G01N 2035/0465; G01N 2035/1032; G01N 35/0092; G01N 2035/00861; G01N 35/0099; G01N 2035/0405; G16H 10/40; Y02A 90/10
  See application file for complete search history.

(56) References Cited

U.S. PATENT DOCUMENTS

| | | |
|---|---|---|
| 5,876,668 A | 3/1999 | Kawashima et al. |
| 5,985,215 A | 11/1999 | Sakazume et al. |
| 6,027,691 A | 2/2000 | Watts et al. |
| 6,138,521 A | 10/2000 | Basch et al. |
| 6,146,592 A | 11/2000 | Kawashima et al. |
| 6,162,399 A | 12/2000 | Martinell |
| 6,253,807 B1 | 7/2001 | Jones |
| 6,261,521 B1 | 7/2001 | Mimura et al. |
| 6,267,927 B1 | 7/2001 | Longedo et al. |
| 6,290,907 B1 | 9/2001 | Takahashi et al. |
| 6,293,750 B1 | 9/2001 | Cohen et al. |
| 6,335,166 B1 | 1/2002 | Ammann et al. |
| 6,521,183 B1 | 2/2003 | Burri et al. |
| 6,551,833 B1 | 4/2003 | Lehtinen et al. |
| 6,588,625 B2 | 7/2003 | Luoma, II et al. |
| 6,599,749 B1 | 7/2003 | Kodama |
| 6,635,488 B1 | 10/2003 | Saito |
| 6,723,288 B2 | 4/2004 | Devlin, Sr. et al. |
| 6,730,517 B1 | 5/2004 | Köster et al. |
| 6,752,960 B1 | 6/2004 | Matsubara et al. |
| 6,776,961 B2 | 8/2004 | Lindsey |
| 6,793,887 B2 | 9/2004 | Itoh |
| 6,849,236 B2 | 2/2005 | Spitz |
| 6,919,044 B1 | 7/2005 | Shibata et al. |
| 6,982,063 B2 | 1/2006 | Hamel et al. |
| 7,015,042 B2 | 3/2006 | Devlin, Sr. |
| 7,033,543 B1 | 4/2006 | Panzer et al. |
| 7,185,288 B2 | 2/2007 | McKeever |
| 7,206,667 B2 | 4/2007 | Kleinschmitt |
| 7,220,385 B2 | 5/2007 | Blecka |
| 7,288,228 B2 | 10/2007 | Lefebvre |
| 7,326,386 B2 | 2/2008 | Sasaki et al. |
| 7,354,510 B2 | 4/2008 | Fujimoto et al. |
| 7,368,084 B2 | 5/2008 | Sklar et al. |
| 7,384,601 B2 | 6/2008 | Matsubara et al. |
| 7,390,458 B2 | 6/2008 | Burow et al. |
| 7,402,282 B2 | 7/2008 | Lacourt et al. |
| 7,462,328 B2 | 12/2008 | Fritz et al. |
| 7,501,094 B2 | 3/2009 | Bysouth |
| 7,572,638 B2 | 8/2009 | Pressman et al. |
| 7,579,190 B2 | 8/2009 | Ostgaard et al. |
| 7,585,678 B2 | 9/2009 | Sigrist |
| 7,666,355 B2 | 2/2010 | Alavie |
| 7,687,033 B2 | 3/2010 | Itoh |
| 7,700,042 B2 | 4/2010 | Matsumoto et al. |
| 7,727,469 B2 | 6/2010 | Takahashi et al. |
| 7,807,446 B2 | 10/2010 | Macisaac et al. |
| 7,814,788 B2 | 10/2010 | Halaka et al. |
| 7,854,892 B2 | 12/2010 | Veiner et al. |
| 7,858,041 B2 | 12/2010 | Muraishi et al. |
| 7,867,768 B2 | 1/2011 | Ryan et al. |
| 7,879,292 B2 | 2/2011 | Nagai et al. |
| 7,885,077 B2 | 2/2011 | Sass et al. |
| 7,939,020 B2 | 5/2011 | Nogawa et al. |
| 7,972,579 B2 | 7/2011 | Brunner |
| 7,985,375 B2 | 7/2011 | Edens et al. |
| 7,998,409 B2 | 8/2011 | Veiner et al. |
| 8,034,293 B2 | 10/2011 | Kumar et al. |
| 8,100,266 B2 | 1/2012 | Lackner et al. |
| 8,206,663 B2 | 2/2012 | Nagai |
| 8,142,719 B2 | 3/2012 | Matthias et al. |
| 8,148,163 B2 | 4/2012 | Hofstadler |
| 8,158,060 B2 | 4/2012 | Nagai |
| 8,178,043 B2 | 5/2012 | Burkhardt |
| 8,211,701 B2 | 7/2012 | Spence et al. |
| 8,226,889 B2 | 7/2012 | Nakaya |
| 8,252,232 B2 | 8/2012 | Neeper et al. |
| 8,257,650 B2 | 9/2012 | Chow et al. |
| 8,277,729 B2 | 10/2012 | Matsuo et al. |
| 8,278,108 B2 | 10/2012 | Wada et al. |
| 8,282,895 B2 | 10/2012 | Miller et al. |
| 8,329,103 B2 | 12/2012 | Wakamiya et al. |
| 8,337,755 B2 | 12/2012 | Bendele et al. |
| 8,357,538 B2 | 1/2013 | Self et al. |
| 8,383,411 B2 | 2/2013 | Kawamura |
| 8,386,195 B2 | 2/2013 | Feingold et al. |
| 8,431,079 B2 | 4/2013 | Rosenberg et al. |
| 8,431,404 B2 | 4/2013 | Spence |
| 8,455,256 B2 | 6/2013 | Yamoto et al. |
| 8,480,977 B2 | 7/2013 | Gunji |
| 8,496,877 B2 | 7/2013 | Yamazaki et al. |
| 8,529,836 B2 | 9/2013 | Winther et al. |
| 8,535,607 B2 | 9/2013 | Wakamiya et al. |
| 8,545,760 B2 | 10/2013 | Yamamoto et al. |
| 8,551,404 B2 | 10/2013 | Nagai et al. |
| 8,557,599 B2 | 10/2013 | Koyata et al. |
| 8,616,072 B2 | 12/2013 | Boeke et al. |
| 8,632,725 B2 | 1/2014 | Yamazaki et al. |
| 8,652,832 B2 | 2/2014 | Kondo |
| 8,658,417 B2 | 2/2014 | Godsey et al. |
| 8,679,421 B2 | 3/2014 | Sano et al. |
| 8,703,492 B2 | 4/2014 | Self et al. |
| 8,731,712 B2 | 5/2014 | Hagen et al. |
| 8,747,745 B2 | 6/2014 | Kitaoka |
| 8,758,685 B2 | 6/2014 | Komatsu et al. |
| 8,778,268 B2 | 7/2014 | Takehara et al. |
| 8,778,281 B2 | 7/2014 | Holenstein et al. |
| 8,778,696 B2 | 7/2014 | Gutmann et al. |
| 8,784,735 B2 | 7/2014 | Winther et al. |
| 8,784,750 B2 | 7/2014 | Gunji |
| 8,883,078 B2 | 11/2014 | Humada et al. |
| 8,894,930 B2 | 11/2014 | Mizumoto |
| 8,926,902 B2 | 1/2015 | Pedrazzini |
| 8,945,470 B2 | 2/2015 | Kuwano et al. |
| 8,951,805 B2 | 2/2015 | Fritchie et al. |
| 8,956,569 B2 | 2/2015 | Hamada et al. |
| 8,965,558 B2 | 2/2015 | Haas et al. |
| 9,028,756 B2 | 5/2015 | Yamamoto et al. |
| 9,034,257 B2 | 5/2015 | Covey et al. |
| 9,057,672 B2 | 6/2015 | McKeen et al. |
| 9,063,103 B2 | 6/2015 | Pedrazzini |
| 9,103,806 B2 | 8/2015 | Massaro |
| 9,114,399 B2 | 8/2015 | Knight et al. |
| 9,117,192 B2 | 8/2015 | Clark et al. |
| 9,134,332 B2 | 9/2015 | Frey et al. |

(56) References Cited

U.S. PATENT DOCUMENTS

| | | | |
|---|---|---|---|
| 9,134,334 B2 | 9/2015 | Gunji | |
| 9,140,632 B2 | 9/2015 | Furrer | |
| 9,164,019 B2 | 10/2015 | Geach | |
| 9,164,115 B2 | 10/2015 | Davis et al. | |
| 9,180,447 B2 | 11/2015 | Schlegel et al. | |
| 9,248,422 B2 | 2/2016 | Ching et al. | |
| 9,335,338 B2 | 5/2016 | Ochranek et al. | |
| 9,506,943 B2 | 11/2016 | Müller et al. | |
| 10,101,349 B2 | 10/2018 | Antoni et al. | |
| 2003/0000597 A1* | 1/2003 | Ganz | B01L 9/523 141/130 |
| 2004/0142486 A1 | 7/2004 | Weselak et al. | |
| 2004/0184959 A1 | 9/2004 | Itoh | |
| 2005/0047963 A1 | 3/2005 | Safar et al. | |
| 2005/0158212 A1 | 7/2005 | Yavilevich | |
| 2006/0204997 A1 | 9/2006 | Macioszek et al. | |
| 2006/0210435 A1* | 9/2006 | Alavie | G01N 21/253 422/65 |
| 2007/0098597 A1 | 5/2007 | Brunner | |
| 2007/0134131 A1 | 6/2007 | Watson et al. | |
| 2007/0290004 A1 | 12/2007 | Lee et al. | |
| 2009/0047179 A1 | 2/2009 | Ping et al. | |
| 2010/0126286 A1* | 5/2010 | Self | G01N 35/026 73/863.81 |
| 2011/0091364 A1 | 4/2011 | Voit | |
| 2011/0306051 A1 | 12/2011 | Belz et al. | |
| 2011/0306053 A1 | 12/2011 | Ochsenbein et al. | |
| 2012/0318076 A1 | 12/2012 | Kappelhoff et al. | |
| 2013/0065797 A1 | 3/2013 | Silbert et al. | |
| 2013/0116102 A1* | 5/2013 | Hansen | G01N 35/026 494/10 |
| 2013/0230860 A1 | 9/2013 | Park et al. | |
| 2014/0050637 A1 | 2/2014 | Giovanoli et al. | |
| 2014/0112843 A1 | 4/2014 | Thomas et al. | |
| 2014/0241946 A1 | 8/2014 | Self et al. | |
| 2015/0273468 A1 | 10/2015 | Croquette et al. | |
| 2015/0343439 A1 | 12/2015 | Burroughs et al. | |
| 2017/0248626 A1 | 8/2017 | Procyshyn et al. | |

FOREIGN PATENT DOCUMENTS

| | | |
|---|---|---|
| EP | 2333559 A1 | 6/2011 |
| EP | 3078972 A1 | 10/2016 |
| JP | 5781557 U | 5/1982 |
| JP | H02167473 A | 6/1990 |
| JP | H0618531 A | 1/1994 |
| JP | H07229904 A | 8/1995 |
| JP | H08304408 A | 11/1996 |
| JP | 2001504229 A | 3/2001 |
| JP | 2002340912 A | 11/2002 |
| JP | 2008532048 A | 8/2008 |
| JP | 2010536332 A | 12/2010 |
| JP | 2011123066 A | 6/2011 |
| JP | 2015511313 A | 4/2015 |
| JP | 2015131260 A | 7/2015 |
| JP | 2017517000 A | 6/2017 |
| WO | 9503548 A1 | 2/1995 |
| WO | WO 2009/024560 A1 | 2/2009 |
| WO | WO 2011/101467 A1 | 8/2011 |
| WO | WO 2013168559 A1 | 11/2013 |
| WO | 2015108164 A1 | 7/2015 |

OTHER PUBLICATIONS

Notice of Reasons for Refusal issued in corresponding JP Patent Application No. 2018-555526 dated Feb. 2, 2021, 13 pp.

International Search Report and Written Opinion from corresponding International Application No. PCT/US2017/018346 dated May 11, 2017.

International Search Report and Written Opinion from corresponding International application No. PCT/US2017/018298 dated Jul. 12, 2018.

International Search Report and Written Opinion from corresponding International application No. PCT/US2017/018358 dated Nov. 7, 2017.

Held, P. G., et al., "Automated Procedures For The Quantitation of Protein", Biotechniques Rapid Dispatches, Informa Healthcare, US, vol. 17, No. 5, XP000474857, (Nov. 1, 1994), pp. 988-991.

Simport, "PCR—The assurance of highly accurate and contaminant-free proceduresLean-Driven Innovation11", URL:http://www.simport.com/documents/PCR2014Web.pdf/, (Mar. 30, 2016).

Thermofischer, ""Howto Use MicroAmp (TM) Reaction Plates, Tube Strips, and Tubes For use with: Applied Biosystems (TM) thermal cyclers and real-time PCR systems Publication No. 100033471 Revision A—How to use MicroAmp (TM) plates How to use MicroAmp"", XP055487397, Retrieved from the Internet: URL:https://assets.fishersci.com/TFS-Asset s/LSG/manuals/100033471_MicroAmpReactionPlates_TubeStrips_Tubes_UB.pdf [retrieved on Jun. 25, 2018] Aug. 25, 2015, (Aug. 25, 2015), pp. 1-8.

Full Examination Report for corresponding Australian Patent Application No. 2017220028 dated May 14, 2021, 3 pp.

Japanese Notice of Refusal dated Jan. 27, 2021 in JP Application No. 2018-555453.

Extended European Search Report for corresponding European Patent Application No. 21166097.2 dated Jun. 22, 2021, 9 pp.

* cited by examiner

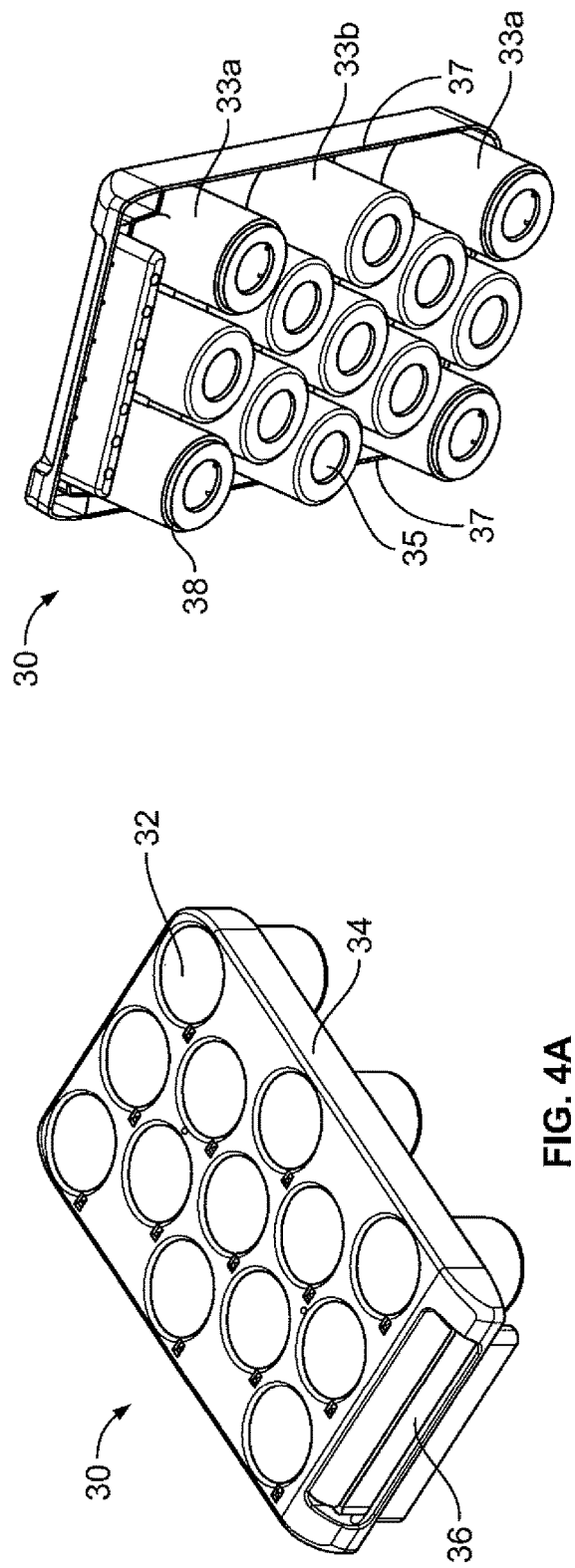
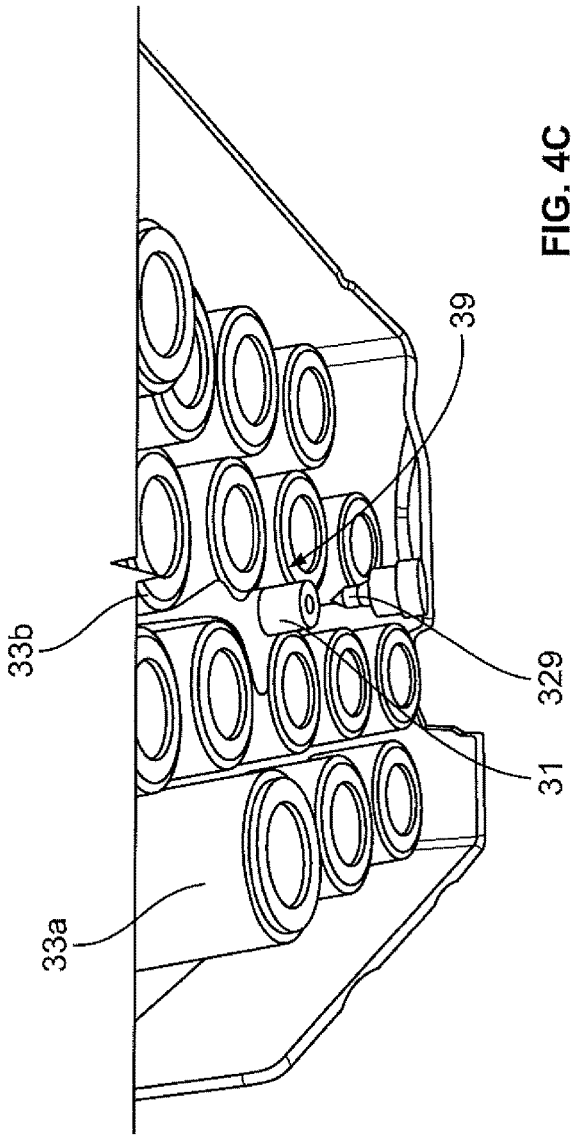
FIG. 4A
FIG. 4B
FIG. 4C

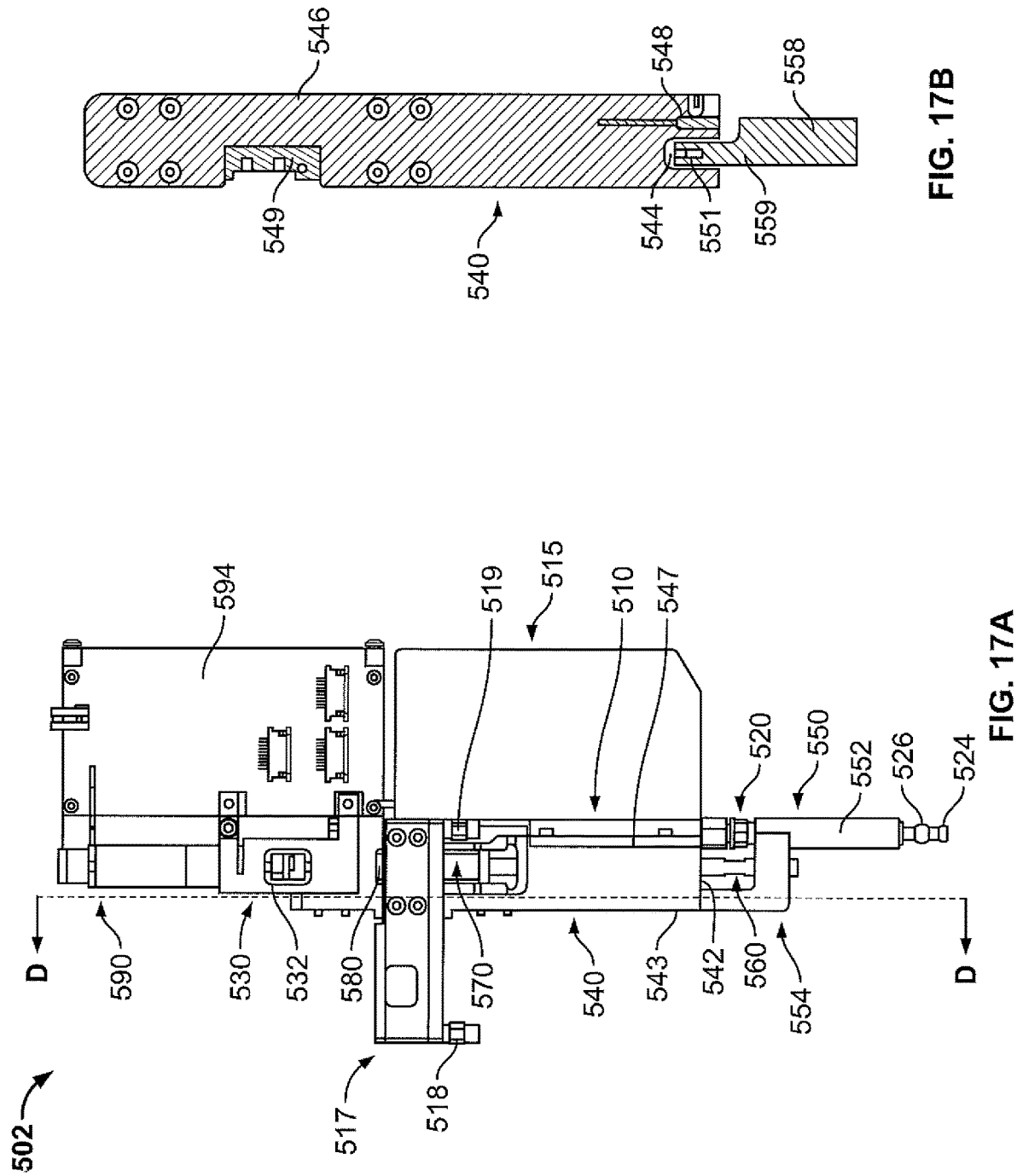

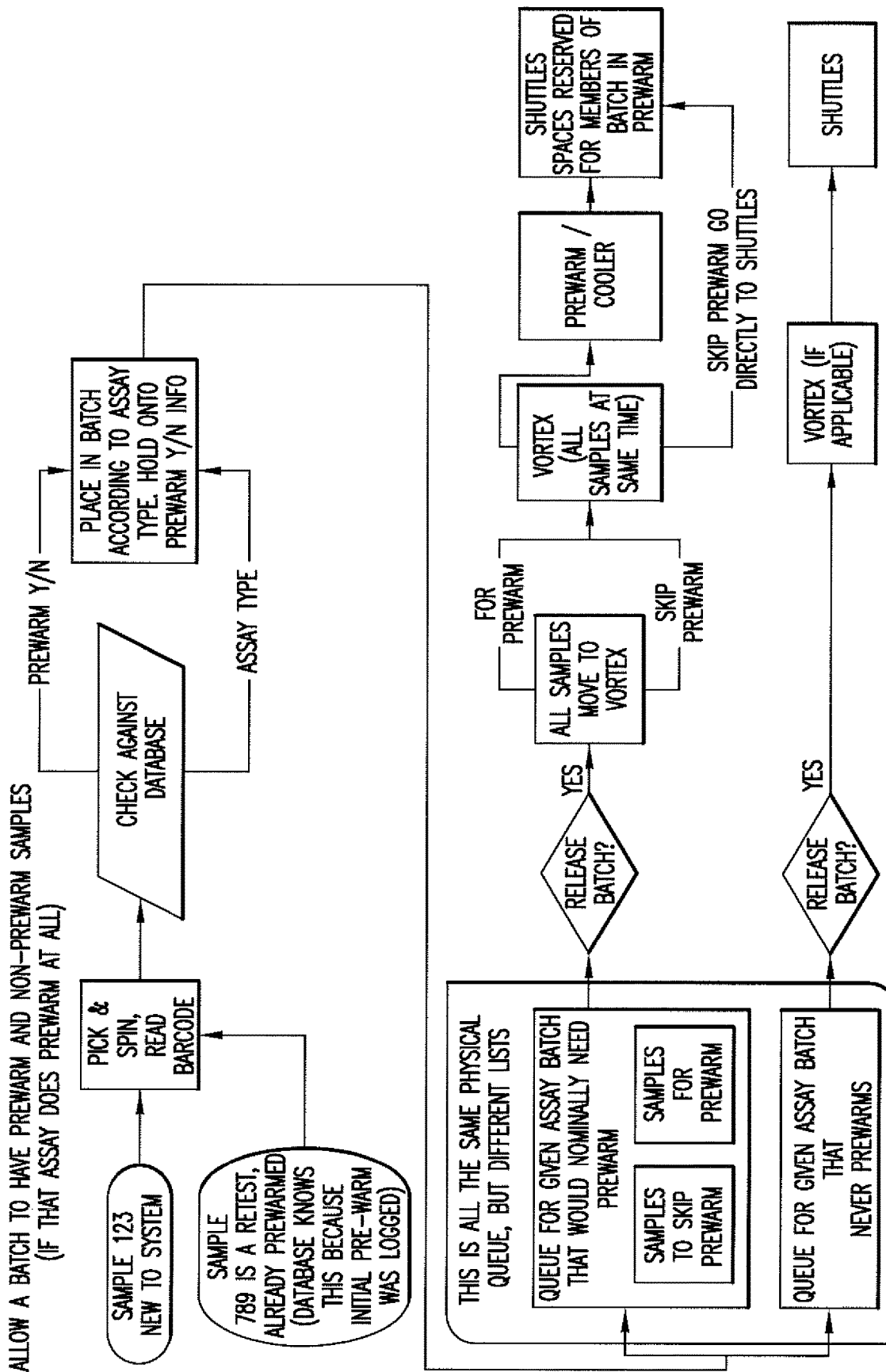

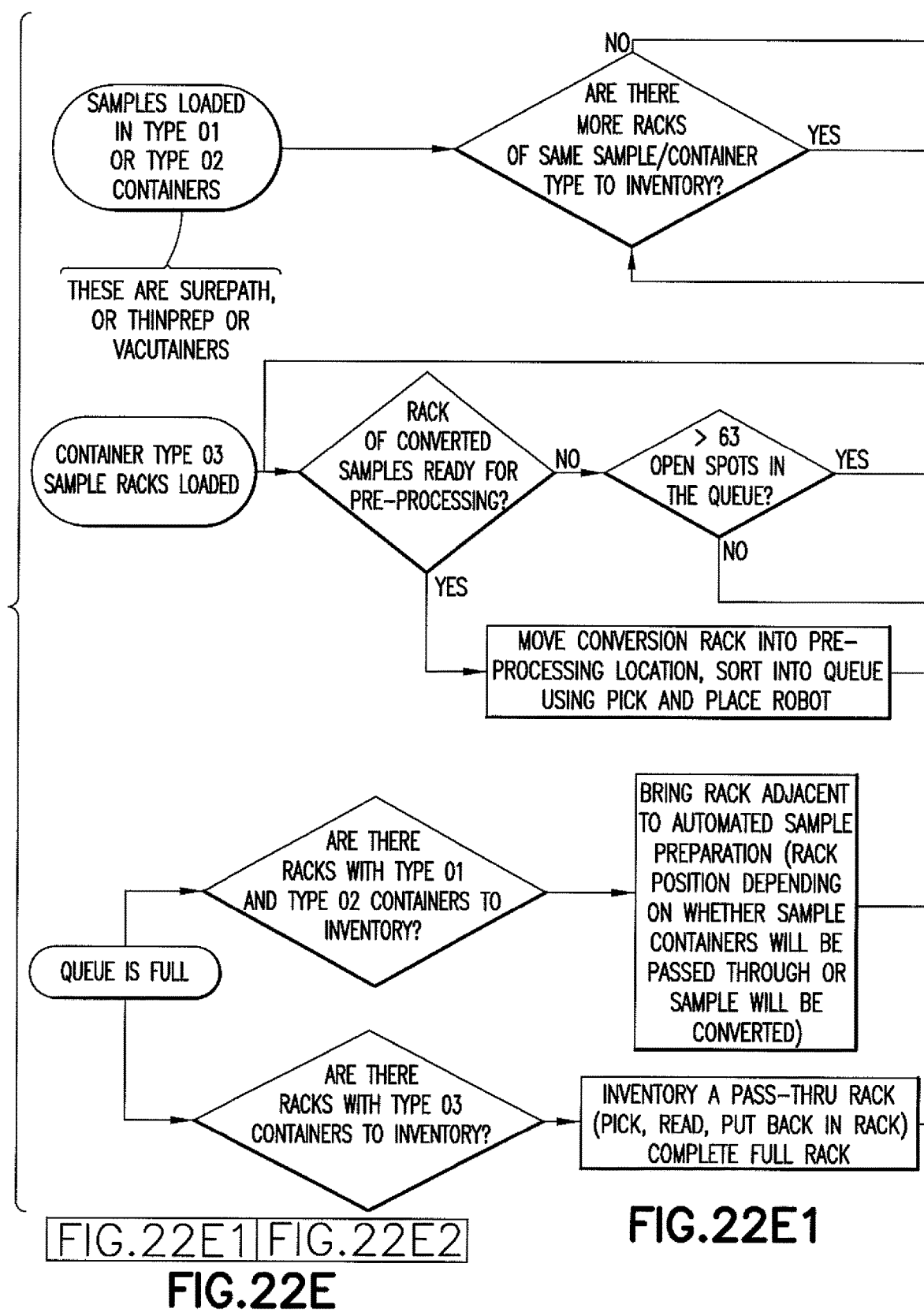

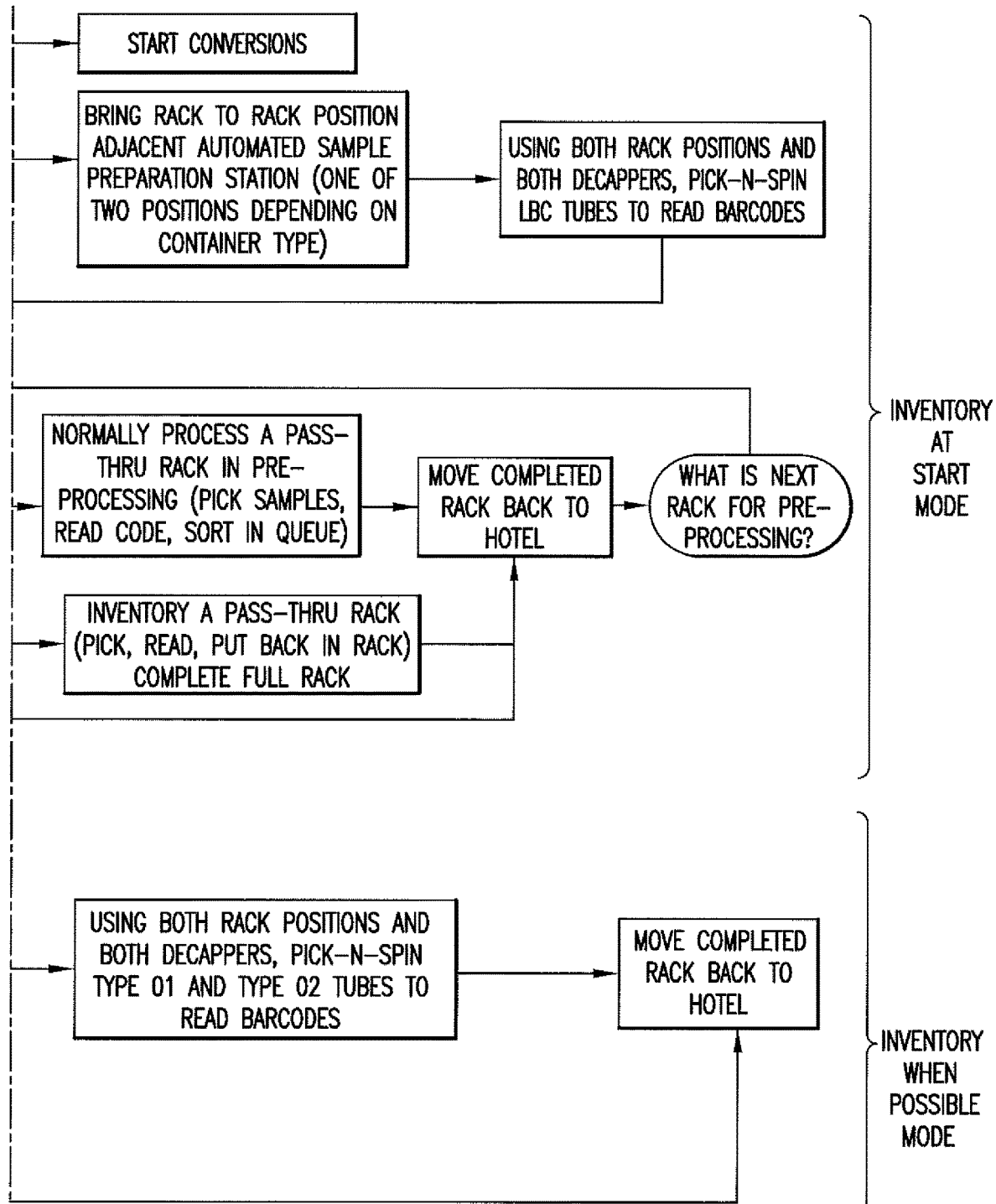
FIG.22E2

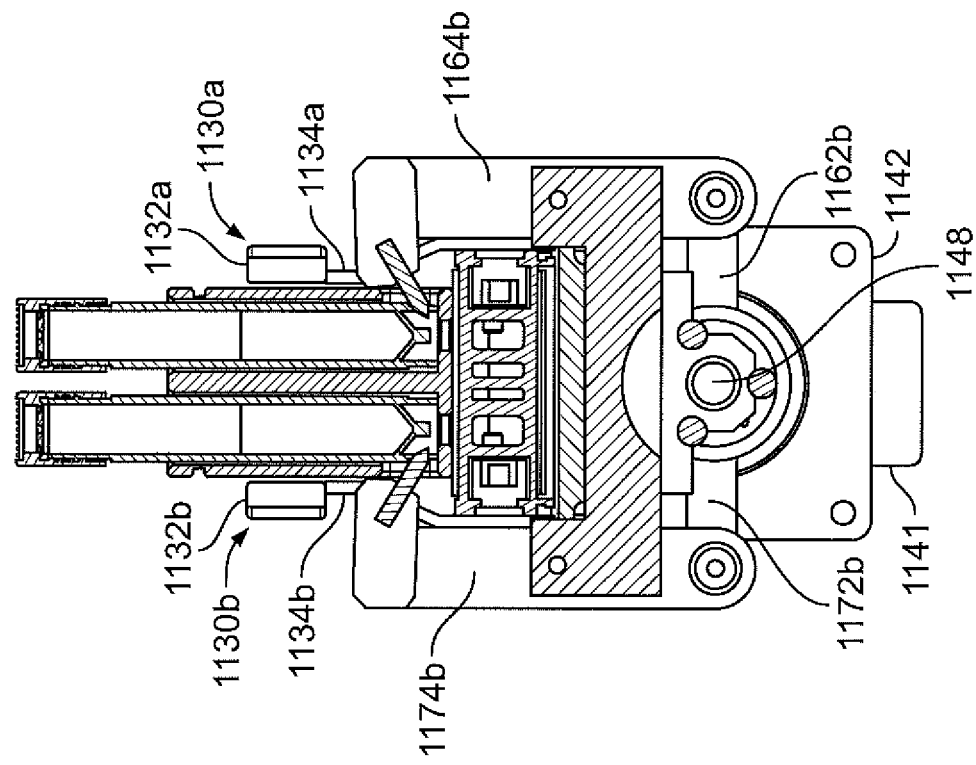
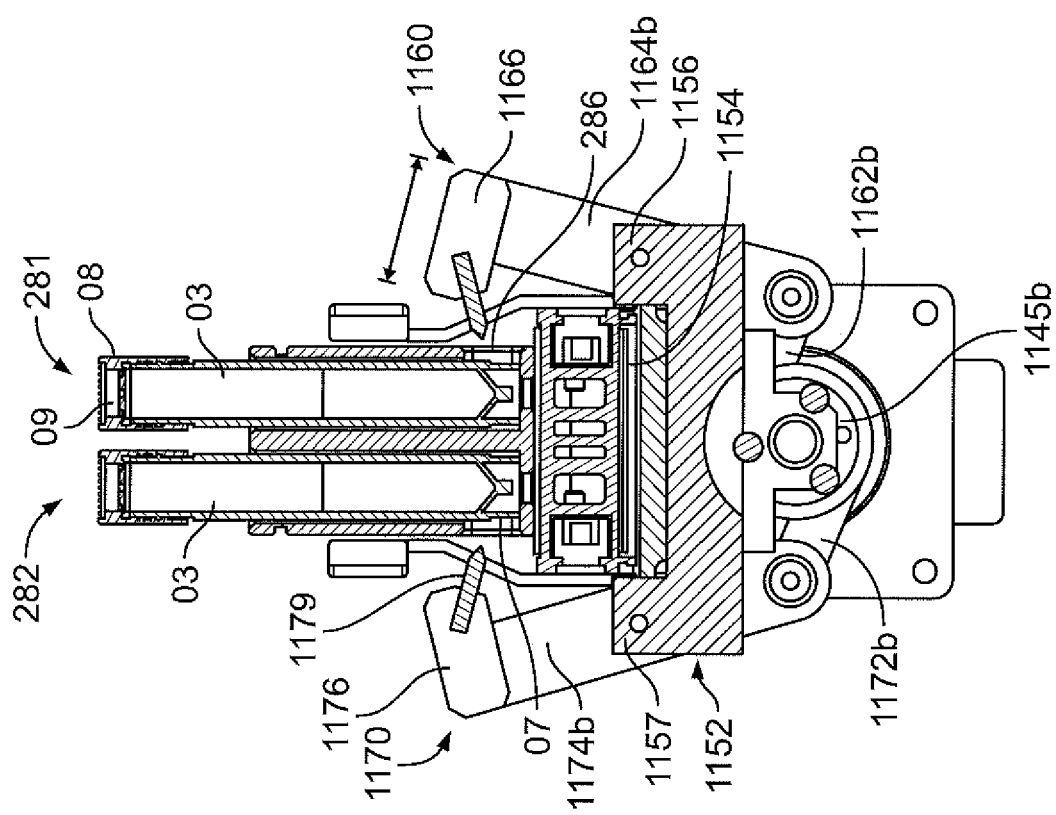

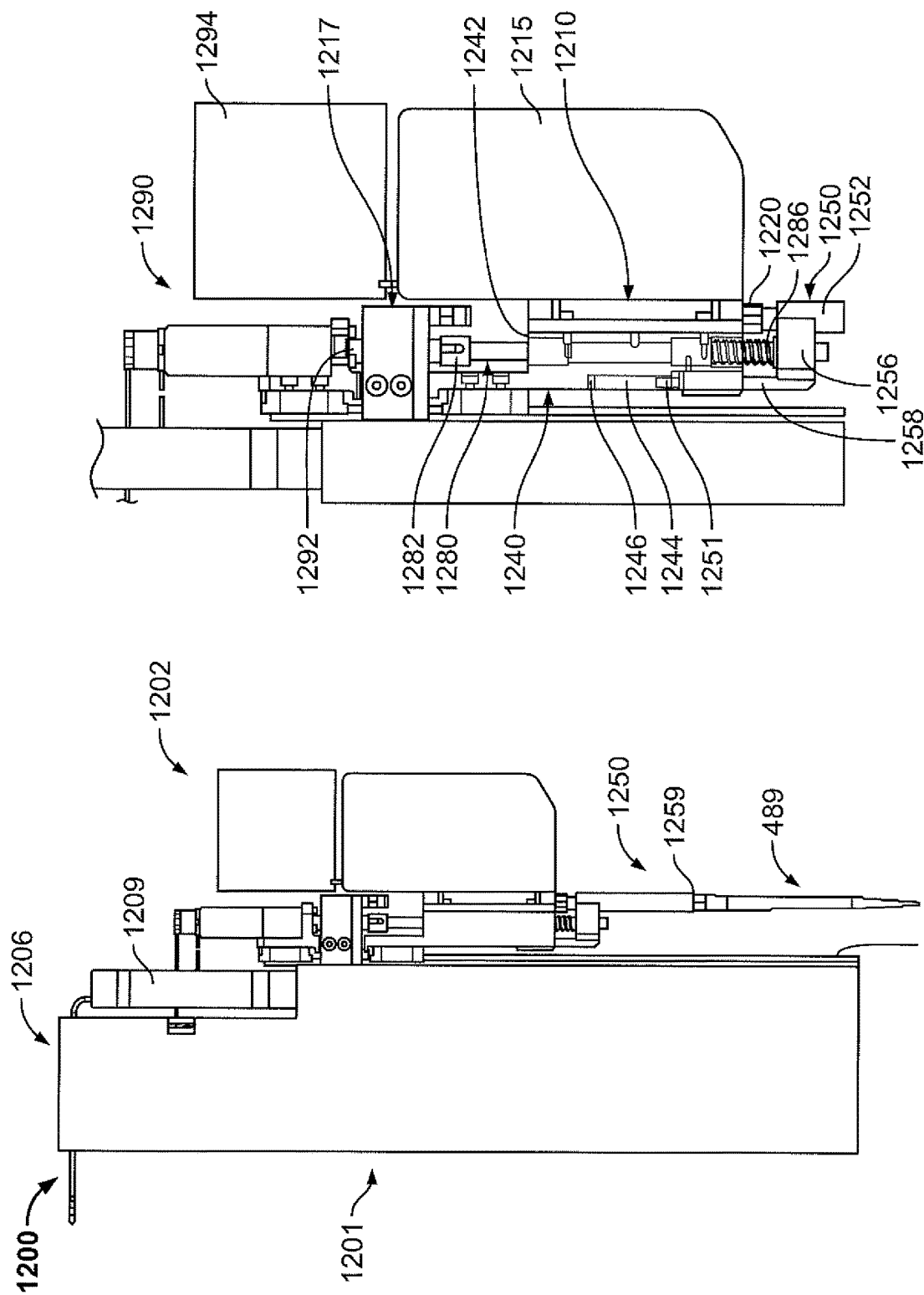

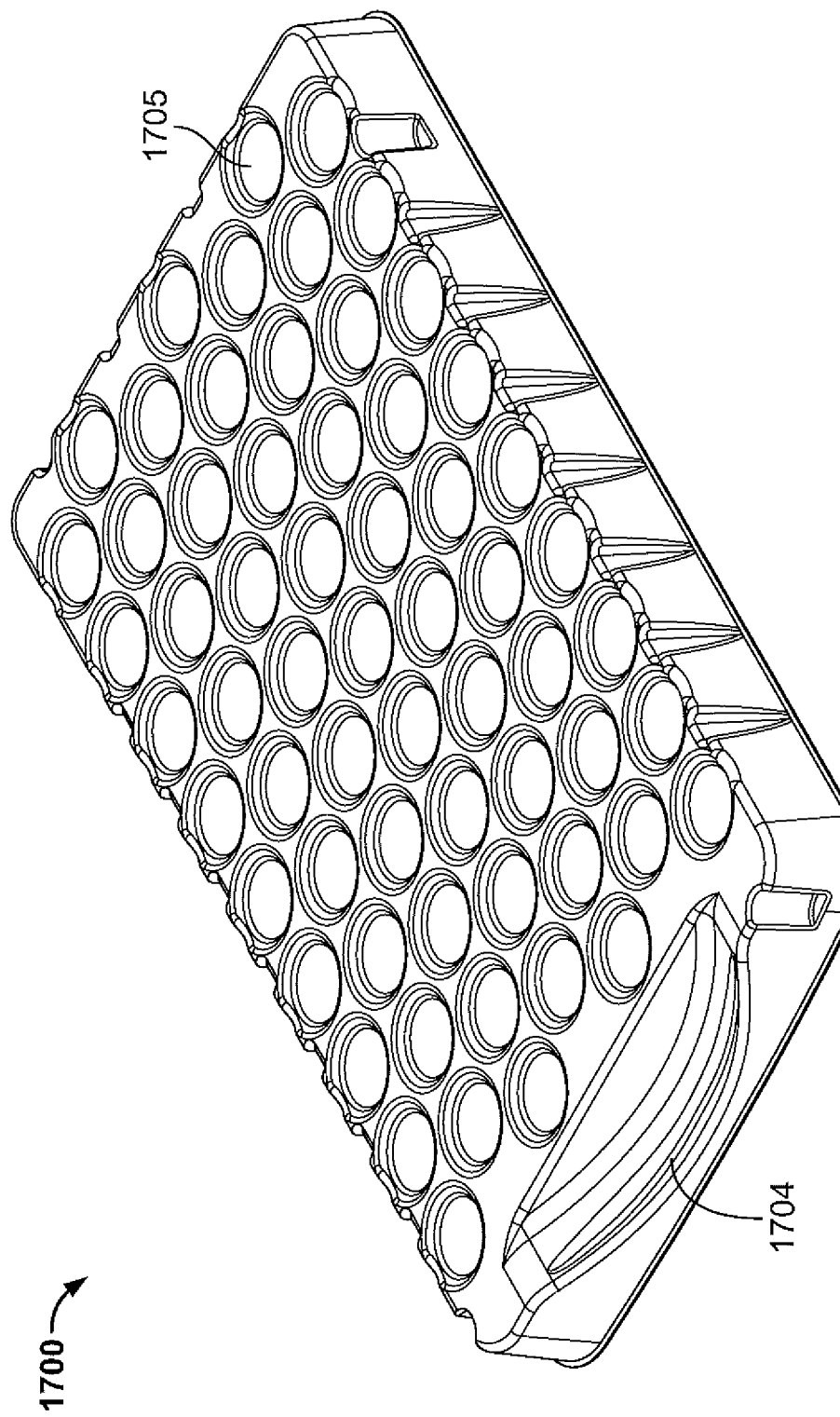

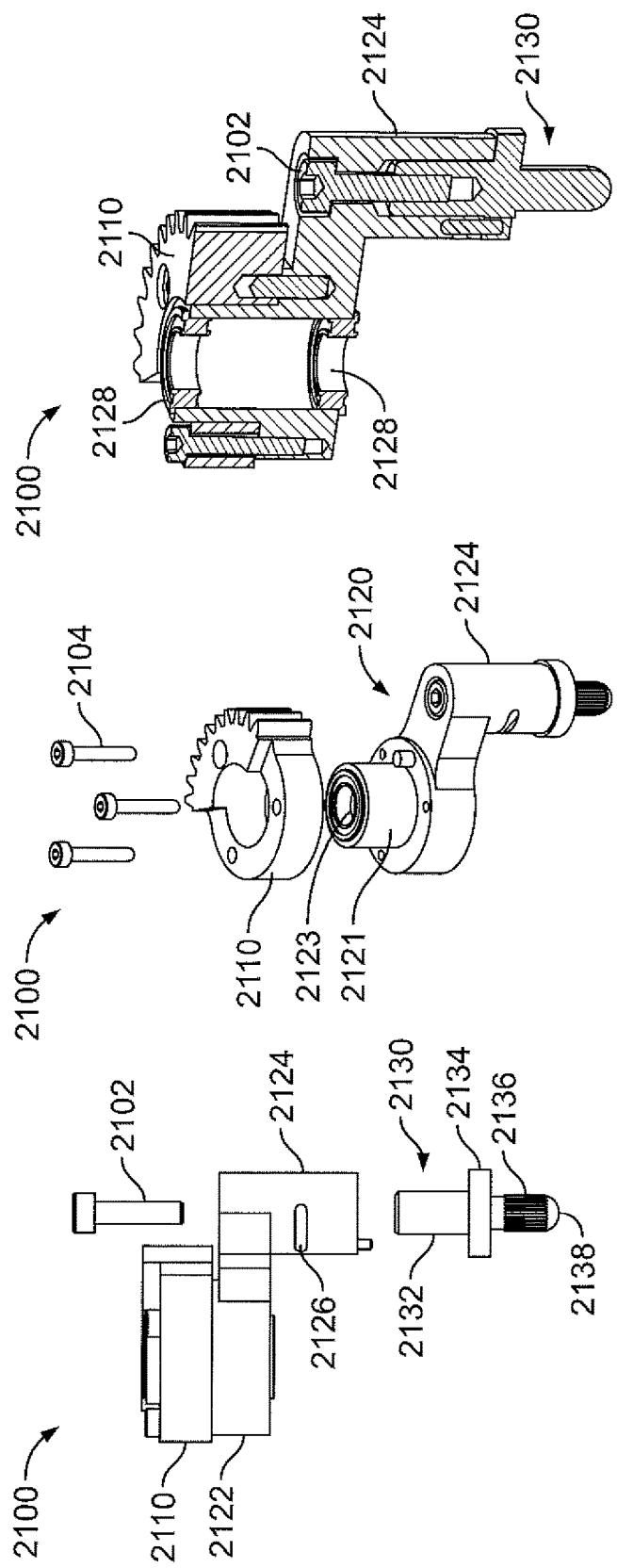
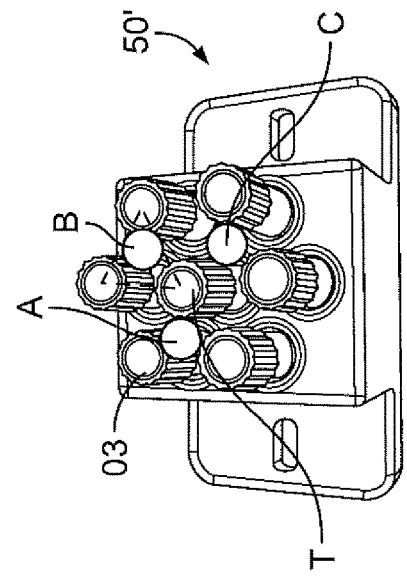
FIG. 31I
FIG. 31J
FIG. 31H
FIG. 31G

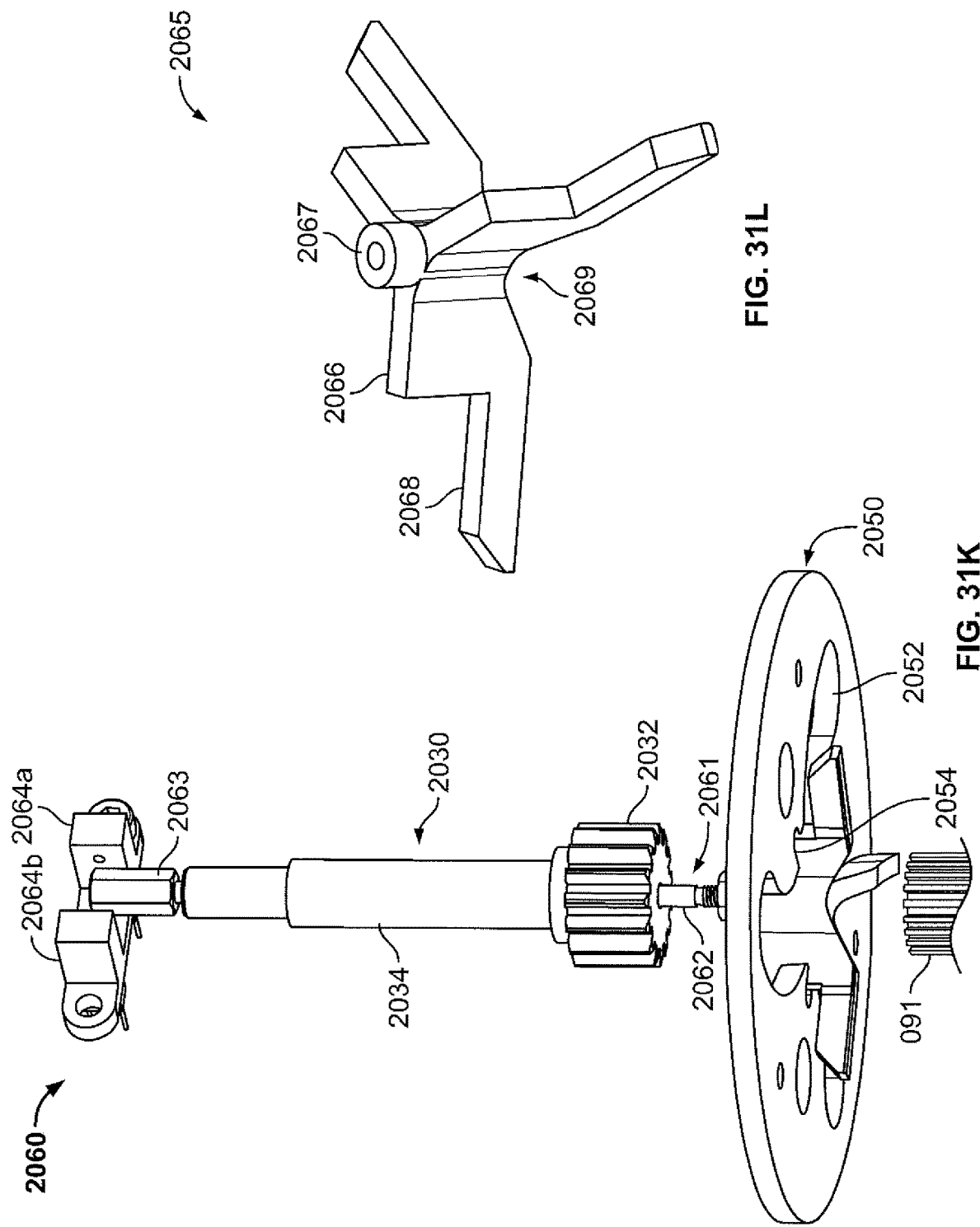

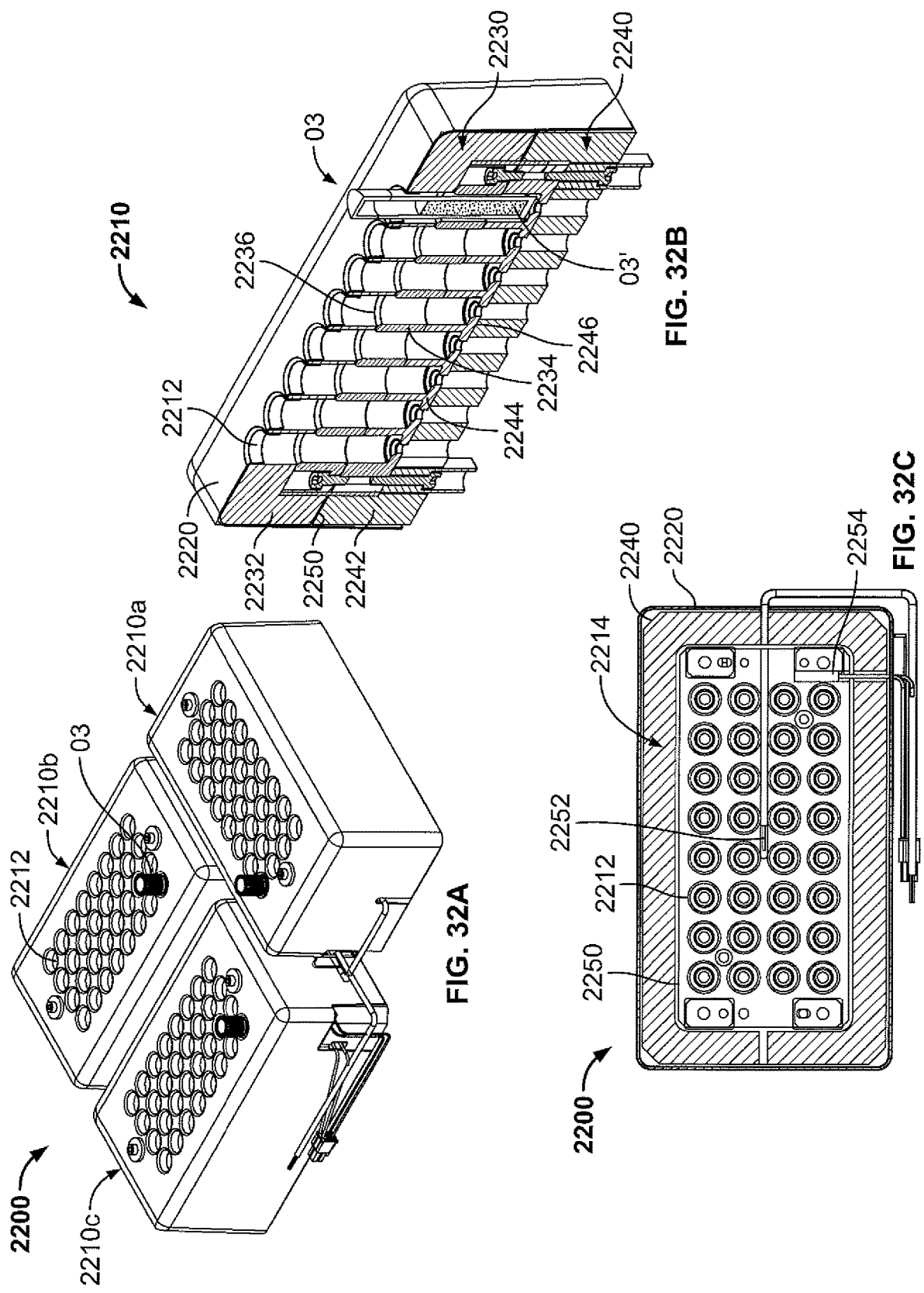

AUTOMATED SAMPLE PREPARATION SYSTEM FOR DIAGNOSTIC TESTING OF SAME

CROSS-REFERENCE TO RELATED APPLICATIONS

The present application is a national phase entry under 35 U.S.C. § 371 of International Application No. PCT/US2017/018358, filed Feb. 17, 2017, published in English, which claims the benefit of the filing dates of U.S. Provisional Application No. 62/409,013, filed Oct. 17, 2016, and U.S. Provisional Application No. 62/296,349, filed Feb. 17, 2016, the disclosures of which are hereby incorporated by reference herein.

BACKGROUND OF THE INVENTION

Diagnostic testing of biological samples is instrumental in the health care industry's efforts to quickly and effectively diagnose and treat disease. Clinical laboratories that perform such diagnostic testing already receive hundreds or thousands of samples on a daily basis with an ever increasing demand. The challenge of managing such large quantities of samples has been assisted by the automation of sample analysis. Automated sample analysis is typically performed by automated analyzers that are commonly self-contained systems which perform multistep processes on the biological samples to obtain diagnostic results.

Several current automated clinical analyzers offer a user an array of automated tests that can be performed on a provided sample. However, when samples arrive at the laboratory, they are often not ready for analysis. In order to prepare a sample for testing with an automated analyzer, a lab technician typically transfers an aliquot of the sample from a primary container, as received by the laboratory, to a secondary container which is amenable to the analyzer. In addition, the technician typically must know what tests are to be performed on the sample so that the technician can select a test specific reagent or diluent to be paired with the sample. This can be time consuming and can lead to operator error and exposure to communicable diseases.

Pre-analytical systems meant to help prepare a sample for analysis and further remove the operator from the workflow between the laboratory's receipt of a sample and the analyzer's test results also exist. However, many of these systems still require significant technician time and involvement. For example, technicians are required to interact with such systems when loading samples in the pre-analytical system and again when the samples have been prepared by the pre-analytical system and need to be removed and again once the analyzers have completed analysis (if the pre-analytical system is integrated with an analyzer).

For example, some pre-analytical systems may automatically transfer an aliquot of sample from a first container to a second container. However, such systems often require a technician to manually pair identification codes of the first and second containers prior to loading them into the system, which can be time consuming and is prone to error.

In addition, many of these systems are not capable of being integrated with one or more analyzers. In this regard, a technician must be present to manually transfer the samples from the pre-analytical system to an analyzer and from the analyzer to a storage location once analysis is complete. This redirects skilled labor to menial tasks and can create distractions in that the technician must be ever mindful of the progress of the samples within the pre-analytical system and analyzer so that the technician is prepared to transfer samples when ready in order to minimize downtime.

Moreover, current pre-analytical systems generally prepare samples at different rates than the analyzers which further complicate the integration between pre-analytical systems and analyzers. In this regard, a technician may be required to continuously keep track of samples prepared by the pre-analytical system until a full batch of samples is accumulated for manual transfer to an analyzer. Alternatively, technicians may transfer partial batches to an analyzer, which can reduce the analyzer's productivity.

Thus, while current automated pre-analytical systems are beneficial to the clinical laboratory, there is room for further improvements.

BRIEF SUMMARY OF THE INVENTION

The present disclosure describes devices, systems, and methods for sample preparation and pre-analytical processing that reduces user interaction and increases sample throughput over current systems. In particular, a pre-analytical system is described. The pre-analytical system is configured to perform pre-analytical processing that includes both sample handling and sample preparation. As used herein, sample handling is any manipulation of the sample in a container. Sample handling can include, but is not limited to, heating, cooling, vortexing and conveying sample containers. Sample preparation, by contrast is processing of the sample itself, as distinguished from the container in which the sample is disposed. Examples of sample preparation include sample aspiration from one type of container and sample dispense into another sample container, sample dilution, etc. . . . . Such sample preparation is also referred to as sample conversion herein. When a sample is received by a laboratory in a container not suitable for use in an analyzer, the pre-analytical system prepares the sample by transferring an aliquot of the sample from the primary container to a secondary container that is amenable for processing by the analyzer. The sample that is received by the pre-analytical system is referred to as the primary sample herein. The sample so prepared or converted is referred to herein as a secondary sample.

A further function performed by the pre-analytical system is sample distribution to analyzers integrated with the pre-analytical system. Some analyzers are configured to perform certain specific assays while other analyzers are configured to perform a range of other assays. The presently described pre-analytical system identifies the assay to be performed and automatically distributes prepared and preprocessed samples to the appropriate analyzer for analysis. In addition, the system is configured to receive/retrieve used samples from the one or more analyzers and distribute the used samples to the user at the user's behest. In this regard, the pre-analytical system can store samples until requested by the user.

More particularly, the pre-analytical system is configured as a hub between a user and one or more analyzers. In this regard, the system is coupled to one or more analyzers and can receive samples within various types of sample containers from a user. The pre-analytical system prepares and preprocesses the samples and distributes them to the analyzers where the samples are analyzed. Once the samples are analyzed, the pre-analytical system receives/retrieves the samples from the analyzers and outputs them to the user when commanded.

The pre-analytical system is also configured to allow the user to randomly access the samples while also being configured to distribute prepared and preprocessed samples in batches to the analyzers. This allows a user to load the system with samples and walk away for an entire shift. However, if additional samples are received by the laboratory throughout the day, the user can load these samples into the pre-analytical system at any time.

In one aspect, an exemplary pre-analytical system is described, which includes an exemplary layout and exemplary instruments utilized by the pre-analytical system for performing sample preparation and preprocessing. The pre-analytical system may include multiple levels, such as a storage level, first deck level, second deck level, and deck robot level. Various instruments that may be located on these levels are described. In addition, various robots that manipulate samples and sample containers are described.

In another aspect, the described instruments and system levels are partitioned into modules, which perform various sample preparation and preprocessing operations. Such modules include an input/output and post analysis module, a sample conversion/sample preparation module, one or more sample handling modules, a sample transfer module, and a consumable inventory module.

In a further aspect of the disclosure, a control system of the pre-analytical system is described. Such control system coordinates all of the activities within the pre-analytical system and interactions with one or more analyzers. Such control system may include one or more processors, a component interface/bus, and memory/data storage. The memory/data storage may include stored data and processor control instructions. Stored data can include sample container type, sample container location, sample rack location, patient information, and other information associated with each sample, such as the assay to be performed and preprocessing parameters.

In yet a further aspect of the disclosure, a method of operation is described. In the method, the pre-analytical system may be loaded with racks by a user through a single port/window with the consumables utilized in the method. Such racks carry, for example, empty secondary sample containers, test controls, and primary sample containers. The types of sample containers are identified by the system and the consumables are moved to a storage deck within the system where they are stored temporarily until retrieved for pre-analytical processing including secondary sample preparation, sample handling and/or distribution to one or more analyzers.

The method of operation at this point may differ based on the type of container within which the primary sample is contained when received by the pre-analytical system. Where the primary sample container is not amenable for use by a downstream analyzer, the primary sample container is retrieved from the storage deck and the primary sample is prepared/converted from the primary container to a secondary sample disposed in secondary container. Such secondary sample preparation may include diluting the sample with an assay specific diluent. The secondary container with the secondary sample disposed therein may then be placed in a batch-accumulation area where batches of samples are accumulated for handling and/or transport to an analyzer.

Where the primary container is amenable for use with an analyzer, the primary container bypasses sample preparation and is sent directly for handling as required by the pre-analytical system. In some embodiments such handling includes placing the primary container in batch of primary containers to be sent to the same analyzer destination. In one embodiment, the pre-analytical system includes a batch-accumulation area where the sample containers are assembled into batches for the analyzers.

Where a sample, depending on the assay to be performed, requires handling, the sample containers are retrieved from the batch-accumulation area and the ordered pre-analytical processing may include vortexing, pre-warming and cooling the sample disposed in the containers. Thereafter, the sample containers may be transported to the analyzers.

Samples that are ready for transport to the analyzers are placed into shuttles that may contain a sufficient number of receptacles to hold an entire batch. In some embodiments multiple shuttles will be required to transport all of the sample tubes in one batch to an analyzer. In other embodiments, there may be more receptacles in a shuttle than there are sample tubes in a single batch. The shuttles are then transported to one or more analyzers depending on the assay to be performed on the samples within the batch.

Once the analyzers have obtained the test sample for analysis, the sample containers are no longer needed by the analyzer and the used sample containers are transported back to the pre-analytical system in the shuttle. The sample containers are placed back into the storage deck. Ultimately, the rack containing the returned sample containers will be dispensed from the pre-analytical system either as part of the periodic clearance of processed samples or by operator action. A user can retrieve any sample container from the storage deck on command.

BRIEF DESCRIPTION OF THE DRAWINGS

The features, aspects, and advantages of the present invention will become better understood with regard to the following description, appended claims, and accompanying drawings in which:

FIG. 4A is a top perspective view of a sample container rack according to one embodiment of the present disclosure.

FIG. 4B is a bottom perspective view of the sample container rack of FIG. 4A.

FIG. 4C is another bottom perspective view of the sample container rack of FIG. 4A and an engagement member thereof.

FIG. 17A is a front view of a pipette assembly of a pipette head of the sample handling assembly of FIG. 16A according to one embodiment of the present disclosure.

FIG. 17B is a cross-sectional view taken at line D-D of FIG. 17A.

FIG. 24C is a side view of the sample tube retention assembly of FIG. 24C in a first position.

FIG. 24D is a side view of the sample tube retention assembly of FIG. 24C in a second position.

FIG. 25A is a front view of a pipette head according to another embodiment of the present disclosure.

FIG. 25B is a front transparent view of the pipette head according to FIG. 25A.

FIGS. 30A-E illustrate a tray for receiving consumables that permits easy transition of the consumables into a rack configured to be received by the system described herein.

FIG. 31G is an exploded elevational view of a gripper assembly of the decapper assembly of FIG. 31A.

FIG. 31H is a perspective exploded view of the gripper assembly of FIG. 31G.

FIG. 31I is a sectional view of the gripper assembly of FIG. 31G.

FIG. 31J is a sample container array depicting gripper finger pick-up positions.

FIG. 31K is a perspective view of a sample container contact sensor assembly of the decapper assembly of FIG. 31A.

FIG. 31L is a perspective view of a plunger cap of the sensor assembly of FIG. 31K.

FIG. 32A is a perspective view of a batch warmer array according to an further embodiment of the present disclosure.

FIG. 32B is a sectional view of a batch warmer taken along a midline thereof.

FIG. 32C is a top-down sectional view of a batch warmer taken directly above a heater thereof.

DETAILED DESCRIPTION

Definitions

Figure 1A:
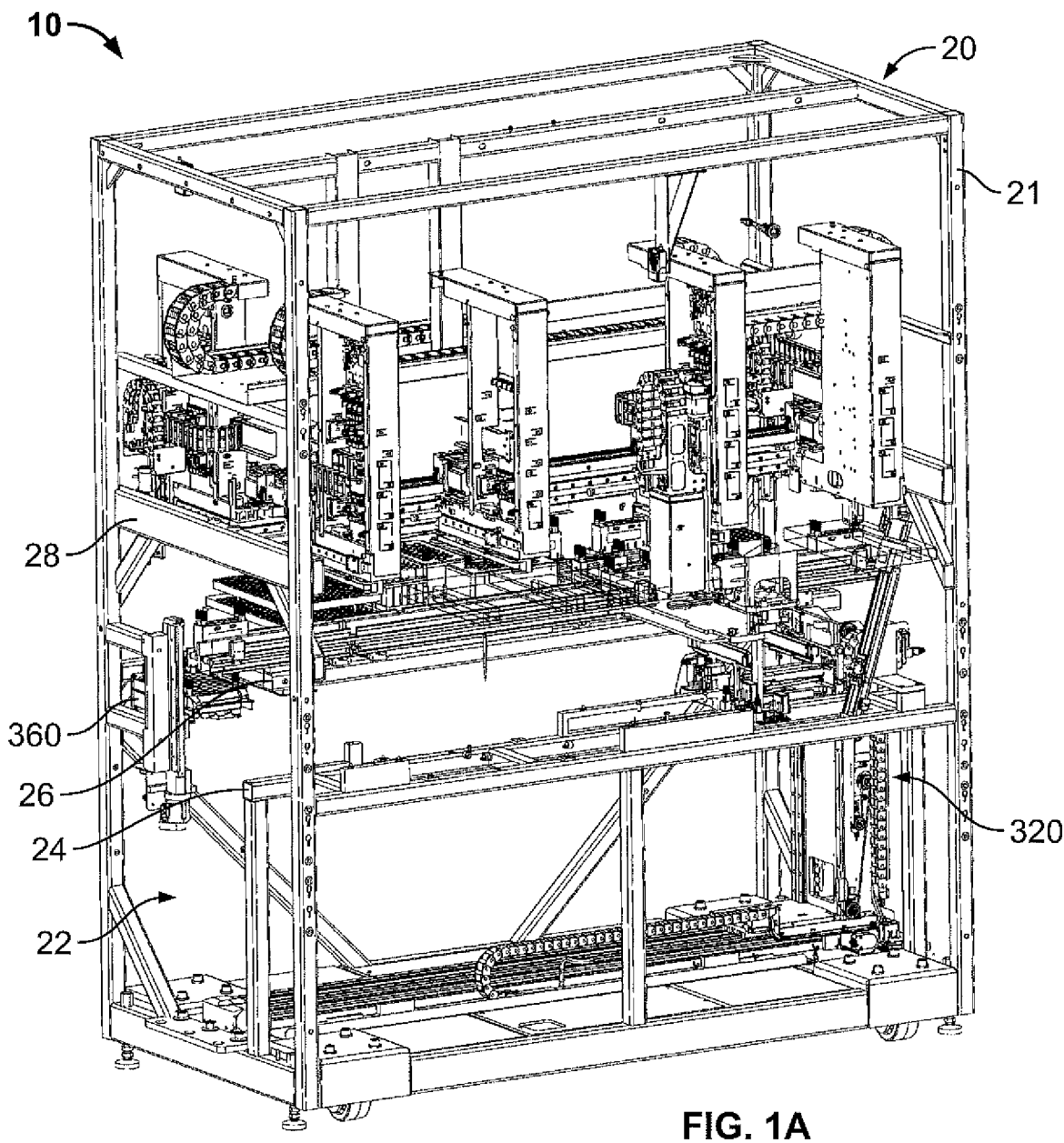
FIG. 1A is a front perspective view of a pre-analytical system according to one embodiment of the present disclosure.
Figure 1B:
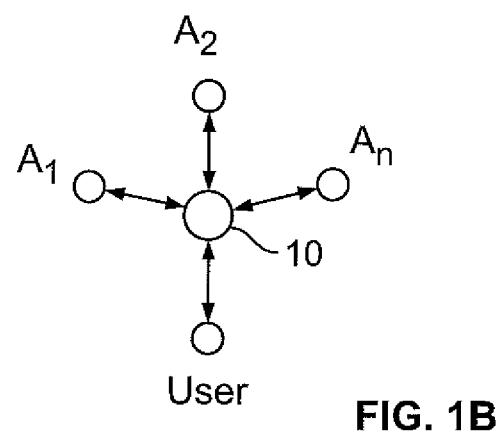
FIG. 1B is a schematic representation of the pre-analytical system of FIG. 1A in an exemplary application within a hub-and-spoke distribution network.

As used herein, "primary sample container" means any container in which a sample, such as a biological sample, as it is received by the pre-analytical system. In addition, "secondary sample container" is intended to mean any container that holds a sample after being transferred out of the primary sample container. In some examples "primary sample container" refers to those containers that can be handled directly by the pre-analytical system described herein without the need to transfer the sample from the primary container to a secondary container. As used herein, the terms "about," "generally," and "substantially" are intended to mean that slight deviations from absolute are included within the scope of the term so modified.

The term "shuttle" as used herein broadly includes any structure that can carry a plurality of sample containers and has a plurality of receptacles, each configured to receive a single sample container. Conventional other terms that can be used to describe the shuttle include, for example, racks, conveyance, carrier, etc.

Also when referring to specific directions, such as left, right, front, back, up and down, in the following discussion, it should be understood that such directions are described with regard to the perspective of a user facing the below described system during exemplary operation.

System Generally

FIGS. 1A-3 depict the general structure and layout of a pre-analytical system 10 according to one embodiment of the present disclosure. As illustrated in FIG. 1B, system 10 is configured to act as a hub in a hub-and-spoke distribution network involving a user and one or more analyzers $A_1 \ldots A_n$, such as the BD Viper™ LT System (Becton Dickinson, Franklin Lakes, N.J. or the BD MAX™ System). System 10 is a high-throughput platform that automates sample preparation and preprocessing for any number of analytical tests or assays performed by the one or more analyzers. For example, system 10 can prepare and preprocess samples for assays involving the determination of blood viral loads and the detection of human papilloma virus (HPV), *Chlamydia trachomatis, Neisseria gonorrhoeae, Trichomonas vaginalis*, group B *streptococcus*, enteric bacteria (e.g., *Campylobacter, Salmonella, Shigella, Escherichia coli, Shigella dysenteriae*), and enteric parasites (e.g., *Giardia lamblia, Cryptosporidium, Entamoeba histolytica*). System 10 is also capable of preparing and preprocessing several categories of samples including blood, mucus, sputum, urine, feces, liquid based cytological samples and the like.

Sample Containers

In addition, system 10 can accommodate a variety of sample containers including, but not limited to, ThinPrep® cervical sample/liquid based cytology containers (Hologic, Inc., Bedford, Mass.), SurePath™ cervical sample/liquid based cytology containers (Becton Dickinson, Franklin Lakes, N.J.), blood sample containers and blood collection containers such as, for example, BD Vacutainer® blood collection tubes, and penetrable-cap containers, such as BD MAX' sample buffer tubes with pierceable caps (Becton Dickinson, Franklin Lakes, N.J.) and APTIMA® Transport Tubes (Gen-Probe Inc., San Diego, Calif.).

Figure 8A:
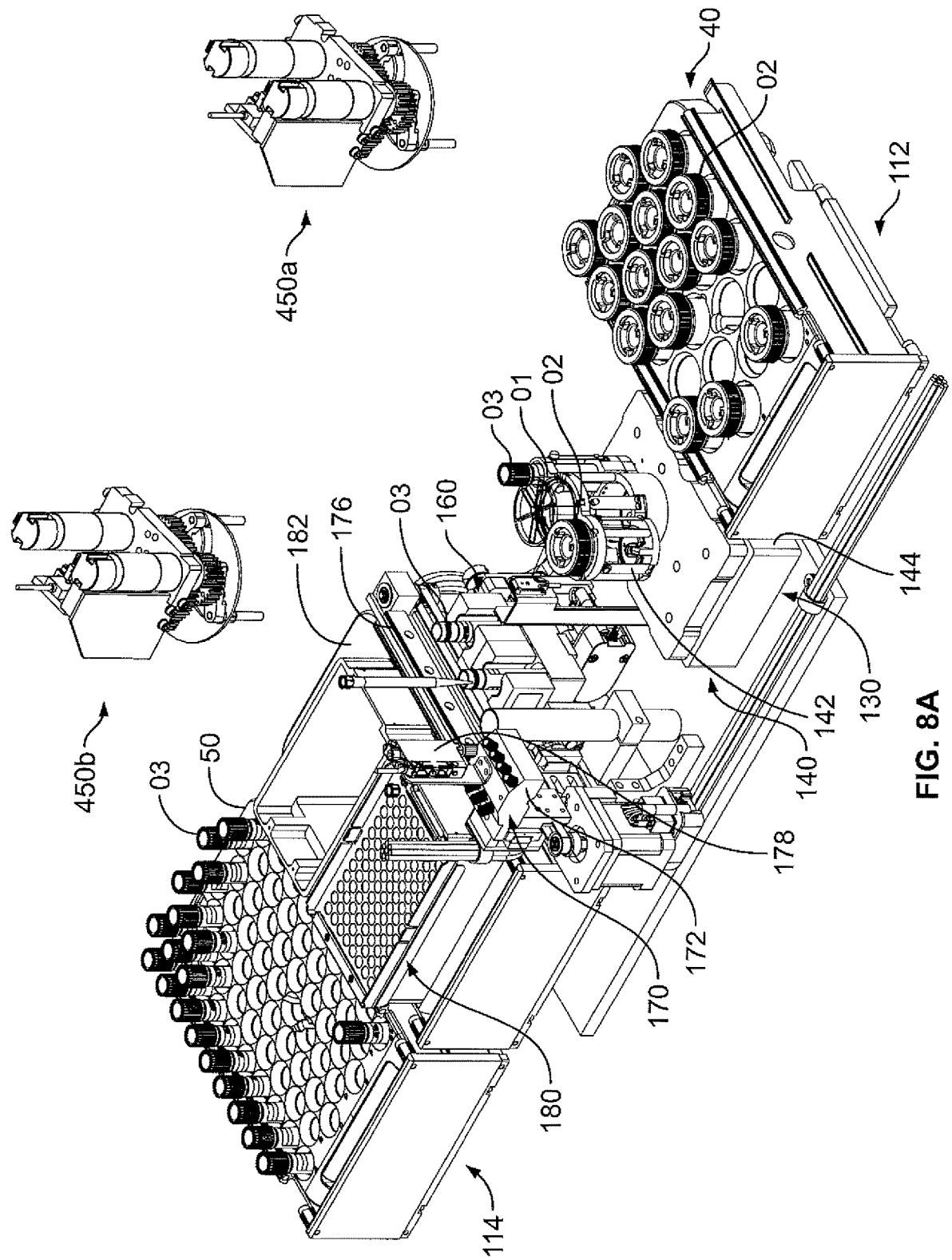
FIG. 8A is a perspective view of a sample conversion module of one of the sample pre-analytical processing decks of FIG. 7 according to one embodiment of the present disclosure.

For simplicity, the remainder of this disclosure refers to first-type, second-type, and third-type sample containers 01, 02, and 03. Exemplary first-type, second-type, and third-type containers 01, 02, 03 are depicted in FIG. 8A. First type containers 01 are analogous to ThinPrep® containers, second type containers 02 are analogous to SurePath™ containers, and third type containers 03 are analogous to BD MAX™ mL sample buffer tubes. The ThinPrep® containers and SurePath™ containers are referred to collectively as liquid based cytology (LBC) containers. Each of these types of containers differs in size such that the first-type 01 is the largest and the third-type 03 is the smallest. However, this particular size distribution is not necessary and is only meant to be illustrative of the container handling capabilities of system 10. As such, it should be understood that the first-type, second-type, and third-type containers 01, 02, 03 may be the same size or differ in size other than what is described directly above. In addition, third-type sample container 03 is particularly adapted for use by the one or more analyzers that can be coupled to system 10. For example, third-type sample container 03 may have a penetrable cap, such as a cap having a foil septum, or some other cap or structural feature particularly suited for use in the one or more analyzers $A_1 \ldots A_n$.

These containers are also referred to as primary first-type container 01, primary second-type container 02, and primary third-type container 03. These descriptions refer to containers 01, 02, and 03 in the role of a primary sample container. In addition, third-type container 03 is occasionally referred to as secondary third-type container 03, which refers to the third-type container's role as a secondary sample container.

System Frame

System 10 includes a structural frame 20 comprised of several support components 21, such as segments of metal tubing, which are configured to support and define various decks or levels for pre-analytical preparation and preprocessing of samples. Such decks or levels include a main storage deck or first accumulation area 22, a first pre-analytical processing deck 24, a second pre-analytical processing deck 26, and a suspended robot deck 28.

System Deck Relationships

Main storage deck 22 is generally the lowest located deck. It is defined at an upper boundary by first and second decks 24, 26. A system shell (not shown) that surrounds and is supported by frame 20 includes an access door (not shown) at a front of system 10 that can be manually and/or automatically operated to access main storage deck 22. However, during normal operations, this access door remains closed.

First preparation deck 24 is located at the front of system 10, and second preparation deck 26 is located at the back of system 10. These decks 24 and 26 are positioned parallel to each other and extend along the length of system 10. First preparation deck 24 is preferably positioned lower than second preparation deck 26.

In some embodiments, second deck 26 may be positioned lower than first deck 24. This height difference allows a robot to access first preparation deck 24 from below. In other embodiments, first and second pre-analytical processing decks 24, 26 may be located at the same height. In such embodiments, a widthwise gap (not shown) may separate first and second preparation decks 24, 26 to provide robot access thereto from below. However, such a gap may increase the front-back width of system 10.

Suspended robot deck 28 is located above first and second pre-analytical processing decks 24, 26 so that robots located within deck 28 can reach downward toward decks 24 and 26. As such, suspended robot deck 28 extends along the length of system 10 in correspondence with first and second pre-analytical processing decks 24, 26.

Consumable Racks for Use in System

FIGS. 4A-6 depict exemplary embodiments of various sample racks that can be utilized in system 10 to help accommodate the above mentioned variety of sample containers. In particular, FIG. 4A depicts a rack 30 adapted for holding first-type sample containers 01 and includes a plurality of uniformly sized receptacles 32 for receipt of containers 01. Rack 30 preferably includes thirteen receptacles 32. However, more or less receptacles 32 may be utilized. Each receptacle 32 defines discrete cylindrical or projecting members 33a and 33b. Cylindrical members 33a are located at the corners of rack 30 and each includes an extension 38 at a bottom thereof that defines an abutment shoulder. Such shoulder is formed by the smaller dimensions of extension 38 relative to cylindrical member 33a.

Cylindrical members 33b are located between cylindrical members 33a. Members 33b do not include extension 38. Thus, extensions 38 extend beyond the length of cylindrical members 33b such that when rack 30 is placed on a flat surface, cylindrical members 33b do not touch the flat surface so as to form a space between cylindrical members 33b and the surface. These extensions 38 are dimensioned to be received within a receptacle 32 of another rack 30 so that multiple racks 30 can be stacked when they are empty. Small indentations (not shown) in the side of the rack allow the rack to lock into position at different locations throughout system 10 to help locate and maintain rack 30 in a specific position.

Openings 35 extend through the bottom of cylindrical members 33a-b and communicate with receptacles 32. These openings 35 can help with rack sanitation and can allow scanners, such as bar code scanners, to scan information that may be located on the bottom of a container located within one of receptacles 32, for example.

As shown in FIG. 4C, an engagement member 39 may be located at a bottom of rack 30. Engagement member 39, as depicted, includes a hollow cylinder 31 that has an opening sized to engage a projection of a rack mover arm (discussed below). Engagement member 39 may be modular so that it can be attached to rack 30 at a bottom end thereof. For example, in one embodiment a shim portion coupled to hollow cylinder 31 may be press-fit into spaces between cylindrical members 33a-b. However, in other embodiments, engagement member 39 may be integrated into the structure of rack 30 such that hollow cylinder 31 extends from a bottom thereof or is recessed between cylindrical members 33a-b. When rack 30 is placed on a surface, a space is formed between the surface and the bottom of cylindrical members 33b due to the extended length of cylindrical members 33a. The rack mover arm engages engagement member 39 which extends from the bottom of the rack 30 but does not interfere with rack stability when the rack 30 is placed on a flat surface. Engagement feature 39 is preferably located at or near a center of mass of rack 30 to help stabilize it when it is retrieved by rack mover arm.

Rack 30 also includes at least a pair of peripheral walls 34 located at opposite sides of rack 30. Such walls 34 each include a downward facing surface 37. Surface 37 is preferably planar and may be utilized by automated devices for engaging and supporting rack 30.

A handle 36 is located on a single side of rack 30 between and transverse to the peripheral walls 34. Although a single handle is shown, multiple handles disposed at opposite sides of rack 30 are contemplated. However, a single handle 36 is preferred in order to keep the overall dimensions of rack 30 to a minimum for efficient storage within system 10. As described below, rack 30 is loaded and retrieved by a user through a single port in system 10. Handle 36, alone, is sufficient to load and retrieve rack 30 from the port, particularly since system 10 delivers rack 30 to the port in the same orientation in which it is loaded.

Figure 5:
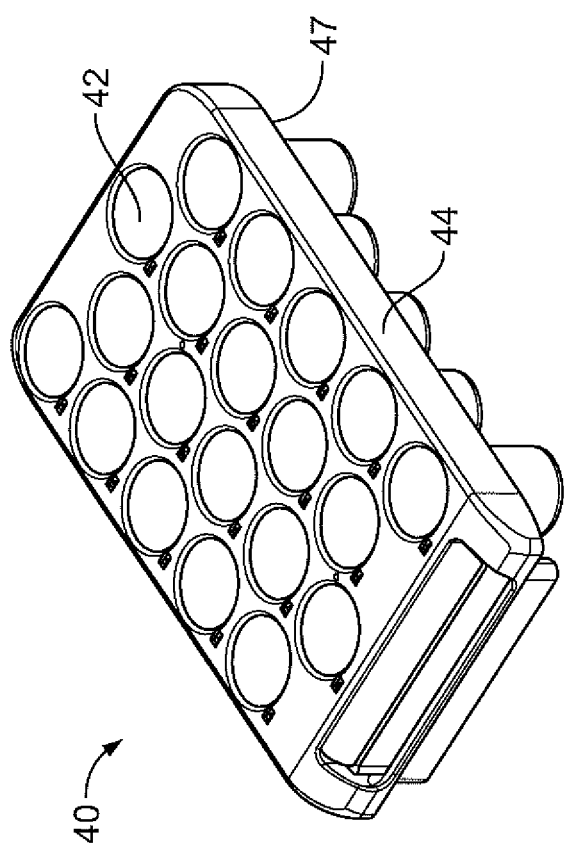
FIG. 5 is a top perspective view of a sample container rack according to another embodiment of the present disclosure.

Rack 40, as depicted in FIG. 5, is similar to rack 30 and includes a plurality of receptacles 42. However, receptacles 42 of rack 40 are smaller than those of rack 30 and are sized to accommodate second-type sample containers 02. Due to the smaller size of receptacles 42, rack 40 can include more of such receptacles 42. In a preferred embodiment, rack 40 includes twenty receptacles 42. However, more or less receptacles 42 are contemplated.

Figure 6:
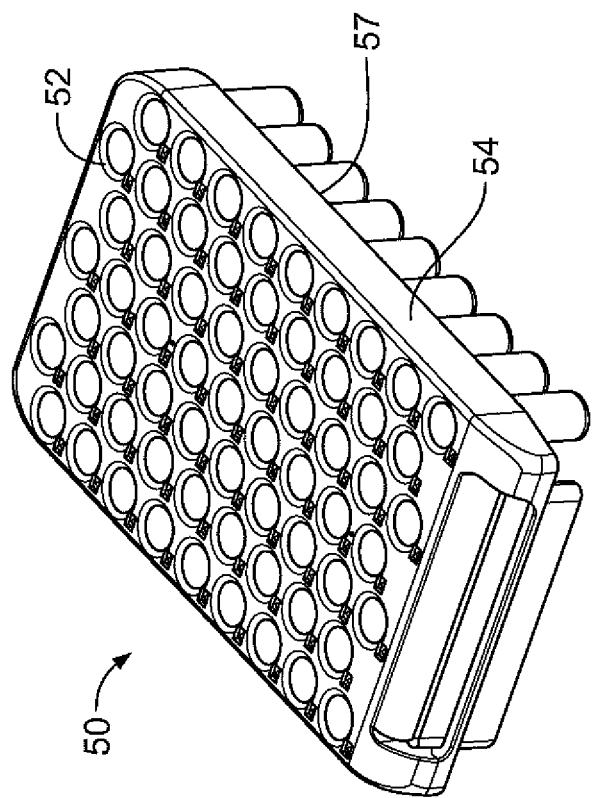
FIG. 6 is a top perspective view of a sample container rack according to a further embodiment of the present disclosure.

Rack 50, as depicted in FIG. 6, is also similar to racks 30 and 40, but includes even smaller receptacles 52 that are sized to accommodate third-type sample containers 03. As such, rack 50 can include sixty-three receptacles. However, again, more or less receptacles 52 are contemplated.

Racks 30, 40, and 50 have substantially the same peripheral dimensions. In addition, each rack 30, 40, 50 includes a bar code, RFID, or some other identification tag which can be scanned upon entry into system 10, such as automatically by system 10 or manually by the user, in order to identify the types of containers disposed therein. In addition, racks 30, 40, and 50 may be color coded so that a user can easily determine the type of container that goes into a particular type of rack.

While each rack 30, 40, 50 includes uniformly sized receptacles for a single size sample container; it is contemplated that a single rack may include receptacles having differing sizes to accommodate various sizes of sample containers. For example, receptacles 32 and 42 can be included into a single rack to accommodate both first and second-type sample containers 01, 02. It is also contemplated, that receptacles 52, sized for a third-type container 03, can be included in a rack along with receptacles 32 and/or 42. However, it is preferable to separate the third-type sample containers 03 (or any containers particularly suited for an analyzer) into their own rack so that the small containers can bypass sample conversion, as described in more detail below. This helps enhance speed and reduce complexity of system 10.

Figure 7:
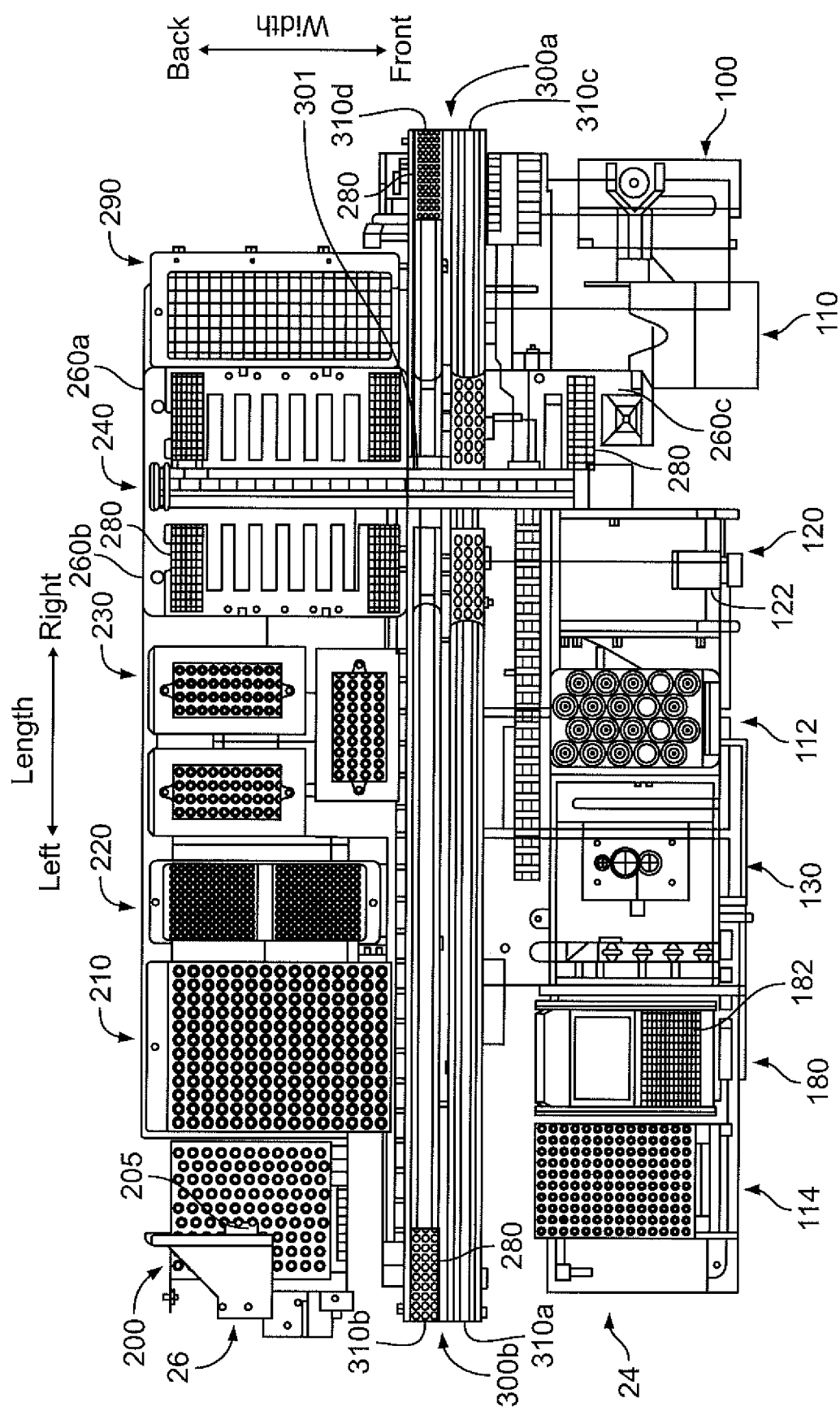
FIG. 7 is a top view of sample pre-analytical processing decks of the analytical system of FIG. 1A.

FIG. 7 depicts a disposable pipette tip rack 182. Disposable pipette tip rack has the same dimensions as racks, 30, 40, and 50. In addition, disposable pipette tip rack 182 includes a plurality of receptacles 184 each sized to receive and suspend a disposable pipette tip so that a pipetting robot can retrieve a pipette tip therefrom.

Also, system 10 is adaptable to accommodate other sample racks having other types of containers. For example, racks similar in structure to those just described directly above may be particularly adapted to retain blood sample containers/vacutainers.

Main Storage Deck

Referring back to FIGS. 2 and 3, main storage deck 22 includes a rack handler robot 320 (see FIG. 14) and rack elevator 360 (see FIG. 15) which are primarily disposed within main storage deck 22 and can traverse main storage deck 22 and into first and second processing/preparation decks 24, 26.

Main storage deck 22 also includes shelving or discrete storage cells for holding consumables in an organized fashion. For example, as shown in FIG. 2, main storage deck 22 includes shelving (not shown) for racks 30, 40, 50, and 182, shelving (not shown) for a pipette tip waste container 12, and shelving (not shown) for bulk diluent containers.

Figure 2:
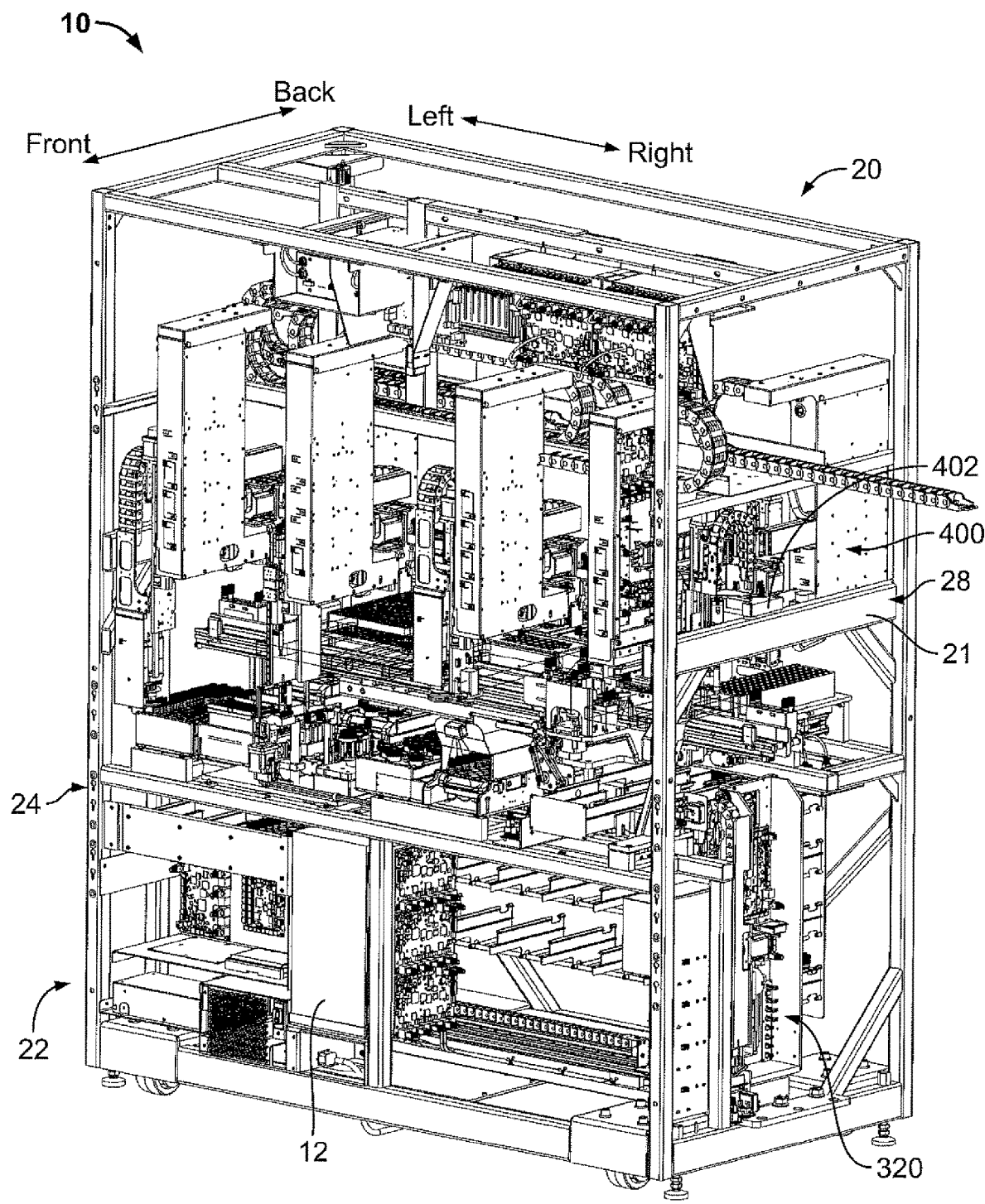
FIG. 2 is another front perspective view of the pre-analytical system of FIG. 1A.
Figure 3:
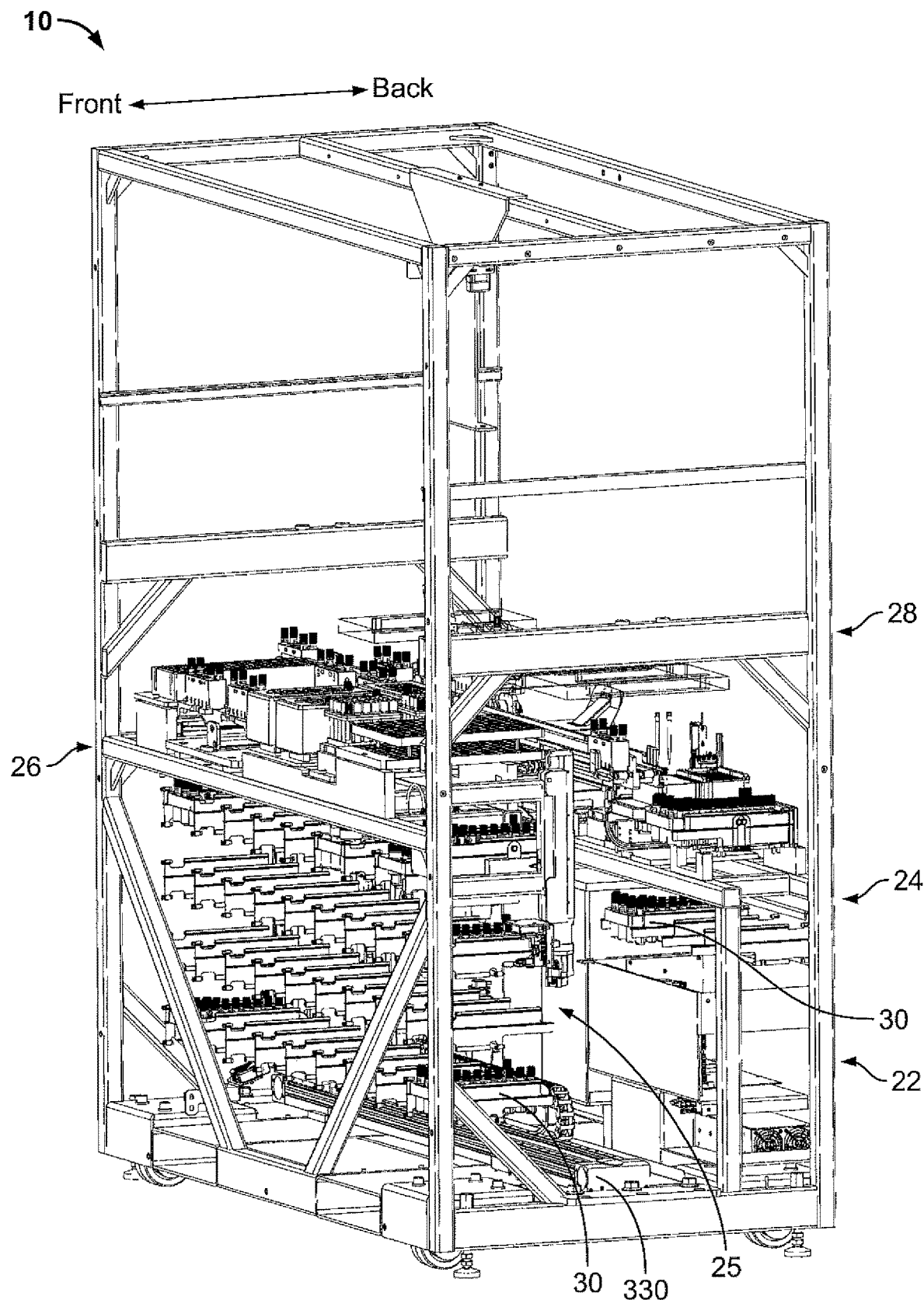
FIG. 3 is a rear perspective view of the pre-analytical system of FIG. 1A.

Referring to FIG. 2, shelving for various consumables and items are located below first and second pre-analytical processing decks 24, 26 (FIG. 3). For example, shelving supports consumable racks 30, 40, 50, 182 (FIG. 7) and define rack storage positions. Such rack storage positions can be below both first and second pre-analytical processing decks 24, 26. In addition, shelving may be provided under first pre-analytical processing deck 24 which supports bulk diluent containers, waste containers for disposable pipette tips, and the like from below. Shelving is arranged so as to form a space or runway 25 (see FIG. 3) extending along the length of system 10 so that robot 320 can traverse this runway 25 and retrieve racks 30, 40, 50, and 182 from either side of runway 25. In this regard, runway 25 extends upward along a back-end of the sample rack storage positions located at the front of system 10 so that runway 25 intersects a back-edge of first preparation deck 24. This allows robot 320 traversing runway 25 to retrieve and deposit racks 30, 40, 50, 182 below first and second preparation decks 24, 26 and also above first preparation deck 24.

Shelving for bulk diluent containers or other items may be statically disposed within storage deck 22 or may be coupled to an access door (not shown) so that when the access door is swung open, bulk diluent containers move with the access door and are presented to a user for easy removal and replacement. Shelving is configured for side-by-side arrangement of the bulk diluent containers. However, shelving may also be configured so that the bulk diluent containers are arranged both side-by-side and vertically.

Storage deck 22 and its configuration is an aspect that allows system 10 to perform high-throughput pre-analytical preparation and preprocessing while providing long walk-away times for a user by accumulating significant quantities of consumables and allowing for automated manipulation thereof when determined by system 10.

FIG. 7 depicts an exemplary configuration of first and second pre-analytical processing decks 24, 26. Decks 24 and 26 include numerous devices and locations for rack/tube placement. As shown, first deck 24 includes, from right to left, an angled elevator 100, a first sample rack space 110, an input/output (I/O") port 120, a second sample rack space 112, a sample conversion assembly 130, pipette tip rack space 180 with pipette tip rack 182, and a third sample rack space 114. Sample rack space 114 is the destination location for sample containers that have been processed through sample preparation/conversion assembly 130. First pre-analytical processing 24 deck also includes an opening (not shown) extending therethrough and positioned above pipette tip waste container 12. Although these devices/spaces are shown disposed on the first pre-analytical processing deck 24 in a particular configuration, it should be understood that each of these device/spaces can be located elsewhere on first pre-analytical processing deck 24 without departing from the invention as described herein.

First Pre-Analytical Processing Deck
Tube Sealer and First Rack Space

Sample rack spaces 110, 112, and 114 can receive any of the sample racks 30, 40, 50 previously described. However, such spaces 110, 112, 114 generally receive particular sample racks with a particular load therein. Such spaces are designated to receive these particular sample racks to optimize robotic movements. However, as mentioned such spaces can receive a multitude of different racks. In addition, each sample rack space 110, 112, and 114 are generally configured to receive a single sample rack 30, 40, 50. Although, it should be understood that system 10 can be configured such that rack spaces 110, 112, and 114 can accommodate more than one sample rack.

In a preferred configuration of system 10, first sample rack space 110 receives sample rack 50 with receptacles 52 empty or partially empty. While located within rack space 110, receptacles 52 are loaded with processed/used sample containers 03 returned from an analyzer. Elevator 100, which is described further below, is placed adjacent to rack space 110 and is configured to raise a rack 50 to second deck 26 to be filled with used sample containers 03 and to lower such rack 50 filled with such used containers 03 down to deck 24 at rack space 110 so that rack handler robot 320 can retrieve the rack 50 from angled elevator 100 and move it to the storage deck 22.

Input Port & Bar Code Scanner

I/O port 120 is located adjacent to rack space 110. I/O port 120 is generally a rectangular enclosure through which sample racks 30, 40, and 50 are deposited and retrieved by a user. All sample racks 30, 40, 50 and sample containers 01, 02, 03 utilized by system 10 pass through this port. I/O port 120 may be dimensioned to be slightly larger than a single rack 30, 40, 50, 182. This helps conserve preparation/processing space and helps position each rack 30, 40, 50 in substantially the same location within I/O port 120 for rack handler robot 320 (described below) to retrieve a rack therefrom. However, it is contemplated that port 120 may be dimensioned to receive multiple racks placed side-by-side or front-to-back. In addition, a bar code scanner (not shown) is located adjacent to or within I/O port 120 to read bar codes located on sample racks 30, 40 and 50 as they are input into system 10.

Sample Preparation/Conversion Instruments

Figure 8B:
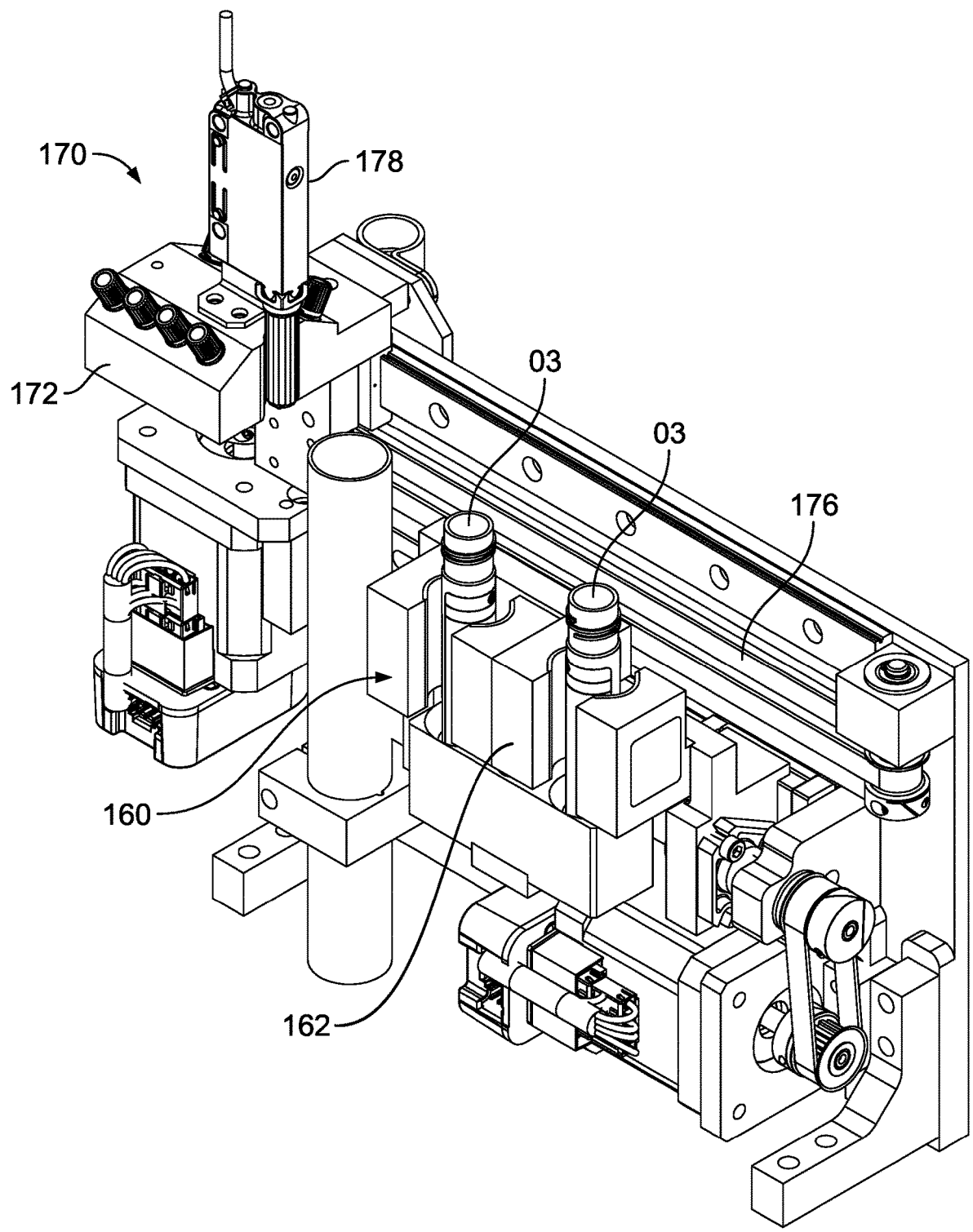
FIG. 8B is a perspective view of a tube clamp assembly of the sample conversion module of FIG. 8A according to one embodiment of the present disclosure.
Figure 8C:
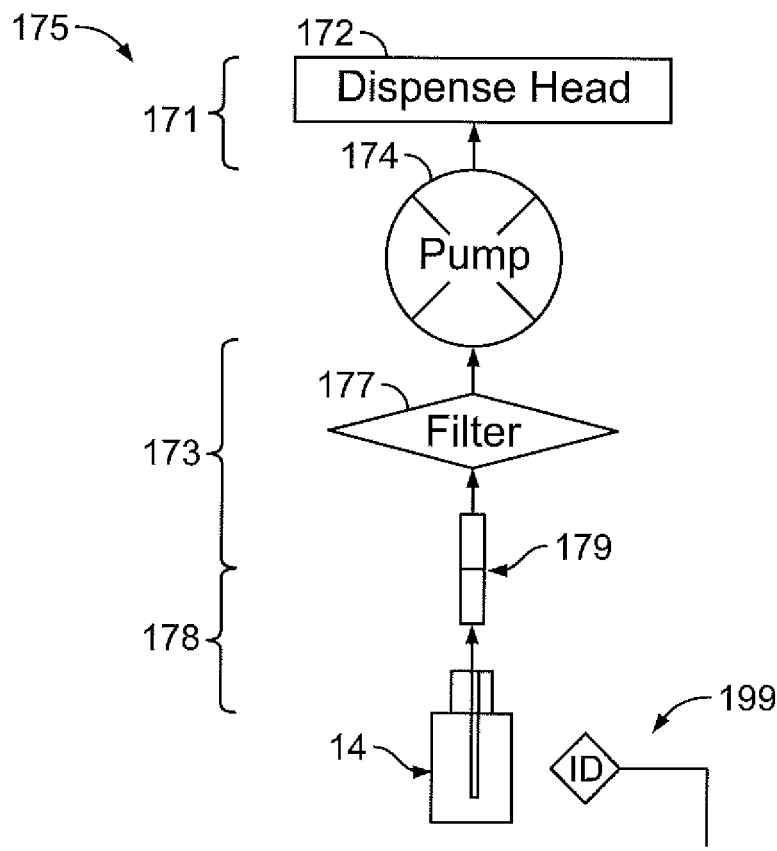
FIG. 8C is a schematic view of a diluent dispense system of the sample conversion module of FIG. 8A according to one embodiment of the present disclosure.

FIGS. 7-8C depict spaces and devices positioned at an opposite side of I/O port 120 from first rack space 110. Sample conversion (described below) takes place at this side of I/O port 120 and includes sample preparation/conversion assembly 130, pipette tip rack space 180, and second, third, and fourth rack spaces 112, 114.

Second sample rack space 112 generally receives either rack 30 or 40 which is filled or partially filled with sample containers 01 or 02, respectively, acting as primary sample containers. However, in some embodiments sample rack space 112 can also receive rack 50 including sample containers 03 that had been previously used by an analyzer. In other words, rack space 112 can receive sample rack 50 in order to run additional tests on a sample without removing it from system 10. Third sample rack space 114 receives sample rack 50 filled or partially filled with empty third-type containers 03, which later act as secondary containers for samples contained in containers 01 and 02 or third-type containers 03 containing control samples. Also, rack space 180 receives pipette tip rack 182.

Preparation/conversion assembly 130 is preferably located between second and third rack spaces 112, 114 and generally includes a bar code scanner (not shown), a primary sample container station 140, a secondary sample container station 160, and a diluent dispenser 170. Also one or more clamp assemblies 162 is optionally provided.

Primary sample container station 140 may include multiple receptacles 142 each dimensioned to receive a different size sample container. For example, a first receptacle may be dimensioned to receive first-type sample container 01 and a second receptacle may be dimensioned to receive second-type sample container 02. In some embodiments, a third receptacle for a third-type sample container 03 may be provided, or a single adjustable receptacle, such as a receptacle with a clamping mechanism, may be provided to accommodate each sample container type 01, 02, and 03. In addition, each receptacle 142 may include engagement features (not shown) located at a bottom thereof for interlocking with corresponding features located at a bottom of sample containers 01 and 02 so as to prohibit sample containers 01 and 02 from rotating therein. Such engagement features allows for a sample container 01, 02 to be de-capped and recapped within a receptacle 142.

Receptacles 142 are also integrated into a motorized base 144. Motorized base 144 includes a motor, such as an eccentric motor, which may be coupled, directly or indirectly, to the structure defining each receptacle such that station 140 can operate as an agitator or vortexer to re-suspend particulates within a sample. However, in some embodiments, an independent agitator/vortexer may be provided adjacent to station 140.

Secondary sample container station 160 is positioned adjacent primary sample container station 140 and adjacent to diluent dispenser 170. As mentioned, sample container station 160 preferably has one or more clamps to receive third-type sample container 03 and, optionally, vacutainers. The clamps hold the third-type container 03 so as to prohibit container 03 from rotating therein while a cap thereon is decapped and recapped by a decapper robot 450*b*, as is described further below. However, in other embodiments passive receptacles can be provided at secondary sample container station 160 to receive the third-type sample containers 03. In such embodiments, the receptacles may include engagement features that are keyed to a container engagement feature that may be located on a side of a container 03 or at a collar of container 03. In this regard, the receptacle engagement features may be correspondingly positioned within receptacles disposed at the secondary sample container station. Thus, when a container 03 is disposed in a corresponding receptacle, the engagement features engage each other to prevent rotation of container 03. In either embodiment just described, secondary container station 160 is configured so that container 03 can be de-capped and recapped while remaining in the same location Similar to station 140, secondary container station 160 may also be configured with a motorized base to act as an agitator/vortexer for third-type sample containers 03.

FIGS. 8A and 8B depict an exemplary clamp assembly that comprises secondary sample container station 160 and diluent dispenser 170 combination. The clamp assembly has moveable jaws that can hold two containers 03 adjacent each other. Such clamp assembly is positioned adjacent to or below a track 176 that includes a belt and pulley mechanism. Diluent dispenser 170 is connected to this track 176 and is moveable along the track 176 so that a multichannel dispense head 172 can be positioned over the clamp assembly and any containers 03 retained by such assembly. Diluent dispenser 170 has multiple dispense nozzles/openings that are angled inward so that when dispense head 172 is positioned over a container 03, a selected channel 175 can dispense a metered amount of diluent into the respective container 03. An ultrasonic sensor 178 verifies that dispense occurred by confirming a volume change.

In another embodiment diluent dispenser 170 may include a column rising from first preparation deck 24 and a spout or dispense head transversely extending from column. Dispenser may also include a plurality of diluent channels. For example, in one embodiment such dispenser may include eight diluent channels, but may include any number of diluent channels. Channels are isolated from one another such that each channel 175 is capable of dispensing a different diluent into an empty third-type sample container 03. The diluent that is dispensed depends on the downstream analysis to be performed on the sample. As such, each channel 175 is separately controlled.

As depicted in FIG. 8C, each channel 175 includes first and second tubing sets 171 and 173 and a pump 174. First tubing set 171 connects the pump to the dispense head 172. The pump 174 may be a dosing pump that precisely controls the quantity of diluent dispensed and also includes a sensor (not shown) to verify fluid volume. Such sensor can include a distance measuring sensor, gravimetric sensor, optical sensor, and the like, for example. The second tubing set 173 connects a bulk diluent container 14 to the pump and includes a filter 177. Filter 177 may be a 50 u inline filter and is positioned downstream of pump 174 to help prevent particles, such as coagulated diluent, from getting into pump 174. Each channel 175 is connected to a bulk diluent container 14 located within main storage deck 22 via a tube cap assembly 178. Cap assembly 178 and second tubing set 173 may also have corresponding components of a quick-connect mechanism 179 that allows bulk diluent containers 14 to be quickly replaced. The cap assembly 178 and pump 174 are arranged beneath deck 24. Additionally, a bar code scanner 199 is positioned beneath deck 24 and may be configured to concurrently read barcodes on each of the bulk diluent containers 14 connected to each of the plurality of diluent channels 175 so as to feed system 10 with real-time information regarding available diluents. Alternatively, a plurality of bar code scanners can be positioned adjacent bulk diluent containers 14 to perform such function.

Dispense head 172 acts as a straight-through manifold (schematically illustrated in FIG. 8C) for the plurality of diluent channels 175 and may have a plurality of nozzles (not shown) each defining a diluent channel 175 terminating at a bottom end of the dispense head to help prevent cross-contamination as the diluent flows therefrom. Such nozzles may be aligned along a single axis or offset in more than one axis. In some embodiments where dispense head 172 is connected to a rotating column, such column may be coupled to a stepper motor that rotates the column back and forth by predetermined angular distances so that a designated diluent channel 175 aligns with an open third-type sample container 03 located at secondary container station 160. For example, each step of the motor may rotate the dispense head an angle equivalent to an angular distance between adjacent channels 175. In other embodiments, the dispense head may be coupled to a linear actuator that moves dispenser 170 back and forth in a linear direction to align a diluent channel 175 with a container 03. In further embodiments, a receptacle at secondary container station 160 may be linearly translated, such as by a moving base via a linear actuator, so that a container 03 disposed therein can be aligned with an appropriate diluent channel 175.

Second Preparation/Processing Deck

Referring again to FIG. 7, second preparation deck 26 includes, from left to right, an empty space 200, batch-accumulation area 210, a plurality of bulk vortexers 220, a warmer 230, a shuttle handling assembly 240, a cooler 290, and a pair of shuttle transport assemblies 300a-b. Second deck 26 also includes a bar code scanner 205 configured to scan the bar code of a sample container. Although these devices/spaces are shown disposed on the second pre-analytical processing 26 deck in a particular configuration, it should be understood that each of these device/spaces can be located elsewhere on the second pre-analytical processing deck 26 without departing from the invention as described herein.

Rack Elevator Space

As depicted in FIG. 7, empty space 200 is sized to receive sample rack 50. Also, as previously mentioned rack elevator 360 (described below) is partially disposed within storage deck 22 and operates between storage deck 22 and second pre-analytical processing deck 26. Rack elevator 260 is disposed in the back, left corner of system 10 and serves to fill empty space 200 with sample rack 50. Sample rack 50, when occupying this space typically includes third-type sample containers 03 which can be either primary or secondary containers, as is described in more detail below.

Batch-Accumulation Area

Batch-accumulation area 210 includes an array of receptacles 212. For example, area 210 includes about 200 receptacles but can include more or less. Receptacles 212 are sized to receive third-type sample containers 03 and are arranged in a rectangular configuration such that they border bulk vortexers 220 along two sides thereof. Such shape helps conserve space and minimizes the distance between receptacles 212 and bulk vortexers 220. However, receptacles 212 can be arranged in any geometric configuration, such as a rectangular or circular shaped arrangement of receptacles 212. Batch-accumulation area 210 receives and accumulates containers 03 in batches based on their assay designation. The total number of receptacles 212 for batch accumulation area may vary. However, the total number should be sufficient to maintain sufficient stock of containers 03 to feed analyzers $A_1 \ldots A_n$ as the analyzers become available in order to reduce downtime.

Batch-accumulation area 210 is a second accumulation area in addition to storage deck 22 which is a first accumulation area. These accumulation areas 22, 210 provide system 10 reserves of accumulated samples/consumables that can be drawn upon when needed. This allows a user to randomly load and unload system 10 while also allowing complete batches of prepared and preprocessed samples to be distributed to an analyzer as soon as an analyzer becomes available, thereby minimizing downtime.

Bar code scanner 205 is arranged adjacent to batch-accumulation area 210 and near empty space 200. This allows containers 03 to be scanned by scanner 205 as containers 03 are moved from a rack 50 at space 200 to a receptacle 212.

Bulk Vortexer

Figure 9:
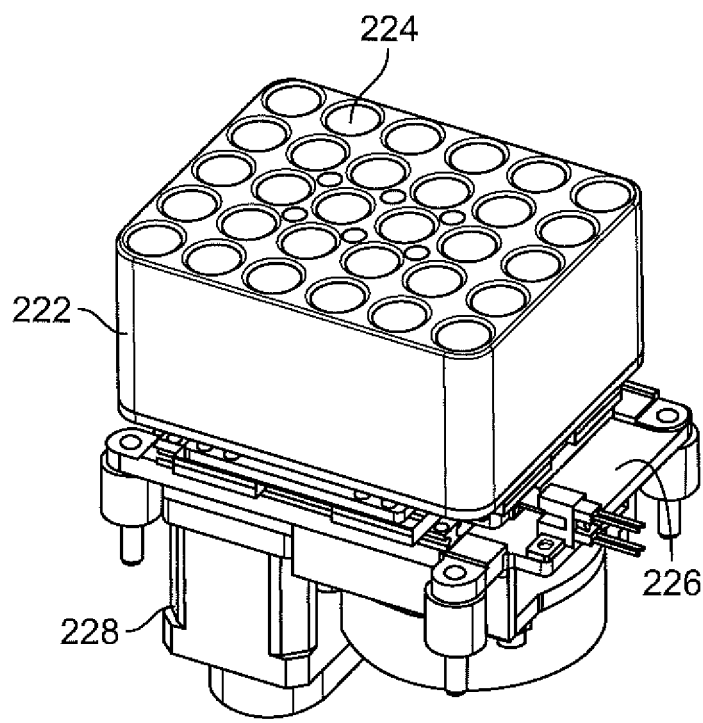
FIG. 9 is a front perspective view of a bulk vortexer according to one embodiment of the present disclosure.
Figure 10:
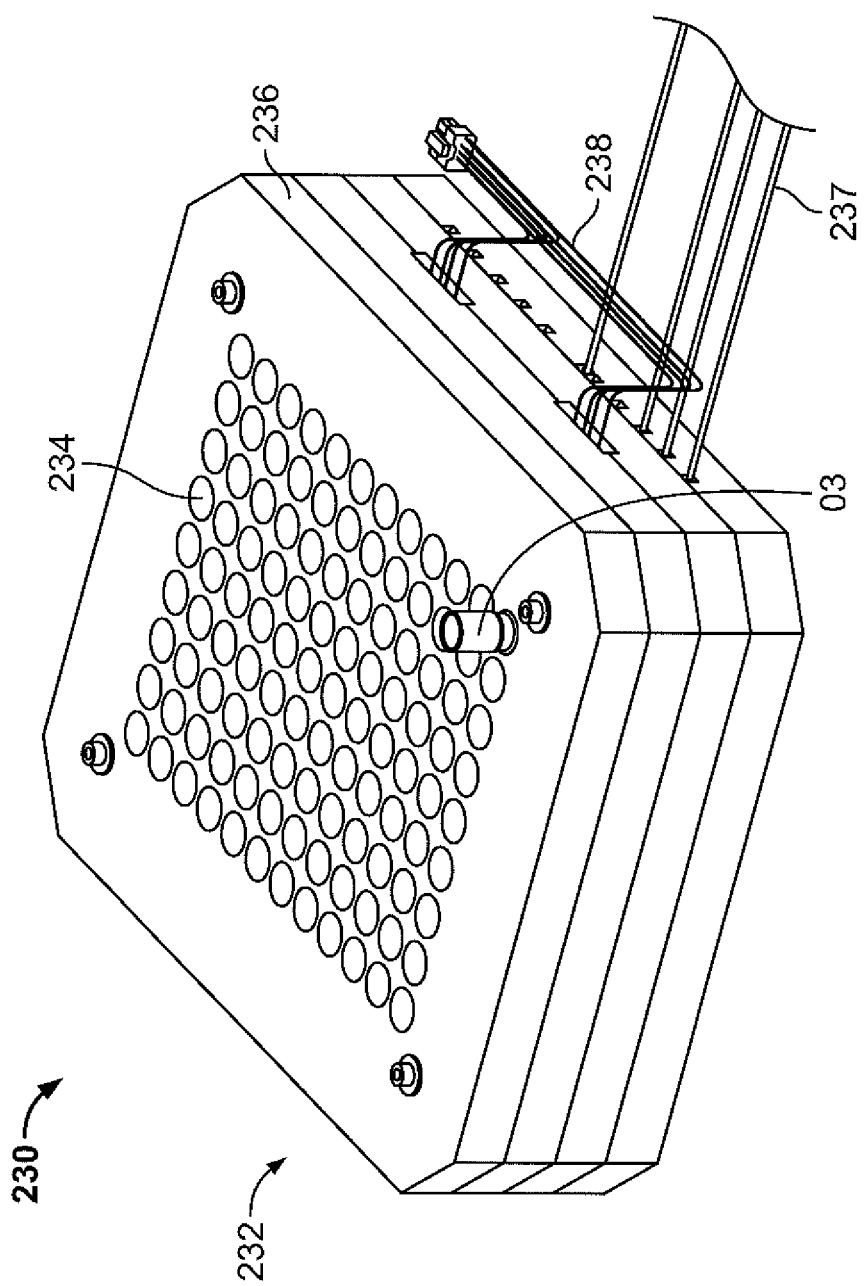
FIG. 10 is a front perspective view of a warmer of one of the sample pre-analytical processing decks of FIG. 7 according to one embodiment of the present disclosure.

As depicted in FIG. 7, second pre-analytical processing deck 26 includes two or more bulk vortexers 220 (in FIG. 7, four bulk vortexers are arranged in two rows of two) located between batch-accumulation area 210 and warmer 230. However, more or less bulk vortexers 220 may be included and in alternative arrangements. For example, in one embodiment of system 10, two bulk vortexers 220 may be arranged on second pre-analytical processing deck 26. Each bulk vortexer 220 generally includes a body 222, platform 226 and motor 228 (best shown in FIG. 9). Body 222 includes a plurality of receptacles 224 arranged in a quadrilateral array of about thirty receptacles or less. Each receptacle 224 is sized to receive a third-type container 03 therein and may contain an engagement feature (not shown) disposed at a bottom-end thereof for engaging a bottom-end of containers 03 to prevent rotation within receptacles 224 during use. Body 222 is arranged on platform 226 which is coupled to motor 228, such as an eccentric motor. Motor 228, when turned on, oscillates platform 226 and body 228 to re-suspend particulates within each sample. Motor 228 is controlled to operate for a predetermined time interval which may be determined by the type of samples contained within sample containers 03.

System 10 also includes a vortex controller. When a sample is ready to be handed off to a vortexer 220, the controller determines if vortexer 220 can receive the sample. The programmer/controller also instructs vortexer 220 to operate at a certain speed for a predetermined time interval. The vortex controller has a feedback loop that continuously monitors vortexer operating conditions and sends an error message if a vortexer operating condition fails to match an input instruction. For example, if a particular operating speed is instructed, the feedback loop monitors the actual operating speed. If the operating speed does not match the instructed speed, then there is an error which generates an error message. In addition to generating a first error message, if there is an error, the vortexer is reinitialized. If a second error message is received then a command for vortexer service/replacement is issued. Thus, auto correction is first attempted, and then a request for user intervention is sent if the auto correction is not successful. In all cases a pick and place robot, such as robot 410a or 410b, removes container 03 from vortexer 220 upon completion.

Warmer

Warmer 230 is disposed between bulk vortexers 220 and shuttle handling assembly 240, as shown in FIG. 7. Warmer 230 heats samples at a specified temperature for a specified period of time as determined by the assay to be performed. For example, in one embodiment, warmer 230 heats samples to within about 100° to 115° Celsius for about 9 to 17 minutes after equilibration at 100° Celsius.

Warmer 230 generally includes a body 232 comprised of a plurality of warming plates 236 made from thermally conductive materials and stacked in a tight arrangement on top of one another. A plurality of receptacles 234 extend through warming plates 236 from a top surface of body 232 and are arranged in a quadrilateral array of about 110 receptacles or less. For example, warmer may include 96 receptacles (which can be more or less), which can hold multiple batches of 24 or 32 containers at any given time. Heating elements 237 are sandwiched between each plate 236 so as to distribute heat evenly throughout body 232. A temperature sensor 238, such as thermocouple, resistance temperature detector ("RTD"), or thermistor, is located at about mid-height of body 232 and measures temperatures therein. Temperature sensor 238 and heating elements 237 may be coupled to a proportional-integral-derivative ("PID") controller to help maintain constant set-point temperatures.

Cooler

Figure 11:
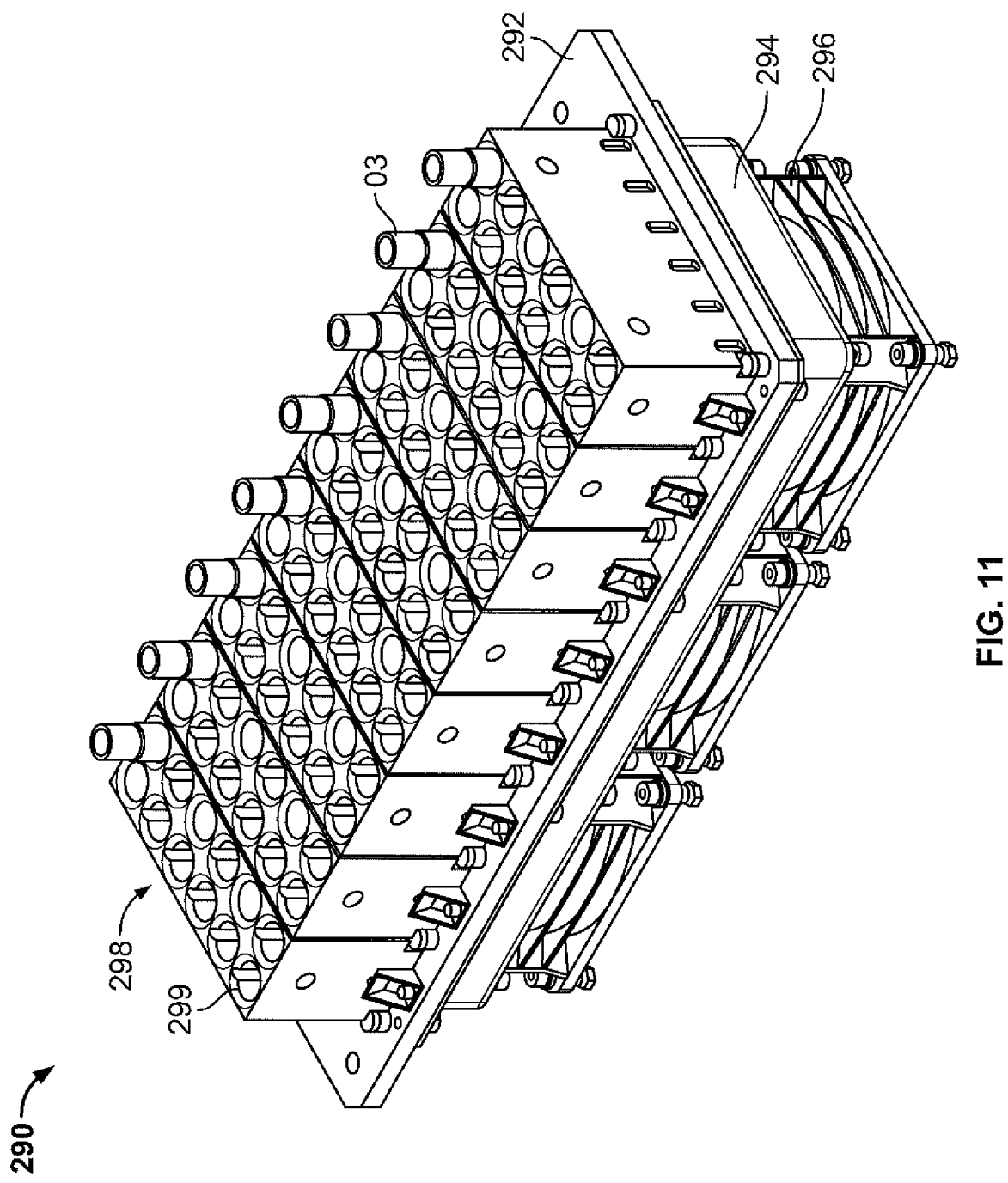
FIG. 11 is a front perspective view of a cooler of one of the sample pre-analytical processing decks of FIG. 7 according to one embodiment of the present disclosure.

Cooler 290, as depicted in FIG. 11, generally includes fans 296, one or more plenum 294, a platform or mounting plate 292 and cooling racks 298. Fan units 296 are positioned directly above second pre-analytical processing deck 26 and are partially surrounded at an upper-end thereof by plenum 294. Platform 292 sits atop of plenum 294 and includes openings (not shown) that allow air to pass therethrough. Cooling racks 298 are positioned over the openings of platform 292. Cooling racks 298 can be shuttles 280 or structures integrally formed into platform 292. Cooling racks 298 include a plurality of receptacles 299 sized to receive third-type containers 03 therein. Openings (not shown) extend through a bottom-end of cooling racks 298 and communicate with receptacles 299. These openings are smaller than receptacles 299 so that containers 03 do not fall therethrough. This arrangement allows air to be drawn into fans 296 from below and to the sides of fans 296 and expelled upwardly through plenum 294 and into cooling racks 280 to convectively cool sample containers 03. This bottom-up cooling approach helps prevent contaminants from being deposited on the caps of containers 03 and allows for containers 03 to be easily moved in and out of cooling racks 280.

Cooler 290 is disposed at the back, right corner of system 10 and adjacent to shuttle handling assembly 240, as shown in FIG. 7. Cooler 290 is generally located at this position so that shuttle handling assembly 240 acts as a buffer between warmer 230 and cooler 290. This helps prevent airflow around cooler 280 from affecting the heat distribution within warmer 230.

Shuttle Handling Assembly

Figure 12A:
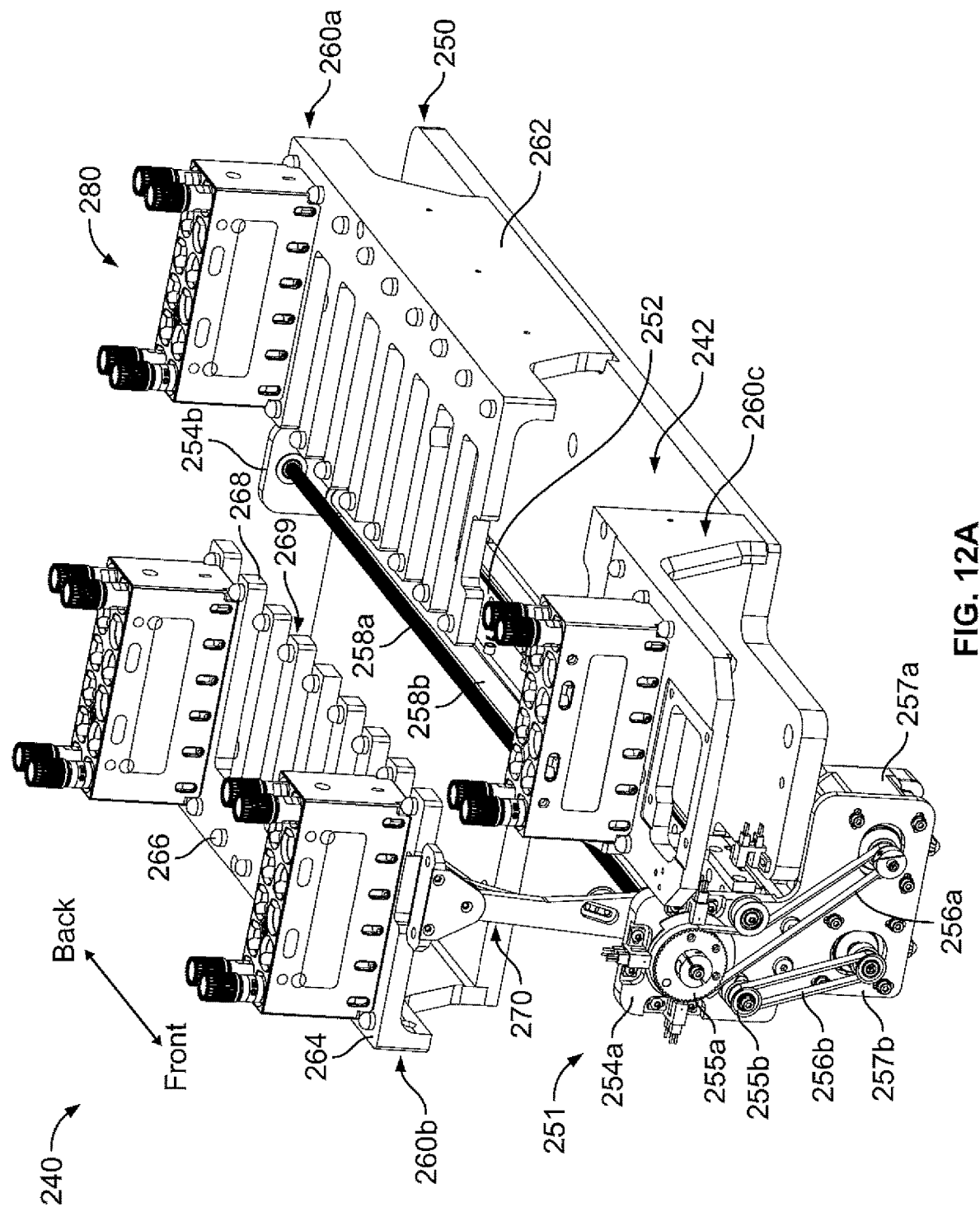
FIG. 12A is a front perspective view of a shuttle handling assembly of the pre-analytical system of FIG. 1A according to one embodiment of the present disclosure.
Figure 12B:
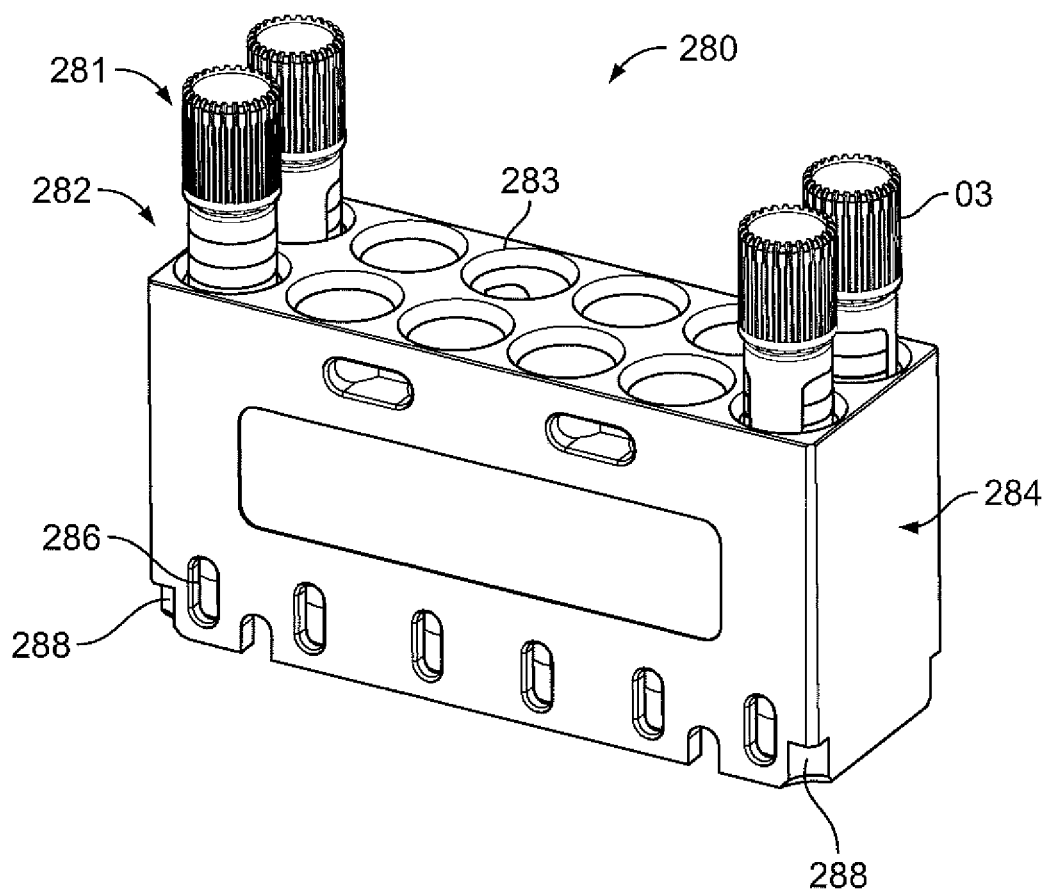
FIG. 12B is a shuttle of the shuttle handling assembly of FIG. 12A according to one embodiment of the present disclosure.
Figure 12C:
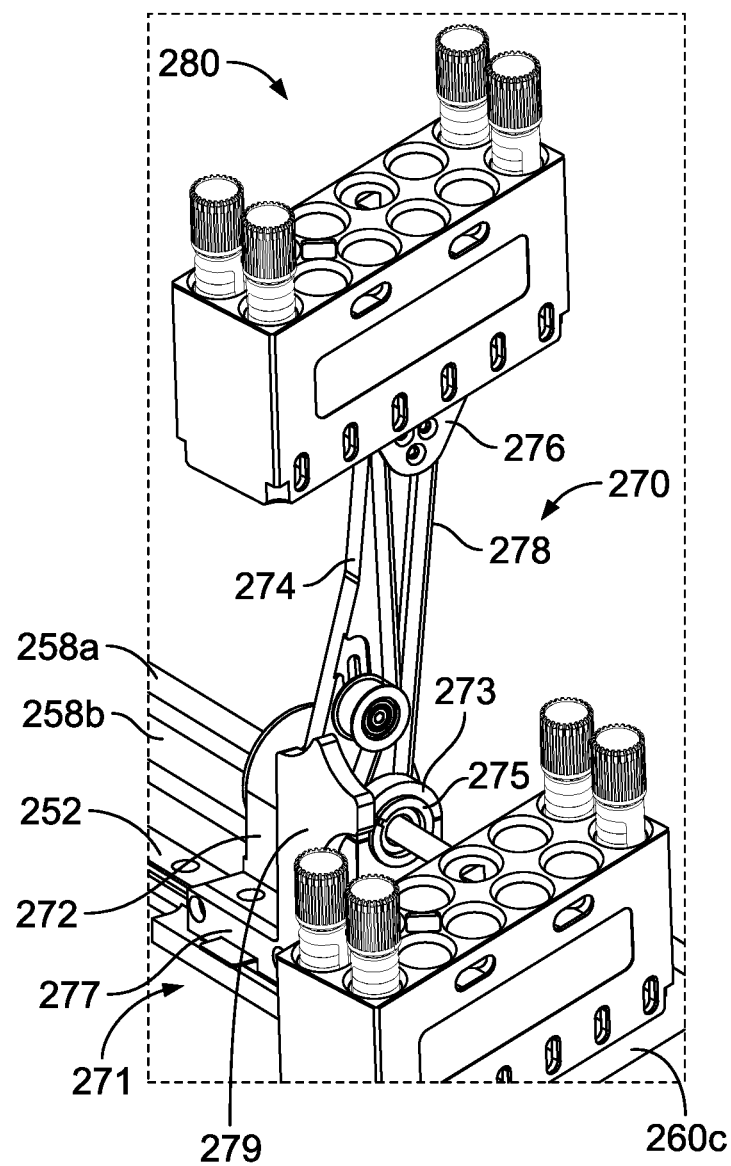
FIG. 12C is a partial rear perspective view of the shuttle handling assembly of FIG. 12A.

FIGS. 12A-12C depict a shuttle handling assembly 240. Shuttle handling assembly 240 generally includes a plurality of shuttles 280, a base 250, a plurality of shuttle docking stations 260*a-c* extending from base 250, a drive mechanism 251, a transfer arm assembly 270, and a barcode scanner (not shown). Shuttle handling system 240 is configured to retain sample container shuttles 280 until they are at least partially filled and to transport shuttles 280 to and from a shuttle transport assembly 300 (described below).

Shuttle 280, as best shown in FIG. 12B, includes a body 284 and a plurality of receptacles 283 extending into body 284 from a top surface thereof. The shuttle 280 depicted includes twelve receptacles 283 which are each sized to receive a third-type sample container 03. However, other embodiments may include more or less receptacles 283 depending on the capacity of an analyzer coupled to system 10. Additionally, receptacles 283 are arranged in two linear rows 281, 282. While receptacles 283 can be arranged in more than two linear rows, two rows are preferable.

A plurality of transverse openings 286 extends through body 284 at opposite sides thereof. More particularly, each transverse opening 286 intersects a corresponding receptacle 283 such that receptacles 283 in first row 281 are intersected by transverse openings 286 extending through a first side of body 283, and receptacles 286 in second row 282 are intersected by transverse openings 286 extending through a second side of body 284. These transverse openings 286 are disposed at a lower end of shuttle 284 and provide access to and communication with a lower end of containers 03 disposed within receptacles 283.

A plurality of notches 288 extends into a bottom surface of body 284. There are preferably four notches 288 symmetrically distributed about body 284, although more or less notches 284 can be provided. For example, three notches 288 may extend into body 284 which may help ensure shuttle 280 is placed in a desired orientation throughout system 10. Each notch 284 generally has a semi cylindrical geometry. These notches 284 are configured to engage cylindrical or frustoconical projections extending from a surface of the shuttle handling system in order to retain shuttle 280 on such surface. Although, shuttle 280 includes semi cylindrical notches 288 to correspond with cylindrical or frustoconical projections, any notch geometry matching a surface projection can be selected.

One or more slots (not shown) also extend into the bottom surface of body 284 generally near the center of body 284. These slots correspond with engagement features or flanges (not shown) of transfer arm assembly 270 to help transfer arm assembly 270 pickup and hold shuttle 280.

Base 250 is a structural member which supports drive mechanism 251, transfer arm assembly 270, and shuttle docking stations 260*a-c*. Drive mechanism 251 operates transfer arm assembly 270 and generally includes a pair of motors 257*a-b* and a pair of drive shafts 258*a-b*. The first drive shaft 258*a* is an elongate shaft that has a torque applying geometry. For example, first drive shaft 258*a* may be a square shaft, hexagonal shaft, or a splined shaft. The second drive shaft 258*b* is generally an elongate leadscrew. Drive shafts 258*a-b* are rotatably connected to a pair of end-plates 254*a-b* that extend from base 250 at a front-end and back-end thereof. Drive shafts 258*a-b* are disposed parallel to each other in a vertical arrangement above base 250 such that first drive shaft 258*a* is located directly above second drive shaft 258*b*. A rail 252 is provided on the top surface of base 250 and is disposed directly below second drive shaft 258*b*.

A first and second pulley 255*a-b* or sheaves are connected to first end plate 254*a*, although they can be connected to second end plate 254*b*, and are offset from each other in a front-back direction. First pulley 255*a* is directly connected to first drive shaft 258*a*, and second pulley 255*b* is directly connected to second drive shaft 258*b* such that rotation of these pulleys 255*a-b* rotates shafts 258*a-b*. First and second motors 257*a-b* may be rotating stepper motors and are connected to base 250. First motor 257*a* is connected to first pulley 255*a* via first belt 256*a*, and second motor 257*b* is connected to second pulley 256*b* via a second belt 256*b*. First and second motors 257*a-b* are independently operable and may have the same or different angle of rotation per step.

Transfer arm assembly 270, as best shown in FIG. 12C, includes a carriage 271 and transfer arm rotatably connected to carriage 271. Carriage 271 includes a first flange member 272 and a second flange member 273 extending from a support member 277. Support member 277 is slidingly connected to rail 252. Flange members 272 and 273 are offset from each other to form a gap therebetween. First flange member 272 includes first and second openings (not shown). The first opening is configured to slidingly receive first drive shaft 258*a* while also being configured to allow drive shaft to freely rotate therein such as by a correspondingly shaped bushing disposed within the first opening. For example, where first drive shaft 258*a* is a square shaft, the first openings may include a rotatable bushing with a square opening, and where first drive shaft 258*a* is a splined shaft, the first opening may include a rotating bushing having splines configured to engage with drive shaft 258*a*. The second opening of the first flange member 272 is threaded, such as by a threaded nut being disposed therein and threadedly engages second drive shaft 258*b* such that rotation thereof drives carriage 271.

Second flange member 273 also includes first and second openings (not shown). These openings may be similar to the first and second openings of first flange member 272. As such, the first opening of second flange member 273 receives first drive shaft 258*a* such that drive shaft 258*a* is slidable and rotatable relative to flange member 273. Also, the second opening of second flange member 273 may be threaded to threadedly receive second drive shaft 258*b*. In some embodiments, second flange member 273 may not include a second opening and may instead be shaped, such as L-shaped, to be positioned partially about drive shaft 258b to avoid any engagement thereof.

The transfer arm is comprised of a first arm member 274 and second arm member 276. First arm member 274 is an elongate linkage that includes an opening at a first end thereof. This opening is configured to slidingly receive first drive shaft 258a while also being configured to receive torque applied therefrom so as to rotate first arm member 274 in conjunction with rotation of drive shaft 258a. For example, the opening of first arm member 274 may be square shaped, hexagonal shaped, or have splines configured to engage corresponding geometry of drive shaft 258a. The first end of first arm member 274 is disposed within the gap between first and second flange members 272, 273 such that the opening of arm member 274 is coaxial with the first openings of first and second flange members 272, 273.

Second arm member 276 is rotatably attached to a second end of first arm member 274. Second arm member 276 includes engagement features (not shown) at an end remote from first arm member 274 that are configured to engage slots at a bottom end of shuttle 280.

Belt 278 is engaged with bearing 275 of second flange member 273 between second flange member 273 and first arm member 274. Belt 278 is also engaged to second arm member 276 such that rotating bearing 275 in a first direction rotates second arm member 276 relative to first arm member 274 in the first direction, and rotating bearing 275 in a second direction rotates second arm member 276 in the second direction.

Shuttle docking stations 260a-c, as best shown in FIG. 12A, each include a support wall 262 extending from base 250 and a transverse support member 264 cantilevered to and extending from support wall 262. Transverse support member 264 includes a plurality of fingers 268 each partially defining a space 269 between an adjacent finger 268. Adjacent fingers 268 and a single space 269 define a docking position for single shuttle 280. Thus, each finger 268 is sized to support two shuttles 280 positioned side-by-side. Each space 269 is sufficiently large to receive first and second arm members 274, 276 (FIG. 12C) of transfer arm assembly 270, yet sufficiently small to prevent shuttle 280 from falling therethrough when positioned on adjacent fingers 268.

Each finger 268 includes at least two cylindrical projections 266 extending from a top surface thereof. Each projection 266 has a diameter sufficiently large to partially fit within adjacent recesses 288 of two shuttles 280 positioned side-by-side. In other words, a single finger 268 supports a portion of two shuttles 280 positioned next to each other and each projection 266 may be shared by such adjacent shuttles 280. Projections 266 help retain shuttle 280 on a transverse support member 264 and help precisely position shuttle 280 for pickup by transfer arm assembly 270.

First and second docking stations 260a and 260b are positioned opposite of each other such that their respective fingers 268 point towards each other. First and second docking stations 260a-b are separated by a gap so as to form a runway for transfer arm assembly 270 to traverse base 250 in a front-back direction. First and second docking stations 260a-b may also include the same number of docking positions to hold an equal number of shuttles 280. For example, as depicted, first docking station 260a and second docking station 260b each include eight docking positions for a total of sixteen docking positions. However, in some embodiments each docking station 260a-b may include more or less docking positions and first docking station 260a may include more or less positions than second docking station 260b.

Third docking station 260c is aligned with first docking station 260a and positioned closer to the front of system 10 than first docking station 260a. Third docking station 260c generally includes less fingers 268 and spaces 269, and consequently less docking positions, than first docking station 260a. First and third docking stations 260a, 260c are offset from each other by a gap so as to form a transverse space 242 for a first transport assembly 300a, as described below. Although third docking station 260c is depicted as being aligned with first docking station 260a, third docking station 260c can be positioned in a number of other locations, such as aligned with second docking station 260b. Also, in some embodiments a fourth docking station (not shown) can be provided opposite third docking station 260c and aligned with second docking station 260b.

Figure 22A:
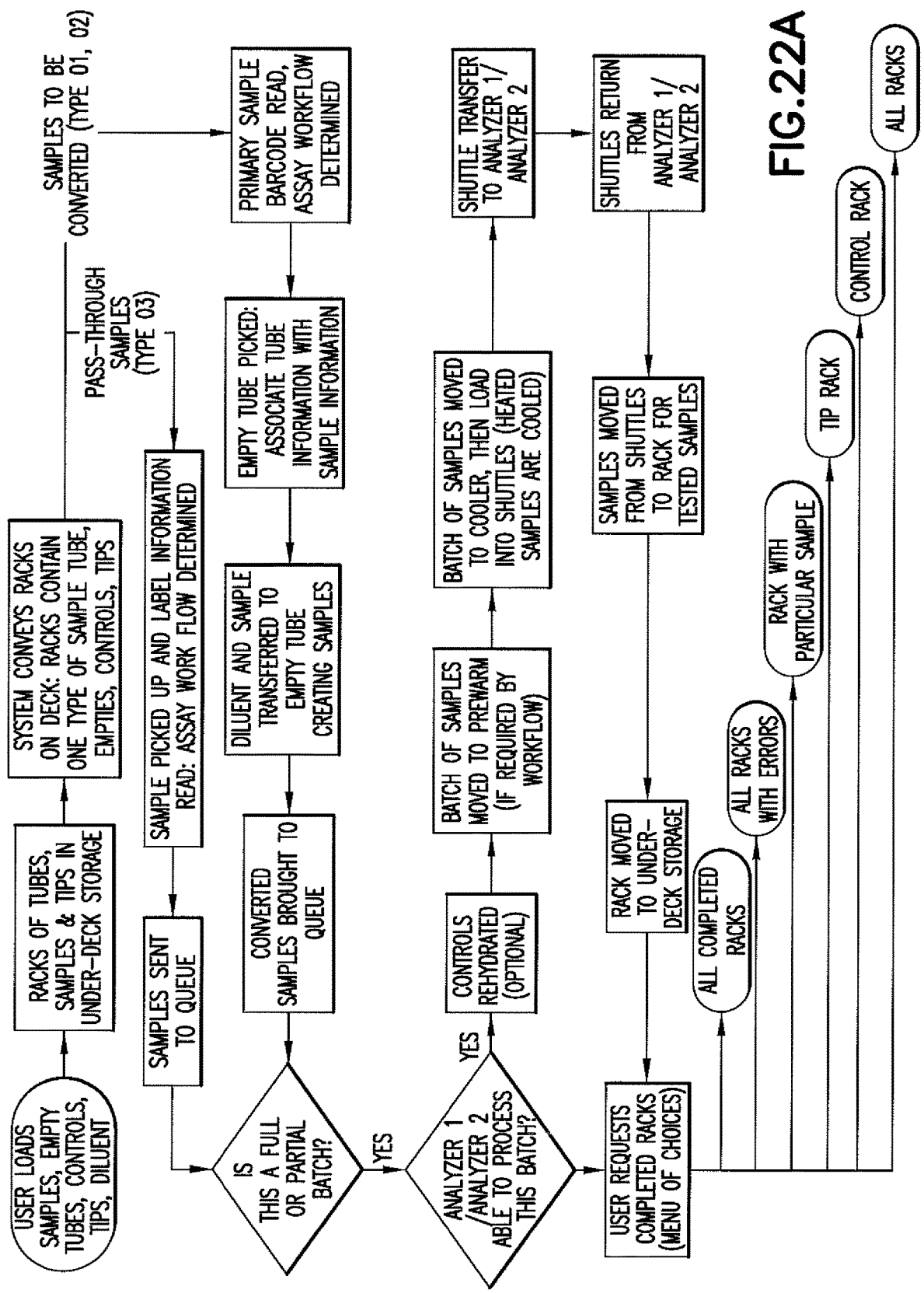
FIGS. 22 A-G are embodiments of workflows that are supported by the pre-analytical system

The pre-analytical system controller determines the placement of samples in the shuttle. The shuttles are loaded so that that the shuttles can be transported to any of the analyzers associated with the pre-analytical system. Referring to FIG. 22F, the controller has a shuttle address associated with each shuttle receptacle. These "positions" (designated as 1, 2, . . . n in FIG. 22F), For example, if positive/negative controls are loaded on to the shuttle, then the control containers are placed in locations 1 and 2 in the tray. Note that locations 1 and 2 have different positions relative to the shuttle handling assembly 240 in that the controls are in the distal positions of the rack relative to the shuttle robot position for the racks on one side and locations 1 and 2 are proximate to the shuttle robot assembly when on the other side. Loading in the manner will allow any shuttle to be transported to any analyzer. To enable intelligent loading with knowledge of shuttle orientation the shuttles have a bar code that is read by the pre-analytical system. The pre-analytical system is programmed to know the location of the shuttle receptacles from the location of the bar code. As illustrated in FIG. 22F, if the analytical system is to the right of the pre-analytical system, the 1 and 2 positions in the shuttle are in-board (i.e. the first portion of the shuttle to enter the analyzer). If the analytical system is to the left of the pre-analytical system, then the 1 and 2 positions in the shuttle will be outboard as the shuttle enters the analyzer.

Referring to FIG. 22D, there is illustrated a shuttle operation for samples for which tests from more than one analyzer have been ordered by the workflow computing device 1330 that orchestrates the operation of the pre-analytical system 20 and the two or more analyzers. As noted herein the sample when received by the pre-analytical system has a unique identifier label. That unique identifier is referred to as an accession number herein. The shuttle carries the sample to the first analyzer. Workflows for routing samples to a second analyzer As noted above, when the shuttle returns from the first analyzer, the shuttle is unloaded. In one embodiment, the shuttle is completely unloaded. In other embodiments, some or all of the sample containers may remain in the shuttle to be routed to an analyzer for a second test. The analyzer for the second test can be the same as or different from the analyzer that performed the first test. Once emptied, the shuttle is returned to the parking lot 260a-c. If there are empty receptacles in the shuttle for a second assay, the "QUEUE MANAGER" will retrieve other samples from the batch accumulation area 210 to populate the shuttle for the designated test. Once the shuttle is loaded with a batch of sampled for the test, it will then be placed on the shuttle transport assembly by the shuttle handling assembly 240.

As illustrated in FIG. 7, shuttle handling assembly 240 is generally located between warmer 230 and cooler 290. Also, while shuttle handling assembly 240 is positioned at second deck level and mostly positioned at the back of system 10, a portion of shuttle handling assembly 240 is positioned on the same side, or front side, of system 10 as the instruments of first pre-analytical processing deck 24. More particularly, shuttle handling assembly 240 extends towards the front of system 10 such that third docking station 260c is positioned adjacent I/O port 120 and first sample rack space 110, while first docking station 260a is positioned adjacent cooler 290 and second docking station 260b is positioned adjacent warmer 230. This allows sample containers 03 located at second pre-analytical processing deck 26 to be easily loaded into shuttles 280 on first and second docking stations 260a-b for distribution to an analyzer, and for shuttles 280 returning from an analyzer to be placed on third docking station 260c so that containers 03 therein can be easily loaded into rack 50 at space 110.

Shuttle Transport Assembly

Figure 13:
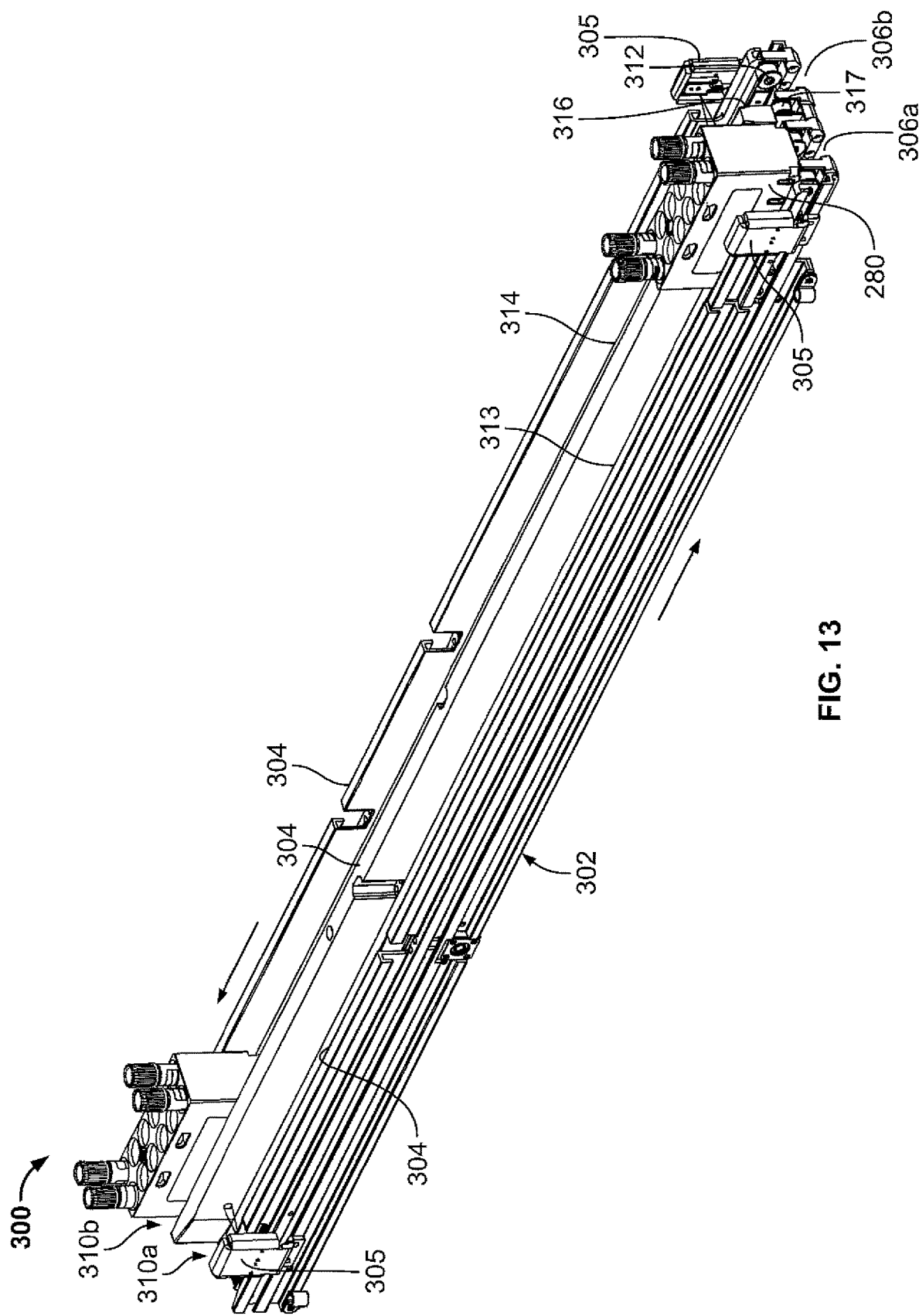
FIG. 13 is a shuttle transport assembly of the pre-analytical system of FIG. 1A according to one embodiment of the present disclosure.

FIG. 13 depicts a shuttle transport assembly 300. Shuttle transport assembly 300 generally includes a base frame 302 having a first and second transport track 310a-b. However, in some embodiments shuttle transport assembly may have only one transport track. Transport tracks 310a-b are defined by sidewalls 304 that are slightly wider than a width of shuttle 280. These sidewalls 304 help prevent shuttle 280 from moving off of one of tracks 310a-b as it is being transported. A pair of recesses 306a and 306b extends into one end of base frame 302 such that each recess extends a short distance along a corresponding track 310a-b. These recesses 306a-b form a clearance space for transfer arm assembly 270 as it rotates downward to deposit shuttle 280 onto one of tracks 310a-b and rotates upward to retrieve shuttle 280 from one of tracks 310a-b.

A plurality of pulleys 312 is located on sidewalls that define recesses 306a-b. Such pulleys 312 are each connected to an elongate belt. For example, for second track 310b, a pair of pulleys are connected to respective belts 316 and 317. In this regard, track 310b includes a pair of opposing belts that extend adjacent to and along recess 306b. This allows a shuttle to be advanced along this section of track 310b without obstructing recess 306b. Track 310a is similarly situated. Thus, each track 310a-b includes at least two belts at an end thereof. This configuration allows belts to reach as close to the recessed end of transport assembly 300 as possible to help ensure shuttle 380 is placed on belts 313, 314 when deposited thereon by transfer arm 270.

The pair of opposed belts at extend along a portion of their respective tracks 310a and 310b and terminate near an end of recesses 306a-b. Such opposed pairs of belts then transition to a single belt so that a single belt 314 extends along the majority of the length of track 310b, and a single belt 313 extends along a majority of the length of track 310a. Belts 313, 314, 316, and 317 comprise a conveyor and are driven by one or more motors to move shuttle 280 along each track. In the depicted embodiment, the conveyors of the first and second transport tracks 310a-b move in opposite directions. For example, the conveyor of second transport track 310b is operable to move shuttle 280 away from shuttle handling assembly 240 and toward an analyzer coupled to system 10. Conversely, the conveyor of the first transport track 310a is operable to move shuttle 280 away from the analyzer and towards shuttle handling assembly 240.

Base frame 302 also includes presence sensors 305 at each end thereof for each track 310a-b. Thus, each track 310a-b has a pair of presence sensors 305. These sensors 305 may be optical sensors and can detect the presence of shuttle 280 when it breaks an optical field. When sensor 305 is activated due to the presence of shuttle 280, a signal is sent to a computing system (described below) thereby notifying system 10 that shuttle 280 has been transferred to either track 310a or 310b. The computing system can then determine next steps, such as whether or not the conveyor should be turned on or off.

As depicted in FIG. 7, system 10 includes two shuttle transport assemblies 300a and 300b which can each feed shuttles 280 to a respective analyzer $A_1 \ldots A_n$. Although two is depicted, it should be understood that system 10 can be configured to include more shuttle transport assemblies 300 to feed more than two analyzers. First and second shuttle transport assemblies 300a-b are located at about the same height as second pre-analytical processing deck 26. In addition, first and second shuttle transport assemblies 300a-b extend along the length of system 10, are aligned with each other, and are separated by a gap 301 (best shown in FIG. 7). This gap 301 allows transfer arm assembly 270 of the shuttle transport assembly 240 to position itself within gap 301 in order deposit shuttle 280 onto one of the first or second transport assemblies 300a-b. Additionally, first transport assembly 300a extends between first and third shuttle holding stations 260a, 260c such that first and third shuttle holding stations 260a, 260c are disposed on opposite sides of transport assembly 300a.

Methods of Shuttle Handling and Transportation

In a method of shuttle handling and transportation, shuttle handling assembly 240 moves a loaded shuttle 280 to and from one of the shuttle transport assemblies 300a-b. The shuttle transport assemblies 300a-b transport the shuttle to and from an analyzer.

In one particular example, an empty shuttle 280 sits on adjacent fingers 268 of first shuttle docking station 260a such that projections 266 are partially disposed within recesses 288. Each receptacle 280 of shuttle 280 has a container 03 disposed therein (particular details of this is described below).

Once shuttle 280 is populated with containers, first motor 257a is turned on which rotates first pulley 255a and first shaft 258a in a first direction. At this point, transfer arm assembly 270 is generally positioned in alignment with transverse space 242 (best shown in FIG. 12A). As first shaft 258a rotates, first arm member 274 rotates in the first direction toward transverse space 242 while second arm member 276 rotates in a second direction away from transverse space 242, which keeps engagement features of second arm member 276 pointing generally upward. First arm member 274 is continuously rotated such that it passes into transverse space 242 between first transport assembly 300a and first shuttle docking station 260a (See FIG. 7). First motor 257a is operated until first arm member 274 is positioned at about 90 degrees and generally parallel to base 250.

Thereafter, second motor 257b is turned on and rotates second pulley 256 and second shaft 258b in the first direction, which causes transfer arm assembly 270 to be driven toward the back of system 10. Due to first arm member's generally horizontal position, first and second arm members 274, 276 pass under transverse support member 264 of first shuttle docking station 260a as transfer arm assembly is driven to the back of system 10. Second motor 257b is stopped when first and second arm members 274, 276 are aligned with space 269 underneath shuttle 280.

First motor 257a is then turned on such that first pulley 255a and first drive shaft 258a are rotated in the second direction. This causes first and second arm members 274, 276 to rotate toward shuttle 280. Second arm member 276 remains pointing upward and engages the bottom of shuttle 280 as first arm member 274 is continuously rotated toward a vertical position. Shuttle 280 is then lifted off of first shuttle docking station 260a while second arm member 276 points upwardly keeping shuttle 280 upright. Once first arm member 275 reaches a vertical position, first motor 257a stops.

Thereafter, second motor 257b is turned on such that second pulley 255b and second shaft 258b rotate in the second direction which drives transfer arm assembly 270 toward the front of system 10. Due to the first arm's generally vertical position, transfer arm assembly 270 moves freely through the gap between first and second shuttle docking stations 260a-b. Second motor 257b is operated until transfer arm assembly 270 reaches second transport track 310b of second shuttle transport assembly 300b and first and second arm members 274, 276 are aligned with second recess 306b.

Once transfer arm assembly 270 is in this position, first motor 257a is turned on such that it rotates first arm member 274 toward second track 310b and rotates second arm member 276 away from second track 310b so that shuttle 280 remains upright. First and second arm members 274, 276 pass through recess 306b and one end of shuttle 280 touches down onto conveyor belts of second track 310b. As shuttle 280 is touching down, it crosses an optical field of sensor 305, which notifies system 10 of its presence on second track 310b. System 10 then determines whether to turn on second track 310b depending on other circumstances, such as another shuttle 280 being located at the other end of track 310b. Once shuttle 280 touches down, it is disengaged with second arm member 276 and is moved toward an analyzer coupled to a left flank of system 10 until it reaches an end of second track 310b where another sensor 305 is activated thereby notifying system 10 of the shuttle's location. At this point shuttle 280 may be inside the analyzer or near the analyzer depending on whether or not assembly 300b extends into the analyzer.

Once analysis of the samples by the analyzer is completed, shuttle 280 is placed on first track 310a activating a sensor 305 located at one end thereof. This notifies system 10 of the shuttle's presence on first track 310a where instructions for further operation are determined/provided. Shuttle 280 moves toward the recessed end of first track 310a where shuttle 280 trips the other sensor 305. Belts 313 and 314 are turned off such that a portion of the shuttle 280 sits over recess 306a.

Transfer arm assembly 270, with first arm member 274 in a generally horizontal position, is driven by second drive shaft 258b into alignment with first track 310a such that first and second arm members 274, 276 are positioned beneath transport assembly 300b. First motor 257a is activated and first arm member 274 rotates toward a vertical position. As this takes place, second arm member 276 passes through first recess 306a and engages the bottom of shuttle 280 thereby lifting shuttle 280 off of first track 310a until first arm member 274 is vertical.

Thereafter, second motor 257b is again activated to drive transport assembly 270 toward the front of system 10 until it is aligned with a space 269 of third docking station 260c. First motor 257a then rotates first and second arm members 274, 276 toward transverse support member 264 of the third docking station 260c which then pass between adjacent fingers 268 and docks shuttle 280 to third docking station 260c. When the belt is clear, transfer arm assembly 270 may be indexed to return to a position aligned with transverse space 242.

This method is one example of the shuttle's movement to and from an analyzer using transfer arm assembly 270 and transport assembly 300b. It should be understood that transfer arm assembly 270 can move a shuttle 280 in any sequence between first, second and third docking stations 260a-c and first and second transport assemblies 300a-b by intermittently rotating first and second arm members 274, 276 through various angles within a 180 degree arc and driving carriage 271 forward and backward along base 250.

Shuttle Transport Monitoring and Error Protocols

System 10 has a shuttle processor that controls operation of a shuttle processing or transport module/subsystem 750 (see FIG. 19), which may include shuttle handling assembly 240 and shuttle transport assemblies 300a-b. Such processor may be associated with the one or more processors 804 of the computer control device 802 of system 10 described in more detail below. The shuttle processor has processing logic that identifies processing errors, sends notices to the operator and shuts down the subsystem in response to certain detected processing errors. For example, handling assembly 240, transport assembly 300a and/or transport assembly 300b may be shut down. However, in response to certain conditions, subsystem operation continues but with adjustments (retries, operating at half speed, etc.) to avoid shutting down in response to every detected error. In response to certain detected conditions, the subsystem executes preprogrammed routines to determine the source of the error (i.e., a broken sensor, a shuttle 280 in the wrong location, etc.). For example, the shuttle processor has an initialization protocol to ensure that the shuttle transport assemblies 300a-b are operating correctly on start up. Motion failure indications allow for one retry before an error message is issued in response to which the shuttle processor enters a failed state and a service call issues. The shuttle belts 313, 314 are initialized periodically during operation to ensure that they are operating correctly. Again, when motion failures are detected there is retry before a failure is indicated, which is reported by the system 10 to an operator.

The shuttle processor also monitors and coordinates the operation of the shuttle transport assemblies 300a-b with respective analyzers. When a shuttle transport assembly 300a-b receives a request that an analyzer is ready for a batch of preprocessed samples, a shuttle 280 is retrieved and placed on the belt of either assembly 300a or 300b that will transport the shuttle to the designated analyzer module ($A_1$, $A_2$, or $A_n$). System 10 ensures that the belt is clear before proceeding to transfer a shuttle 280 to the selected shuttle transport assembly and that the respective analyzer is ready to receive the samples. If not, system 10 waits until the prior batch is cleared.

Furthermore, movement of the shuttle handling assembly 240 is monitored to ensure compliant operation. When motion errors or encoder count mismatches, such as encoder counts of motors 257a-b, are detected for movement of transfer arm assembly 270, a retry is permitted at reduced speed after which, if errors in movement or response are detected and end module operation error issues, the operator is notified. A shuttle barcode reader (not shown) is proved at assembly 240 to not only verify that the correct shuttle 280 is transported, but to ensure that the assembly 240 itself is operating properly. If a barcode is still not read after one retry, the shuttle 280 is moved to a position to determine if the error is the barcode or an absence of a shuttle 280. If the barcode is read but it is not the expected bar code, the shuttle 280 is transported to the shuttle unloading area 260c where its contents are placed in an output rack disposed at rack space 110.

Similarly, sensors provide information to the shuttle processor of the handoff of the shuttle 240 from the analyzer to system 10. The respective belts 313, 314 of assemblies 300a-b are monitored for correct operation. If belt errors are detected, the handoff operation is ended and a service call is indicated. When motion errors are detected at the transition from the analyzer to the pre-analytical system 10, one retry at reduced belt speed is permitted before handoff operation is halted and notification of an error is sent to the operator. Sensors are provided at the interface between the analyzer ($A_1$, $A_2$, $A_n$) and the pre-analytical system 10 to detect shuttle passage from one to the other.

The analyzer provides a hand off message to the pre-analytical system 10 when a shuttle 280 is returned from the analyzer to the pre-analytical system 10. If there is no handoff message, this indicates a problem with the analyzer. Consequently, all remaining shuttles 280 (if any) associated with the batch of samples being processed by the analyzer are sent to the output rack 260c where the samples are unloaded into a rack 50 at space 110 and designated "unprocessed." If a handoff message is received from the analyzer, the return belt of one of assemblies 300a-b from the analyzer back to the pre-analytical system 10 is turned on. Sensors communicate belt operation and, if a motion error is detected, the belt 113, 114 is paused and an error message sent.

Sensors also indicate if a shuttle 280 is present at the interface between the analyzer and the pre-analytical system 10. If the analyzer sent a hand off message and the pre-analytical system 10 is ready to receive a shuttle 280, then the belt 113, 114 is started. If no shuttle is received, then handoff is stopped and a notice is sent to the operator that service is required. If a shuttle 280 is detected at the interface then the shuttle processor sends a signal to the analyzer ($A_1$, $A_2$, $A_n$) that hand off is complete. If such a message is received then the process is completed. If no message is received, this indicates an error such as a stuck shuttle, a sensor problem, etc. and the operator is notified.

Certain errors may have specific protocols that may differ from other errors. For example, if a pipette tip used by an analyzer is stuck in a sample container within a shuttle 280, the analytical module ($A_1$, $A_2$, $A_n$) flags the shuttle as having a stuck tip. Logic is provided by shuttle processor that causes such a shuttle 280 to be conveyed to a holding area, such as docking station 260c. In addition, the operator is notified that the shuttle requires special processing. If the holding area is full, then the pre-analytical system 10 will not receive any more shuttles until the holding area is emptied.

Once the shuttle 280 has been conveyed to the spot where it will be unloaded, a message is sent to the analytical module ($A_1$, $A_2$, $A_n$) acknowledging receipt of the shuttle 280. If the shuttle 280 is not detected in the unloading spot 260c, placement is retried, verifying presence of the shuttle 280 via the barcode reader. If shuttle 280 is still not detected then the system 10 issues an error that the unload sensor is broken. The shuttle processor then instructs the pick and place robot 410a to unload the third type sample containers 03 from the shuttle 280 (one by one) and place the third type x containers 03 in the rack 50 at space 110.

The system 10 monitors for errors in processing when an analyzer ($A_1$, $A_2$, $A_n$) sends an indication to the pre-analytical module 10 that it is ready to receive a batch of samples. In response, the pre-analytical system 10 (i.e. the processor) sends the relevant shuttle 280. In the event of a system disruption (e.g. manual operator intervention), the system 10 verifies that the correct shuttle 280 is sent by reading the bar codes on the shuttles 280 loaded with samples and parked awaiting processing. The location of each shuttle 280 is stored in a memory, such as memory 804 described below, and a command is sent to the shuttle handler 240 to retrieve the relevant shuttle 280 from its known location and place it on the appropriate shuttle transport assembly 300a-b.

The pre-analytical system 10 already has stored in memory an association between a particular shuttle 280 and its "parking spot." If there is a detected mismatch, the shuttle 280 is lifted from its current position and moved to a test position and evaluated to determine if there is an actual error or a sensor error. If a sensor error has occurred, then the pre-analytical system 10 puts the shuttle 280 in an empty location, such as on one of docking station 260a-c, and proceeds with processing. If a shuttle 280 is determined to be present when it should not be, or determined not to be present when it should be, there is a system error registered and shuttle transport is halted.

If the system 10 determines that the inventory of shuttles 280 matches the inventory sensor readings, a routine is entered to determine if the transfer arm assembly 270 of the shuttle handling assembly 240 is on the correct side. In other words, the routine determines if transfer arm assembly 270 is in a position to retrieve a shuttle 280 from the designated docking station 260a-c. For example, if assembly 270 is rotated so that it is positioned underneath docking station 260b, assembly 270 is not in a correct position to retrieve a shuttle 280 from docking station 260a. A routine is provided to move the assembly 270 to the correct side as needed. If a motion error is detected, the logic allows for a retry at reduced speed before an error message is sent.

The movement of the transfer arm assembly 270 continues to be monitored as it positions to pick up shuttle 280, picks up shuttle 280, moves shuttle 280 to a bar code reader and places shuttle 280 on the transport assembly 300a or 300b to be sent to an analyzer (A1, A2, $A_n$). If motion errors are detected, the motion is tried at reduced speed. If the motion error occurs again, the run is ended and the operator is notified of the error. If the barcode reader cannot read the bar code of the shuttle or reads a code that it does not expect, then the code is read again. If the error persists then the system 10 will determine that the shuttle 280 that was obtained was not the correct shuttle. The operator will be notified that intervention is needed.

When the shuttle 280 is placed on the belt, sensors detect its presence. If the sensor does detect a shuttle 280, the transfer assembly conveys the shuttle 280 to the analytical module. Sensors are also provided on the transfer assemblies 300a and 300b to monitor the progress of the shuttle 280 toward the designated analyzer. If the sensors determine that the shuttle 280 has not been conveyed to the analyzer, there is a retry at reduced speed before the system 10 transmits a message for customer intervention.

System 10 is also capable of automatically managing shuttle transport upon reboot in the event of a power loss. In one embodiment, the pre-analytical system 10 has sensors and logic that perform a sequence of functions for shuttle power recovery prior to returning to normal operations involving: i) I/O and post analysis module 710 (described further below); ii) shuttle transport assemblies 300a-b; iii) shuttle handling assembly 240; iv) shuttle docking stations 260a-b; and v) a shuttle penalty box. Examples of routines that are initiated by the pre-analytical system 10 in the event of a power loss are as follows. Generally these routines, along with sensors and the last known state of system 10 recalled from a memory thereof are used to return the system 10, including subsystem 750, to a ready state following an unexpected power loss.

Regarding I/O and post analysis module 710, a flag is set for normal processing until all shuttles 280 are emptied and the sample tubes contained therein at shutdown are disposed in an output rack 50 at station 110. Holding positions at station 260*c* are also sensed for the presence of a shuttle 280. If a shuttle is in a holding position, the shuttle is retrieved by arm 270, its barcode is read and the shuttle 280 is returned to docking station 260*c*.

Regarding the shuttle transport assemblies 300*a-b*, the sensors thereof are scanned for indications that a shuttle 280 is located on its belt. If no shuttle 280 is detected, the transport belts 113, 114 are run. If an inboard sensor (i.e., a sensor nearest to assembly 240) is triggered, then a shuttle 280 is detected. If the sensors indicate a shuttle 280 is present at the pick-up/drop off shuttle location adjacent gap 242, then the shuttle barcode is read and the shuttle 280 is placed in queue for unloading of its sample containers to a rack 50 at location 110. If a shuttle 280 is detected at the delivery/return position adjacent an analyzer, the tracks 113, 114 are run and, if the inboard sensor is triggered then the shuttle is associated with a barcode and placed in queue for unloading. If the inboard sensor is not triggered by a shuttle 280, then a sensor or track error is indicated.

The shuttle processor resets the shuttle handling assembly 240. Arm assembly 270 of the shuttle handling robot 240 is placed in its home position. If arm 270 is in an upright position, and the arm 270 may have a shuttle 280 connected thereto that needs to be cleared. In this regard, the arm assembly 270 along with shuttle 280 is then moved to the barcode reader so that the shuttle bar code can be read. Thereafter, the shuttle 280 is then placed on a shuttle transport assembly 300*a-b* (if available). However, if the barcode cannot be read then shuttle inventory is updated. The shuttle handling assembly 240 is then available.

Regarding docking stations 260*a-b*, such docking stations 260*a-b* are cleared using the shuttle handling assembly 240 to lift a shuttle 280 from the lot, present it to the barcode reader and return the shuttle to its respective docking station after the barcode is read and the inventory is updated. If no barcode is read, the system 10 has a sensor that determines if there was a shuttle present or not. If a shuttle 280 is present, it is placed back in the space from which it was retrieved and the system brings the problem to the operator's attention. If there is no shuttle 280, then the parking spot is marked empty in inventory. In either event, the inventory is updated with the information.

Before start up, all shuttles 280 are moved from the tracks 300*a-b* to either the unload position or the parking lot 260*a-c* as appropriate.

A shuttle penalty box has a sensor that initiates a process for determining how to instruct an operator about the shuttle 280 in the penalty box. If a shuttle 280 is detected, a message is sent to the operator and the system 10 enters pause. The operator can then open the system 10 and remove the shuttle 280, or hand scan the sample containers in the shuttle 280, after which the operator indicates that the shuttle 280 has been removed/replaced. If a shuttle 280 is not detected, the operator is again messaged to address and retry to return the shuttle 280. If no shuttle 280 is detected, the system 10 is shut down, the operator is notified and the error is reported. If the shuttle 280 has been fixed or replaced, the doors of system 10 will close and the system 10 will resume operation. If the doors fail to close, system 10 operation ceases and a door sensor failure is reported to the operator. If the doors are closed, the shuttle handling system 240 will barcode scan the sample containers and move it to the unload position, where the containers will be unloaded and barcoded.

It should be understood that the sensors described above with respect to the described shuttle transport error protocols and power loss protocols can include sensors that are well understood in the art. For example, optical sensors can be used to determine the presence or non-presence of a shuttle, and motor encoders can be used to determine belt positions of assemblies 300*a-b* and transport arm assembly 270 of rack handling assembly 240.

Shuttle Clamp

Figure 12D:
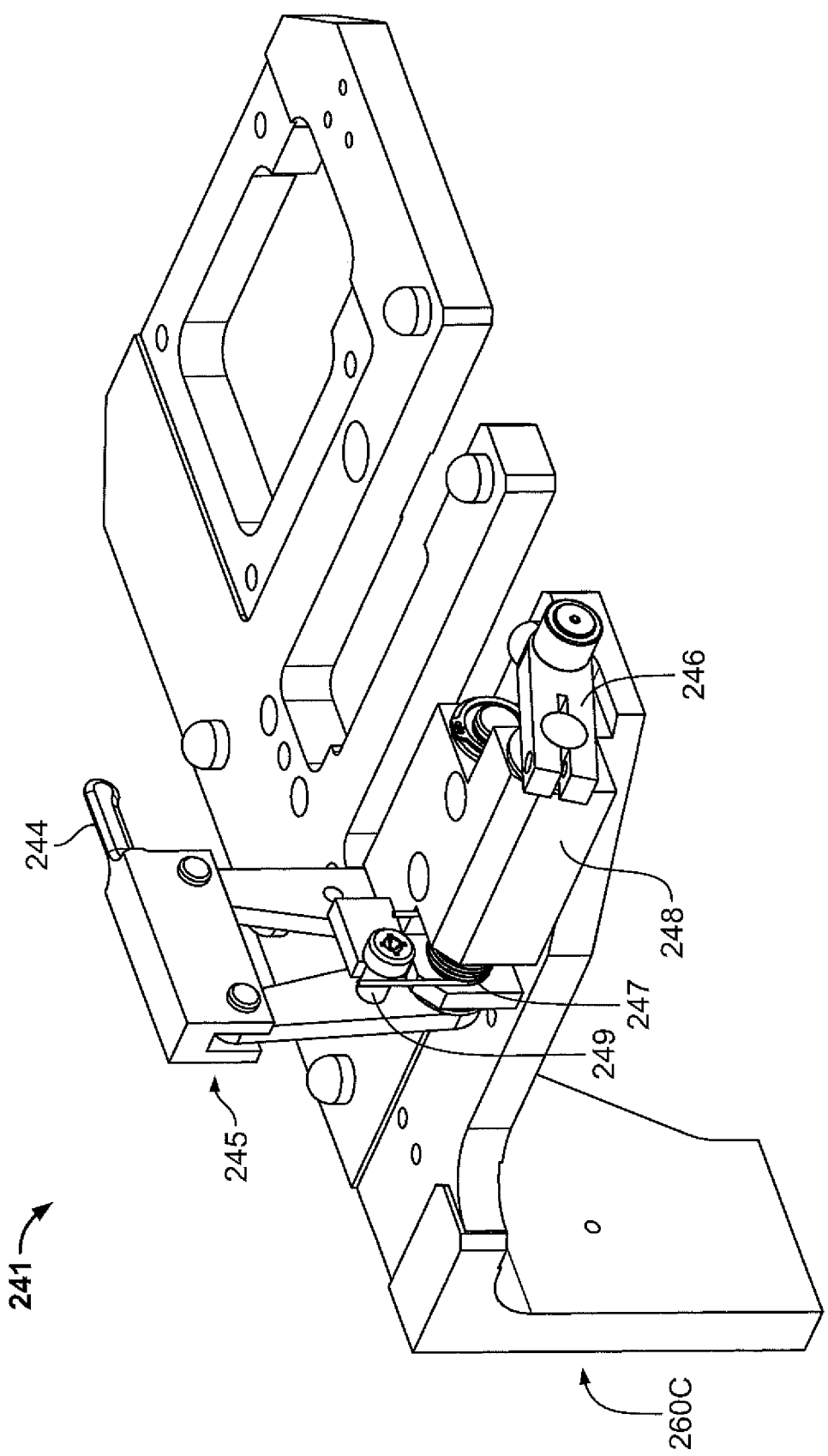
FIG. 12D is a perspective view of a shuttle docking station including a shuttle clamping mechanism.

As shown in FIG. 12D, docking station 260*c* may optionally include a shuttle clamp mechanism 241. This mechanism 241 may be utilized to help restrain a shuttle 280 docked at station 260*c* so that shuttle 280 is not incidentally lifted off of its parking spot while individual, used containers 03 are being removed from it. Clamp mechanism is not powered by a power source and includes a clamp arm 245, an actuating arm 246, a base 248, and a torsional spring. The clamp arm 245 includes a projection 244 which, when in the clamped position, engages a side slot 286 of a shuttle 280. Clamp arm 245 is connected to the torsion spring 247 and is biased in a clamped position via engagement between a lever 249 that projects from clamp arm 245 and torsion spring 247, as shown. Clamp arm 245 may be locked in an un-clamped position, not shown, via a clutch within base 248. Movement of clamp arm 245 between the clamped and unclamped position is achieved via engagement between actuating arm 246 and a paddle 279 that extends from arm assembly 270. Thus, when arm assembly 270 moves in a front direction past actuating arm 246, it moves actuating arm 246 to an unclamped position. In this regard, arm assembly 270 can deposit or remove a shuttle 280 at docking station 260*c*. When arm assembly 270 moves in a back direction, paddle 279 trips the actuating arm 246 releasing the clutch and allowing clamp assembly 241 to engage a shuttle 280 if present at docking station 260*c*.

Angled Elevator

Figure 12E:
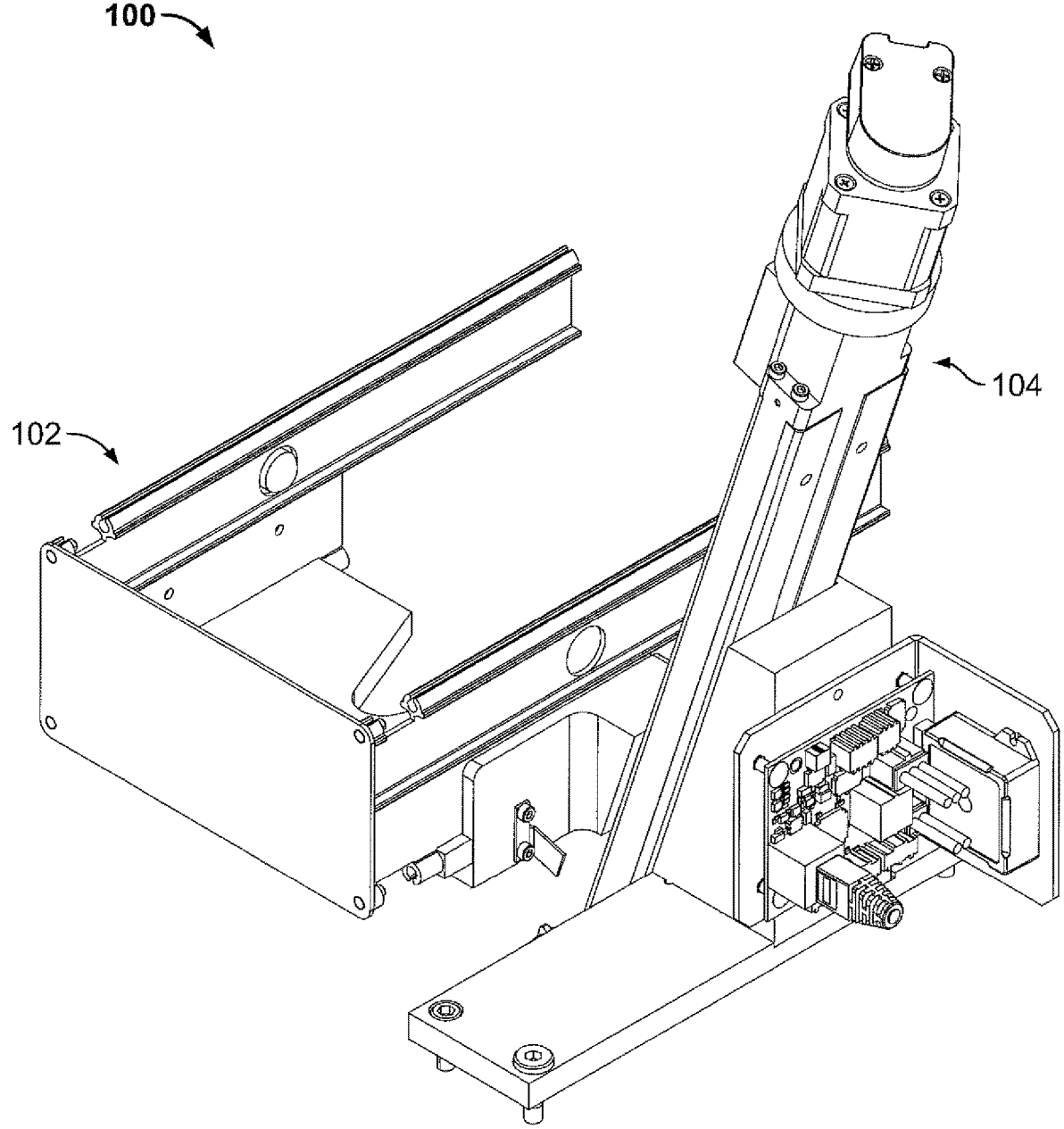
FIG. 12E is a perspective view of an angled elevator according to an embodiment of the present disclosure.

FIG. 12E depicts an angled elevator 100. Angled elevator raises and lowers a rack 50 between decks 24 and 26. Thus, when containers 03 are offloaded from a shuttle 280 at station 260*c*, the containers 03 are loaded onto a rack 50 held by elevator 100. In this regard, elevator 100 includes a rack holding structure 102 which is connected to an elongate member 104 that extends along an oblique axis. The rack holding structure 102 moves along the elongate member 104 between station 110 at deck 24 and a position adjacent station 260*c*.

Interdeck Robots

Figure 14A:
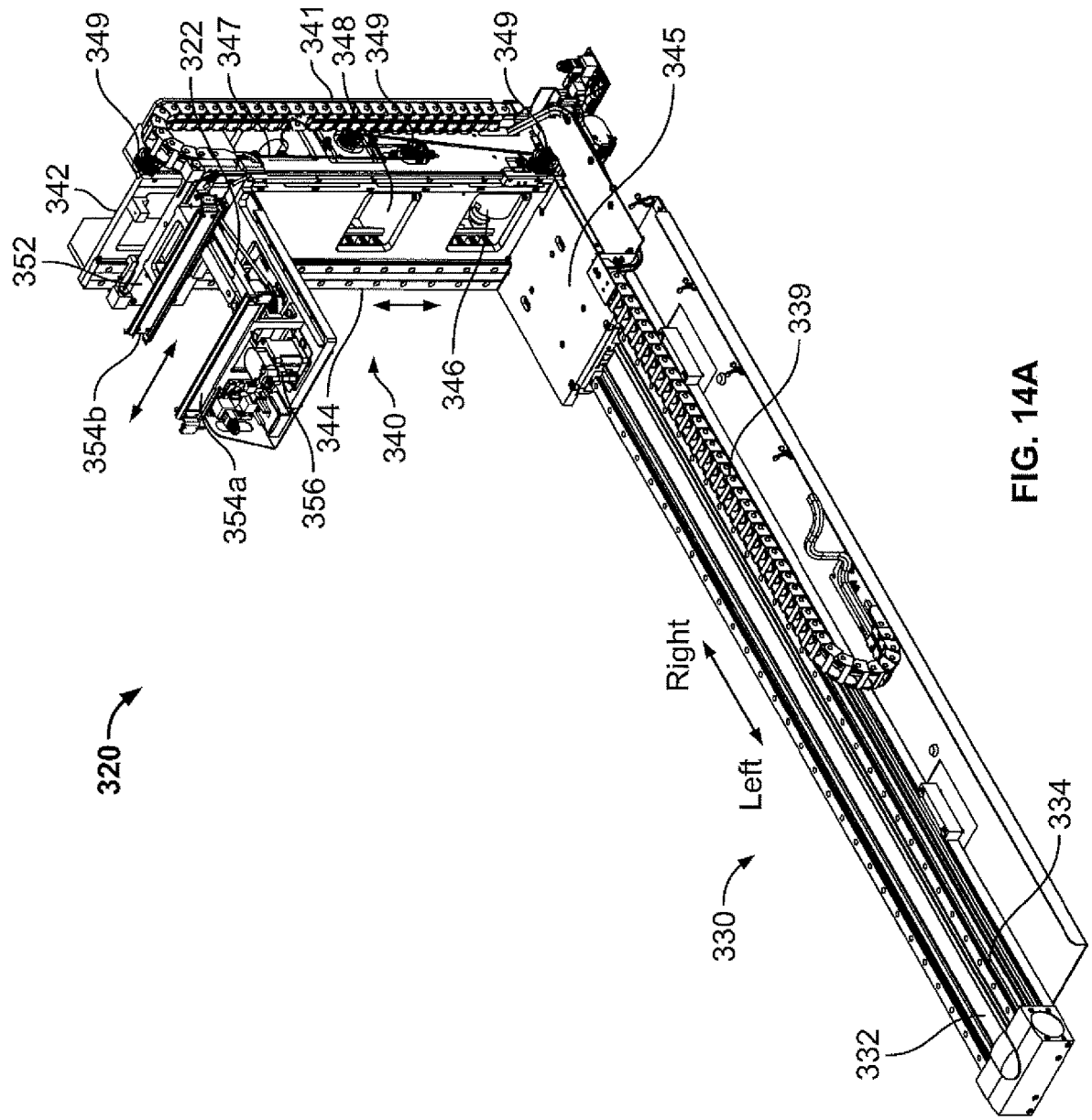
FIG. 14A is a front perspective view of a rack handler robot of the pre-analytical system of FIG. 1A according to one embodiment of the present disclosure.
Figure 14B:
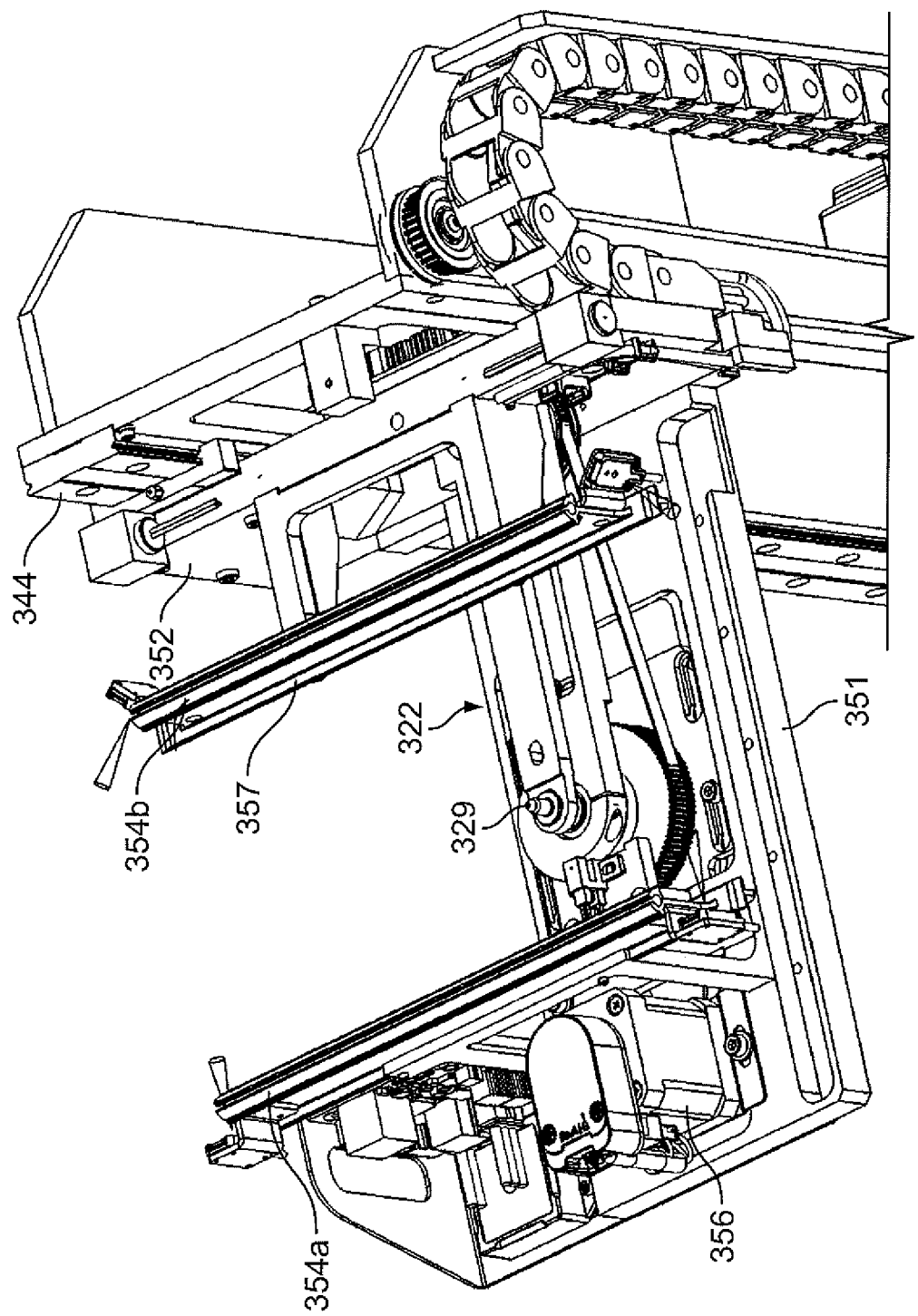
FIG. 14B is a top enhanced view of a carriage of the rack handler robot of FIG. 14A including a rack mover arm.
Figure 14C:
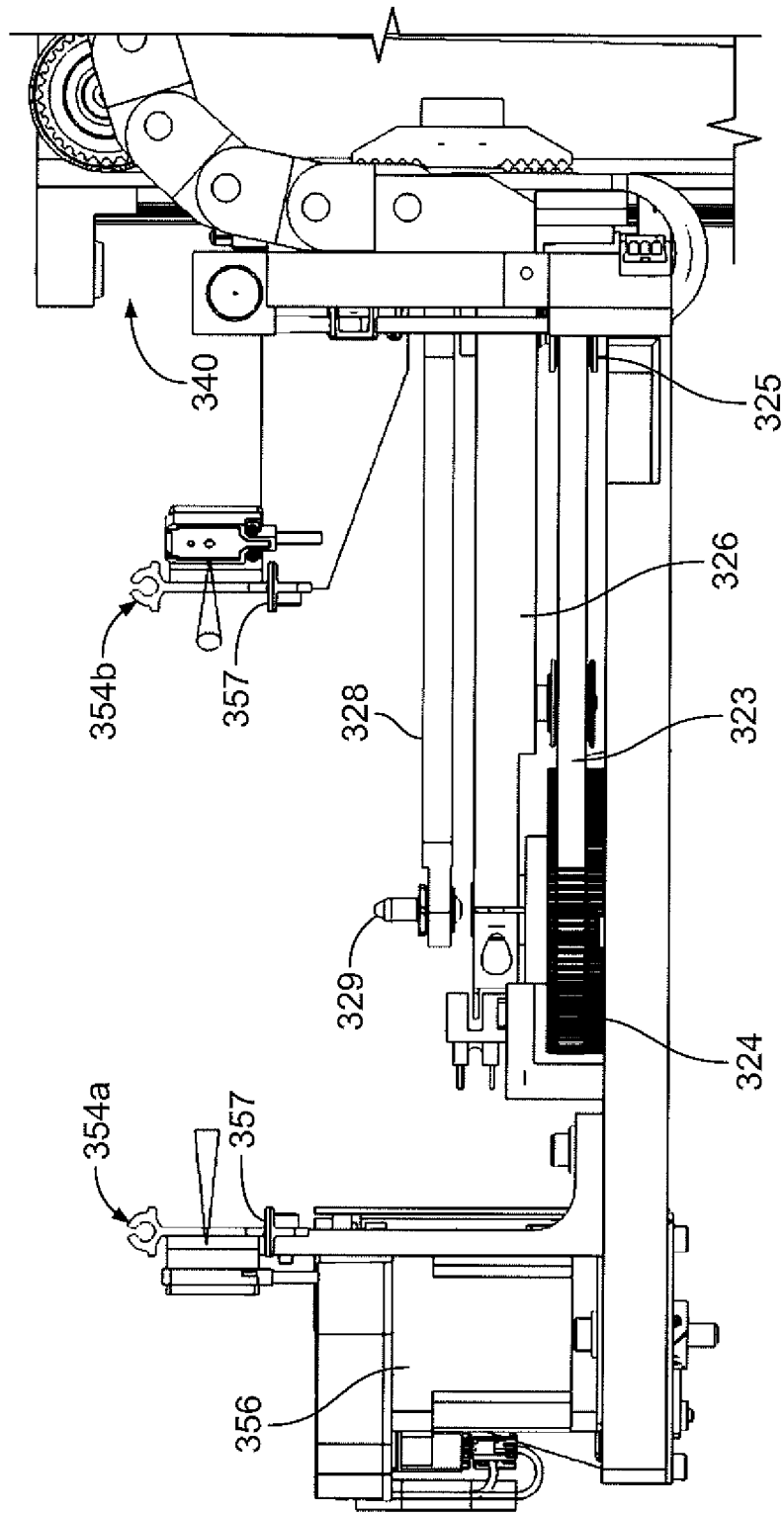
FIG. 14C is a side enhanced view of the rack mover arm of FIG. 14B.
Figure 14D:
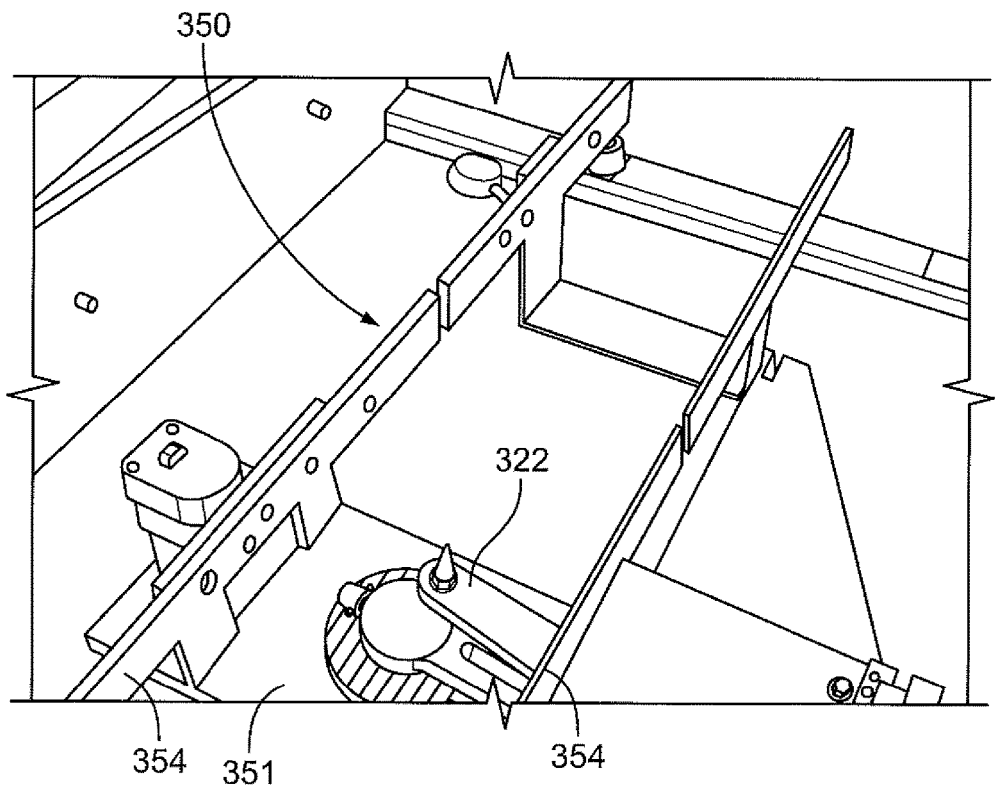
FIG. 14D is a top perspective view of the rack mover arm of FIG. 14B in an intermediate position.
Figure 14E:
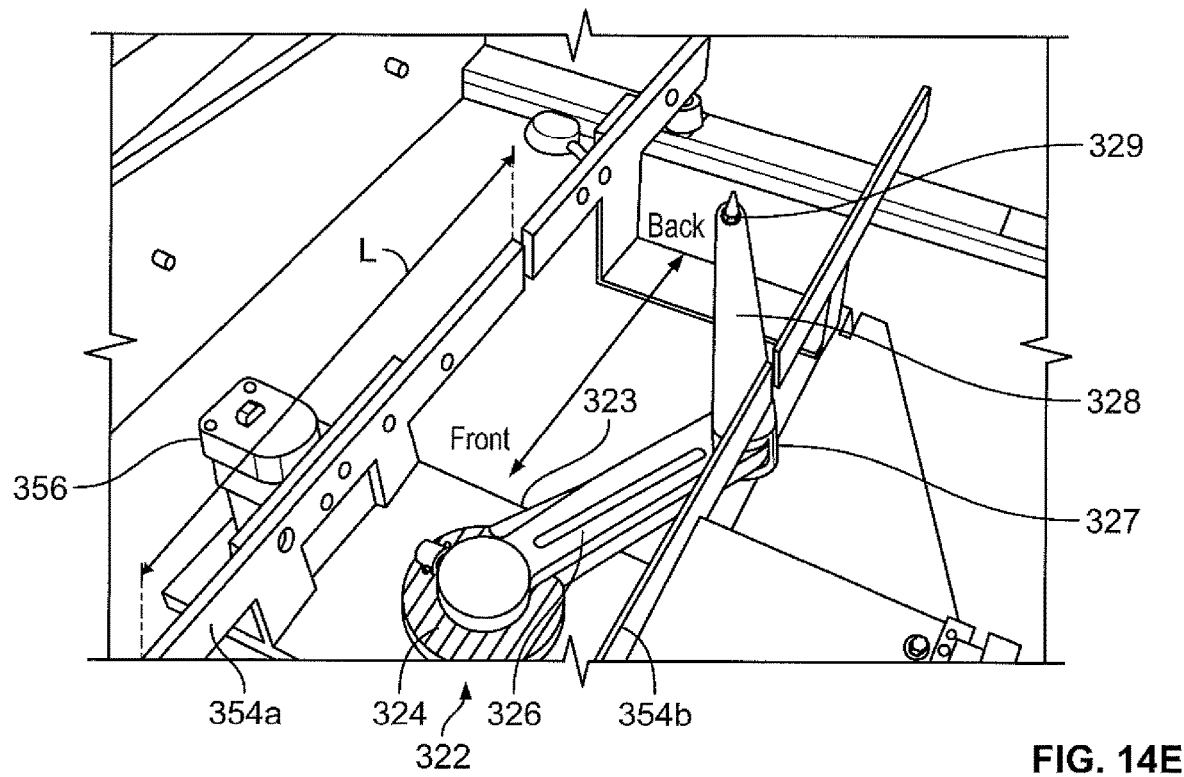
FIG. 14E is a top perspective view the rack mover arm of FIG. 14B in a back position.
Figure 14F:
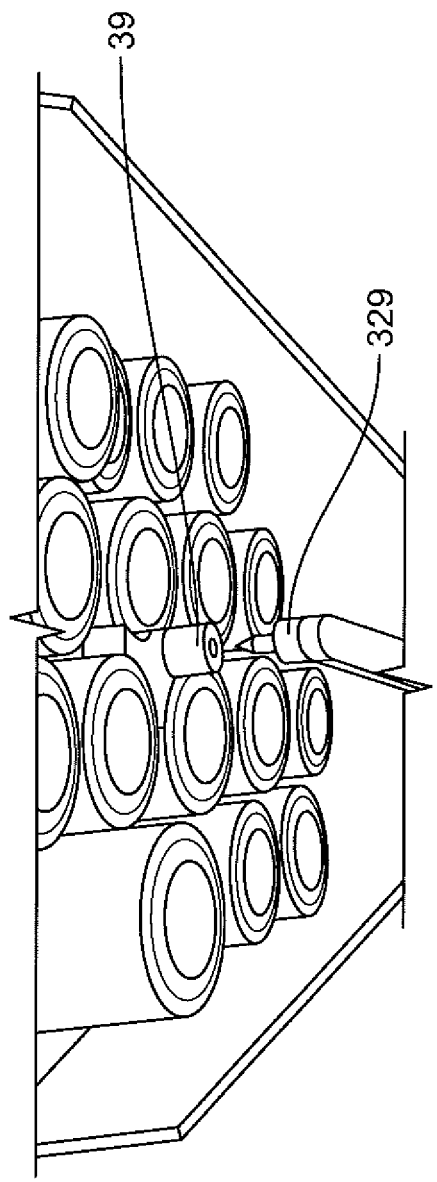
FIG. 14F is a bottom perspective view of the rack mover arm of FIG. 14B in front position and in relation to the sample rack container rack of FIG. 4A.
Figure 14H:
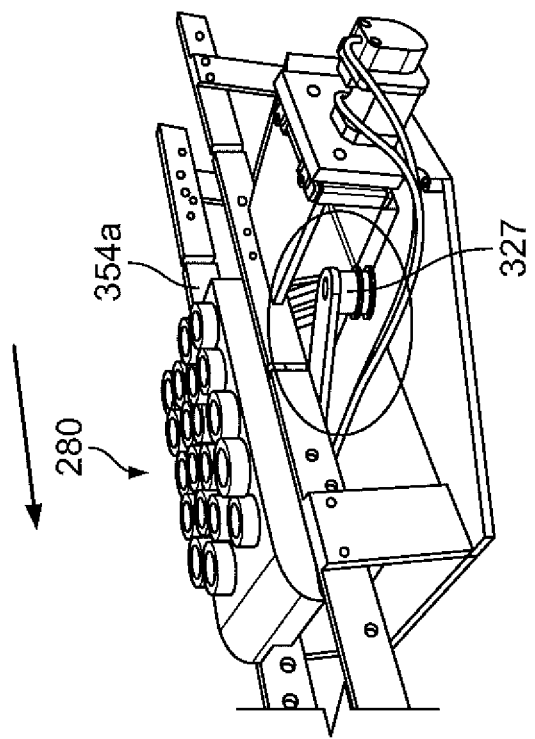
FIGS. 14G and 14H show the rack mover arm of FIG. 14B moving a sample rack container from a back position to a front position.
Figure 14G:
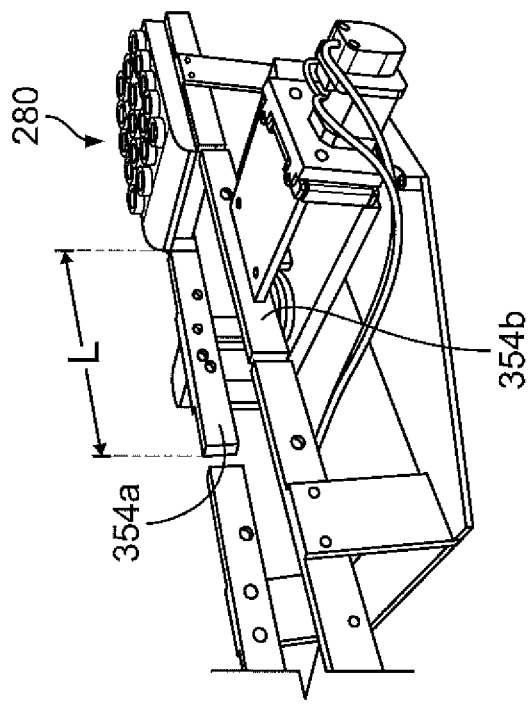
Figure 15:
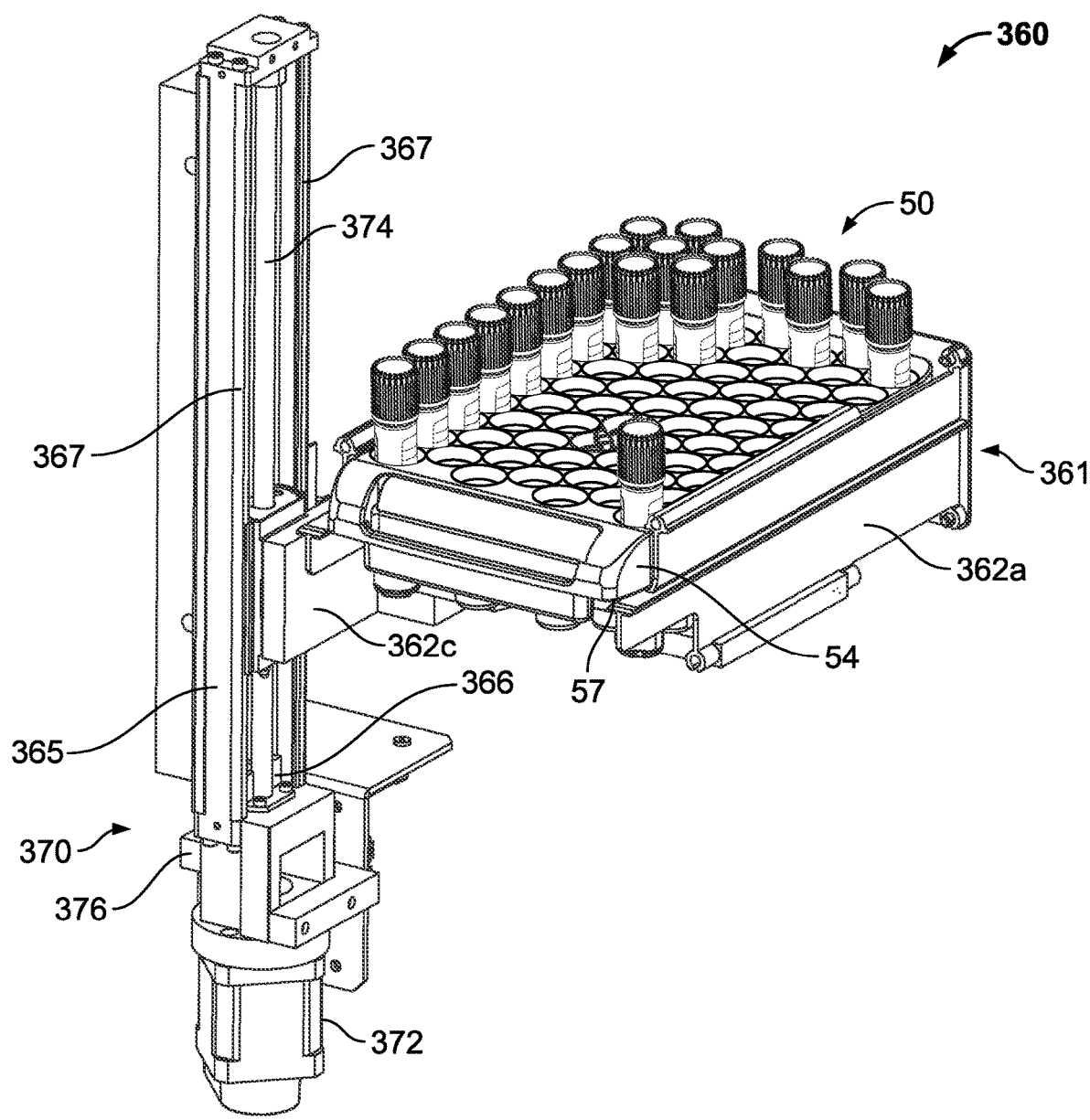
FIG. 15 is a front perspective view of a rack elevator of the pre-analytical system of FIG. 1A according to one embodiment of the present disclosure.

FIGS. 14 and 15 depict a rack handler robot 320 and a rack elevator 360, respectively. Rack handler robot 320, rack elevator 360, and angled rack elevator 100 (described above) comprise inter-deck robots or a rack elevator robot system. Such rack elevator robot system can transport racks 30, 40, and 50 between decks 22, 24, and 26. For example, rack handler robot 320 moves racks 30, 40, and 50 between storage deck 22 and first pre-analytical processing deck 24. In addition, rack elevator 360 transports rack 50 between storage deck 22 and second pre-analytical processing deck 26, and angled rack elevator 100 transports racks 50 between deck 24 and deck 26. However, it should be understood that in a pre-analytical system where decks 24 and 26 are not located at different vertical heights, the rack elevator robot system may only include rack handler robot 320. In other words, the vertical height difference between decks 24 and 26 helps minimize the front-back width of system 10 as system 10 is stretched vertically. Thus, elevators 100 and 360 help account for this vertical elevational difference. However, system 10 can be configured such that decks 24 and 26 are at the same height and are provided with a horizontal gap between them that allows for robot 320 to reach both decks.

Rack Handler Robot

Rack handler robot 320 generally includes a horizontal track member 330, vertical track member 340, and rack carriage 350. Horizontal track member 330 includes an elongate base 332 and one or more rails 334 extending from a surface of base 332 along a length thereof. Vertical track member 340 similarly includes an elongate base 342 and one or more rails 344 extending from a surface of base 342 along a length thereof. Vertical track member 340 is slidingly connected to rails 334 of horizontal track member 330 via a horizontal rail mount 345 that is connected to and extends from a bottom of vertical member 340. Vertical track member 340 is connected to horizontal rail mount 345 in this way so that vertical member 340 extends vertically and generally orthogonally relative to horizontal member 330 and such that vertical member 340 can slide in a left-right direction along horizontal member 330.

Vertical track member 340 is magnetically driven along horizontal member 330 via a linear motor, such as by a Festo Linear Motor Actuator ("FLMA") (Festo AG & Co. KG Esslingen Neckar, Germany), for example. A cable sleeve 339 may be provided adjacent to horizontal member 330 for electrical cables in order to protect the cables and keep them in place as vertical track member 340 is moved. In an alternative embodiment, pulleys or sheaves are attached to base 332 of horizontal member 330 and to horizontal rail mount 345 and are used in conjunction with a belt to move vertical track member in a right-left direction.

Rack carriage 350 includes a base 351, a vertical rail mount 352, first and second rack support members 354a-b, and a rack mover arm 322. Carriage 350 is generally disposed directly above horizontal rail mount 345 and is moveable relative thereto via vertical rail mount 352. Vertical rail mount 352 is slidingly connected to rails 344 of vertical member 340 and base 351 is cantilevered to vertical rail mount 352.

First and second rack support members 354a-b are elongate beams that include planar, upward facing surfaces 357 that are configured to engage downward facing surfaces 37, 47, and 57 of racks 30, 40 and 50. Rack support members 354a-b are substantially parallel to each other and each have substantially the same length "L" (best shown in FIG. 14E). In this regard, first rack support member 354a is connected to base 351 and second rack support member is connected to vertical rail mount 352 such that first and second rack support members 354a-b are spaced a distance substantially equal to a distance between opposing peripheral walls 34, 44, and 54 of racks 30, 40, and 50, respectively (best illustrated in FIG. 14B). This provides a gap for a portion of racks 30, 40, 50 to fit therein and for rack support members 354a-b to engage and support racks 30, 40, 50 via their peripheral walls. In addition, this gap between first and second rack support members 354a-b opens in a front-back direction. The front-back length of the gap is delimited by the length "L" of rack support members 354a-b.

As best shown in FIGS. 14B-14F, a rack mover arm 322 is disposed within the gap between rack support members 354a-b and is connected to a motor 356 attached to base 351. Motor 356 is operable to extend rack mover arm 322 outwardly in one of two directions which are transverse to the length of horizontal track member 330. In the depicted embodiment, rack mover arm 322 includes first and second elongate members 326, 328. First elongate member 326 is connected to a rotating coupling 324 disposed on base 351. The rack mover arm 322 is positioned between support members 354a-b. Second elongate member 328 is rotatably connected to an end of first elongate member 326 remote from rotating coupling 324 which forms an elbow 327. Second elongate member 328 includes an engagement feature or a projection 329 at an end thereof remote from first elongate member 326. Engagement feature 329 projects upwardly and is configured to engage engagement member 39 of rack 30 and also the engagement members of racks 40 and 50 so that rack mover arm 322 can pull a rack onto rack support members 357a-b and push a rack of off rack support members 357a-b.

In this regard, a pulley 325 is fixedly attached to second arm 328 and rotatably attached to first elongate arm 326 at elbow 327. A belt 323 is connected to pulley 325 and rotating coupling 324 such that rotation of rotating coupling 324 via operation of motor 356 causes second elongate member 328 to rotate relative to first elongate member 326. This configuration allows rack mover arm 322 to move a rack 30, 40, 50 from one side of horizontal track member 330 to the other as best illustrated in FIGS. 14E and 14F. As such, rack mover arm 322 has at least three different positions: a front position, a back position, and an intermediate position.

In the intermediate position, first and second elongate members 326, 328 are generally aligned perpendicular to the length "L" of rack support members 354a-b and engagement feature 329 is situated within the gap between rack support members 354a-b. In this position, elbow 327 may project beyond support member 354a in a left-right direction (see FIG. 14F as an example). In the particular embodiment depicted, elbow projects into a covered space within vertical track member 340. Rack mover arm 322 generally assumes the intermediate position when a rack is located on rack support members 354a-b and/or to traverse runway 25.

In the back position (best shown in FIG. 14E), second elongate member 328 is obliquely angled relative to first elongate member 328 and engagement feature 329 is positioned outside of the gap beyond the length "L" of rack support members 354a-b in the front-back direction. It is noted that elongate members 326 and 328 are configured so that when rack mover arm 322 is moved from the intermediate position to the back position, engagement feature 329 moves in a linear direction parallel to rack support members 354a-b and remains situated between rack support members 354a-b as it is advanced through the gap. The front position is similar to the back position with the difference being that engagement feature 329 is positioned at an opposite end of rack support members 354a-b than when rack mover arm 322 is in the back position. Rack mover arm 322 generally assumes one of these positions when transferring a rack off of rack support members 354a-b or moving a rack onto rack support members 354a-b.

As mentioned above, vertical mount 352 is connected to vertical track member 340. A plurality of pulleys 349 or sheaves are connected to one or more side surfaces of horizontal member 342 and to vertical mount 352. These pulleys 349 are connected via one or more belts 347. A motor 348 is attached to vertical member 340, which drives belt 347 and pulleys 349 allowing for vertical mount 352 to be driven along rails 344 of vertical track member 340 in two linear directions (i.e., up and down). This allows carriage 350 to be moved vertically. A cable sleeve 341 may be provided adjacent to vertical track member 340 for electrical cables that feed motor 348 in order to protect the cables and keep them in place as carriage 350 is moved.

Rack handler robot 320 is positioned within runway 25 located within storage deck 22 such that horizontal track member 330 extends along the length of system 10 in a left-right direction. In addition, vertical member 340 extends upwardly beneath first and second rack transport assemblies 300a-b so that an end of vertical track member 340 remote from horizontal track member 330 extends above first pre-analytical processing deck 24. The height difference between first and second pre-analytical processing decks 24, 26 allows carriage 350 to reach first pre-analytical processing deck 24 to retrieve racks 30, 40, 50 therefrom and place racks thereon 30, 40, 50. Thus, as described, carriage 350 can move in a left-right direction through storage deck 22, in an up-down direction between storage deck 22 and first pre-analytical processing deck 24, and can reach out to retrieve or place a rack 30, 40, 50 in a front-back direction.

Rack Elevator

Rack elevator 360, as shown in FIG. 15, generally includes a guide member 365, carriage 361, and carriage drive mechanism 370. Guide member 365 includes a base 366 and at least one rail 367 (two are illustrated) extending along a surface of base 366.

Carriage 361 includes three support members (only first support and third members are shown) connected together in the shape of a "U". The first and third support members 362a, 362c are disposed opposite each other and extend in generally the same direction. First and third support members 362a, 362c are spaced a distance substantially equal to a distance between opposing peripheral walls 54 of rack 50. This provides a gap for a portion of racks 50 to fit therein and for support members 362a, 362c to engage and support rack 50 via their peripheral walls (best shown in FIG. 15). Third support member 362c is slidingly attached to rails 367 of guide member. The second support member provides a backstop for a rack 50 disposed between first and third support members 362a, 362c.

Drive mechanism 370 includes a motor 372 and drive shaft 374. Motor 372 is attached to a lower end of base 366 via a bracket 376. Drive shaft 374 is connected to motor 372 and to third support member 362c at an end of drive shaft 374 remote from motor 372. Motor 372 may be a linear magnetic motor configured to manipulate drive shaft 374 in an up-down direction. Alternatively, motor 372 may be a rotating stepper motor and drive shaft 374 may be threaded and threadedly engaged to third support member 362c. Such stepper motor may be configured to rotate in opposite directions which would rotate drive shaft 374 in opposite direction to drive carriage 361 in an up-down direction along rails 367.

As mentioned above, rack elevator 360 is positioned in the back, left corner of system 10 and is partially disposed within storage deck 22 beneath second pre-analytical processing deck 26 and partially disposed within space 200 so that elevator 360 can position a rack 50 within space 200 from below.

Methods of Rack Handling and Transportation

In a method of rack handling and transportation, rack handler robot 320 moves a rack 30, 40, or 50 between a designated rack storage position within rack storage deck 22 and first pre-analytical processing deck 24. Rack handler robot 320 also moves a rack 50 among first pre-analytical processing deck 24, storage deck 22 and rack elevator 360. Rack elevator 360 moves a rack 50, once received from rack handler robot 320, between storage deck 22 and second pre-analytical processing deck 26.

In one particular exemplary method, a rack 30 is placed into I/O port 120 by a user. Motor 346 is turned on which operates pulleys 336 and belt 338 to drive carriage 350 and vertical member 340 along rails 334 in a direction toward I/O port 120. When carriage 350 is aligned with I/O port 120 in a front-back direction, motor 346 is turned off.

Motor 348 is turned on which operates pulleys 349 and belt 347 to move vertical rail mount 352 upward from storage deck 22 toward first pre-analytical processing deck 24. Motor 348 can be operated concurrently with motor 346, such as while carriage 350 and vertical member 340 are moving in a left-right direction, or sequentially, such as once carriage 350 and vertical track member 340 have stopped.

Once rack support members 354a-b reach a position in which they are aligned with peripheral walls 34 of rack 30 and slightly below downward facing surfaces 37, motor 348 is stopped. At this point, support members 354a-b are separated from rack 30 by a distance which is overcome by operating motor 356. This moves rack mover arm 322 across such distance in a forward direction toward rack 30 and into the front position in which engagement feature 329 is positioned slightly below engagement member 39 (best shown in FIG. 14D). Mover arm 322 then engages rack 30 via the moveable arm's engagement feature 329. This may be achieved by moving carriage 350 slightly upwardly so that engagement feature 329 catches engagement member 39. Motor 356 is then operated in an opposite direction into the intermediate position such that moveable arm 322 moves in a backward direction to pull rack 30 onto support members 354a-b such that downward facing surfaces 37 rest on upward facing surfaces 357. Once fully positioned thereon, motor 356 stops.

Motor 346 is then turned on such that carriage 350, rack 30, and vertical member 340 move in a left-right direction toward a rack storage position within storage deck 22. When rack 30 is aligned with a designated rack storage position, motor 346 is turned off. Motor 348 is turned on, either concurrently or sequentially to motor 346, to move carriage along rails 344 and to move rack 30 downward toward a rack storage position within deck 22. Motor 356 then operates to move rack mover arm 322 outwardly either forward or backward into the front or back position, depending on the location of the rack storage position, which slides rack 30 off of support members 354a and 354b and into the designated rack storage position.

In another exemplary method of rack handling and transportation, rack handler robot 320 repeats the above described process of concurrent or sequential motor operation to move carriage 350 up to first pre-analytical processing deck 24 in alignment with a rack 50 positioned at third sample rack space 114. Rack mover arm 322 is extended in a forward direction into the front position and toward third sample rack space 114 and engages rack 50. Moveable arm 322 is then operated to pull sample rack 50 in a backward direction and places rack 50 onto support members 354a-b.

Carriage 350 is then moved toward rack elevator 360 (FIG. 15) such that support members 354a-b of rack handler 320 align with support members 362a, 362c of rack elevator 360. Rack mover arm 322 is then moved from the intermediate position to the back position such that moveable arm slides rack 50 off of carriage 350 in a backward direction and onto carriage 361 until rack 50 abuts the backstop provided by the second support member of carriage 361. In other words, rack mover arm 322 hands-off rack 50 to rack elevator 360.

Thereafter, motor 372 of rack elevator 360 is operated to drive carriage 361 along rails 367 in an upward direction to fill space 200. Sample containers 03 located with rack 50 are unloaded and motor 372 is operated in a reverse direction to lower rack 50. Rack handler 320 again aligned with rack elevator 360 and retrieves rack 50 from therefrom. Rack handler 320 then transports rack 50 to a rack storage position within storage deck 22 or up to first pre-analytical processing deck 24 where it is removed from carriage 350.

The sequence of motor operation is implemented by a computing system which is described below. Although it is contemplated that rack handler robot 320 could perform the functions of rack elevator 360 (i.e., insert rack 50 into space 200 at second pre-analytical processing deck 26) such robots are complementary in that rack elevator 360 frees-up rack handler robot 320 to perform the above described functions while sample containers 03 are being removed from rack 50.

In addition, the methods described immediately above with regard to rack handler 320 and rack elevator 360 are examples illustrating the movement of and interplay between rack handler robot 320 and rack elevator 360. In this regard, it should be understood that rack handler robot 320 can move racks 30, 40, and 50 to and from any location within storage deck 22 and first pre-analytical processing deck 24.

Rack Transport Monitoring and Error Protocols

System 10 has a rack processor that controls operation of rack handler robot 320 and rack elevator 360. Such processor may be associated with the one or more processors 804 of the computer control device 802 of system 10 described in more detail below. In one embodiment, operational logic is provided via processor for the control of the rack handler robot 320 so that that system 10 "knows" when a rack, such as rack 30, 40, and 50, has been successfully transferred to and from the rack handler robot 320. For example, there is a feedback loop provided so that, after an instruction has been issued to the robot 320 to transfer a rack from either the main storage deck 22 or the rack elevator 360 to the robot 320, the system 10 will know whether or not the transfer has been successful. In this embodiment, the robot 320 is provided with sensors that signal whether or not the rack mover arm 322 of the robot 320 is in the front, back or intermediate positions. The robot 320 is also provided with fore and aft sensor that can sense where a rack is positioned on the rack carriage 350. Such sensors can be optical sensors or any other sensor known in the art. With these sensors, the following combinations of signals suggest the following actions:

| Arm Home Sensors (In, Out, NA) | In | In | In | In | Motion Error | In | In | In |
|---|---|---|---|---|---|---|---|---|
| Fore FD-11 sensor (Y, N) | Y | N | Y | N | any | N | Y | N |
| Aft FD-11 sensor (Y, N) | Y | N | N | Y | any | N | N | N |
| Relevant Mailbox Inventory FD11 (Y, N) | N | Y | Y | Y | any | N | N | N |
| Status | Rack successfully moved onto robot | Rack still in rack storage location | Rack only partially moved onto robot (if rack being moved from front to back on robot) | Rack only part way moved if being moved from the back of the robot to the front of the robot for transfer | Arm stuck part way | Fore FD11 sensor failure | Aft FD11 sensor failure | Not determined |
| Action | OK | Message to user to check rack and reinsert; after retry limit call service | Service Call, if moving | Service Call, if moving | Service Call | Service Call | Service Call | Service Call |

The following conditions after the command to move the rack from the rack handler robot 320 into the rack storage area 22 or the elevator 360 indicates the following actions.

| Arm Home Sensors (In, Out, NA) | Out to Encoder Count | Out to Encoder Count | Out to Encoder Count | Out to Encoder Count | Motion Error | Out to Encoder Count | Out to Encoder Count | Out to Encoder Count | In; Motion Error |
|---|---|---|---|---|---|---|---|---|---|
| Fore FD-11 sensor (Y, N) | N | Y | Y | N | any | N | Y | N | Y |
| Aft FD-11 sensor (Y, N) | N | Y | N | Y | any | Y | N | N | Y |

-continued

| Arm Home Sensors (In, Out, NA) | Out to Encoder Count | Out to Encoder Count | Out to Encoder Count | Out to Encoder Count | Motion Error | Out to Encoder Count | Out to Encoder Count | Out to Encoder Count | In; Motion Error |
|---|---|---|---|---|---|---|---|---|---|
| Relevant Mailbox Inventory FD11 (Y, N) | Y | N | Y | Y | any | Y | Y | N | N |
| Status | Move to Rack Storage or Elevator OK | Rack Still on Robot | Rack part way moved; if moving rack out to fore side. | Rack part way moved; if moving out to aft side | Arm Stuck part way | Fore F11 failure | Aft FD11 failure | Not determined | Arm failure |
| Action | OK | Message to User to Check Rack and reinsert; After Retry Limit Call Service | Service Call | Service Call | Service Call | Service Call | Service Call | Service Call | Service Call |

Sensors are also provided in rack storage area 22 and I/O port 120 to determine if a rack has been successfully transferred from the rack storage area 22 or I/O port area 120 to the robot 320. The following conditions after execution of a command to "move the rack onto the robot from the rack storage area" cause the specified status and actions.

| | | | | | | | | | | |
|---|---|---|---|---|---|---|---|---|---|---|
| IO Slot Sensor Out (Closer to User) | N | Y | N | Y | any | any | any | N | N | N | Y |
| IO Slot Sensor In (Closer to Robot). | N | N | Y | Y | any | Y | any | N | N | N | Y |
| Arm Home Sensors (In, Out, NA) | In | In | In | In | In | In | Motion Error | In | In | In | Motion Error |
| Fore FD-11 sensor (Y, N) | Y | Y | Y | N | Y | Y | any | N | Y | N | Y |
| Aft FD-11 sensor (Y, N) | Y | Y | Y | N | any | any | any | Y | N | N | Y |
| Mailbox Inventory FD11 (Y, N) | N | N | N | Y | Y | any | any | N | N | N | N |
| Status | Move into robot OK | IO Sensor Out failure | IO Sensor In failure | Rack Still in mailbox | Rack part way moved | Rack part way moved | Arm stuck part way | Fore FD11 failure | Aft FD11 failure | Not determined | Arm failure |
| Action | OK | User Message to check IO Slot; Service | User Message to check IO Slot; Service | Message to User to Check Rack and Re-insert After Retry Limit Call Service | Try to Eject Rack; Message to check rack and reload; Home Robot; After retry limit Call Service | Try to Eject Rack; Message User to check rack and reload; After retry limit Call Service | Drop down in Z; Home Arm; Message to user to reload rack; Close IO Gate; Wait for customer reload; | Service Call | Service Call | Service Call | Drop down in Z; Home Arm; Message to user to reload rack; Close IO Gate; Wait for customer reload; Retry Once; Service Call |

|  |  |  |  |  |  |  | Retry Once; Service |
|---|---|---|---|---|---|---|---|

The system 10 provides the following actions in response to an instruction to the robot 320 to move the rack into location in the rack storage area 22 or I/O port 120.

the system 10 to instruct the rack handler robot 320 to retrieve the rack from storage 22 and convey it to the I/O slot 120 of the system 10.

| | | | | | | | | | | | |
|---|---|---|---|---|---|---|---|---|---|---|---|
| IO Slot Sensor Out (Closer to User) | Y | N | Y | N | any | any | any | Y | N | N | Y |
| IO Slot Sensor In (Closer to Robot) | Y | Y | N | N | any | Y | any | Y | N | N | Y |
| Arm Home Sensors (In, Out, NA) | Out to encoder count | Out to encoder count | Out to encoder count | Out to encoder count | Out to encoder count | Out to encoder count | Motion error | Out to encoder count | Out to encoder count | Out to encoder count | Motion Error |
| Fore FD-11 sensor (Y, N) | N | N | N | Y | any | any | any | N | Y | N | Y |
| Aft FD-11 sensor (Y, N) | N | N | N | Y | N | N | any | Y | N | N | Y |
| Relevant Mailbox Inventory FD11 (Y, N) | Y | Y | Y | N | Y | any | any | Y | N | N | N |
| Status | Move To Rack Storage OK | IO Sensor Out failure | IO Sensor In failure | Rack Still on robot | Rack part way moved; Arm failure | Rack part way moved; Arm failure | Arm stuck part way | Fore FD11 fail | Aft FD11 fail | Unknown | Arm fail |
| Action | OK | Service; Can run rest of rack in Systems and unload; Cannot load | Service; Can run rest of rack in Systems and unload; Cannot load | Service | Drop down in Z; Home Arm; Message to user to unload; Service | Drop down in Z; Home Arm; Message to user to unload; Service | Drop down in Z; Home Arm; Message to user to unload; Service | Service | Service | Service | Retry Once; then Service |

The first pre-analytical processing deck 24 is equipped with a vision system in one embodiment. In this embodiment a camera acquires an image of the racks on the processing deck. The image is evaluated to identify errors in the way the racks were loaded. Examples of such errors include pierced sample tubes, capping errors or racks with mixed container types. The image is compared with information stored in the system 10 regarding the rack 30, 40, or 50, to ensure that the rack in the image is the correct rack. If the rack is determined to have an error, it is associated with an error in the system software and routed to rack storage 22. The system 10 notifies the operator (via a graphical user interface 820 or GUI described elsewhere herein) through any conventional notification channel (audio/visual, text message, email, etc.) and advises that the rack with the associated error should be removed from the system. The user can then enter a request that the rack be returned via the interface 820 which causes Suspended Robot Assembly Referring back to FIGS. 1-3, suspended robot deck 28 includes a suspended robot assembly 400 which is configured to handle samples and sample containers located on first and second pre-analytical processing decks 24, 26.

Figure 16A:
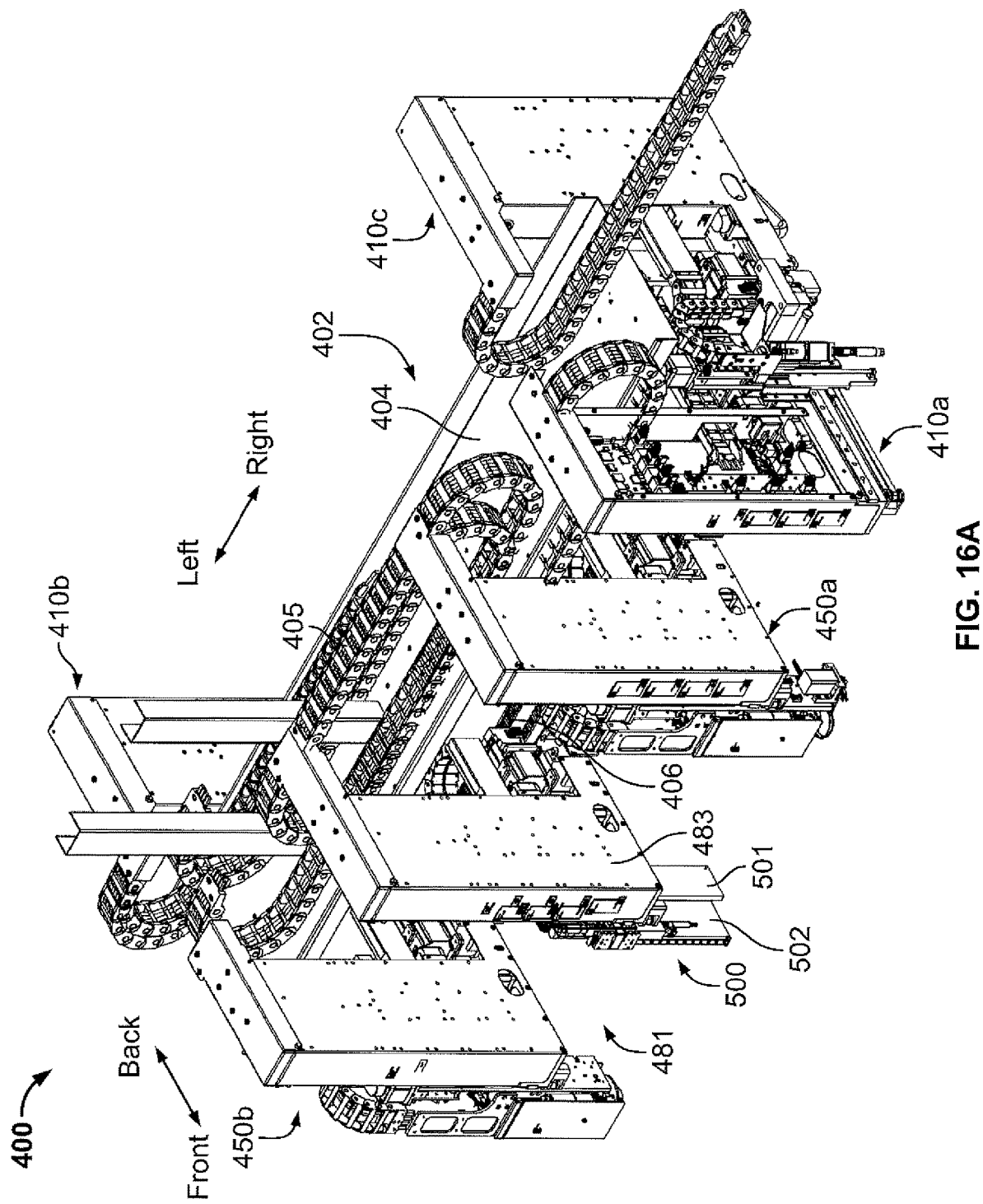
FIG. 16A is a front perspective view of a suspended robot assembly of the pre-analytical system of FIG. 1A according to one embodiment of the present disclosure.

Suspended robot assembly 400, as shown in FIG. 16A, includes a plurality of robots and a support beam or gantry 402. Support beam 402 is a support beam that spans the length of system 10 in a left-right direction and is mounted to support components 21 of structural frame 20 at opposite ends of support beam 402. When supported by frame 20, support beam 402 includes a front-side and a back-side. A rack 406 (of a rack and pinion mechanism) and a rail (not shown) disposed directly below rack 406 extend along the length of both the front and back-sides. A tray 404, for cable management, is disposed at a top-side of support beam 402 and extends along its length. This tray 404 is configured to receive cable sleeves 405 for electric cables feeding each robot as the robots move along support beam 402.

The plurality of robots includes three pick-and-place robots 410a-c, two decapper robots 450a-b, and a pipetting robot 481. From right to left, front-side of support beam includes first pick-and-place robot 410a, first decapper robot 450a, pipetting robot 481, and second decapper robot 450b. Addition, from left to right, the back-side of support beam 402 includes second pick-and-place robot 410b and third pick-and-place robot 410c. As described in detail below, each decapper robot 450a-b performs discrete functions within the pre-analytical system 10. In one embodiment, the first capper/decapper is for the LBC type containers (types 01 and 02) and the second is for the sample buffer tubes (the third type 03 containers).

Pick-and-Place Robots

Figure 16B:
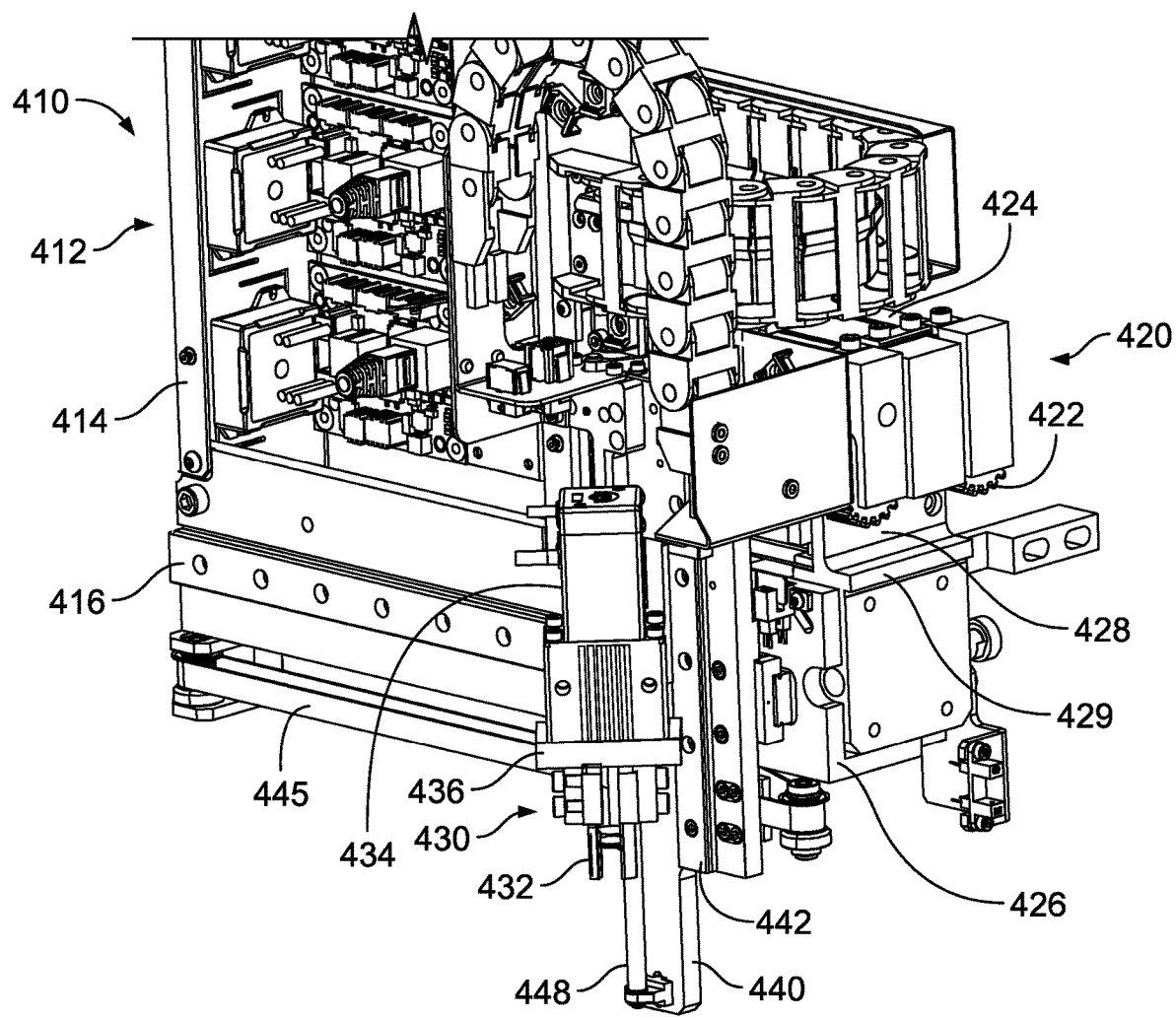
FIG. 16B is a rear perspective view of a pick and place robot of the suspended robot assembly of FIG. 16A according to one embodiment of the present disclosure.

FIG. 16B depicts a pick-and-place robot 410, which are virtually identical for robots 410a-c. The difference between these robots is that pick-and-place robots 410b and 410c are configured to have a shorter length of travel than robot 410a to retrieve items from second pre-analytical processing deck 26 as this deck 26 is elevated relative to first pre-analytical processing deck 24 over which robot 410a operates. Pick-and-place robot 410 generally includes a housing 412, control box 414, gripper assembly 430, and transport mechanism 420.

Transport mechanism 420 is mounted to housing 412 and extends from an open-end thereof. Transport mechanism 420 includes a motor 424, one or more pinions/idlers 422 (of the rack and pinion mechanism mentioned above), and a rail mount 426. Motor 424 is connected to the one or more pinions 422 and is configured to rotate pinions 422 in any one of two angular directions. Motor 424 is mounted with a spring bracket (not shown) which keeps pre-load on the motor's gear and pinions 422. This creates a zero-backlash or reduced backlash setup. Rail mount or linear profile bearing 426 is connected to housing 412 beneath pinions 422 so as to form a lipped opening 428 between rail mount 426 and pinions 422 which is sized to receive rack 406 so that rack 406 indexes with pinions 422. A lip 429 partially defining lipped opening 428 creates a channel that helps keep rack 406 aligned within lipped opening 428 when disposed therein. Rail mount 426 is configured to slidingly attach to a rail (not shown).

Gripper assembly 430 is attached to a side of housing 412. In particular, the side of housing 412 includes a horizontal rail 416 disposed at a bottom-end of housing 412. A sliding plate 440 is slidingly attached to horizontal rail 416 and includes a vertical rail 442. When mounted to horizontal rail 416, sliding plate 440 and vertical rail 442 extend below horizontal rail 416 to extend a z-direction reach of gripper assembly 430. A belt and pulley mechanism 445 is attached to sliding plate 440 and drives sliding plate 440 forward and backward along horizontal rails 416a-b.

Gripper assembly 430 includes a carriage 436 which is slidingly attached to vertical rail 442 and drive shaft 448. Drive shaft 448 is operated by a motor (not shown) which is attached to a top-end of sliding plate 440 and moves with the sliding plate 440 when belt and pulley mechanism 445 is operated by another motor (not shown). Gripper assembly 430 also includes gripper fingers 432, such as two gripper fingers, which are operated by yet another motor 434 such that gripper fingers 432 move away from and toward each other to grip sample containers of various sizes, such as containers 01, 02, and 03. However, the gripper as utilized in system 10 typically grips and transports container 03.

Control box 414 is mounted to the inside of housing 412 and is electrically coupled to a computing system (described below) and the motors of pick-and-place robot 410. Control box 414 includes electronics that receive instruction signals from the computing system, converts them into operating signals, and sends the operating signals to the various motors of pick-and-place robot 410 to perform the instructed operations. Control box 414 also sends signals back to the computing system regarding position of gripper assembly 430, task completion, and the like.

In an exemplary method of operation, the computing system sends instructions to control box 414 to pick up a container, such as container 03, from a first location and transport it to another location. These locations may be preprogramed or determined through optical sensors or other means disposed throughout system 10 that determine the precise location of the target container. Control box 414 receives these signals and converts them into operating signals which are sent to the motors of pick-and-place robot 410 to perform the instructed tasks. The motors are then operated concurrently or sequentially to move robot 410 along support beam 402, sliding plate 440 along horizontal rails 416, carriage 436 along vertical rail 442, and gripper fingers 432 until the container is picked up and moved to the designated location.

Pick-and-Place Monitoring and Error Protocols

System 10 has a pick-and-place processor that controls operation of pick-and-place robots 410a-c. Such processor may be associated with the one or more processors 804 of the computer control device 802 of system 10 described in more detail below. Also, as described below in more detail, when a shuttle 280 is received from an analyzer module after the samples contained therein are analyzed, a rack 50 is provided on the processing deck at location 110 for unloading the sample containers 03 from the shuttle 280 to the rack 50. The pick-and-place robot 410a, as controlled by the processor, unloads the containers 03 from the shuttle 50. A feedback loop monitors the pick-and-place robot 410a to determine if a sample container is unloaded from a position in the shuttle 280 to a position in the rack 50. If feedback indicates that no sample container was unloaded from a position in shuttle 280, the system 10 will send an error message.

If a container 03 has been successfully gripped, a feedback loop is provided to ensure that the container 03 remains gripped. If the container 03 is dropped, the system 10 pauses and an error message is sent. If system 10 determines that the barcode on the sample container needs to be read, the pick-and-place robot 410a moves the container to a container spinner (not shown) and deposits the container 03 therein so that the container 03 can be spun in front of the scanner so that the container can be read. Feedback loops are provided to determine if the pick-and-place robot 450a moved the container 03 to the spinner/reader, seated the container 03 in the spinner, released the container 03, and whether or not the container 03 was spun and the barcode was read. If motion errors occurred at these steps there is one retry before a failure is indicated. In the above, there could be a gantry z/y-movement failure, a gantry Z-movement failure, a gripper finger failure or a spinner failure. All failures, if indicated with cause the system 10 to stop operation.

If the barcode is not read successfully, then there may be a motor encoder error of the spinner. In retry, the container 03 is spun and read again. If retry is unsuccessful the container 03 is picked from the spinner. The empty spinner is subjected to a bar code test. If the read fails, the sequence is stopped and the failure data is stored. If the barcode read test is successful, the container 03 is replaced in the spinner and barcode read is retried. If read is successfully, the process continues and the container chain of custody is reported. If the container 03 is not read successfully the container 03 is flagged.

Once read, the container 03 is placed in a rack 50 at location 110. Again, the container 03 is moved to particular x, y coordinate, then moved down (in z) to be placed in its predetermined location in the rack 50. The gripper 432 releases the container 03 and the gripper then moves back up in z to its travel height. If motion errors are detected for any of these motions, then there is one retry. If still unsuccessful then there is a failure, and a stop operation occurs and the failure data is stored. Once the container 03 is released the grippers 432 are no longer monitored for droppage. Once the shuttle 280 is determined to be empty, it is returned to either docking station 260a or 260b.

Pick-and-place robot 410a has its own power recovery protocol from a system pause or stop. Again the discrete acts performed are to close the gripper 432 to retain a held container, send the robot 410a to home on the x, y and z axis. If motion errors are detected there is one retry before the system issues a stop operation and the failure data is stored. There is also recovery of the barcode reader. In this regard, there is then an empty spinner barcode retest. If read is unsuccessful, it is determined that there is a failure. A successful read will indicate that the barcode reader is ready.

Robot 410a is moved in to the empty barcode spinner location and, if successful, the container 03 is seated in the spinner and if successful the gripper 432 is moved home. Motion errors, if detected, will allow for one try prior to failure. If the barcode is successfully read then, the container in the spinner it is removed, and the container is moved to its designated rack position and placed in rack 50 as described above. Once the sequence is complete, the empty robot 410a is moved to its safe location, power recovery is complete and the robot is ready for operation.

The tube spinner and barcode reader described herein has a diagnostic self-test. As described elsewhere herein for other discrete components/apparatus/subsystems, the diagnostic self-test is performed in communication with a processor/controller and sensors that report motion errors at which time the processor/controller initiates a retry. If the retry is unsuccessful a report is given to the operator and, depending upon the programmed instructions, the module, apparatus or system may enter pause or shut down until the error is corrected.

Although, the above error protocols are described with respect to pick-and-place robot 410a, it should be understood that robots 410b-c may also be operated with such protocols to perform diagnostic self-tests to resolve errors similar to the above.

Decapper Robots

Figure 16C:
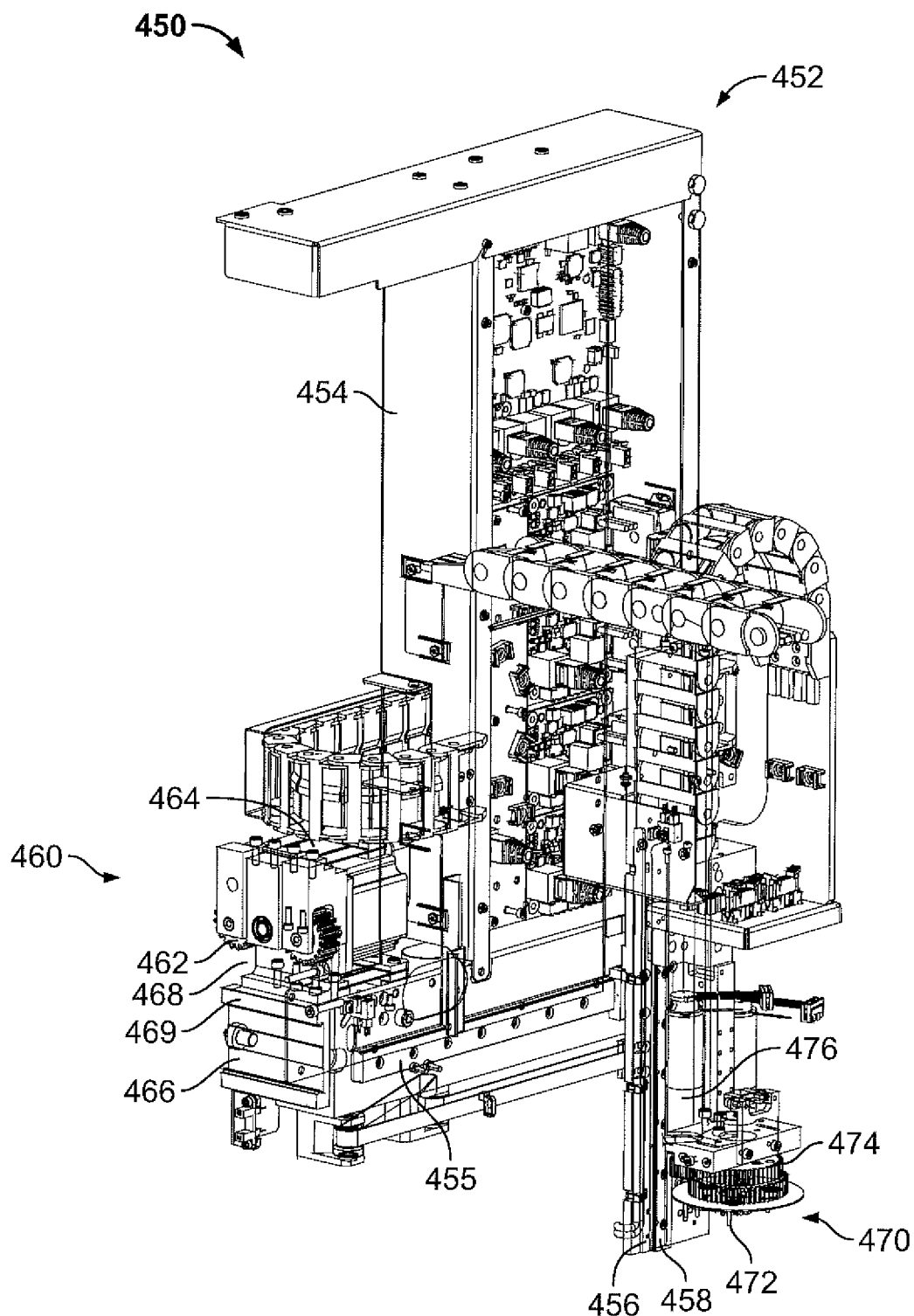
FIG. 16C is a rear perspective view of a decapper robot of the suspended robot assembly of FIG. 16A according to one embodiment of the present disclosure.

FIG. 16C depicts a decapper robot 450, which is identical for robots 450a-b. Decapper robot 450 generally includes a housing 452, control box 454, decapper assembly 470, and transport mechanism 460.

Transport mechanism 460 is mounted to housing 452 and extends from an open-end thereof. Transport mechanism 460 includes a motor 464, one or more pinions 462 (of the rack and pinion mechanism mentioned above), and a rail mount 466. Motor 464 is connected to the one or more pinions 462 and is configured to rotate pinions 462 in any one of two angular directions. Rail mount 466 is connected to housing 452 beneath pinions 462 so as to form a lipped opening 468 between rail mount 466 and pinions 462 which is sized to receive rack 406 so that rack 406 indexes with pinions 462. A lip 469 of lipped opening 468 creates a channel that helps keep rack 406 aligned within lipped opening 468 when disposed therein. Rail mount 466 is configured to slidingly attach to a rail adjacent to rack 406. Decapper assembly 470 is suspended at a lower-end of housing 452 and generally includes two elongate fingers 472 attached to a series of gears 474. Gears 474 are driven by a driveshaft (not shown) and a decapper motor 476 which moves fingers 472 closer or further away from one another and also rotates all of fingers 472 about a central axis to de-cap/recap a container. Decapper motor 476, which may be disposed in its own housing, and decapper assembly 470 are attached to a sliding plate 456 via a vertical rail 458 located on a surface of sliding plate 456. Sliding plate 456 is slidingly attached to a horizontal rail 455 located on a support structure within housing 452. A series of other motors (not shown) drive sliding plate 456 along horizontal rail 455 in a front-back direction and decapper assembly 470 along vertical rail 458.

Control box 454 is mounted to the inside of housing 452 and is electrically coupled to a computing system (described below) and motors 464, 476 and the ones not shown. Control box 454 includes electronics that receive instruction signals from the computing system, converts them into operating signals, and sends the operating signals to the various motors to perform the instructed operations. Control box 454 also sends signals back to computing system regarding decapper position, task completion, and the like.

In an exemplary method of operation, computing system sends instructions to control box 454 to pick up a container, such as one of containers 01, 02, and 03, from a first location (e.g., rack spaces 112, or 114), transport it to another location (e.g., primary or secondary container station), and de-cap and recap the container. These locations may be preprogramed or determined through optical sensors or other means disposed throughout system 10 that can determine the precise location of the target container. Control box 454 receives these signals and converts them into operating signals which are sent to motors 464, 476 and the ones not shown to perform the instructed tasks. The motors are then operated concurrently or sequentially to move robot 450 along support beam 402, sliding plate 456 along horizontal rails 455, motor 476 and decapper assembly 470 along vertical rail 458, and decapper fingers 472 together until the container is picked up and moved to the designated location. The designated location preferably includes engagement features, such as those within primary or secondary container stations 140, 150, or a clamping mechanism, such as clamp assembly 162 that restrains the container from rotation. Once the container is constrained, decapper assembly 470 is rotated to de-cap container. Fingers 472 hold onto the cap and recap the container when ready.

Decapper Monitoring and Error Protocols

System 10 has a decapper processor that controls operation of decapper robots 450a-b. Such processor may be associated with the one or more processors 804 of the computer control device 802 of system 10 described in more detail below. In addition, the decapper processor has processing logic that identifies errors and implements preprogrammed error process flows. As described elsewhere herein, as part of the error process flow, motions of each decapper 450a-b are monitored for motion errors. If motion errors are detected, then one retry is permitted before there is an error message or corrective action taken. When a decapper is instructed to move its gripper fingers 472 to the pre-grip/home position, the decapper is directed to a location and settings based upon the type of container to be capped or de-capped. If a z-motion error is detected, a retry is performed before an error message issues as noted above. If the decapper stalls in the z-motion, the grippers 472 are all re-homed. Motion errors detected on re-homing allow for one retry with ensuing error message upon detecting a second motion error. Other motions monitored for motion errors include x and y movements to a container barcode reader, rotational/spin movements (for reading barcodes) and the barcode read itself. Also, the movement of the container's cap is monitored to detect a dropped cap should it occur.

The spin motion of the decapper is also monitored for motion errors. If rotation stalls repeatedly (more than twice in a row), the operator is notified of a potential problem (e.g. a container size mismatch). Specifically, if rotation stalls this can indicate that the container is not seated properly in the container receptacle (i.e. the nest for the container).

The recap error flows also monitor for motion errors and only issue error messages if the error occurs after one retry. The recap sequence causes the decapper 450 to proceed to an x, y position above the container to be re-capped, followed by transfer of a drip tray to ensure that it does not impede motion of the decapper. This is further followed by moving the decapper 450 into position in the z direction. If there is a motion error in z, the decapper moves back to home in z.

The decapper 450 also has the ability to determine if a container is properly re-capped by monitoring motor encoder counts and motor current at appropriate segments during the re-cap routine. If the number of recap fails exceeds a certain threshold, the system 10 may stop and inform the operator. The container is cleared. After clearing, the decapper 450 is rehomed. Failure to return home indicates that the decapper 450 or the decapper assembly 470 needs to be replaced.

Once the cap is successfully tightened onto the container, the cap is released by the decapper 450.

The pre-analytical system 10 described here, in one embodiment, has a pre-programmed routine for rebooting the decapper after a power outage. The decapper 450 has preset home positions (e.g. home position in x, y and z) to which the decapper 450 moves during a reboot/power restore. If the decapper 450 was in the process of de-capping or re-capping during power failure, rotation is activated to uncap fully, and then the decapper returns to the home position in z.

Pipetting Robot

Referring back to FIG. 16A, pipetting robot 481 includes a pipette arm 483 and a pipette head 500. Pipette arm 483 includes a housing, a control box, and transport mechanism similar to that of pick-and-place robot 410. As such, transport mechanism includes a pinion and rail mount (not shown) that mounts to rack 406 and a rail of support beam 402 at a front-side thereof for traversing support beam 402 in a left-right direction. In addition, pipette arm 481 includes horizontal rails (not shown) and a sliding plate (not shown) slidingly attached to the horizontal rails similar to that of pick-and-place robot 410. Pipette head 500 is connected to a vertical rail (not shown) of the sliding plate and to a motor (not shown) via a drive shaft 487. The motor is attached to the sliding plate so as to move with pipette head 500 as sliding plate 484 is driven along the horizontal rails in a front-back direction via a belt and pulley mechanism (not shown). Thus, as shown, pipette head 500 is coupled to pipette arm 483 via a z-axis drive mechanism that includes a vertical rail motor, and drive shaft 487.

Pipette head 500 generally includes a main board 501 and a pipette assembly 502 (best shown in FIG. 16A). Pipette assembly 502 is comprised of a pipette channel assembly and a pipette tip ejector assembly (best shown in FIGS. 17A-17D). The pipette channel assembly includes a channel housing 510, pipette tip adaptor 520, control unit 515, and connector arm 517.

Figure 17D:
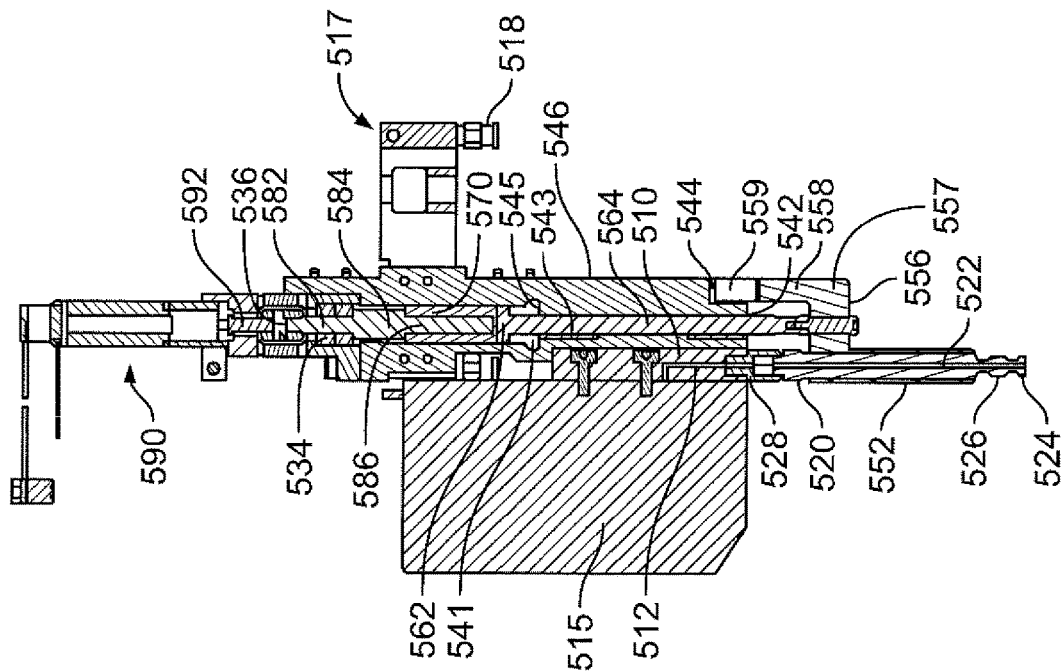
FIG. 17D is a cross-sectional view taken at line F-F of FIG. 17C.
Figure 17C:
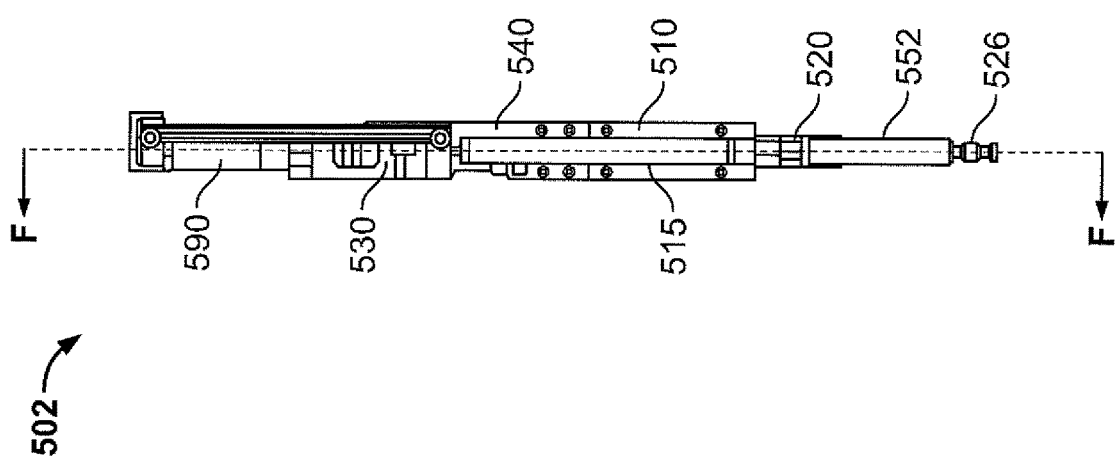
FIG. 17C is a side view of the pipette assembly of FIG. 17A.

Channel housing 510 includes a pipette channel 522 extending therethrough (best shown in FIG. 17D). Housing 510 has a first side surface which is configured for connection to an ejector housing 540, and a second side surface which is configured to connect to control unit 515. As depicted, channel 512 extends through a bottom end of housing 510, extends along a portion of the length of housing 510, turns at an angle (such as between 90 and 180 degrees) and extends through the second side surface of housing 510.

Pipette tip adaptor 520 extends from the bottom of channel housing 510 such that a channel 522 of pipette tip adaptor 520 is in fluid communication with channel 510 of channel housing 510 to form a unitary pipette channel In the embodiment shown, an isolator 528 for capacitive sensing couples pipette tip adaptor 520 to channel housing 510. However, in other embodiments, tip adaptor 520 may be directly connected to channel housing 510.

At a bottom end of pipette tip adaptor 520 remote from channel housing 510, pipette tip adaptor 520 includes first and second pipette tip engagement features 524, 526. In the embodiment depicted, these engagement features 524, 526 are spherical bulbs that project radially outwardly from adaptor 520. First engagement feature 524 has a smaller diameter than second engagement feature 526. This helps create an interference fit with a disposable pipette tip for retaining such tip to adaptor 520. In other embodiments, engagement features 524, 526 can be conical portions like that of a Leuer lock or some other tapering geometric feature.

Control unit 515 is connected to the second surface of channel housing 510 and extends therefrom. Pipette channel 512 extends into control unit 515 where a valve, such as a solenoid valve (not shown), selectively opens and closes channel 512. In one embodiment, differential pressure flow sensors (not shown) are located upstream of the valve and measure air flow to channel 512 to help control aspiration and dispense of a sample in conjunction with the valve.

Connector arm 517 is coupled to control unit 515 and in particular to channel 512. Connector arm 517 may be directly connected to control unit 515 or may be located remote of control unit 515. Connector arm 517 includes two inlet ports 518, 519. First inlet port 518 is a positive pressure port. Second inlet port 519 is a vacuum port. Positive and negative pressures of air across these ports 518, 519 help drive aspiration and dispense of a sample.

Pipette tip ejector assembly generally includes a first ejector housing or upper ejector housing 530, a second ejector housing or lower ejector housing 540, a tip ejector 550, control unit 594 and a tip ejector drive mechanism.

First or upper ejector housing 530 includes an opening extending therethrough from a first end to second end thereof. The opening is dimensioned to receive a motor drive shaft 592 through the first end, an angular contact bearing 534 within the second end, and a shaft coupling 536 within housing 530 between the first and second ends. A transverse port 532 extends into housing 530 and intersects the opening such that when shaft coupling 536 is disposed within first ejector housing 530, shaft coupling 536 is exposed. This allows a motor 590 to be decoupled from pipette head 500 and replaced with minimal disassembly. Housing 530 is also configured to connect to control unit 594 at one side thereof.

Second or lower ejector housing 540 is connected to the second end of upper ejector housing 530 such that a longitudinal opening 542 of lower ejector housing 540 is in fluid communication with the opening of upper ejector housing 530. Longitudinal opening 542 extends through the entire length of lower ejector housing 540 from a first end or upper end to a second end or lower end. Longitudinal opening 542 has a first portion or lower portion 543 smaller than a second portion or upper portion 541 so as to form a shoulder 545 therebetween (see FIG. 17D). A recess 544 extends into the second end of housing 540. A Hall Effect sensor 548 is embedded in housing 540 adjacent to recess 544.

A side surface 546 extending along the length of housing 540 is connected to main board 501 (FIG. 16A). Main board 501 may include electrical connections and other connections for pipette head 500 and connects pipette head 500 to pipette arm 483 via the z-axis mechanism. The connection between pipette assembly 502 and main board 501 may be a rigid connection or hinged connection, such as via a hinge located in a notch 549, so that pipette assembly can be rotated about a vertical axis into other positions. In addition, housing 540 has a cut-out portion 547 at one side thereof which receives a portion of pipette channel housing 510.

Tip ejector 550 includes a cannulated body 552 and an arm 554 extending from body 552. Cannulated body 552 has an opening extending therethrough from a first to second end and is dimensioned to slidingly receive tip adaptor 520. Arm 554 extends from an upper end of cannulated body 552 and has an elbow 557 defining a curve in arm 554 of about 90 degrees, which forms a horizontal portion 556 and a vertical portion 558. Horizontal portion 558 is configured to attach to a floating shaft 560. A terminal end 559 of vertical portion 558 remote from horizontal portion 556 is sized to be partially received in recess 544 of lower ejector housing 540. In addition, a magnet 551, configured to cooperate with Hall Effect sensor 548, is located in terminal end 559 of vertical portion 558. This magnet 551 cooperates with Hall Effect sensor 548 to determine whether a pipette tip is retained on tip adaptor 520.

The tip ejector drive mechanism includes a motor 590, lead screw 580, pusher nut 570, and floating shaft 560. Motor 590 is an electric motor which may include an encoder and gearbox integrated therewith. A motor drive shaft 592 extends from motor 590.

Lead screw 580 includes an upper portion 582, lower portion 586, and intermediate portion 584. Upper portion 582 and lower portion 586 have a smaller diameter than intermediate portion 584 which helps retain bearing 534 and provides a backstop for pusher nut 570. In addition, upper portion 582 is configured to attach to drive shaft 592 via coupling 536 and has generally smooth outer surfaces for rotation within angular contact bearing 534. Lower portion 586 is threaded along its length for driving pusher nut 570.

Pusher nut 570 is internally threaded and externally dimensioned to be received within upper portion 541 of longitudinal opening 542. A lower end of pusher nut 570 has generally flat surfaces for pushing against floating shaft 560.

Floating shaft 560 has a head 562 with a larger diameter than a shank 564 thereof. The shank diameter is sufficiently small as to be slidingly received within lower portion 543 of longitudinal opening 542. Head 562 has a diameter sufficiently large as to prohibit being received within lower portion 543 of longitudinal opening 542 while sufficiently small as to be slidingly received within upper portion 541 of longitudinal opening 542. A lower end of shank 564 remote from head 562 is configured to attach to horizontal portion 556 of tip ejector 550, such as by receiving a fastener extending from horizontal portion 556.

Control unit 594 is connected to upper ejector housing 530 and has an output coupled to motor 590 for driving motor 590 in one of two rotational directions. Control unit 594 also has an input connected to Hall Effect sensor 548 and an output that is coupled to the computing system (described below) to notify a user that a pipette tip has fallen off of tip adaptor 520. Additionally, control unit 594 can be a switch interface board ("SIB") to provide switching functionality to pipette assembly 502.

As assembled, the pipette channel assembly is connected to the pipette ejector assembly via channel housing 510 being received in cutout portion 547 of lower ejector housing 540 and is connected thereto. In this regard, tip adaptor 520 extends below both channel housing 510 and lower ejector housing 540.

Shank 564 of floating shaft 560 is received within lower portion 543 of longitudinal opening 542 such that an end of shank 564 extends from lower ejector housing 540. Tip adaptor 520 is received within the opening of the cannulated body 552, horizontal portion 556 is connected to an end of shank 564, and terminal end 559 of vertical arm 558 is received within recess 544 of lower ejector housing 540.

In this regard, floating shaft 560 and tip ejector 520 have a tip-off position and tip-on position. In the tip-off position, no pipette tip is connected to tip adaptor 520, and in the tip-on position, a pipette tip is connected to tip adaptor 520.

When in the tip-off position, head 562 of floating shaft 564 rests against shoulder 545 of lower ejector housing 540. This positions cannulated body 550 at its lowest extent or near its lowest extent relative to tip adaptor 520 such that body 552 surrounds one or both of first and second engagement features 524, 526. In addition, terminal end 559 and magnet 551 are positioned at their lowest extent within recess 544.

When in the tip-on position, a pipette tip pushes cannulated body 552 upward such that cannulated body 552 is positioned above first and/or second engagement feature 524, 526, terminal end 559 of vertical portion 558 is positioned above its lowest extent within recess 544, and head 562 of floating shaft 550 is positioned a distance above shoulder 545. It should be understood that when no pipette tip is attached to tip adaptor 520 (illustrated), floating shaft 560 and tip ejector 550 are positioned in the tip-off position under their own weight. Also, when a pipette tip is attached to tip adaptor 520, the weight of floating shaft 560 and tip ejector 550 are countered by the holding force between tip and tip adaptor 520 so as to position floating shaft 560 and tip ejector 550 in the tip-on position.

Continuing with the assembly, pusher nut 570 is positioned above head 562 of floating shaft 560 within upper portion 541 of longitudinal opening 542. Lower portion 543 of leadscrew 580 is threaded to pusher nut 570 and extends therefrom such that upper portion 582 of leadscrew 584 extends through angular bearing 534 positioned within the second end of upper ejector housing 530. Upper portion 582 of leadscrew 580 is coupled to motor drive shaft 592 via coupling 536, and motor 590 is mounted to the first end of upper ejector housing 530.

Pusher nut 570 has an eject position and a stand-off position. In the eject position, the threads of leadscrew 580 position pusher 570 within longitudinal opening 542 such that pusher nut 570 forces floating shaft 560 and tip ejector 550 into the tip-off position. In the stand-off position, the threads of leadscrew 580 position pusher 570 within longitudinal opening 542 such that floating shaft 560 has sufficient space to allow a pipette tip to be connected to tip adaptor 520.

A method of operation of pipette head 500 is now described. In the method, robot 481 is moved along support beam 402 to pipette tip racks located at space 180. Tip adaptor 520 is aligned with a pipette tip 489 (tip is depicted in FIG. 25A) and a motor (not shown) drives pipette head 500 toward the pipette tip until tip adaptor 520 engages an opening of pipette tip 489. The motor further drives tip adaptor 520 into the opening of pipette tip 489 so as to engage one or both engagement features 524, 526 in a locking fashion. As this occurs, an end of pipette tip 489 pushes against cannulated body 552 which drives floating shaft 560 upwardly so that head 562 lifts off of shoulder 545 to form a distance therebetween. In addition, terminal end 559 of vertical portion 558 moves upwardly within recess 544 and magnet 551 interacts with Hall Effect sensor 548 which sends a signal to control unit 594 that indicates a pipette tip 489 is engaged. At this stage, floating shaft 564 and tip ejector 550 are in the tip-on position.

Robot 481 then moves along support beam 402 to aspirate a sample from a container. If at any time pipette tip 489 inadvertently falls off of tip adaptor 520, floating shaft 564 and tip ejector 550 automatically move into the tip-off position. The movement of magnet 551 into this position signals control unit 594 that tip 489 has fallen off of tip adaptor 520 and a user is warned of this occurrence. Stated another way if tip 489 accidentally falls off of tip adaptor 520, the weight of tip ejector 550 and floating shaft 560 causes cannulated body 552 to slide downwardly along tip adaptor 520, floating shaft 560 to drop so that head 562 contacts shoulder 545, and terminal end 559 to move downwardly within recess 544 which triggers a tip-off warning.

Once robot 481 reaches an open sample container, the motor drives tip adaptor 520 down until tip 489 contacts the sample which triggers a capacitive or pressure-based liquid level detection sensor causing aspiration to begin. After a sample has been aspirated and dispensed in another container, pipette head 500 is moved to an opening located through first pre-analytical processing deck 24. With pipette tip 489 aligned over the opening, motor 590 turns on which drives leadscrew 580 in a first direction from a stand-off position to an eject position. The threads of leadscrew 580 push pusher nut 570 toward head 562, which is positioned above shoulder 545. When pusher nut 570 contacts head 562, pusher 570 is further driven which pushes floating shaft 560 downward. Shank 564 pushes on horizontal portion 556, which consequently pushes body 552 downwardly along tip adaptor. Body 552 drives pipette tip 489 off of engagement features 524, 526 so that pipette tip 489 is ejected from tip adaptor 520. When ejection occurs, the weight of floating shaft 560 and tip ejector 550 causes head 562 to fall whatever remaining distance there is left between head 562 and shoulder 545, which signals that tip 489 has been successfully removed. Since tip 489 is ejected over an appropriate waste opening, no alarm is signaled. Motor 590 is then operated in a second direction which returns pusher nut 570 to the stand-off position so that another pipette tip can be attached to tip adaptor 520.

If the robotic pipettor drops a pipette before it reaches the waste receptacle, the robotic pipettor returns to its home position and open containers are recapped, prior to the capper/decapper robots 450 returning to their respective home positions.

Pipette Monitoring and Error Protocols

System 10 has a pipettor processor that controls operation of pipetting robot 481. Such processor may be associated with the one or more processors 804 of the computer control device 802 of system 10 described in more detail below. Pipettor processor/controller provides both power restore protocols and error control protocols to the pipettor 481. As noted previously herein, errors in motion, when detected, are given one retry before the system logs an error and informs an operator. Additional pipettor errors include aspiration and clogged pipette tips.

During sample preparation/conversion, the pipettor 481 is instructed to retrieve a pipette tip 489. The pipettor 481 conducts various checks prior to and after picking up a tip, including flow check of the newly picked up tip as the pipettor 481 is advanced to the sample container to obtain an aliquot of sample for preparation/conversion. When called to eject a tip, if the tip fails to eject after the first try, the controller runs a preprogrammed routine for a tip eject failure. If the tip sensor 548 indicates an error with the tip pick up, the pipettor 481 is returned to home, and there is a retry. If the tip sensor 548 again indicates that there was an error with tip pick up, a different rack of pipette tips is tried. If the error persists, or another rack of tips is not available, preparation/conversion is paused until the problem is solved.

Sample containers 01, 02, and 03 are de-capped using the procedures and error control protocols described elsewhere herein. The diluent bottles 14 (see FIG. 8C) are monitored and, if the bulk diluent bottle level is low, a message is sent to the operator. The diluent contained in such bottles 14 is then dispensed into the third-type containers 03 for sample preparation/conversion. The dispense head 172 is used to dispense diluent into a container and to monitor the level of diluent in the container. If a motion error is detected, there is a level check retry and if the error persists then the bulk diluent head 172 is evaluated for errors. If the bulk diluent dispense head 172 successfully checks the level of the diluent dispensed into the container, then the sample container is de-capped. If the diluent level is too low or too high, there is one retry followed by, if unsuccessful, a message to the operator to stop using the channel 175 if the level is too high and the container 14 is discarded. If the level remains too low, the container 14 is discarded.

The z-motion of the pipettor 400 is monitored. If the pipettor 400 fails to encounter the liquid level surface for an aspiration, there is one retry before the sample is recapped, returned to the sample storage area 22 and designated as a bottle with no sample. The container 03 into which the sample was to be dispensed is discarded.

If the liquid level surface is in contact with the pipette tip 489, the Z position of the pipette tip 489 is reported and compared with a minimum threshold for the container type. If below the minimum threshold, the pipette tip 489 is moved to the bottom and then raised about 0.5 mm in the z-direction. During aspiration the pipette tip 489 can either remain at a z-coordinate or travel downward in the z-direction as aspiration progresses and the liquid level declines. Z-motion errors and aspiration errors initiate further protocols. Z-motion errors will allow one retry before entering an error protocol for pipette channel z failure. Aspiration errors will cause a retry in which the pipettor 481 will move incrementally in x, y, or z directions after which aspiration will occur at a lower rate. If aspiration errors continue and the liquid level is below threshold than the pipette tip 489 contents are redispensed into the sample container which is recapped and sample reported as low volume. If the liquid level is not below threshold, then the sample is redispensed and the sample is replaced and the aspiration error is reported as a clog.

Upon successful aspiration, the pipettor 481 will pull a travel air gap and, after a pause to let drips fall into the container, the pipettor 481 will move to the dispense location. If there is an x, y or z motion error, there is one retry before an axis error is indicated.

The dispense is then monitored for errors. If a dispense error occurs, the container 03 designated to receive the dispensed liquid is discarded. The tip 489 is then discarded. If no dispense error, the tip 489 is discarded, the sample container and prepared sample container are recapped and moved to their respective racks. If the prepared sample container is prepared correctly it is recorded in the system 10 as such and sample preparation is complete and a secondary sample is obtained for further pre-analytical processing.

Main Deck Robot Operating Envelopes

Figure 18:
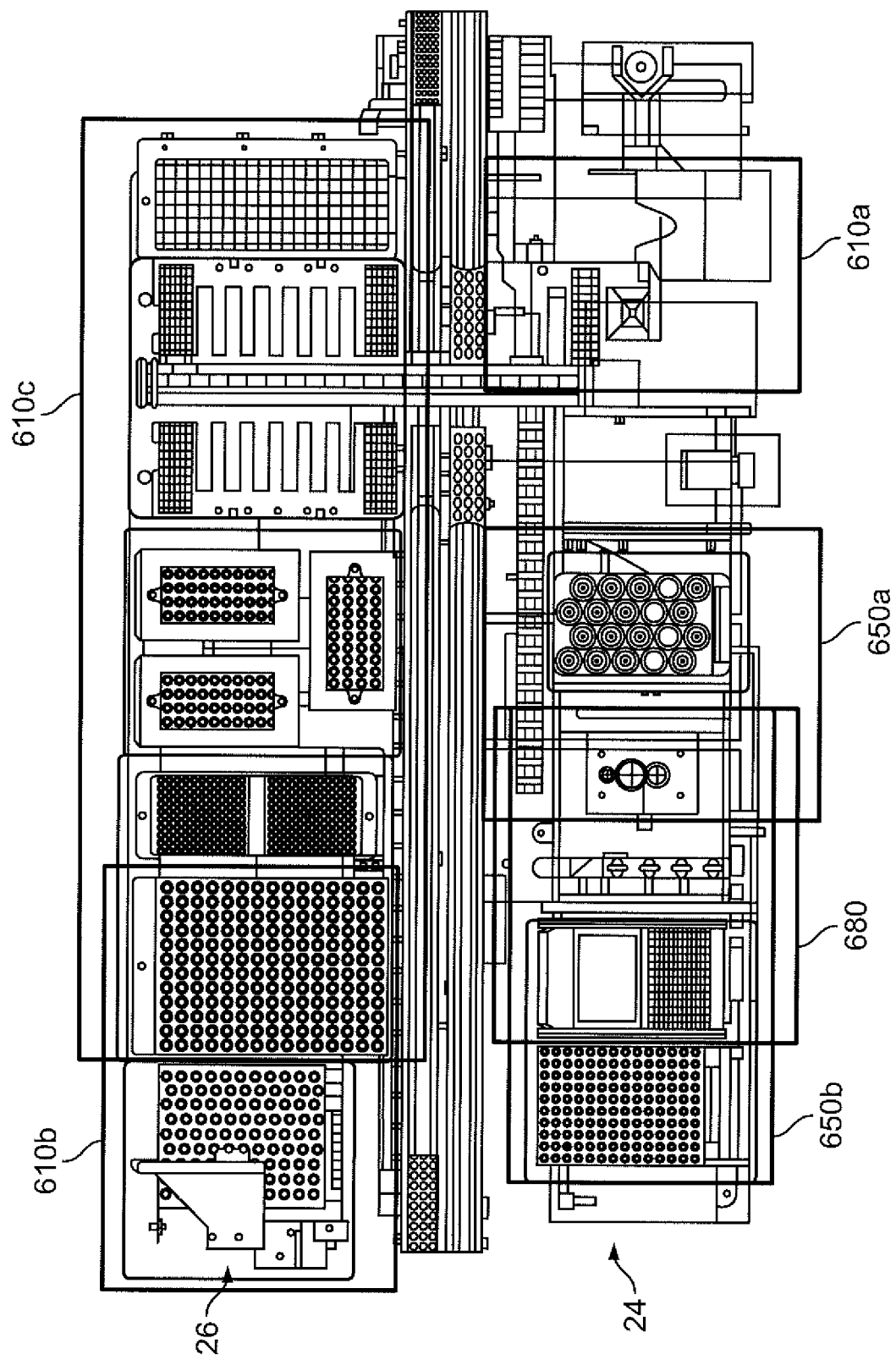
FIG. 18 is a top view of the preparation/processing decks of FIG. 8A schematically representing the operating envelope of the robots of the support beam robot assembly of FIG. 16A.

FIG. 18 depicts the operating envelopes 610*a*-*c*, 650*a*-*b*, and 680 of each robot 410*a*-*c*, 450*a*-*b*, and 481 of suspended robot assembly 400 relative to first and second pre-analytical processing decks 24, 26. Robots 410*a*-*c*, 450*a*-*b*, and 481 generally perform their assigned responsibilities within these envelopes which facilitates efficient performance as the envelopes help minimize the distance robots 410*a*-*c*, 450*a*-*b*, 481 must travel to perform their assignments and helps coordinate robot movement as they traverse support beam 402. While these robots generally operate within these envelopes they are not prevented from travelling outside of the envelopes.

As shown, operating envelope 610*a* for pick-and-place robot 410*a* is established over first pre-analytical processing deck 24 and about first sample rack space 110 and third shuttle docking station 260*c* of shuttle handling assembly 240. Robot 610*s* operates within this envelope 610*a* to transfer sample containers 03 from a shuttle 280 at third shuttle docking station 260*c* (FIG. 12A) to a rack 50 located at first sample rack space 610*a*.

Operating envelope 650*a* for first decapper robot 450*a* is established over first pre-analytical processing deck 24 and about second sample rack space 112 and sample preparation/conversion assembly 130. Robot 450*a* operates within this envelope 650*a* to transfer containers 01 and 02 between racks 30 and 40, respectively, and primary sample container station 140. Decapper 450*a* also de-caps and recaps containers 01 and 02 within this envelope 650*a*. In addition, decapper 450*a* positions these containers 01 and 02 in view of a barcode scanner (not shown) at preparation/conversion assembly 130 so that the barcode scanner can scan the containers.

Operating envelope 680 for pipetting robot 481 is established above first pre-analytical processing deck 24 about pipette tip rack space 180 and sample preparation/conversion assembly 130. Robot 481 operates within this envelope 680 to retrieve and dispose of disposable pipette tips and to aspirate and transfer an aliquot from a primary first-type or second-type container 01, 02 at primary sample container station 140 to a secondary first-type container 03 at the secondary sample container station.

Operating envelope 650*b* for second decapper robot 450*b* is established about sample preparation/conversion assembly 130, pipette tip rack space 180, and third and fourth sample rack spaces 114. Robot 450*b* operates within this envelope 650*b* to transport empty third-type containers 03 and third-type containers 03 inoculated with a control from a rack 50 located at third rack space 114 to and from the secondary sample container station 160. Second decapper robot 450*b* also de-caps and recaps these containers within this envelope 650*b*. In addition, decapper 450*b* positions these containers in view of a barcode scanner so that barcode scanner can scan an identifying barcode.

Operating envelope 610*b* for second pick-and-place robot 410*b* is established over second pre-analytical processing deck 410*c* and about space 200, barcode scanner 205, batch-accumulation area 210, and vortexers 220. Robot 410*b* operates within this envelope 610*b* to transfer primary and secondary third-type containers 03 among a rack 50 located at space 200, receptacles 212 within batch accumulation area 210, and bulk vortexers 220. In particular, robot 410*b* generally transfers containers 03 from space 200 to the batch accumulation area 210 and from batch accumulation area 210 (or directly from space 200) to bulk vortexers 220. Robot 410*b* also positions these containers 03 in view of a barcode scanner (not shown) at preparation/conversion assembly 130 so that the barcode scanner can scan the containers.

Operating envelope 610*c* for third pick-and-place robot 410*c* is established over second pre-analytical processing deck 26 and about batch-accumulation area 210, bulk vortexers 220, warmer 230, cooler 290 and first and second shuttle docking stations 260*a*, 260*b*. Robot 410*c* operates within this envelope 610*c* to transfer primary and secondary third-type containers 03 among the above identified instruments and locations. In particular, robot 410*c* generally transfers container 03 from batch accumulation area 210 and bulk vortexers 220 to warmer 230, cooler 290 and shuttle handling assembly 240. So while second pick-and-place robot 410*b* generally transfers containers 03 to bulk vortexers 220 and batch-accumulation area 210, third pick-and-place robot 410*c* generally transfers containers 03 away from bulk vortexers 220 and batch accumulation area 210.

System Modules

Figure 19:
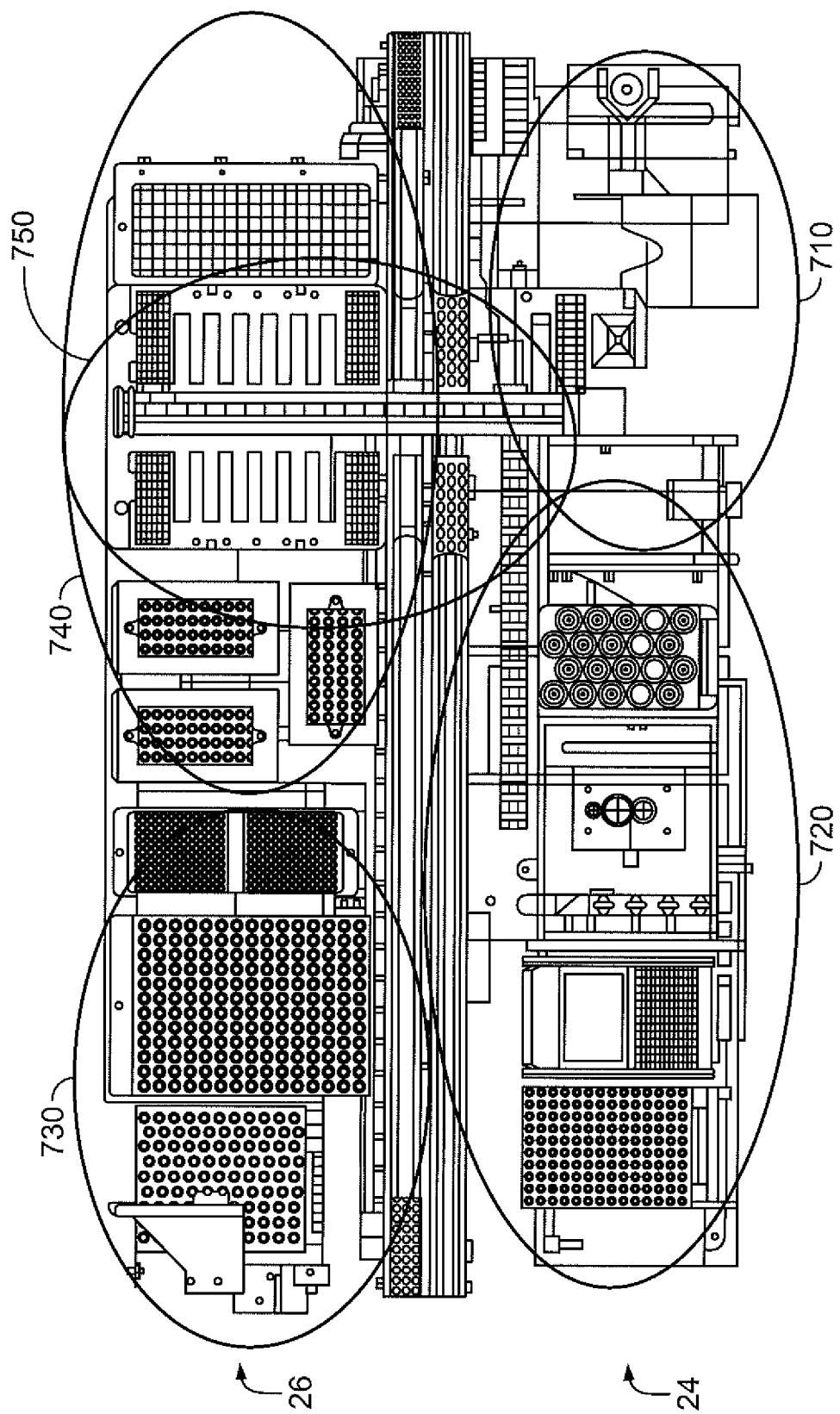
FIG. 19 is a top view of the preparation/processing decks of FIG. 8A schematically representing various modules of the pre-analytical system of FIG. 1A.

FIG. 19 depicts several modules 710, 720, 730, 740, 750 that are groups of many of the above identified instruments and locations/spaces that work together as subsystems within system 10 to perform general functions. In other words, each instrument and location/space is assigned one or more specific functions and when operated in conjunction with other instruments and locations/spaces within a module, more general functions are achieved which further the total operation of system 10. As shown, system 10 includes an I/O and post analysis module 710, sample conversion/preparation module 720, pre-preprocessing module 730, preprocessing module 740, shuttle processing module 750, and consumable accumulation module 760.

Input/Output and Post Analysis Module

I/O and post analysis module 710 is both a start-point and end-point of system 10. Stated another way, consumables enter into system 10 through module 710 and flow through system 10 within one of several routes which leads back to this module 710, thereby closing a travel loop. Module 710 includes I/O port 120, first sample rack space 110, container elevator 100, third shuttle docking station 260*c*, and first pick-and-place robot 410*a*.

Within this module 710, I/O port 120 receives every rack and sample container from a user and outputs these racks to a user when commanded. For example, I/O port receives sample racks 50 with empty third-type containers 03 later to be used as secondary sample containers, sample racks 50 with third-type containers 03 inoculated with controls, sample racks 50 with primary third-type sample containers 03, sample racks 30 with primary first-type sample containers 01, sample racks 40 with primary second-type sample containers 02, and pipette tip racks 182 loaded with disposable pipette tips.

I/O port 120 also outputs sample racks 50 with used primary third-type containers 03 that have gone through an analyzer, sample racks 50 with used primary third-type containers 03 that have gone through an analyzer, sample racks 50 with used third-type containers 03 with controls therein that have gone through an analyzer, sample racks 30 with primary first-type sample containers 01 that have had an aliquot extracted therefrom, sample racks 40 with primary second-type sample containers 02 that have had an aliquot extracted therefrom, and empty disposable pipette tip racks 182.

Module 710 also receives shuttles 280 returning from one or more analyzers $A_1 \ldots A_n$ and optionally seals containers disposed therein for storage. For example, a shuttle 280 is received at third shuttle docking station 260c and containers therein are transferred to a rack 50 at first sample rack space 110 where they are sealed by elevator 100.

Sample Conversion/Preparation Module

Sample conversion/preparation module 720 includes second, third and fourth rack spaces 112, and 114, pipette tip rack space 180, sample preparation/conversion assembly 130, decapper robots 450a-b, and pipetting robot 481. Module 720 converts samples from primary containers to secondary containers. Sample preparation/conversion generally includes matching barcodes of primary and secondary containers, transferring an aliquot from a primary container to a secondary container, diluting the aliquot with an assay specific diluent, and vortexing the containers. This module 720 also fills a rack 50 at third space 114 with secondary third-type containers 03 and mixes in one or more controls as desired. Such rack 50 is moved from sample conversion/preparation module 720 to pre-preprocessing module 730.

Pre-Preprocessing Module

Pre-preprocessing module 730 includes space 200 for a rack 50, batch-accumulation area 210, barcode scanner 205, bulk vortexers 220 and second pick-and-place robot 410b. Pre-preprocessing module 730 vortexes and accumulates secondary third-type containers 03 and controls after they leave conversion module 720. In addition, pre-preprocessing module 730 vortexes and accumulates primary first-type containers 03 that bypass preparation/conversion module 720 (discussed further below). These containers 03 are accumulated into batches for ultimate distribution to an analyzer. For example, an analyzer may have a capacity to perform a particular assay on a batch of up to 36 containers. Pre-preprocessing module 730 identifies the assay to be performed for samples within each container 03, suspends particulates within the samples, determines whether the samples require preprocessing, and accumulates assay specific batches of 36 containers 03 or less prior to being moved to preprocessing module 740 and/or sample transfer module 750. For example, pre-processing module may accumulate a batch of 12 or 24 primary and/or secondary containers 03. In another example, pre-processing module may accumulate batches containing 30 primary and/or secondary containers 03 and two control containers.

Preprocessing Module

Preprocessing module 740 preprocesses a portion of the sample containers 03 that leaves pre-preprocessing module 730. Preprocessing includes pre-warming and cooling samples prior to distribution to an analyzer. Although in some embodiments of system 10 other preprocessing operations can be included within this module, such as inoculation of samples with magnetic beads. Module 740 includes warmer 230, cooler 290, and third pick-and-place robot 410c. Whether or not samples are preprocessed generally depends on the assay to be performed on the batch of samples. In addition, the amount of time the samples are pre-warmed and cooled generally depends on the assay to be performed. For example, warming may be performed at about 100 to 115 degrees Celsius for about 9 to 17 minutes after equilibration at 100 degrees Celsius. In addition, cooling may be performed for about 20 minutes or less or until the samples reach a temperature of about 40 degrees Celsius.

Shuttle Processing Module

Shuttle processing/transport module 750 loads batches or partial batches of samples leaving pre-preprocessing module 730 or preprocessing module 740 into shuttles 280 and distributes them to analyzers. Shuttle processing module 750 includes shuttle handling assembly 240 and shuttle transport assemblies 300a-b.

Consumable Accumulation Module

Consumable accumulation module 760 (shown in FIG. 2) includes storage deck 22, rack handler robot 320, and rack elevator 360. Module 760 stores and accumulates system 10 consumables and distributes them to and from first and second pre-analytical processing decks 24, 26. For example, module 760 stores and accumulates about 40 racks or less, but preferably 36 or less, and about 8 or less bulk diluent containers. Such racks can include sample racks 30, 40, and 50 and pipette tip racks 182. This module helps provide inventory sufficient to allow for unattended operation of the apparatus for up to an entire work shift. It also allows a user to input and retrieve racks at random intervals throughout the work shift so that a lab technician can quickly move on to other tasks.

Computing System

Figure 20:
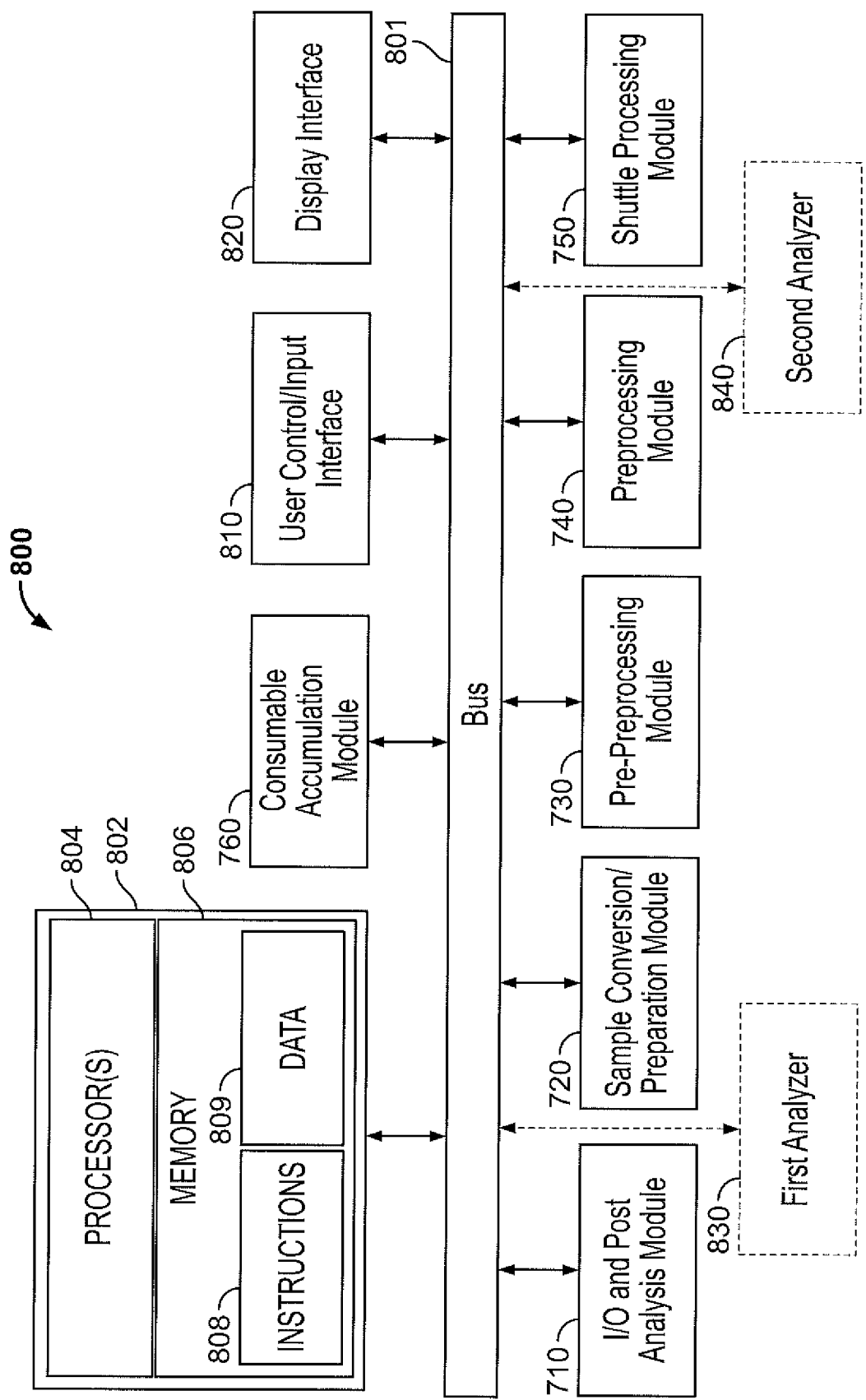
FIG. 20 is a block diagram of an example architecture of a computing system involving the pre-analytical system of FIG. 1A including example components suitable for implementing methodologies of the present disclosure.

FIG. 20 depicts a general architecture of an internal computing system 800. Computing system 800 includes one or more computer control devices 802, a user control/input interface 810, display interface 820 and a bus 801. Bus 801 connects user interface 810, computer control device 802, and modules 710, 720, 730, 740, 750 so that user interface 810 and the modules can communicate back and forth with computer control device 802. In addition, analyzers 830, 840 can be modularly connected to bus so that analyzers can communicate back and forth with processor 804.

Computer Control Device & Processor

Computer control device 802 may be any general purpose computer and may contain a processor 804, memory 806 and other components typically present in general purpose computer control devices. Although computer control device 802 can include specialized hardware components to perform specific computing processes. Processor 804 may be any conventional processor, such as a commercially available CPU. Alternatively, processor 804 may be a dedicated component such as an application specific integrated circuit ("ASIC") or other hardware-based processor.

Memory

Memory 806 may store information accessible by processor 804, including instructions 808 that can be executed by processor 804. Memory 806 can also include data 809 that can be retrieved, manipulated or stored by processor 804. Memory 806 can be of any non-transitory type capable of storing information accessible by processor 804, such as a hard-drive, memory card, ROM, RAM, DVD, CD-ROM, write-capable, and read-only memories.

Instructions 808 can be any set of instructions to be executed directly, such as machine code, or indirectly, such as scripts, by processor 804. In that regard, the terms "instructions," "application," "steps," and "programs" can be used interchangeably herein. Instructions 808 can be stored in object code format for direct processing by processor 804, or in any other computing device language including scripts or collections of independent source code modules that are interpreted on demand or compiled in advance.

In one embodiment of system 10, computing system 800 may include several sets of instructions that are each associated with a mode of operation. For example, computing system 800 may include a load mode and unload mode.

The load mode includes a set of load instructions that instruct the processor, in conjunction with user inputs, to perform certain tasks relating to loading consumables into system 10. For example, when a user selects input mode, processor 804 may run a set of instructions 808 in which processor 804 asks the user, via display interface 820, to identify the contents of the sample containers (e.g., controls, empty sample containers, or samples) and then digitally tags a rack holding these containers with the user identified information when it is loaded into system 10 through I/O port 120 by the user. Further load instructions operate rack handler robot to move the rack to a rack storage position in rack storage space 22. Processor 804 is further instructed by the set of load mode instructions to digitally tag each subsequent rack loaded into system 10 and to move such rack to storage deck 22 the same way until a user selects another option or changes the mode.

The unload mode is a set of instructions that instruct processor 804 to perform certain tasks relating to unloading consumables from system 10 in conjunction with user inputs. For example, when a user selects unload processor 804 asks the user, via display interface 820, which sample container the user would like to unload. After the user inputs the desired information, further unload instructions operate rack handler robot 320 to deliver the rack containing the sample container to I/O port 120.

The user loads the samples without having to individually interact with each tube. The system individually scans each sample tube and looks up what tests have been ordered for that tube by interacting with computing system 800. Consumables, such as pipettes, for example are those items that are used by the instrument to perform testing but are not patient samples or used to transport patient samples to and from an assay, are not managed by the computing system 800 or known to the computing system 800. The difference between Samples/Empties will be indicated by the user at the front of the machine (default to sample, special selection for empties) and will be confirmed by the instrument. Controls will be loaded in a rack with the same size and shape but will have a special barcode so that the instrument will know that the user is loading controls.

Data is entered and viewed through a graphical user interface ("GUI"). Data includes, but is not limited to, diluent composition of bulk diluent containers, sample container type, aliquot volume, assay to be performed, patient information, preprocessing parameters (e.g., warming time, warming temperatures, cooling time, and cooling temperatures), dilution parameters for a sample (e.g., diluent composition and volume), and analyzer information (e.g., analyzer location relative to system 10, analyzer assay menu, and analyzer batch capacity).

This data can be digitally tagged to particular identification codes (e.g., barcode serial numbers) in a field implemented or relational database, which may also be stored in memory 806. This helps system 10 keep track of various consumables within system 10 and helps provide certain information to processor 804 during the execution of processor instructions 808 without the need for user input. For example, a rack 30, 40, or 50 may have an identification code which may be tagged with certain stored data such as the type of containers disposed therein. In another example, a sample container 01, 02, or 03 may have an identification code which may be tagged with certain stored data such as patient name, assay to be performed, preprocessing parameters and diluent parameters. In a further example, an analyzer coupled to system 10 may have an identification code which may be digitally tagged with analyzer information.

Although FIG. 20 functionally illustrates processor 804, memory 806, and other elements of computer control device 802 as being within the same block, computer control device 802, processor 804, and/or memory 806 can be comprised of multiple processors, computer control devices, and memories, respectively, which may or may not be stored within the same physical housing. For example, memory 806 can be a hard drive or other storage media located in housings different from that of computer control devices 802. Accordingly, references to processor 804, computer control device 802, and memory 806 should be understood to include references to a collection of processors, computer control devices, and memories that may or may not operate in parallel.

Display Interface

Display interface 820 includes a monitor, LCD panel, or the like (not shown) coupled to a front panel of a housing surrounding system 10 or located remote from system 10. Display interface 820 displays the GUI, user prompts, user instructions and other information that may be relevant to a user.

User Control/Input Interface

User control/input interface 810 allows a user to navigate the GUI, provide commands, and respond to prompts or instructions provided to the user. This can be a touch panel, keyboard, or mouse, for example. In addition, input interface 810 can be integrated into display interface 820 such that the same device that displays prompts and the like is the same device that allows a user to respond to said prompts.

Connections

As depicted in FIG. 20, modules 710, 720, 730, 740, 750 and 760 are connected to computer control device via bus 801. More particularly, processor 804 of computer control device 802 operates each operable device within each module to output an action based on a processor instruction 808 or to receive information. For example, with relation to I/O and post analysis module 710, computer control device 802 is connected to first pick-and-place robot 410a, elevator 100, and a barcode scanner (not shown). With regard to sample conversion/preparation module 720, computer control device 802 is connected to first and second decapper robots 450a-b, pipetting robot 481, clamp assembly 162, diluent dosing valves 176, primary and secondary sample container stations, and a barcode scanner (not shown). With regard to sample pre-preprocessing module 730, computer control device 802 is connected to second pick-and-place robot 410b, barcode scanner 205, and bulk vortexers 220. With regard to preprocessing module 740, computer control device 802 is connected to third pick-and-place robot 410c, warmer 230 and cooler 290. With regard to shuttle processing module 750, computer control device 802 is connected to rack handler assembly 240, barcode scanner (not shown), and shuttle transport assemblies 300a-b. With regard to consumable accumulation module 760, computer control device 802 is connected to rack handler robot 320 and rack elevator 360. Computer control device 802 may also be connected to other sensors distributed around system 10 which may be used to locate and track items within system 10.

Methods of System Operation

As mentioned above system 10 has an I/O port 120 that receives all consumables with the exception of bulk diluent containers 14 located in storage deck 22. System 10 identifies the consumables with limited assistance of a user and then determines how the consumables are to be handled therein. In this regard, each consumable has a path through system 10 which starts and ends at I/O port 120 and may include a detour to an analyzer. The following describes a method of operation of system 10.

Figure 21:
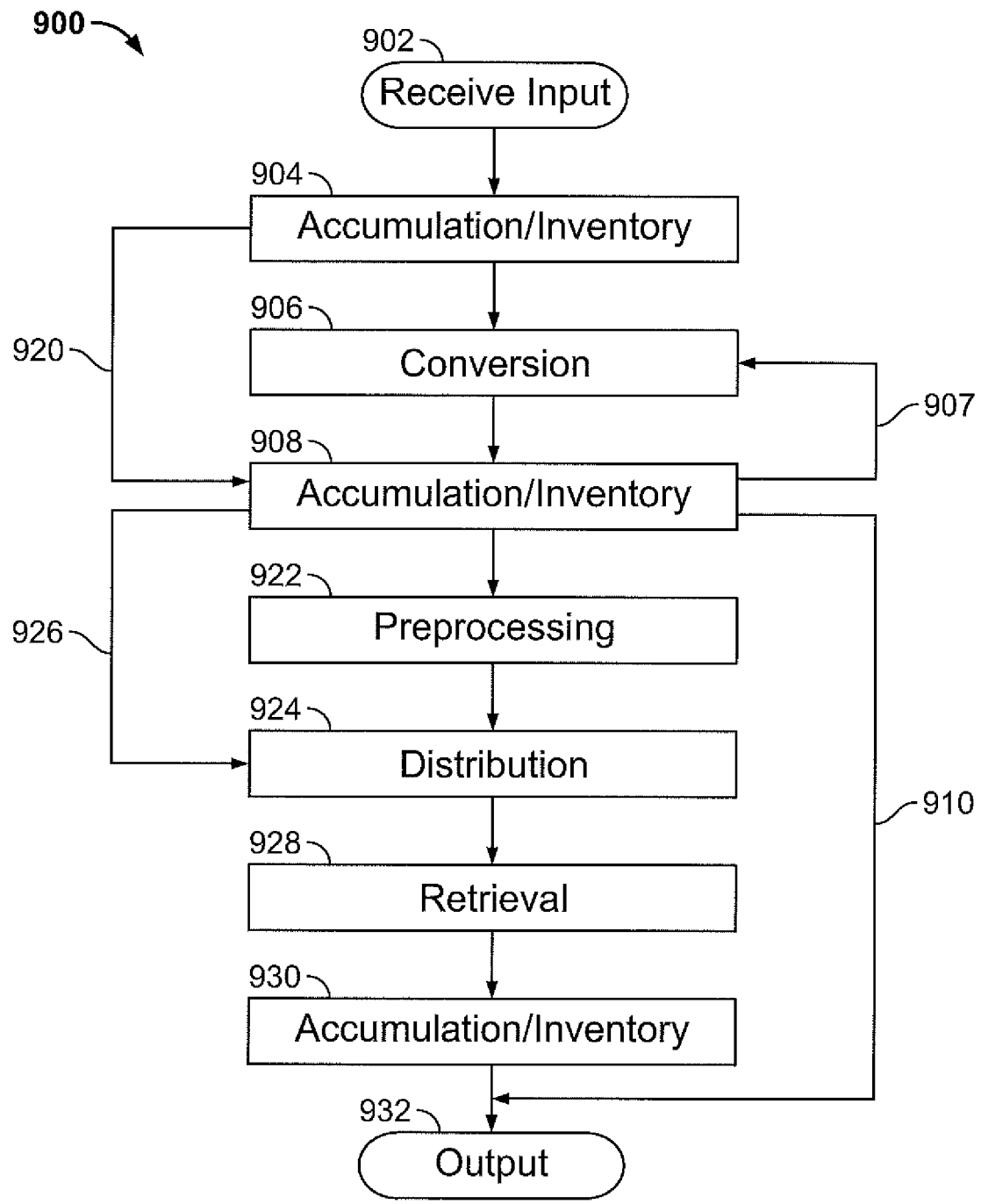
FIG. 21 is a flow diagram of a method of using the pre-analytical system of FIG. 1A according to one embodiment of the present disclosure.

As depicted in FIG. 21, method 900 generally includes receiving 902 consumables through I/O port 120 of I/O and post analysis module 710. The consumables are then sent to consumable accumulation module 760 where they are accumulated 904 or queued in a first accumulation area 22 for further operation.

Some of the consumables, such as pipette tips, controls, empty secondary containers, and certain primary containers are moved to sample preparation/conversion module 720 where aliquots of samples are transferred 906 from a primary container to a secondary container.

When sample preparation is completed and a secondary sample has been created, the secondary containers and controls are transported to pre-preprocessing module 730 where they are accumulated 908 at a second accumulation area 210. The other consumables located within conversion module 720, such as the primary sample containers and empty racks, are returned to consumable accumulation module 760 where they are accumulated 908 within first accumulation area 22. These consumables returned back to first accumulation area 22 may be retrieved by a user and outputted from system 10 at any time. Also, if desired, primary sample containers can be returned to conversion module 720 from the first accumulation area 22 for extraction of another aliquot.

Some primary sample containers bypass 920 conversion 906 and are sent directly to pre-preprocessing module 730 from consumable accumulation module 760. These primary sample containers are accumulated 908 at second accumulation area 210 with the other containers that were sent there from conversion module 720.

Once complete batches of primary and secondary sample containers and controls are accumulated at second accumulation area 210, or when a user actively or passively requests immediate preprocessing of incomplete batches, the batches are sent to preprocessing module 740 where the samples/controls are preprocessed, such as pre-warmed and cooled. The device is configured to provide a wide array of processing conditions well known to one skilled in the art. Specific processing conditions are not described herein. An active processing request can include the user inputting a real-time request into system 10 via user interface 810. A passive processing request can include a preprogramed request to immediately preprocess an incomplete batch when certain conditions are satisfied. For example, a user may preprogram immediate preprocessing of a batch, whether complete or incomplete, every Friday at 5:00 μm. Thereafter, the batches are sent to sample transfer module 750 where they are loaded into shuttles and distributed 924 to an analyzer.

Where preprocessing is not required, the batches bypass 926 preprocessing 922 and are directed to shuttle processing module 750 where they are loaded into shuttles 280 and distributed 924 to one of one or more analyzers.

When analysis is completed, the used batches are retrieved 928 from the analyzer and sent to I/O and post analysis module 710 where the used sample containers are removed from shuttles 280, placed in racks 50, optionally sealed, and then transported to consumable accumulation module 760 where they are again accumulated 930 in first accumulation area 22. The used batches of containers can be outputted 932 to a user from first accumulation area 22 upon request at any time.

Receipt/Input & First Accumulation

In a more particular description of method 900, consumables are received 902 by system 10. Such consumables includes racks 30 carrying primary first-type sample containers 01, racks 40 carrying primary second-type sample containers 02, racks 50 carrying primary third-type sample containers 03, racks 50 carrying third-type sample containers 03 inoculated with controls, racks 50 carrying empty third-type containers 03, and racks 182 carrying disposable pipette tips 489.

These racks are loaded into system 10 via I/O port 120 in any order the user wishes. System 10 automatically determines the type of consumables being loaded. In this regard, when a user loads rack 182 carrying disposable pipette tips through I/O port 120 a barcode scanner (not shown) at I/O port 120 scans a barcode on rack 182. The associated identification number is recognized by system 10 as being associated with pipette tips. This ID number is then stored in memory 806 and tagged with a "pipette tip" tag within memory 806. This helps processor 804 determine process flow for rack 182. Rack handler robot 320, as instructed by the processor 804, traverses system 10 to I/O port 120 and removes rack 182 from I/O port 120 via engagement arm 322. Rack handler robot 320 then carries rack 182 to first accumulation area 22 (rack storage deck) and deposits rack 182 into a rack storage position therein. The coordinates of this rack storage position is tagged to the rack's identification number within memory 806. This helps rack handler robot 320 later locate rack 182.

When user inputs a rack 30 containing primary first-type containers 01 into I/O port 120, the barcode scanner at I/O port 120 scans a barcode on rack 30. Processor 804 recognizes sample rack 30, via its identification numbers, as carrying containers that require conversion as first-type sample containers 01 are not compatible with an analyzer. The identification number of rack 30 is stored in memory 806 and tagged with a "conversion required" tag. This helps processor 804 determine process flow for rack 30. Rack handler robot 320, as instructed by the processor 804, traverses system 10 to I/O port 120 and removes rack 30 from I/O port 120 via engagement arm 322. Rack handler robot 320 then carries rack 30 to first accumulation area 22 and deposits rack 30 into a rack storage position. The coordinates of this rack storage position are tagged to the rack's identification number within memory 806. A rack 40 containing primary second-type containers 02 is handled in the same manner as rack 30 as second-type containers 02 carried by rack 40 are also not compatible with an analyzer. As such, a rack 40 input into system 10 through I/O port 120 is scanned, recognized as containing primary second-type containers 02, tagged as "conversion required," and stored within storage deck 22. Such tagging allows processor 804 to determine the process flow for racks 30 and 40.

On the other hand, as mentioned above, rack 50 may include empty third-type sample containers 03, primary third-type containers 03 with sample contained therein, or third-type sample containers 03 each containing a control. In this regard, system 10 can automatically determine which one of these loads is carried by rack 50 when input into system 10 or with the assistance of the user. For example, in one embodiment, each rack 50 may have an identification number associated with the type of load. As such, a rack 50 containing empty containers 03 may have an ID number recognizable by system 10 as such. The same would apply to racks 50 containing samples and controls. Alternatively, system 10 can identify rack 50 at I/O port 120 via a scan of the rack itself and then transport rack 50, once identified as a rack 50, to conversion module 720 or pre-preprocessing module 730 where a container 03 within rack 50 is removed by a decapper robot or a pick-and-place robot and individually scanned to further determine the type of load contained in rack 50. Thus, automatic identification of a rack 50 and its load can occur via information extracted from the rack itself or a combination of information from the rack and its individual containers.

In another embodiment, system 10 may have a default setting in which system 10 defaults to the assumption that a rack 50 inserted through I/O port 120 contains primary third-type containers 03 containing samples therein. A user may override the default setting via user interface 810. For example, a user may load a rack 50 containing empty containers 03 and may select an "empty container" option provided on user interface 810 either just before inserting rack 50 into I/O port 120 or immediately after, thereby overriding the default setting. In yet another embodiment, a user may identify the type of load being carried by a rack 50 for each rack 50 inputted into system 10.

Once rack 50 is scanned at I/O port 120 and its load determined, rack handler robot 320 transports rack 50 to a rack storage position within first accumulation area 22. The coordinates of this rack storage position is tagged to the rack's identification number within memory 806.

System 10 can be configured to handle dozens of the above described racks. For example, system 10 can accumulate up to 36 racks in first accumulation area 22 by loading each rack through I/O port 120 as described above. This allows a user to simply fill a rack with sample containers, controls, empty containers, or pipettes and input it into system 10. "Input mode" can be selected at the beginning of a work shift, for example, and each rack can be loaded until system 10 reaches full capacity. The user can then walk away for the entire shift. However, "input mode" can be selected periodically throughout the day as needed to load straggler samples or other consumables.

Once the above identified racks, particularly racks 30, 40, and 50, are received by system 10, they are placed in a queue for further preparation and preprocessing. Generally, such racks and consumables therein are placed in the queue in an order in which it was received by system 10. However, a user can identify a rack as being a "priority" in which the rack is moved up in the queue to be immediately prepared and preprocessed. This may be performed by the user via user interface 810.

The system 10 has a processor 804 with logic that detects and responds to errors in rack handling. The placement of a rack in the I/O port 120 triggers a sensor that causes the pre-analytical system 10 to ask the operator if the rack is empty or is carrying containers (empty or containing sample or reagents). The information provided by the operator is forwarded to the rack manager. The containers in the rack are scanned and the scanned information is forwarded to the processor 804 managing the operation of the pre-analytical system 10. The system data is read to determine if there is space for the rack.

If the rack is a tip rack 182, the tip rack's barcodes are read. If the barcodes cannot be read the tip rack 182 is returned to the I/O port 120. If the tip code is correct or the tip rack was not scanned, the tip rack is moved into the pre-analytical system if there is determined to be room for the rack. If there is no room, the tip rack 182 is moved back to the I/O port 120.

The I/O port 120 has two sensors (not shown). A front sensor indicates that a rack (30, 40, 50, 182) has been placed in the port 120, and a rear sensor determines if the rack has been placed far enough into the port 120 for further movement of the rack within the pre-analytical system 10. If the back sensor does not detect a rack, an error message results and the operator is notified. The pre-analytical system 10 determines if there is room for the rack. The rack robot 320 then retrieves the rack from the I/O port 120 when the robot 320 is available to do so. The rack robot 320 moves to the I/O port 120 to retrieve the rack. If a motion error is detected, the rack robot 320 gets one retry at slow speed before module operation ceases and an operator is notified. A rack stop in the I/O port 120 is disengaged prior to rack loading. If a motion error regarding the rack stop is detected, there is one retry before module operation ceases and an operator is notified. The rack handling robot 320 engages the sample rack and pulls it out of I/O port 120 and onto carriage 350. If a motion error is detected regarding this handoff, there is one retry before module operation ceases and an operator is notified.

The status of the I/O port 120 presence sensors, the hotel sensors and the rack handling robot sensors are evaluated and compared with a logic table. If the sensor readings are not consistent with the readings associated with further rack processing, an end module operation is started. If the sensor readings are consistent, then the rack handling robot 320 brings mover arm 322 to its home or intermediate position. If the arm 322 will not move back to home, an error message results. A sample rack stop is engaged when the rack handling robot 320 is aligned with the location in the rack storage area 22 in which the rack is to be placed. If a motion error is detected, there is one retry at slower speed before module operation ceases and an operator is notified. The sample rack is then positioned for unloading to the designated location in the rack storage area 22. If a motion error is detected, then there is one retry at slower speed before module operation ceases and an operator is notified. Prior to unloading the rack in the rack storage area 22, the rack storage area 22 is evaluated to determine if it is empty. If not empty, there is a failure and module operation ceases. If a rack position is empty, the rack robot 320 slides the rack into the rack position in the rack storage area 22. If a motion error is detected, there is one retry at slower speed before module operation ceases and an operator is notified. Sensors are provided to verify that the rack was properly placed in the right location in the rack storage area. If the sensors do not so indicate, the module operation ceases and the operator is notified.

Sensors are provided to detect if rack mover arm 322 of the rack robot 320 retracts to its intermediate/home position after disengaging from the rack. If the arm 322 does not retract, an error message is sent and the module operation ceases. A rack inventory is then updated.

Similar operations and logic are provided in response to a command to move a rack from the rack storage area 22 to the I/O port 120. If there is a command, the system 10 interrogates the I/O sensors to check and see if the I/O port 120 is occupied. The rack handling subsystem enters pause if there is a rack in the I/O port 120. If there is no rack in the I/O port 120, the system 10 determines if robot 320 is available. If not, the system 10 waits. The rack robot 320, when available, then travels to the rack position within storage area 22 to retrieve the rack. If a motion error is detected, there is one retry at slower speed before module operation ceases and an operator is notified. The system 10 verifies that the sensor feedback from the location in the rack storage area 22 matches the rack inventory information. If the sensor indicates the position is empty, there is a failure that ends operation and an operator is notified. If the position is occupied, then the sample rack is engaged by the sample rack handler robot 320 as described elsewhere herein. The rack storage sensors and front and back sensors on the rack robot 320 will indicate whether or not the rack was successfully transferred to the rack handling robot 320. Mover arm 322 retracts with the rack connected thereto, but if it does not, a mechanism failure is indicated. If arm 322 retracts properly to its intermediate position, the robot 320 moves the rack to the I/O port 120 where the sensors thereof cooperates to determine if the rack is successfully unloaded from the rack robot 320 to the I/O port 120. Once placed in the I/O port 120, the operator is alerted to remove the rack.

The system 10 also includes sensors and routines to identify errors that occur when a rack is transferred from on location in the rack storage area 22 to another. As described above, sensors in the rack positions of rack storage area 22 and on the rack handling robot 320 inform the system 10 of the presence (or absence) of racks in the specified locations. Each movement is monitored for motion error. If motion error occurs, the motion is retried at a lower speed. If an error occurs again, the module operation is terminated and an operator informed. As noted above, when the rack is moved from one position to another, the rack inventory is updated with the new information.

Sample Preparation/Conversion

Once racks are loaded into first accumulation area, system 10 begins preparing and preprocessing samples. This includes sample conversion 906. With regard to conversion 906, rack handler robot 320, as instructed by processor 804, removes a pipette tip rack 182 from its rack storage position and places it on first pre-analytical processing deck 24 at space 180. Rack handler robot 320 also automatically removes a rack 50 containing controls from its rack storage position and places it at rack space 114. Similarly, rack handler robot 320 removes rack 50 containing empty third-type containers 03 from its rack storage position and places it at third rack space 114. Also, rack handler robot 320 removes a rack 30 from its rack storage position and places it on first pre-analytical processing deck 24 at second rack space 112. Although, it should be understood, that a rack 40 or a rack 50 with containers having previously penetrated caps may also be placed at second rack space 112 for conversion.

Thereafter, first decapper robot 450*a*, as instructed by processor 804, grips a primary first-type container 01, lifts it from rack 30 and places it in front of a barcode scanner (not shown) within conversion module 720 such that a barcode located on container 01 is read. This barcode notifies processor 804 of the assay to be performed on the sample located within container 01 which is stored in memory 806. Decapper 450*a* then deposits container 01 into receptacle 142 at primary sample container station 140. Processor 804 may then operate a motor within motorized base 144 to vortex container and re-suspend sample. Whether or not container 01 is vortexed may depend on the assay to be performed. In addition, vortexing conditions (e.g. duration and speed) may vary depending on the container type and assay to be performed. Such determinations are made by processor 804. Decapper 450*a* re-grips and de-caps container 01 (best shown in FIG. 8A).

Similarly, second decapper robot 450*b*, as instructed by processor 804, grips an empty third-type container 03 within rack 50, lifts it from rack 50, and places it in front of the barcode scanner within conversion module 720 such that a barcode located on container 03 is read. Processor 804 then associates the identification number of primary first-type container 01 with empty third-type container 03 which includes associating the assay to be performed with container 03. Decapper 450*b* deposits empty third-type container 03 between clamping jaws within the secondary sample container station 160. Decapper 450*b* de-caps container 01. At this point, opened third-type container 03 is disposed beneath dispense head 172 of diluent dispenser 170. Based on the assay to be performed, processor 804 operates a dosing pump 174 on a channel 175 of a select bulk diluent container 14 which contains a diluent that is suitable for the particular assay to be performed. A controlled dose of the diluent is dispensed from the select channel 175 into third-type container 03.

Thereafter, pipetting robot 481 retrieves a disposable pipette tip 489 from rack 182 and aspirates an aliquot from primary first-type container 01 at primary sample container station 140. Pipetting robot 481 then dispenses the aliquot into third-type container 03 which is now secondary third-type container 03. Decapper 450*b* recaps container 03 and processor 804 operates a motor within a motorized base at the secondary station 160 to vortex secondary third-type container 03 to mix diluent with sample and suspend particulates therein.

Primary first-type container 01 is recapped by decapper robot 450*a* and transferred back to rack 30 at space 112. Also, secondary third-type container 03 is transferred from the secondary sample container station 160 back to rack 50 at space 114 via decapper 450*b*. Periodically decapper 450*b* grips a third-type container 03 containing a control and removes it from rack 50 at space 114. The control is placed by decapper into rack 50 at space 114.

Conversion 906 is repeated with other containers in racks 30 and 50 until rack 50 at space 114 is filled with secondary third-type containers. Since rack 30 carries less containers than rack 50, additional racks 30, 40 or 50 may be moved to rack space 112 as needed to continue filling rack 50 with secondary sample containers.

If a container cannot be de-capped, processor 804 instructs decapper robot 450*b* to place container 03 back into rack 50 at space 114. Any further de-cap failures are arranged in a right-to-left or left-to-right arrangement along consecutive rows beginning with a front row or rack 50. Processor 804 alerts a user via display interface 820, who can then recall rack 50. The arrangement of de-cap failures allows the user to easily identify the defective containers for troubleshooting once rack 50 is output from system 10.

If the third-type sample container 03 cannot be recapped, the uncapped sample is held over a drip tray. The sample container from which the primary sample for preparation was obtained is recapped and placed back into the input rack (30 or 40). The system 10 enters a pause state when a rack is stuck. Under such a pause state, the rack is placed in a penalty box; all sample conversions in the process are completed after which the conversion robots all retreat to their home positions.

Second Accumulation

Subsequent to sample conversion 906, secondary third-type containers 03 are sent back to first accumulation area 22 where they are queued for further processing and then sent to second accumulation area 210. Alternatively, secondary third-type containers 03, once conversion 906 is completed, are sent directly to second accumulation area 210 from conversion module 720. In this regard, when rack 50 is filled with secondary third-type containers 03 (and controls), rack handler robot 320 removes rack 50 from space 114 and hands it off to rack elevator 360. When received by rack elevator 360, processor 804 operates elevator 360 such that rack 50 is moved upward into pre-preprocessing module 730 at space 200. At this location, second-pick and place robot 310b removes the secondary third-type containers 03 (and controls) from rack 50 individually and places them in view of barcode scanner 205 which identifies the assay to be performed on the sample therein. Pick-and-place robot 310b then places these containers 03 into second accumulation area 210 in groups or batches of the same assay order. For example, sample containers 03 containing samples that require an enteric bacterial assay may be grouped with like containers, while other containers 03 containing samples requiring a Group B *streptococcus* assay may be grouped together into a separate batch. This allows sample containers 03 trickling in from other racks 50 to be batched together for subsequent movement to an analyzer. Although, like containers can be grouped together in batches, like containers can also be placed apart within second accumulation 210 such that containers designated for different assays can be disposed therebetween as computing system 800 knows where each container within a batch is located and can retrieve them accordingly when a sufficient batch is accumulated.

If a container's barcode cannot be read, processor 804 instructs pick-and-place robot 310b to place container 03 back into rack 50 at space 200. Any further barcode scan failures are arranged in a right-to-left or left-to-right arrangement along consecutive rows beginning with a front row or rack 50. Processor 804 alerts a user via display interface 820, who can then recall rack 50. The arrangement of barcode scan failures allows the user to easily identify the defective containers for troubleshooting once rack 50 is output from system 10.

In addition to accumulating secondary third-type containers 03 at second accumulation area 210 subsequent to conversion 906, other consumables utilized in the conversion process 906 are again accumulated in the first accumulation area 22. This may occur when their supply is exhausted or prior to such exhaustion. More particularly, when a pipette tip rack 182 is depleted of disposable pipette tips 489, rack handler robot 320 removes rack 182 from rack space 180 and deposits it in a rack storage position at first accumulation area 22. Similarly when a rack 50 is depleted of controls, rack handler robot 320 removes rack 50 from rack space 114 and deposits it in a rack storage position at first accumulation area 22. These empty racks 50 and 182 may be removed 910 from first accumulation area and outputted 932 to a user at any time at the user's request.

In addition, when an aliquot has been taken from each container 01 (or 02) of rack 30 (or 40), rack handler robot 320 removes rack 30 from rack space 112 and deposits it in a rack storage position at first accumulation area 22. From there, rack 30 may be redirected 907 to conversion module 720 via rack handler robot 320 for removal of another aliquot from one or more of its containers for further analysis. Rack 30 may also be removed 910 from first accumulation area 22 and outputted 932 to a user at the user's request.

While many of the consumables loaded into system 10 pass through conversion module 720, certain containers bypass 920 sample conversion 906 and are sent to be further accumulated 908. In particular, primary third-type containers 03 can bypass 920 conversion 906 as these containers 03 are suitable for an analyzer and, therefore, do not require conversion. In this regards, rack handler 320, as instructed by processor 804, removes a rack 50 containing primary third-type containers 03 from its rack storage position in first accumulation area 22. Rack handler 320 bypasses conversion module 720 and takes rack 50 directly to rack elevator 360. Rack 50 is handed off to rack elevator 360. When received by rack elevator 360, processor 804 operates elevator 360 such that rack 50 is moved upward into pre-preprocessing module 730 at space 200. At this location, second pick-and-place robot 410b removes primary third-type containers 03 from rack 50 individually and places them in view of barcode scanner 205 which identifies the assay to be performed on the samples contained therein. Pick-and-place robot 410b then places these containers 03 into second accumulation area 210 in groups or batches of the same assay. Barcode scan failures are again placed back into rack 50 in a predefined order. When rack 50 is emptied or only contains barcode failures, it is moved by rack elevator 360 and rack handler so as to place rack 50 back into first accumulation area 22.

Thus, as described above, second accumulation area 210 can include primary third-type containers 03, secondary third-type containers 03, and third-type containers 03 containing controls which are distributed among the accumulated batches.

Preprocessing

With batches of containers 03 accumulating at batch-accumulation area 210, complete batches are sent for pre-processing 922 and/or distribution 924 to an analyzer. In this regard, processor 804 keeps track of batch size and when a batch size matches a batch capacity of a designated analyzer, processor 804 instructs second pick-and-place robot 410b to load a batch of containers 03 into bulk vortexers 220. Processor 804 operates vortexers 220 which is provided to re-suspend the samples.

If the samples contained within containers 03 of the batch require preprocessing 922, third pick-and-place robot 410c, as instructed by processor 804, removes each third-type container 03 from bulk vortexers 220 and individually places them into receptacles 234 of warmer 230. When these containers 03 were barcode scanned by scanner 205, information regarding preprocessing was associated with each container's identification number within memory 806. Such information may include warming time, warming temperature, and cooling time. For example, a batch of containers 03 may require samples to be heated to about 100 to 115 degrees Celsius for about 9 to 17 minutes. Processor 804 operates warmer 230 at a processor determined set-point to achieve the designated heating conditions. When the allotted time period has elapsed, containers 03 of the batch are removed in the order they were placed into warmer 230 by third pick-and-place robot 410c and moved to cooler 290. Processor 804 operates fans 296 to convectively cool the batch of sample containers 03 for a time period which may vary depending on the container type and assay to be performed.

If the samples with containers 03 of the batch do not require preprocessing 922, they are removed from bulk vortexers 220 or batch-accumulation area 210 by third pick-and-place robot 410c and transferred to shuttle processing module 750 thereby bypassing preprocessing 922.

Distribution

Once a batch has completed preprocessing 922 or bypasses preprocessing 922, the batch is picked by third pick-and-place robot 410*c* from any location within operating envelope 610*c* and placed into a receptacle 283 of a shuttle 280 docked at one of first or second docking stations 260*a-b*. Each shuttle 280 may have fewer receptacles 283 than an entire batch. Thus, pick-and-place robot 410*c* may load multiple shuttles 280 for a single batch. For example, shuttles 280 may include 12 receptacles 283 and a batch may comprise 24 third-type containers 03. As such, in this example, two shuttles 280 are filled for the batch.

Once the one or more shuttles 280 are filled, transfer arm assembly 270 picks up a shuttle 280 from docking station 260*a* or 260*b* and drives shuttle 280 past a barcode scanner (not shown) located within shuttle processing module 750 which scans a barcode on shuttle 280. Processor 804 links or otherwise associates the shuttle's identification number with those of containers 03 disposed therein which helps track the location of containers 03.

Processor 804 also recalls information regarding the assay to be performed and determines, based on analyzer information that is stored on memory 806, which analyzer coupled to system 10 is suitable to perform the particular assay. For example, a first analyzer 830 coupled to a right side of system 10 may perform a first assay, such as a Gonorrhea assay, while a second analyzer 840 coupled to a left side of system 10 may perform a second assay, such as an HPV assay. If the batch requires the first assay, then processor 804 chooses first analyzer 830 and operates transfer arm 270 so that transfer arm 270 places shuttle 280 onto first shuttle transport assembly 300*a*. First transport assembly 300*a* is then operated to transport shuttle 280 to first analyzer 830. Conversely, if the batch requires the second assay, then processor 804 chooses second analyzer 840 and operates transfer arm 270 so that transfer arm 270 places shuttle 280 onto second shuttle transport assembly 300*b*. Second transport assembly 300*b* is then operated to transport shuttle to second analyzer 840. If a batch is large enough to fill multiple shuttles 280, transfer arm assembly 270 moves the remaining shuttles 280 to the designated transport assembly 300*a* or 300*b* which distributes those shuttles 280 to the appropriate analyzer 830 or 840. Processor 804 communicates with the designated analyzer to notify the analyzer so that it is prepared to receive shuttle 280. This workflow is illustrated in FIG. 22C. As noted above and in the illustrated workflow, when the shuttle returns with the sample containers carrying the remaining portion of the sample. If the sample containers are to be sent to an analyzer for a second test, they may remain in the shuttle while sample containers carrying samples not designated for a second analyzer are unloaded. If there are empty receptacles in the shuttle designated to carry the batch to the second analyzer, additional sample containers designated for the second analyzer can be added.

Retrieval

When analysis is completed shuttle 280 and the sample containers 03 disposed therein is retrieved from analyzer 830 or 840. In this regard, the analyzer communicates with processor 804 notifying system 10 that shuttles 280 are being sent back to system 10 and also identifies any of containers 03 that were incapable of completing the assay, such as a penetrable cap failing to be punctured. This information is stored in memory 806 by processor 804 and associated with the particular container's identification number. Shuttle 280 is then transported along transport assembly 300*a* or 300*b* until it reaches shuttle handling assembly 240. Transfer arm 270, as instructed by processor 804, retrieves shuttle 280 from the appropriate transport assembly and places shuttle 280 on third docking station 260*c*.

Figure 22B:
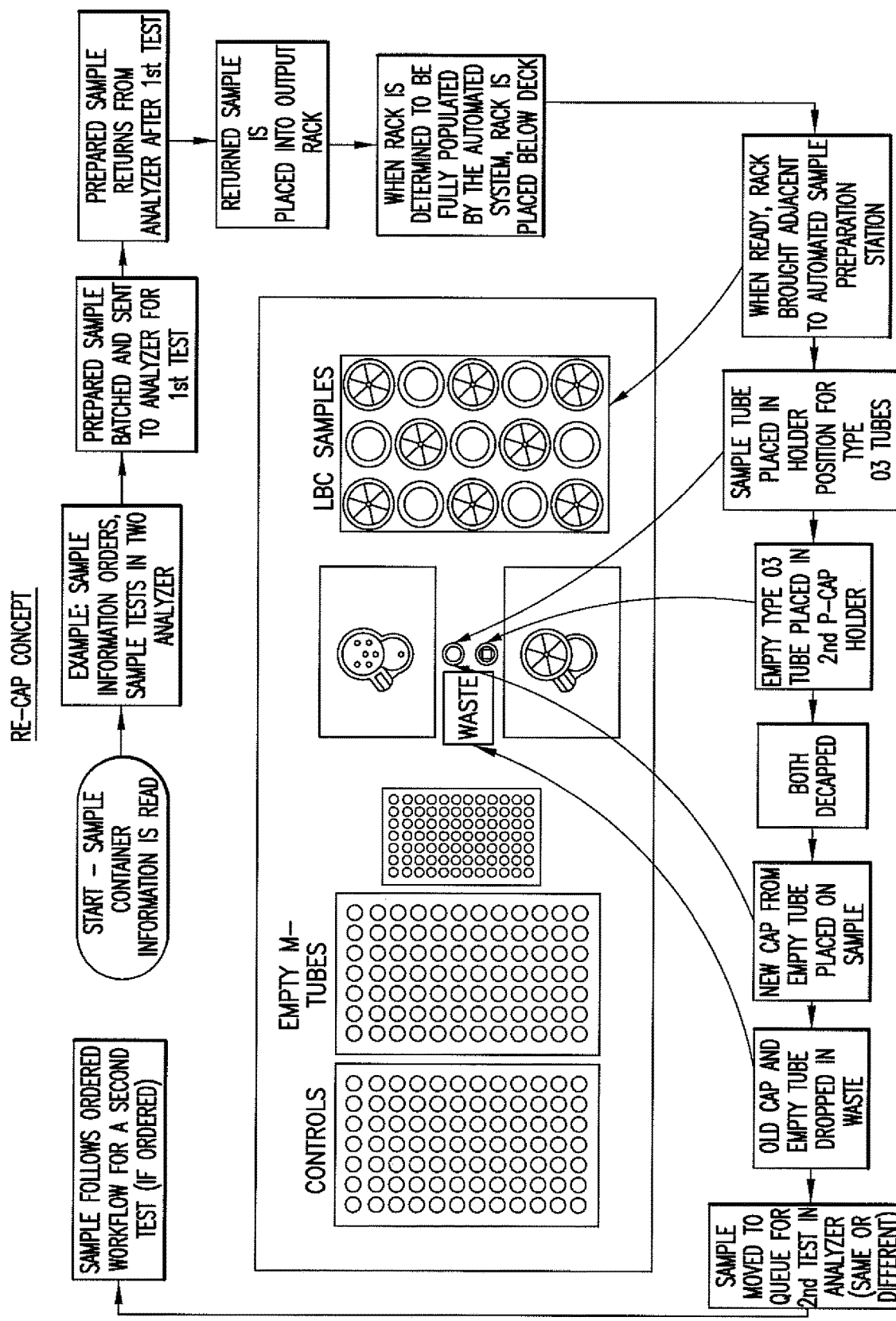
Figure 22C:
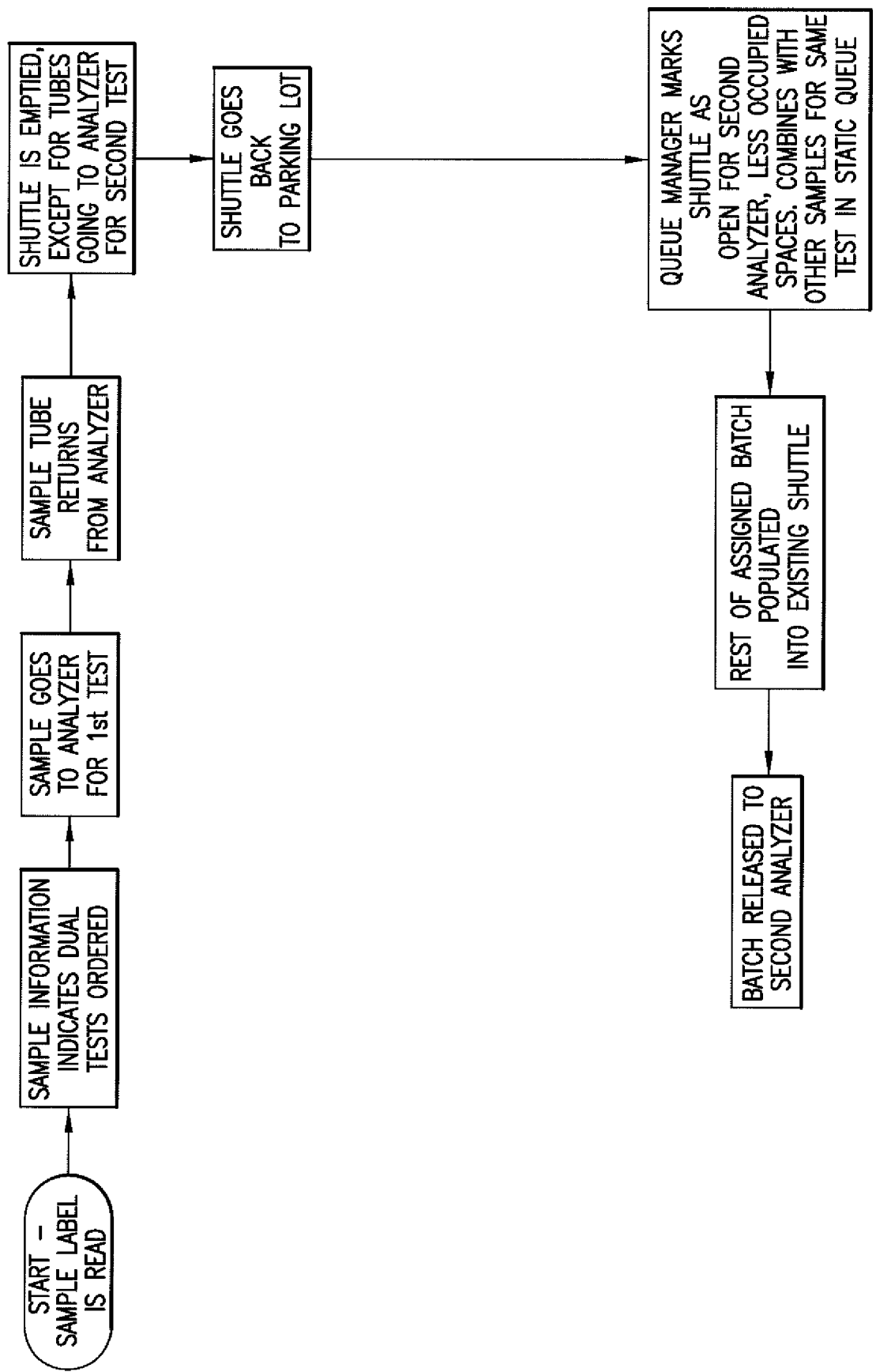
Figure 22F:
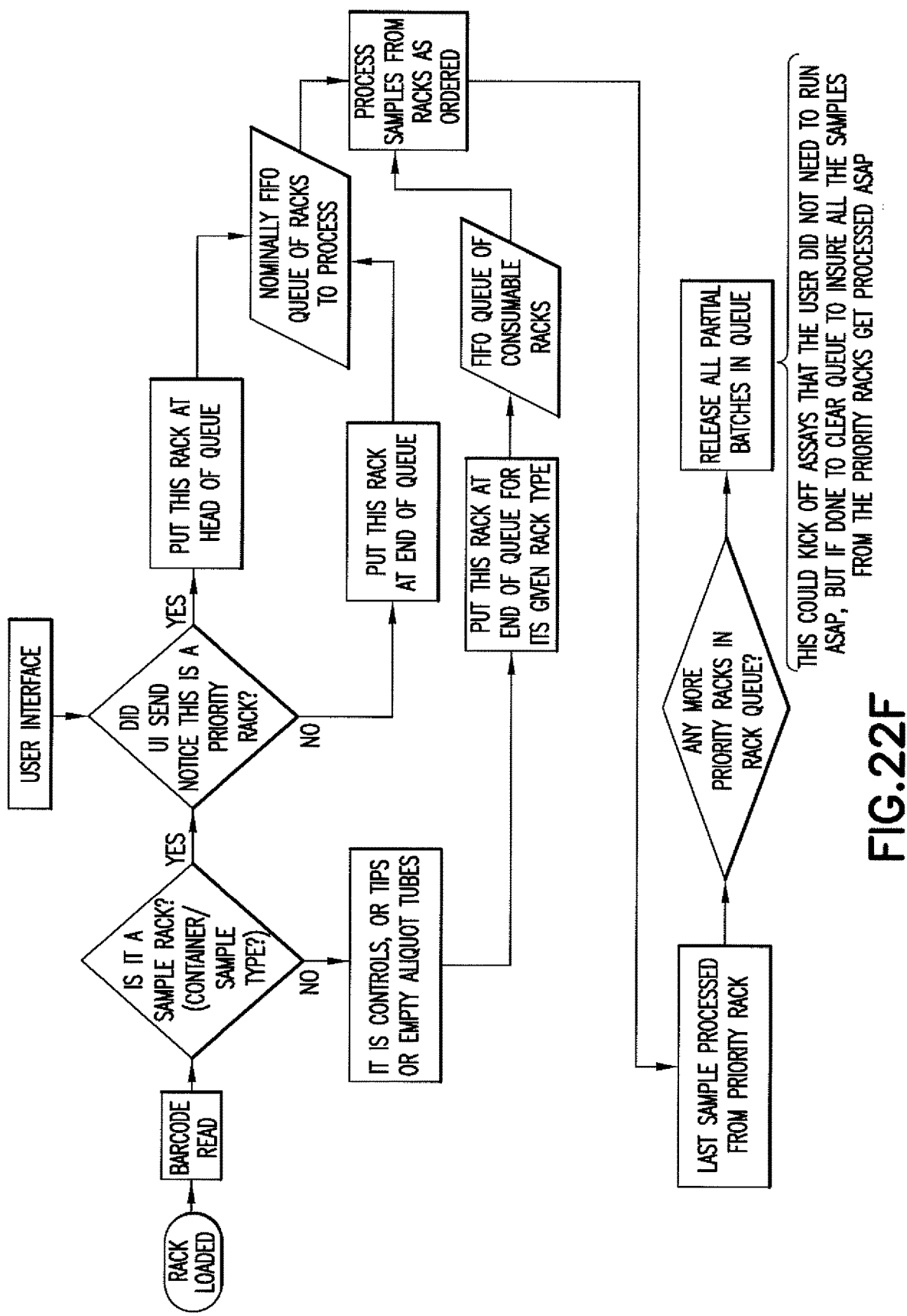
Figure 26:
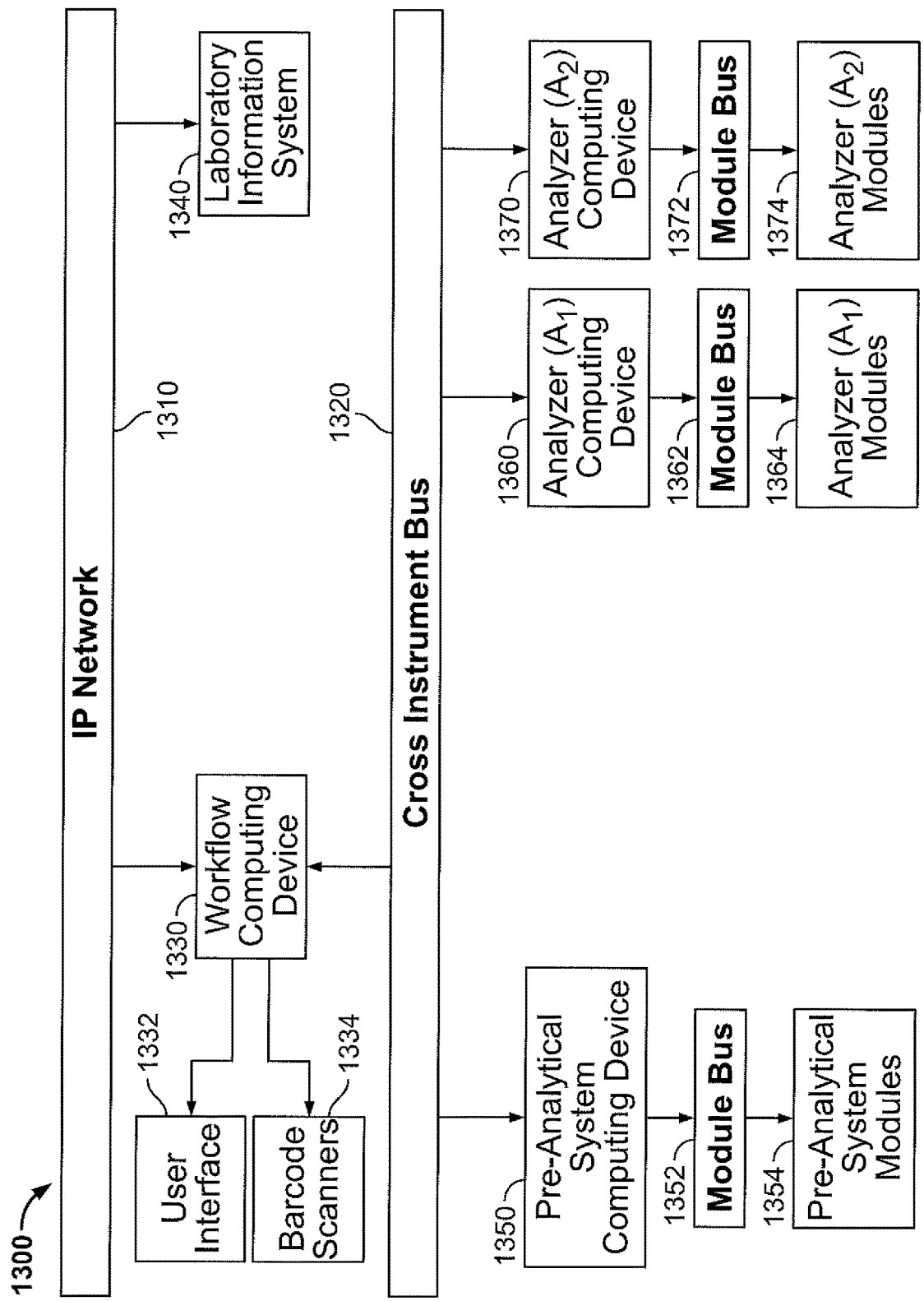
FIG. 26 is a block diagram of an illustrative architecture of a computing system according to another embodiment of the present disclosure.

Referring to FIGS. 22B and 26, when the accession number of the sample container is read and the pre-analytical system computing device 1350, on instructions from the workflow computing device 1330, has the accession number associated with two or more tests to be performed by the same or different analyzers, the sample is prepared and sent to the first analyzer as described herein. When the sample is returned, the sample container is removed from the shuttle 280 and placed in a rack in the embodiment illustrated in FIG. 22B. The sample container barcode is read and the sample container is associated with the rack in which it is placed. When the rack is full, it is placed below deck. When the pre-analytical system processor determines that the sample containers in this rack should be called into the processing queue, the rack is called to rack space 112, where the samples are prepared/handled as described elsewhere herein.

Third Accumulation

At this point, the used third-type containers 03, which may have a punctured cap, are accumulated 930 back in first accumulation area 22. In this regard, an empty or partially empty rack 50 is moved from first accumulation area 22 by rack handler robot 320 and delivered to first rack space 110 on first pre-analytical processing deck 24. First pick-and-place robot 410*a*, as instructed by processor 804, removes each used third-type container 03 from shuttle 280 and places them in front of a barcode scanner (not shown) located at I/O and post analysis module 710 to identify the container 03. If the container 03 is identified as not capable of being analyzed, such container 03 and other containers like it are filled in receptacle rows of rack 50 from front-to-back. If the container 03 is identified as being analyzed by analyzer, then pick-and-place robot places such container 03 and other containers like it in receptacles rows of rack 50 from back-to-front. This allows containers that could not be analyzed to be grouped in an easily identifiable location so that a user can quickly locate the failed containers and troubleshoot the issue.

Once rack 50 is filled at space 110 or close to being filled, elevator 100 optionally seals the punctured containers. Alternatively, each punctured container may be sealed prior to being placed into rack 50. Thereafter, rack handler 320 removes rack 50 from space 110 and moves it to a rack storage position within first accumulation area 22.

Output

Rack 50 with used containers 03 remains in first accumulation area 22 until a user requests its output 932. In this regard, a user may put system 10 into "unload mode" via user control interface 810 which marshals assistance from rack handler robot 320. Processor 804 asks the user via display interface 820 what item the user desires to have unloaded and may provide a predefined list of items to be removed or may provide a search bar that may allow user to query a patient's name or some other identifier tagged in system 10 in association with the item's identification number. When selected by the user, rack handler robot 320 removes a designated rack that may be the item of interest or may contain the item of interest and delivers it to I/O port 120 where the user removes it from system 10.

This method 800 including the accumulation steps of such method provides several benefits. One such benefit is that accumulation creates stores of consumables that can be continuously drawn upon which minimizes downtime as there is frequently a rack or container waiting in a queue for a next step. Another benefit is that accumulation allows a user to provide a large volume of consumables into system 10 which allows the user to walk away for a significant amount of time. A further benefit of accumulation as described is that it allows system 10 to be both a batch processor and random access system. More particularly, sample containers 03 that are prepared for analysis are accumulated in batches corresponding to an analyzer's capacity which maximizes analyzer output. In addition, sample containers that are not on first or second preanalytical processing decks or in an analyzer are accumulated in storage deck 22. This allows a user to randomly output a sample container. Moreover, a user can sporadically input sample containers, pipette tips, and other consumables as desired.

As noted elsewhere herein, each process and sub-process within system 10 has an error handling routine to ascertain and address errors in handling and processing. The error handling routines described herein are for moving individual tubes from a rack, reading the rack information, removing individual sample containers from the rack and reading the container information by spinning the container in front of a bar code scanner.

Each motion of the pick-and-place robots 410a-c and decapper robots 450a-b described herein are monitored. Motion errors are addressed by one retry at slower speed, after which operation is halted and an error in operation is communicated to an operator.

Each subsystem/apparatus/piece of equipment in the larger pre-processing system 10 described herein also has its own power recovery protocol. For example, rack handling robot 320, pre-processing bar code reader, shuttle handling robot 240, vortexer 220, warmer 230 and cooler 290 all have preprogrammed power recovery protocols when power is restored to the system 10. All also have sensors that detect motion errors and are in communication with a processer/controller that will retry, at half speed in some embodiment, the motion. If the motion error persists, the error is reported and, depending upon the criticality of the sub-system/apparatus/device, the analyzer or specific subsystem/apparatus/device may be paused or shut down completely until the error is corrected. Such protocols are described as diagnostic self-test herein. The warmers 230 and coolers 290 are also subjected to diagnostic self-test to ensure proper operation of the heating and cooling elements with real time data checks. For example, the fan units 296 used in the cooler 290 has a tachometer that monitors fan speed. The system 10 will put an operator on notice if fan speed is outside a predetermined range.

Alternatives
Single Tube Transport

Figure 23:
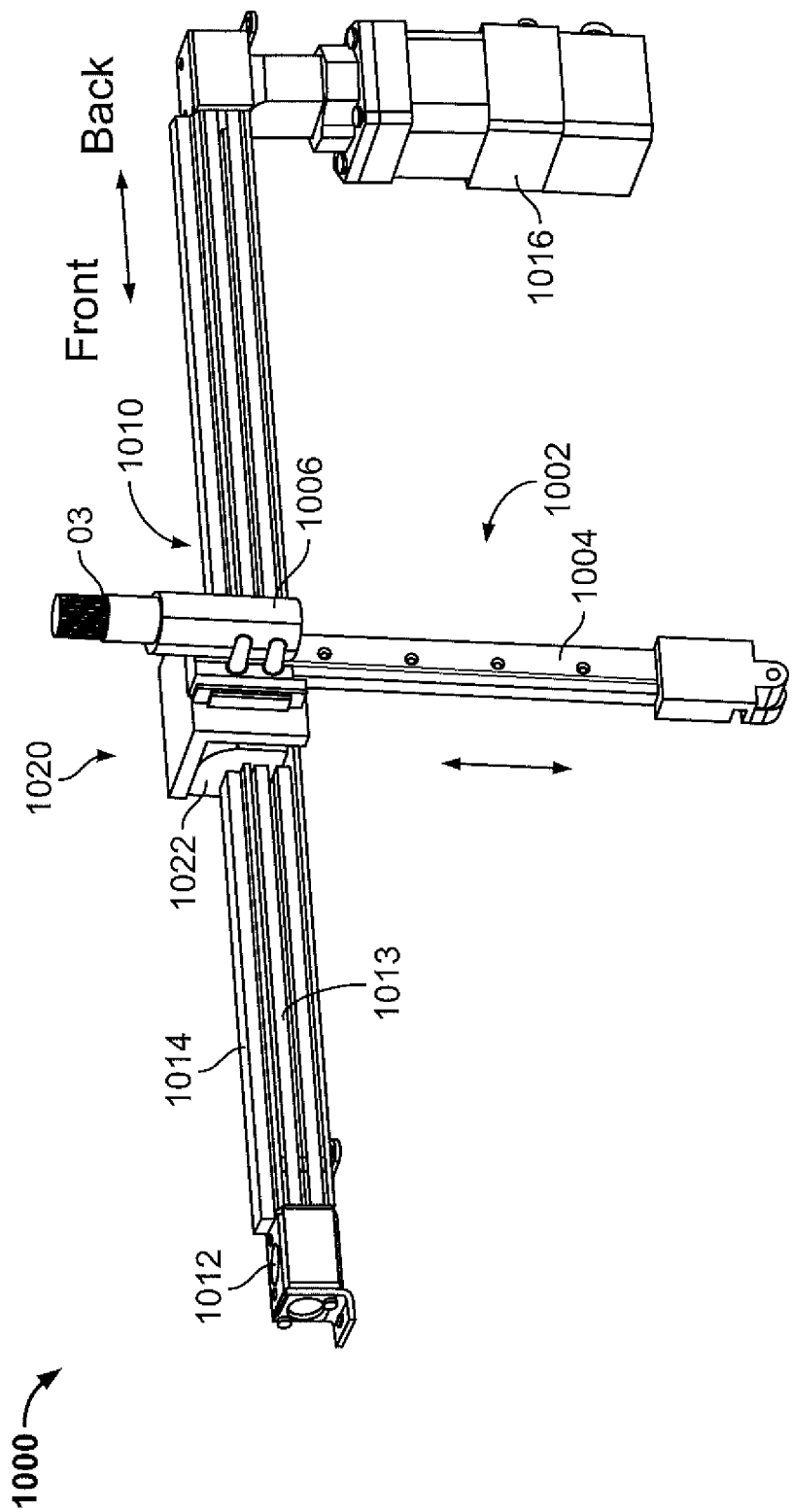
FIG. 23 is side perspective view of an optional single container transport according to another pre-analytical system embodiment of the present disclosure.

Numerous variations, additions and combinations of the features discussed above can be utilized without departing from the present invention. For example, it was described above that an aliquot is transferred from a primary container to a secondary container and that such secondary container is placed into a rack 50. Once rack 50 is filled or partially filled with secondary containers, it is transported to second pre-analytical processing deck 26 from conversion module 720 via rack handler robot 320 and rack elevator 360 where each sample container 03 is removed therefrom. FIG. 23 depicts a single container transport 1000 that can be optionally included in a system 10' to transport secondary third-type containers 03 from conversion module 720 to the second pre-analytical processing deck 26 in lieu of transporting an entire rack 50 filled with secondary containers 03.

Single container transport 1000 generally includes a horizontal rail 1010, vertical rail 1002, carriage 1020, cup 1006 and a motor. The motor is a magnetic linear motor comprised of a power source 1016, stator 1014 and mover 1022. However, in some embodiments, the motor can be a rotating electric motor coupled to a rack and pinion mechanism.

Horizontal rail 1010 includes a base 1012 and the stator 1014. Stator 1014 is connected to base 1012 such that it extends along a length thereof. Elongate slots 1013 also extend along the length of base 1012 at opposite sides thereof. Power source 1016 is connected to one end of base 1012 and energizes stator 1022.

Carriage 1020 is a U-shaped structure that includes engagement members (not shown) extending from sideways facing inner surfaces and mover 1022 which is attached to a downwardly facing inner surface. Carriage 1020 connects to horizontal rail 1010 such that mover 1022 is positioned directly above stator 1014 and the engagement members engage elongate slots 1013.

Vertical rail 1004 is connected to an outer surface of carriage 1020 at one end of vertical rail 1002 such that a portion of vertical rail 1002 hangs lower than carriage 1020 and horizontal rail 1010. Cup 1006 has a receptacle sized to receive a single container 03 therein and is slidably connected to vertical rail 1004. However, it is contemplated that an array of more than one cup can be attached to vertical rail 1004 to transport more than a single container 03 in a single trip. In one embodiment, cup 1006 can be raised or lowered along vertical rail 1004 via a motor (not shown) mounted to carriage 1020. In another embodiment, single container transport 360 may interact with rack elevator 360 to raise cup 1006 along rail 1004.

Single container transport can be connected to a support component 21 at a left-end of system 10 such that horizontal rail 1010 extends in a front-back direction.

In a method of operation, when a primary sample is obtained from a primary first-type or second-type container 01, 02 and transferred to a secondary third-type container 03 to prepare a secondary sample, the secondary container 03 is moved by decapper robot 450b from the secondary container station 160 and into cup 1006. At this point, cup 1006 is positioned near a bottom-end of vertical rail 1004 and a front-end of horizontal rail 1004. Power source 1016 then energizes stator 1014 which moves carriage 1020 toward the back of system 10. Either concurrently with or sequentially to carriage movement, cup 1006 is moved upwardly along vertical rail 1004 until it reaches an upper extent thereof. Once carriage 1020 reaches a back-end of horizontal rail 1010, the motor stops carriage 1020. At this point, container 03 is within reach of pick-and-place robot 410c, which then reaches down and removes container 03 from cup 1006 and moves it to batch-accumulation area 210.

Thereafter, mover 1022 and stator 1014 drives carriage 1020 toward the front of system 10 and cup 1006 is lowered toward a bottom extent of vertical rail 1004 so that cup 1006 can be filled with another secondary third-type container 03. This sequence is repeated as required to support the desired workflow.

Although, single container transport 1000 can be included in system 10' to move secondary containers to second pre-analytical processing deck 24, rack handler robot 320 can be utilized to transport primary third-type containers 03 to rack elevator while single container transport transfers secondary third-type containers 03 to the back.

Sample Container Retention Assembly

FIGS. 24A-24D depicts sample container retention assembly 1100 which is another feature that can be added to system 10. Sample containers 03 may each include a penetrable cap 08 (see FIG. 24C) which is penetrated by an analyzer in order to retrieve a sample therefrom. This can cause a pipette tip or needle to become stuck in the penetrable cap of the sample container 03. As the tip or needle is withdrawn from container 03, the container can be carried by the tip or needle, potentially spilling the contents of the container 03 or removing the container 03 from the workflow, causing loss of sample or contamination issues or both. To secure the sample containers as the pipette needle is withdrawn therefrom, sample container retention assembly 1100 can be coupled to an end of shuttle transport assembly 300*a* and/or 300*b*, which may be disposed within or near a target analyzer, and used to retain sample containers 03 within a shuttle 280 as a pipette or needle is removed therefrom. This helps prevent sample containers 03 from being inadvertently removed from a shuttle 280 and its contents spilled after sample aspiration or dispense.

Sample container retention assembly 1100 generally includes a shuttle transport assembly 1110, clamping assembly 1150, and a motor assembly 1140. The shuttle transport assembly can be any conveyor assembly, such as embodiment 1110 depicted in FIGS. 24A-24D or shuttle transport assembly 300 described above in relation to FIG. 13.

Shuttle transport assembly 1110, as depicted, generally includes an elongate conveyor platform 1112 or track. In some embodiments, conveyor platform 1112 can be incorporated into an analyzer and placed adjacent to an end of shuttle transport assembly 300*a* and/or 300*b* such that a small gap is formed therebetween. In other embodiments, conveyor platform 1112 may span both an analyzer and system 10 such that conveyor platform extends between the two. In even further embodiments, conveyor platform 1112 may only be disposed in system 10. Conveyor platform 1112 includes top and bottom surfaces and side surfaces 1114. A conveyor belt 1116 is wrapped about the top and bottom surfaces and coupled to a belt and pulley mechanism 1118 which moves conveyor belt 1116 relative to the top and bottom surfaces.

Shuttle transport assembly 1110 also includes a backstop 1120 which is comprised of an arm 1122 and bumper and/or position arm. Arm 1122 is attached at a first end thereof to a side surface 1114 of conveyor platform 1112 and is generally curved or angled so that a second end of arm 1122 is positioned over conveyor belt 1116. The bumper includes a bumper portion 1126 and a threaded extension 1124 (see FIG. 24B) extending from bumper portion 1126. The bumper is threadedly engaged to the second end of arm 1122 via threaded extension 1124 such that the position of bumper portion 1126 relative to arm 1122 is adjustable by rotating the bumper in a first or second direction. Such adjustment moves bumper portion 1126 in a direction parallel to a direction of conveyor belt movement and helps properly align shuttle 280 when disposed on conveyor belt 1116.

A first and second guiderail 1130*a-b* extends from corresponding side surfaces 1114 of conveyor platform 1112 such that longitudinal portions 1132*a-b* thereof are spaced a distance slightly larger than a width of shuttle 280. Guiderails 1130, when attached to conveyor platform 1112, each define an opening 1134*a-b* that extends from conveyor platform 1112 to a bottom surface 1134 of longitudinal portions 1132*a-b* (best shown in FIGS. 24A & 24D). These openings 1134*a-b* are sufficiently large as to expose transverse openings 286 of a shuttle 280 when positioned on conveyor belt 1116 and abutting backstop 1120.

Motor assembly includes a motor 1141, gearbox 1142, and drive shaft 1148. Motor 1141 is connected to conveyor platform 1112, such as to side surfaces 1114, so that it hangs beneath the platform's bottom surface without interfering with the movement of conveyor belt 1116 and such that an output shaft extending from gearbox 1142 extends in a direction parallel to a length of conveyor platform 1112. Motor 1141 can be any rotating electric motor capable of operating in two directions. Gearbox may be configured to reduce output speeds and increase output torque of output shaft 1143 relative to motor 1141.

A drive shaft 1148 is coupled at one end thereof to shaft 1143 via a coaxial coupling 1146. Another end of drive shaft 1148 remote from motor 1141 is coupled to a bearing connected to shuttle transport assembly 1110 to help support drive shaft 1148 while allowing rotation thereof. Drive shaft 1148 includes a pair of flanges 1145*a-b* connected thereto and extending radially outwardly. Flanges 1145*a-b* are offset from each other and rotatable in conjunction with drive shaft 1148 and are configured for connection to clamping assembly 1150, such as by having openings for receipt of pins.

Clamping assembly 1150 includes a leverage block 1152 and two arm assemblies 1160, 1170. First arm assembly 1160 includes a pair of driven members 1162*a-b* and a pair of intermediate members 1164*a-b*. In addition, first arm assembly 1160 includes an engagement member 1166.

Driven members 1162*a-b* are bar-linkages that each have a first and second end and a length extending therebetween. Similarly, intermediate members 1164*a-b* are bar-linkages that each have a first and second end and a length extending therebetween.

Engagement member 1166 has a first and second end and a length extending therebetween. In addition, engagement member 1166 has a width orthogonal to its length (see FIG. 24C). The length of engagement member 1166 is about the same as the length of shuttle 280.

Figure 24A:
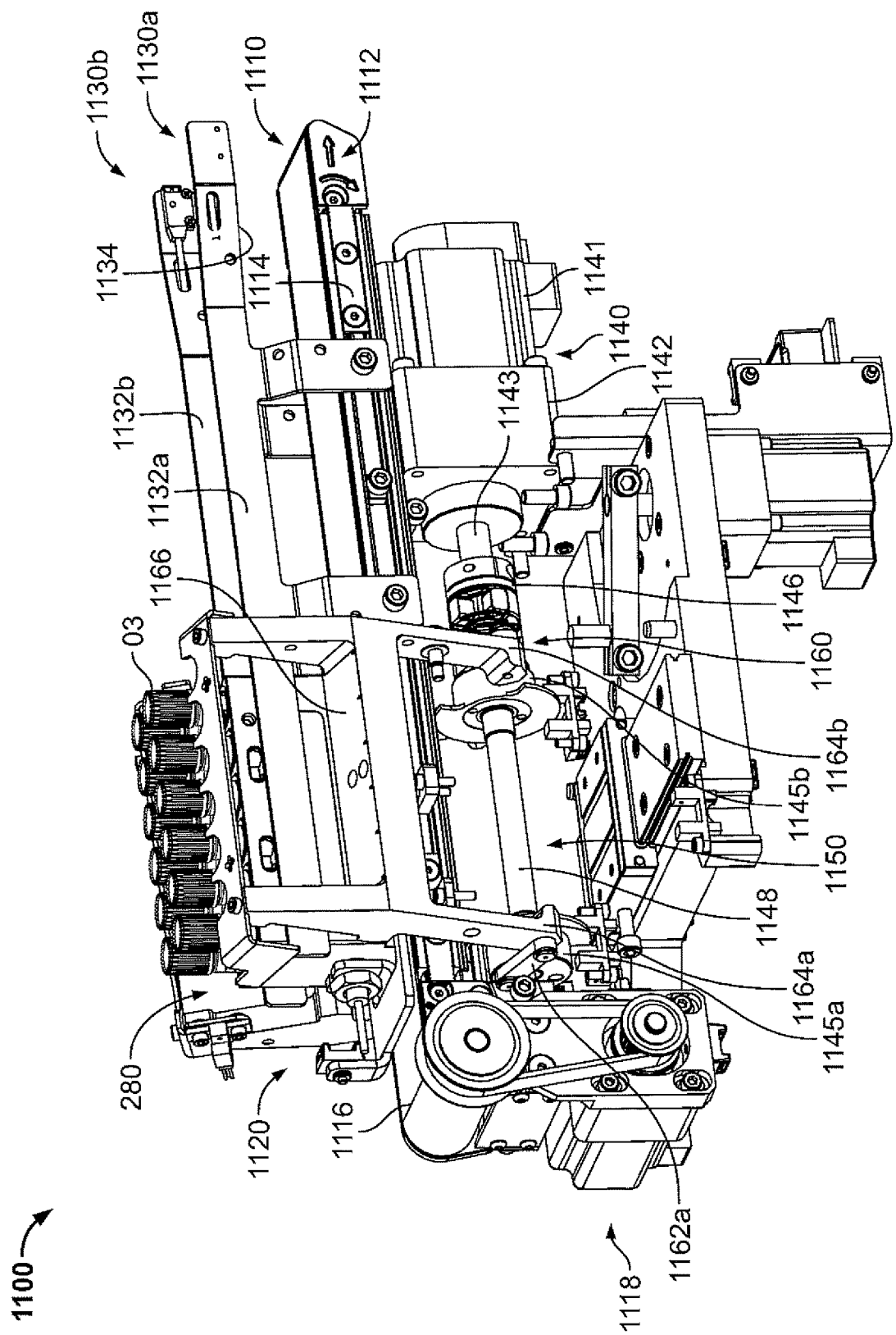
FIG. 24A is a front perspective view of an optional sample tube retention assembly according to one embodiment of the present disclosure.
Figure 24B:
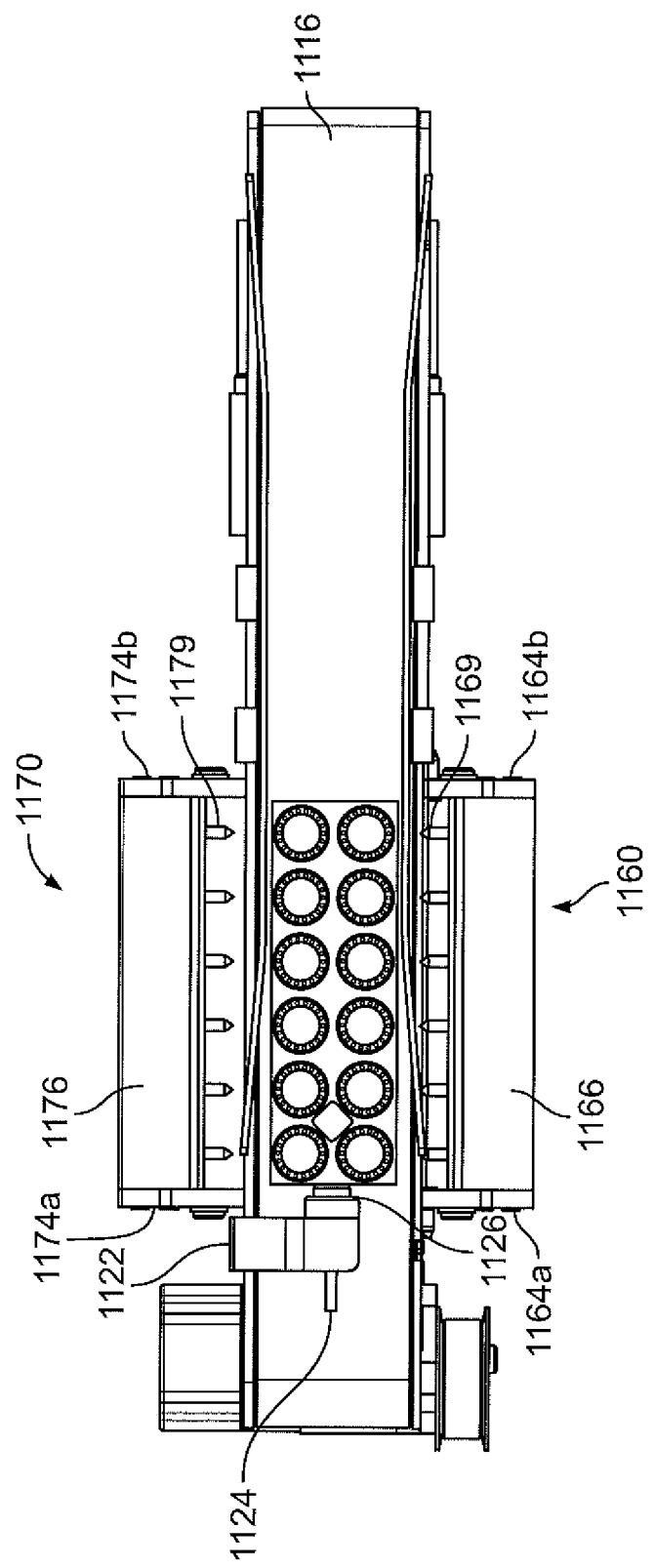
FIG. 24B is a top view of the sample tube retention assembly of FIG. 24A.

Engagement member 1166 also includes an array of pointed members 1169 extending from a side surface thereof at an oblique angle relative to the width of engagement member 1179. The number of pointed members 1169 corresponds to a number of receptacles in a row of shuttle 280. For example, as shown in FIGS. 24A and 24C, shuttle 280 includes a first row 281 of six receptacles 283. As such, the depicted engagement member 1166 includes six pointed members 1169. Each pointed member 1169 is separated from an adjacent pointed member 1169 a distance substantially equal to a distance separating transverse slots 286 of shuttle 280. In addition, each pointed member 1169 has a length and cross-sectional dimension sufficient to pass through transverse slots 286 and pressure contact or otherwise engage a bottom portion of a container 03 disposed within a shuttle 280. A pointed end of each pointed member 1169 is sufficiently sharp to indent, and in some cases even puncture, a bottom of a container 03 in order to secure the containers in the shuttle as the pipette tip is withdrawn therefrom. However, as shown in FIG. 24C, containers 03 preferably have a cylindrical skirt 07 disposed at the bottom portion so that puncturing such skirt 07 does not puncture the portion of the container in which the sample is disposed.

Leverage block 1152 is generally a rectangular block with a rectangular recess 1154 extending along a length thereof. This rectangular recess 1154 has a width slightly larger than a width of conveyor platform 1112 and defines opposing extensions 1156, 1157 which are each attached to side surfaces of conveyor platform 1112 such that leverage block is generally disposed beneath conveyor platform 1112 and spans conveyor platform 1112 from side-to-side. Rectangular recess 1154 forms a space for conveyor belt 1116 to operate unimpeded.

The first ends of driven members 1162a-b are each rotatably connected to a corresponding flange 1145a-b of driven shaft 1148. Intermediate members 1164a-b are each rotatably connected at a first end thereof to the second end of corresponding driven members 1162a-b. Intermediate members 1164a-b extend upwardly at an angle relative to driven members 1162a-b and are each rotatably connected to opposite ends of leverage block extension 1156. This connection may be made by inserting a pin or other fastener through each intermediate member 1164a-b between their first and second ends and into leverage block 1152. In addition, intermediate members 1164a-b are fixedly connected at the second end thereof to opposite ends of engagement member 1166. Engagement member 1116 spans a distance between intermediate members 1164a-b and its length is generally orthogonal to the lengths of intermediate members 1164a-b. The width of engagement member 1166 also extends generally orthogonally relative to a length of intermediate members 1164a-b such that pointed members 1169 are angled downwardly toward conveyor belt 1116 (best shown in FIGS. 24C and 24D).

Second arm assembly 1170 is substantially the same as first arm assembly 1160 and is coupled to drive shaft 1148 and leverage block 1152 in the same manner as first arm assembly 1160 described above. In particular, second arm assembly 1170 includes a pair of driven members 1172a-b, a pair of intermediate members 1174a-b, and an engagement member 1176 that includes an array of pointed members 1179 that match a number of receptacles 283 within a second row 282 of shuttle 280. Driven members 1172a-b are pivotally connected to corresponding flanges 1145a-b at positions opposite driven members 1162a-b of first arm assembly 1160. For example, ends of driven members 1172a-b are connected at a position substantially 180 degrees about flanges 1145a-b from a connection position of driven members 1162a-b.

When arms 1160, 1170 are connected to leverage block 1152 and drive shaft 1148, arms 1160, 1170 generally have two positions. The first position being a release position, and the second position being an engagement position. In the release position (shown in FIG. 24C) drive shaft 1148 is rotated such that the first ends of the driven members 1162a-b are positioned above the first ends of the driven members 1172a-b. Also, in this position, the angle formed between driven arm members 1162a-b and intermediate members 1164a-b of first arm assembly 1160 is acute, while the angle formed between driven arm members 1172a-b and intermediate members 1174a-b of second arm assembly 1170 is obtuse. However, it should be understood that the opposite configuration can also constitute a release position in which driven ends 1172a-b are positioned above driven ends 1162a-b and the angles formed with intermediate members 1174a-b and 1164a-b are acute and obtuse, respectively. In this release position, engagement members 1166, 1176 are pushed outwardly away from platform 1112 so as to allow shuttle 280 to travel down conveyor belt 1116 and contact backstop 1120.

In the engagement position (shown in FIG. 24D), drive shaft 1148 is rotated such that the first ends of the driven members 1162a-b and 1172a-b are aligned in a horizontal plane. Also, intermediate members 1164a-b and 1174a-b, in this position, are generally perpendicular relative to drive members 1162a-b and 1174a-b, respectively. In this position, engagement members 1166, 1176 are pushed inwardly toward platform 1112 such that the widths of engagement members 1166, 1176 are substantially horizontal and pointed members 1169, 1179 extend through openings 1134a-b of guiderails 1132a-b, respectively, and transverse slots 286 of shuttle 280 when disposed on conveyor 1116.

In a method of sample container retention, a shuttle 280 with containers 03 disposed therein is placed on shuttle transport assembly 1110, such as by shuttle handling assembly 240. Belt and pulley mechanism 1118 is operated to move conveyor belt 1116 and shuttle 280 from one end of shuttle transport assembly 1110 to another. Shuttle 280 contacts backstop 1120 and belt 1116 is turned off such that shuttle 280 remains in contact with backstop 1120.

At this point, clamping assembly 1150 is in the release position, as described above. Motor 1141 is then turned on and rotates drive shaft 1148 in a first direction. This causes the first ends of driven members 1162a-b of first arm assembly 1160 to be driven from about a 90 degree position (relative to a horizontal plane bisecting shaft 1148) to a zero degree position, and the first ends of driven members 1172a-b of second arm assembly 1160 to be driven from about a 270 degree position to a 180 degree position (see FIGS. 24C and 24D for contrast). As this occurs, intermediate members 1164a-b and 1174a-b are rotated inwardly by driven members 1162a-b and 1172a-b, respectively, toward platform 1112 and a vertical orientation. Pointed members 1169, 1179 then pass through transverse openings 286 of shuttle 280 and contact skirt 07 of containers 03 disposed therein. Motor 1141 can be operated to further drive pointed members 1169, 1179 into containers 03 so that pointed members 1169, 1179 press into skirt 07 of containers 03.

As shown in FIG. 24D, pointed members 1169, 1179 contact and grip each container 03 from only one side of container 03. Shuttle 280 itself and the opposing, but nearly identical, pressure applied by arm assemblies 1160, 1170 prevent containers 03 from moving while pointed members 1169, 1179 bite into them. This allows pointed members 1169, 1179 to indent or pierce the container's skirt 03 in order to prevent the container from moving vertically out of shuttle 280 during sample aspiration.

Once containers 03 are sufficiently restrained, system 10 communicates to an analyzer that the samples are ready for aspiration or dispense. A pipette (not shown) located in the analyzer pierces caps 08 of sample containers 03 to remove sample therefrom for diagnostic testing or add reagents thereto for sample processing. The pipette may reach into system 10 to access containers 03. Alternatively, and preferably, clamp assembly 1150 and end of shuttle transport assembly 1110 are disposed within the analyzer and the pipette accesses containers 03 within the analyzer. As the pipette withdraws from containers 03 after aspiration or dispense, the pipette drags along the cap's seal 09. Any tendency of the pipette to carry the container along with it is opposed by clamping assembly 1150, thereby securing container 03 in the shuttle 280 during withdrawal of the pipette.

Once the analyzer has completed sample removal, the analyzer communicates with system 10 that shuttle 280 is ready for transport back into system 10. Thereafter, motor 1141 turns drive shaft 1148 in a second direction (or again in the first direction). This causes the ends of driven members 1162a-b of first arm assembly 1160 to return to the 90 degree position and the ends of driven members 1174a-b of second arm assembly 1170 to return to the 270 degree position. Intermediate members 1164a-b and 1174a-b are driven outwardly away from platform 1112 and engagement members 1150 are disengaged from containers 03. Conveyor belt 1116 is then operated and shuttle 280 moves toward shuttle handling assembly 240.

Alternative Tip Ejector

FIGS. 25A-25D depict an alternative pipette head 1200. Pipette head 1200 is similar to pipette head 500 in that it includes a main board 1201 and pipette assembly 1202. However, pipette head 1200 differs in that pipette head 1200 has an integrated z-axis drive mechanism. In other words, the z-axis drive mechanism of pipette head 1200 couples main board 1201 to pipette assembly 1202 whereas the z-axis drive mechanism of robot 481 couples pipette head 500, via main board 501, to pipette arm 483. The z-axis drive mechanism of head 1200 includes a vertical rail 1207 and a motor 1209 which moves pipette assembly 1202 along vertical rail 1207 relative to main board 1201.

Additionally, pipette assembly 1202 is similar to pipette assembly 502 in that it includes a tip ejector assembly and pipette channel assembly. In particular, the pipette channel assembly is similar to the pipette channel assembly of pipette assembly 502 in that it includes a channel housing 1210, tip adaptor 1220 extending from housing 1210, a control unit 1215 connected to housing 1210, and a connector arm 1217 coupled to control unit 1215.

Figure 25D:
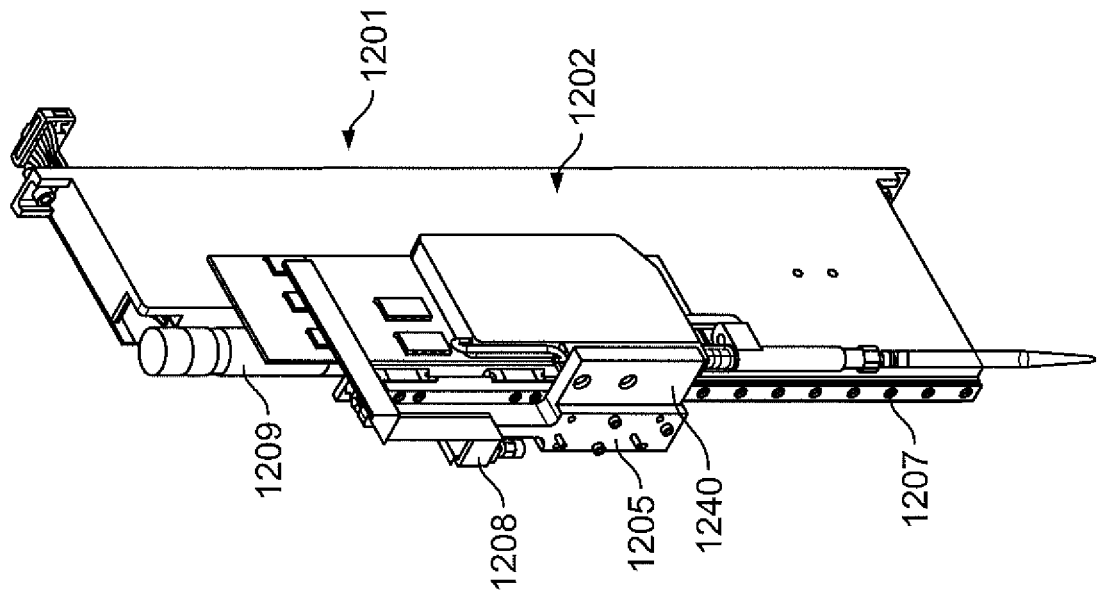
FIG. 25D is a rear perspective view of the pipette head of FIG. 25A in a second position relative to a pipette assembly carriage.

However, pipette assembly 1202 differs from pipette assembly 502 in relation to the tip ejector assembly. In particular, it was previously described with relation to assembly 502 that a leadscrew 540 operates a pusher nut 570 that engages a floating shaft 560 connected to a tip ejector 550 in order to deliberately eject a pipette tip. However, as shown in FIG. 25D, a leadscrew 1280 directly connects to a tip ejector 1250 to eject a tip 489.

Thus, as depicted, the tip ejector assembly of head 1200 includes an ejector housing 1240, motor 1290, tip ejector 1250, and leadscrew 1280. Housing 1240 includes an opening extending through a length thereof and a recess 1244 extending through an end of housing 1240. Recess 1244 does not extend entirely through housing 1240 and, thus, defines a terminal surface 1246 at an end of recess 1244.

Motor 1290 is attached to an upper end of ejector housing 1240 and includes a drive shaft 1292 extending therefrom. Drive shaft 1292 is connected to leadscrew 1280 via a coupling 1282, such as a slip coupling. Leadscrew 1280 extends through the opening such that a threaded portion 1286 extends from a bottom of housing 1240.

Tip ejector 1250 is similar to ejector 550 in that it includes a cannulated body 1252 and an arm 1258 comprised of a horizontal portion 1256 and vertical portion 1258. However, arm 1258 includes an optical sensor 1251 at a terminal end thereof. As assembled, tip adaptor 1220 extends through an opening of cannulated body 1252 and cannulated body 1252 is slidable along a length of tip adaptor 1220. Leadscrew 1280 is threadedly connected to horizontal portion 1256, and vertical portion 1258 extends into recess 1244 such that optical sensor 1251 is directed at terminal surface 1246.

In a method of operation of pipette head 1200, pipette head 1200 is moved into a position over a disposable pipette tip 489 via a pipette arm, such as pipette arm 483. Motor 1209 drives pipette assembly 1202 along a vertical rail 1207 toward tip 489. At this point, leadscrew 1286 and tip ejector 1250 are in a tip-on position in which the leadscrew threads have driven tip ejector 1250 upward such that a bottom edge 1259 of tip ejector 1250 is positioned above engagement features of tip adaptor 1220. In this position, optical sensor 1251 disposed at the terminal end of vertical portion 1258 is near terminal surface 1246 within recess 1244 which generates an output signal indicative of the tip-off position due to the detected closeness of optical sensor 1251 and surface 1246. Motor 1290 further drives head 1200 such that pipette tip 489 connects to tip adaptor 1220 in an interference fit manner.

Pipette head 1200 is now ready for aspiration and dispense. Once aspiration and dispense is completed, pipette head 1200 is positioned over a receptacle opening in first pre-analytical processing deck 24 and tip 489 is ejected. More particularly, motor 1290 is operated in a first direction which rotates leadscrew 1280 in the first direction, thereby driving horizontal portion 1256 of tip ejector 1250 along threaded portion 1286. An edge 1259 of cannulated body 1252 is in contact with tip 489. Motor 1290 continues to drive leadscrew 1280 and cannulated body 1252 pushes tip 489 off of tip adaptor 1220. Optical sensor 1251 determines when tip ejector 1250 is in a tip-off position or has traveled a sufficient distance, which may be predetermined, to eject tip 489 which shuts off motor 1290. Motor 1290 then operates in a second direction which rotates leadscrew 1280 in the second direction thereby raising tip ejector 1250 back into the tip-on position in order to retrieve another pipette tip 489.

Figure 25C:
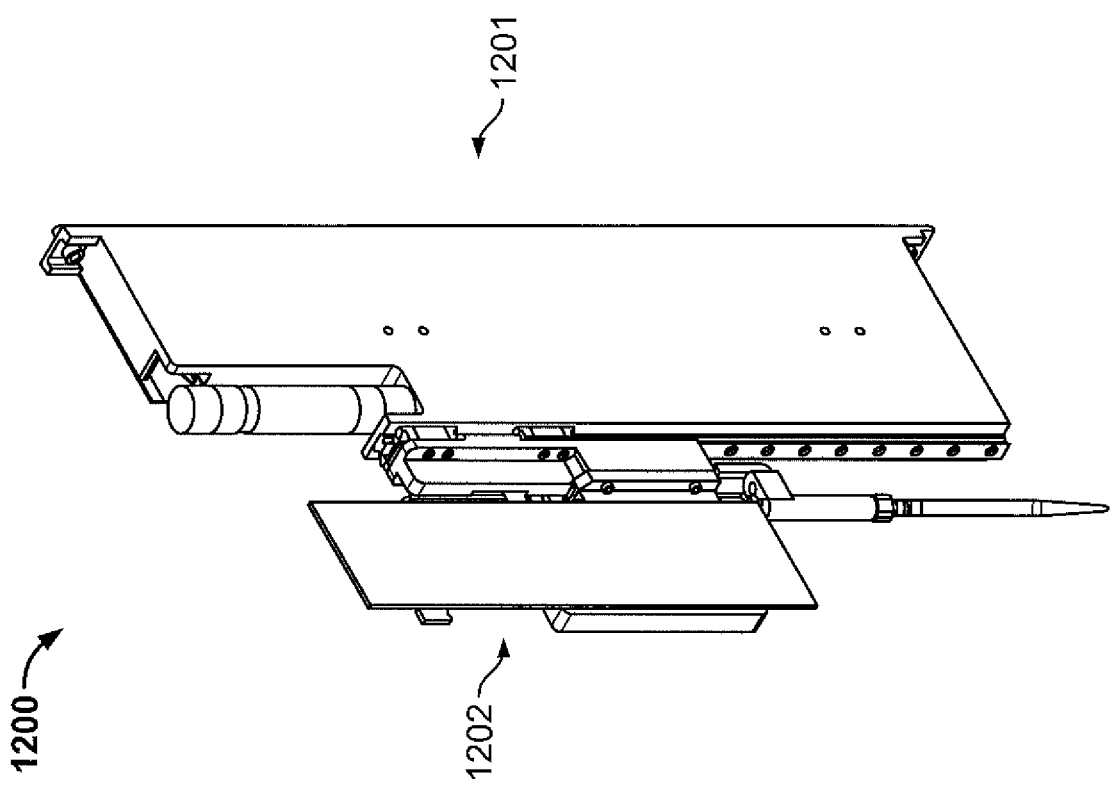
FIG. 25C is a rear perspective view of the pipette head of FIG. 25A in a first position relative to a pipette assembly carriage.

Furthermore, as shown in FIGS. 25C and 25D, pipette assembly 1202 is hingedly connected to main board 1201 such that pipette assembly 1202 can rotate about a vertical axis relative to main board 1201 from a first position to a second position. In particular, pipette assembly is hingedly connected to a carriage 1205 which is slidingly connected to vertical rail 1207. In the first position, as shown in FIG. 25A, ejector housing 1240 is in line with or facing main board 1201. In the second position, pipette assembly 1202 is pivoted about 180 degrees so as to assume a folded relationship with respect to main board 1201 which can reduce the amount of space occupied by pipette assembly 1202. A bracket 1208 can be used to hold pipette assembly 1202 in this position.

Alternative Computing System Architecture

FIG. 26 depicts a computer system architecture 1300 that supports the system according to another embodiment of the present disclosure. Architecture 1300 generally includes a workflow computer control device 1330, a pre-analytical system computer control device 1350, and one or more analyzer computer control devices (illustrated here as two such control devices 1360, 1370; one for each analyzer). As shown, workflow computer control device 1330 is connected to an IP network 1310, which is also connected to a laboratory information system 1340 ("LIS"). LIS 1340 may be an existing generic or customized system associated with a diagnostic laboratory or medical facility that stores and maintains patient records and information, among other things. IP network 1310 allows workflow computer control device 1330 to communicate with LIS 1340 and share information therebetween. Workflow computer control device 1330 is also connected to a cross-instrument bus 1320 along with computer control devices 1350, 1360, and 1370. Although, more or less analyzer computer control devices may be provided depending on the number of analyzers utilized with system 10. This cross-instrument bus 1320 allows computer control devices 1350, 1360, and 1370 to communicate with workflow computer device 1330 and share information.

Workflow computer device 1330 includes one or more processors and memory. A user interface 1332, similar to user interface 810, is connected to workflow computer device 1330 to allow a user to communicate therewith. In addition, barcode scanners 1334, such as scanner 205, which are located within system 10 and within any of the analyzers, are connected to workflow computer control device 1330.

The memory of the workflow computer control device 1330 may include an application stored therein. This application provides instructions to the processor of device 1330 that involve gathering data from various consumers, compiling the data as instructed, and presenting data to various consumers. Such consumers include a user via user interface 1332, LIS 1340, barcode scanners 1334, pre-analytical system computer device 1350, and analyzer computer control devices 1360, 1370. In addition, such exemplary data may include the assay or assays to be performed on a particular sample (data from LIS to devices 1350, 1360 and 1370), instrument and sample status (data from devices 1350, 1360, 1370 to user), and assay results (data from devices 1360, 1370 to user and/or LIS). In this regard, workflow computer control device 1330 acts as an information hub.

Pre-analytical system computer control device 1350 is similar to computer control device 802 in that it includes a processor and memory. Computer control device 1350, in addition to being connected to cross-instrument bus 1320, is connected to a module bus 1352 which is connected to the pre-analytical modules 1354 of system 10, such as modules 710, 720, 730, 740, 750, and 760, allowing computer control device 1350 to communicate therewith. Computer control device 1350 includes an application stored on its memory which provides instructions to its processor involving control of the physical operations utilized in preparation and preprocessing of samples within system 10. In this regard, the application via the processor of computer control device 1350 helps control each instrument/device within pre-analytical modules 1354.

Analyzer computer control device 1360 may also each include a processor and memory. Computer control device 1360, in addition to being connected to cross-instrument bus 1320, is connected to a module bus 1362 which is connected to analyzer modules of an analyzer $A_1$, allowing computer control device 1360 to communicate therewith. Computer control device 1360 includes an application stored on its memory which provides instructions to its processor involving control of the physical operations utilized in analysis of a sample provided to analyzer $A_1$ via system 10. In this regard, the computer control device 1360, via its processor, helps control each instrument/device within the analyzer $A_1$. Computer control device 1370 is similarly configured for its respective analyzer.

Thus, as shown in FIG. 26, workflow computer control device 1330 receives information from multiple inputs and distributes the information as needed. This allows system 10 to be fully integrated with one or more analyzers and with an information sharing network that allows system 10 to smartly perform preparation and preprocessing of multiple different samples contained in multiple different containers. However, full integration is not required. The pre-analytical system can be operated as a stand-alone system and the samples, once prepared, can be removed and carried to an associated analyzer for analysis.

In another embodiment of architecture 1300, pre-analytical system computer control device 1350 may also act as the workflow computer control device 1330. Thus, in such embodiment, device 1350 would be directly connected to IP network and also to user interface 1332 and barcode scanners 1334 as well as cross instrument bus 1320 and module bus 1352.

Workflow Embodiments

Further to FIG. 26, FIG. 22A illustrates one example of the process flow performed by the pre-analytical system module. The process flow allows batch processing of samples that may or may not require conversion (e.g. the samples received in primary sample container type 03 which are processed into secondary containers for batching and transfer to an analytical module(s) for testing) and samples that will require conversion (i.e. the LBC samples in primary container types 01 and 02). Specifically, and with reference to FIG. 22A, the user loads the pre-analytical system with samples and consumables. The samples as received have a unique identifier (i.e. an accession number) thereon. The type of rack informs the system of the type of samples in the rack, but the specifics of the samples are not known to the pre-analytical system until the system reads the information on the particular sample container. Since the objective of the system is batch processing (i.e. aggregating samples together that will be subjected to the same test in one of the analyzers in communication with the analyzer), the samples that are conveyed into the pre-analytical system may be regrouped to meet batch requirements. The pre-analytical system initially aggregates racks of samples and secondary tubes in the consumable accumulation module (760 in FIG. 19B).

When the pre-analytical system retrieves a rack from the consumable accumulation module onto the deck, the rack is scanned for information that indicates whether the sample tubes are to pass through the pre-analytical module directly to an analytical module or if the samples tubes cannot be passed through in which case the primary sample must be drawn from the sample tubes and a secondary sample is prepared for pre-analytical processing. The pre-analytical computing device 1350 will provide different processing instructions depending upon the designation.

The pick and place robot 410 (described elsewhere herein) retrieves a sample container from the rack and places the sample container in primary sample container station 140. The sample preparation/handling of the primary sample container is controlled in the following manner. Using a label reader, the reader sends the accession code for the sample to the pre-analytical computing device 1350, which has been informed of the assay workflow ordered for that sample by the workflow computing device 1330. If the sample is not to be further prepared, the workflow for that sample is determined and it is sent to queue (in rack space 114). If a sample is received in a container that cannot be handled completely by the pre-analytical system, but there is no sample preparation ordered for the sample, that sample container will be flagged as an error and not be processed further.

If the sample is to be prepared, a secondary tube is retrieved by the pick and place robot 410 and its preassigned serial number is associated with the accession number for the sample. As noted elsewhere, a sample is "prepared" if the primary sample itself is removed from the container that carried the sample into the pre-analytical system. For example, a sample that is received by the system in a container that cannot be completely handled by the pre-analytical system, that primary sample is removed from the container in which it was received and placed in a secondary sample container that can be handled by the system. In other examples, the pre-processing instructions for a primary sample will require the pre-analytical system to add pre-processing reagents (e.g. a diluent, a buffer, etc.) to the primary sample to create a secondary sample. In one example, the controller then causes the robotic pipettor to transfer predetermined aliquots of sample from the type 03 sample container into the empty tube thereby creating an ISBT (International Society of Blood Transfusion) 128 standard compliant designation for the secondary sample. The ISBT 128 Standard was specifically designed to meet the special traceability needs of medical products of human origin (MPHO) to provide the donor to patient link of each product. In particular, it incorporates the identification of the donor within the standard to ensure this identification is globally unique and is presented in a standard format to be understood across different device platforms. ISBT 128 is well known to the skill in the art and is not described in detail here. Further information on ISBT 128 can be found at www.iccbba.org/isbt-128-basics. After the rack of ISBT's is completed it is also brought to queue. Here, sensors determine if the queue is full and receives instructions from the controller on what further processing is required.

As described elsewhere herein, the pre-analytical system inquires if an analyzer is available to process a batch of prepared samples. This requires the pre-analytical computing device 1350 to send information to the workflow computing device 1330, which can ascertain the available processing resources for analyzers $A_1$ and $A_2$. Once the pre-analytical computing device 1350 receives a signal that indicates it may prepare a given batch to a designated analyzer, the rack with the batch of samples is moved to the rack location 200 using rack elevator 360. Transfer is controlled by the pre-analytical computing device 1350. The workflow computing device 1330 instructs the pick and place robot 410 to depopulate the sample tubes from the rack into batch accumulation area 210. If workflow computing device 1330 instructs, the pick and place robot 410 places the sample tubes in the warmer 230. The workflow computing device 1330 instructs the pick and place robot 410 to load the shuttles on a batch basis.

The workflow computing device 1330 then coordinates the actions of the pick and place robot and the shuttle handling assembly 240 to assemble a batch of samples into a shuttle. The shuttle handling assembly 240 and the specifics of its operation are described elsewhere herein. The batch itself has been predetermined. Once a batch is assembled in a shuttle, the workflow computing device controls the placement of the shuttle 280 onto the shuttle transport assembly 300.

Additional detail on sample preparation/conversion is illustrated in FIG. 22B (samples are for an HPV assay). A variety of reagents and containers, disposed in racks, are received at the illustrated station. Examples of inputs to the station include racks carrying containers having controls for positive and/or negative assay results (i.e. spiked samples and clear samples). Racks carrying LBC samples requiring preparation/conversion are also input, as are conversion consumables (i.e. type 03 containers). Output of the preparation/conversion are the controls (which may be dried reagents and to which only diluent is added to prepare the controls for analytical processing), the prepared samples and waste. Sample preparation/conversion is controlled by the pre-analytical system computing device 1350 without direction or control from the workflow computing device 1330 that is external to the pre-analytical system.

In one embodiment the pre-analytical system has parallel workflows for: 1) the control samples; 2) the LBC samples; and 3) the non-LBC samples. Note that all samples are placed in the spinner/reader sample container station 140. For the LBC and non-LBC samples, as described in the explanation of FIG. 8A, the sample racks carrying the sample containers are positioned adjacent the sample holder container stations 140, 160 and the sample tubes are placed individually in a receptacle 142 where they are vortexed and decapped. If the samples are not in a primary sample container that can be directly passed to the analyzers, sample is then aspirated from the sample tube in station 140 by controlling the pipetting robot 481 described elsewhere herein by communication between the pre-analytical system computing device 1350 and the pipetting robot 481. As described elsewhere herein, pipetting robot 481 is controlled to travel within envelope 680 to retrieve and dispose of disposable pipette tips and to aspirate and transfer an aliquot from a primary first-type or second-type container 01, 02 at the primary sample container station 140 to the secondary third-type container 03 at secondary sample container station 160.

After aspiration, the pre-analytical computing device 1350 sends instructions to the diluent dispenser 170 to dispense a predetermined aliquot of diluent into the secondary sample containers. Regarding the control tubes, the pre-analytical system, based on the instructions associated with the control sample via the accession number on the sample container (such processing instructions communicated to the pre-analytical computing device 1350 from the workflow computing device 1330) issues instructions to the decapper robot 450 to decap the control sample. After decapping, the pre-analytical computing device 1350 issues instructions to the diluent dispenser 170 to wet the control reagents, after which the control is recapped by the decapper robot 450.

Once the operation for which the sample container has been decapped is complete, the decapper robot 450 receives instructions to recap the sample container. After the sample has been recapped, the pick and place robot 410 receives instructions to place the recapped sample into sample rack 50. In some embodiments, the sample containers with a common batch designation can be grouped together in sample rack 50, but this is only for efficiency and is not required. The pre-analytical computing device 1350 controls the population of the rack 50 by the pick and place robot. Once the rack 50 has been populated according to the instructions provided by the pre-analytical computing device 1350, and that information has been conveyed to the pre-analytical computing device 1350, the rack elevator 360 is activated to convey the rack 50 to space 200 where the sample containers are unloaded to the batch accumulation area 210 by the pick and place robot 410. Again, the unloading of the sample containers to the batch accumulation area is controlled based on instructions from the pre-analytical computing device 1350.

An embodiment of a process flow for whether or not a sample should be pre-warmed in 230 according to such instructions is illustrated in FIG. 22A. Again, the "window" into this workflow is the information about the sample encoded on the sample container. That information, including processing instructions, is provided from a look up table in a processor (e.g. the pre-analytical computing device 1350). Every sample to be transported from a sample rack in space 114 in the first pre-analytical processing deck 24 is read by the scanner in the conversion assembly 130. As noted above, the scanner communicates with a processor such as the pre-analytical computing device 1350. If the sample is a retest, and has already been pre-warmed, the pre-analytical computing device retains this information. If the workflow associated with a particular sample requires a pre-warm, the pre-analytical computing device 1350 so flags the sample in the system. The samples are associated into batches based on the assay information (e.g. a group of samples for an HPV assay are batched together). The pick and place robot 410 places samples read by the scanner 130 into batches and the samples are populated into racks 50 for transport to the batch accumulation area 210. A virtual queue is prepared by the pre-analytical system computing device

1350. The queue is developed for batches where none of the samples require a pre-warming step, where only some require a prewarm step (and some do not) or all require a prewarm step. Once the queue is determined by the pre-analytical computing device, the batch is released. Such release results in instructions being sent to pick and place robot 410. The samples in the released batcher are populated into the vortexer 220. When vortexing is completed, the samples are depopulated from the vortexer 220 and either sent for pre-warm and then to the cooler or, if the pick and place robot is so instructed by the pre-analytical system computing device 1350, the samples are populated directly into a shuttle 280. Shuttle population is controlled by the pre-analytical system computing device 1350 in communication with a pick and place robot. In those instances where only a portion of batch samples requires pre-warming, receptacles in the shuttle are reserved for the samples in the batch that will be populated into the shuttle after pre-warming is completed. If none of the samples in a batch require pre-warming, the samples in the batch are populated directly into shuttles 280 by the pick and place robots after being vortexed from instructions provided by the pre-analytical computing device 1350.

In one embodiment, prior to sample processing of the sample containers in a rack, the pre-analytical system computing device has developed a pre-processing queue and a conversion queue. These queues are developed from batch information and processing information.

The queue instructions from the pre-analytical device cause the rack 50 to be selected from the main storage deck. From the rack type (which identifies the sample container type; e.g. Surepath containers, Tripath containers, etc.), the pre-analytical system computing device instructs the pick and place robot to remove samples that require a dual test and do not require conversion. For those samples requiring conversion, those sample containers are inspected by camera and if any sample tubes lack a cap or are already pierced, the rack is flagged as one with errors and is returned to the hotel. The pre-analytical computing device 1350 is updated with this information.

If the camera detects no errors, the barcodes on the samples are read and are placed in the primary sample container station where they are vortexed. The sample label is inspected to read the accession number. If no accession number is found, the sample is returned to the rack as not capable of being processed and the information about that sample is updated. If the accession number is read, sample conversion is performed in the sample conversion assembly 130 according to the processing instructions provided to the sample conversion assembly 130 from the pre-analytical computing device 1350. This process is repeated for each sample tube in the rack. The number of tubes removed from the rack are incremented, and sample conversion is complete when the incremented number of tubes equals the number of tubes in the rack. When sample conversion is complete for a sample, the secondary sample container is conveyed to a rack in third sample rack space 114. The rack 50 with the sample containers from which the aliquot of sample was obtained for conversion is returned to the hotel.

If the received rack is determined to be a pass through rack (i.e. the samples in containers do not require conversion) that rack is inspected by the camera for the presence of tubes that might require conversion (i.e. blood collection tubes). If the rack is determined to carry blood collection tubes, that information will cause the pre-analytical system computing device 1350 to place that rack in queue for conversion. If the rack contains a mixture of tubes, that rack is flagged as having issues that prevent further processing. Such information is conveyed to both the pre-analytical computing device and the workflow computing device.

If the received rack does not contain any blood collection tubes, the barcode of each sample is read as described above. The barcode information is transmitted to the workflow computing device for sample preparation instructions. If there are tube codes that indicate the tube is empty, the pre-analytical system computing device 1350 determines what assay and sample type are associated with the empty tube. If the tube code is linked to an accession number, the tube is processed according to the assay protocol assigned to the accession number. In the illustrated embodiment the assays are GBS, HPV, urine, etc. If there are no empty tubes codes, the sample is configured for information that will indicate whether or not the tube is a "neat tube." Such tubes contain samples that do not require preparation. Whatever the tube type, the pre-analytical system computing device typically has workflow instructions that will associate with the code or accession number on the sample container. If the sample is not a "neat tube" and it lacks an accession number, then the tube is placed back in the rack without further processing. If there is an accession number, the sample is processed according to the assay or assays linked to the accession number. Depending upon the assigned assay the tube is placed in queue and batched with other samples for that assay. This sorting is determined by the pre-analytical system computing device 1350. The samples are routed to the batch accumulation area and are further processed according to the assay instructions (i.e. vortexing, pre-warm, loading batches into shuttles, etc.) The workflow will depend on the assay assigned to the accession number and the sample type (e.g. urine, swab, LBC, etc.). The HPV assay requires sample processing steps such as pre-warm that other assays do not require. For certain assays, the sample will require preparation even if the primary sample container is a type 03 tube that can be handled completely by the pre-processing system.

The samples are sorted into batches by the pre-analytical system computing device. Such sorting is virtual. When the complete batch is present in the batch accumulation area 210, the pre-analytical computing device determines if a shuttle is available to receive the batch. Any controls in the batch will have been rehydrated (if required) by the pre-analytical system. As previously described, if the assay requires pre-warming, then those samples that so require are prewarmed and then the shuttle is loaded with the batch. Once loaded the shuttle 280 is transported by the shuttle handling assembly 240 to an outbound belt. By this point, the shuttle should be carrying all prepared samples, all samples that did not require preparation (LBC samples) and any controls for the batch (e.g. HPV assay controls). The pre-analytical computing device, in communication with the workflow computing device, has determined that the analyzer needed to perform the assay on the batch is available by exchanging information about the batch with the analyzer computing device. Such information exchanged will be batch identification information, barcode information for the shuttle and the samples in the shuttle. The shuttle is then conveyed by the shuttle transfer assembly to the designated analyzer. During transfer, the pre-analytical system computing device interrogates the belt sensors and then waits for a signal from the analyzer to indicate a completed hand-off. The analyzer computing device 1350 sends a signal to the analyzer computing device 1360 that it is ready to receive the shuttle. Sensors are activated by the pre-analytical system computing device and, when sensor confirm that the belts are working properly, the shuttle is conveyed back to the shuttle handling assembly 240. When received, the pre-analytical computing device receives a signal from the shuttle handling assembly 240 and the pre-analytical computing device 1330 sends a signal to the analyzer computing device 1360 that the shuttle 280 has been received. Since one batch can be more than one shuttle; the pre-analytical system queries whether the shuttle was the last in a batch. If not, the process is repeated.

In one embodiment of a workflow for LBC samples and for sample containers that require conversion, the workflow presumes racks of LBC sample and sample containers that require conversion have been loaded into the system and stored in the hotel. The pre-analytical system computing device then calls for a rack of the LBC samples, which are processes through the sample conversion assembly 130. If there are multiple such racks, they can be placed in the all available rack positions associated with sample conversion assembly. This allows the use of multiple decappers, and pick and spin apparatus to process the plurality of LBC containers. Once there are no more LBC sample racks to process, the pre-analytical system computing device 1330 then orders racks carrying samples that require sample conversion. If there are, such racks are conveyed from the hotel to the sample conversion assembly. The pre-analytical computing device controls conversion of the samples from the sample container into the secondary sample containers for processing. The rack with the samples from which sample aliquots were obtained is then returned to the hotel. If there is no rack ready for conversion, but the pre-analytical computing device determines that there is room in the sample queue, the pre-analytical computing device queries inventory to determine if there are any racks that do not require sample conversion (i.e. a pass through rack). Once samples are processed out of a rack by the sample conversion assembly 130, the racks are returned to the hotel.

When the processing queue is full, the resources of the sample conversion assembly can be used to inventory both LBC sample-containing racks and racks of samples that require conversion. Referring to FIG. 22E, the pre-analytical computing device coordinates the processing of samples out of the rack as described above, but the processed or pass through samples are held in the on the first preparation deck 24 and not transported to the second preparation deck 26 until the queue can accept them. Once the samples are inventoried on the first preparation deck 24 the rack carrying the samples to the sample conversion assembly is returned to the hotel.

In one embodiment of the workflow, the pre-analytical computing device does not know from the accession number the specific assay at the time that the sample is being prepared. So parallel processing occurs when the samples are retrieved from the rack and placed in the sample conversion apparatus 130. The sample is placed in the bar code reader. The barcode is sent to the workflow computing device as the sample is placed in the vortexer of the sample conversion apparatus. During vortexing, the pick and place apparatus 410 retrieves an empty secondary sample processing container, the barcode is read and it is decapped while in the secondary sample container station 160. Parallel to this, the workflow information is received by the pre-analytical system computing device 1350. The computing device waits for a predetermined time and, if no information is received, a second predetermined time. If a reply is received before a time out, the sample tube is decapped using decapper 450; sample is aspirated from the sample tube and inoculated into the secondary sample container using robotic pipettor 481. Diluent is then dispensed into the secondary sample container on instructions from the pre-analytical computing device 1330, after which time the pre-analytical computing device is recapped. The secondary sample container is linked to the primary sample container by the pre-analytical computing device 1350.

If the query to the laboratory information system times out, the sample container is returned to the rack and another sample retrieved. Optionally, the query can be attempted again, and, if a reply is ultimately received, then the sample container will need to be obtained from the rack.

For samples that do not require conversion, there is no parallel processing and the sample is placed in queue while waiting for the workflow information for those samples. If no reply is received from the laboratory information system regarding the assays for the queried sample, the sample is ultimately returned to the rack. The sample can remain in queue until the query to the laboratory information system times out.

A process flow for loading racks is illustrated in FIG. 22F. When a rack is received into the pre-analytical system, there is a bar code reader that reads the barcode on the rack. That information is provided to the pre-analytical system computing device 1350. The pre-analytical computing device determines from the bar code whether the rack contains sample containers or consumables for sample preparation and testing (e.g. assay control reagents, pipette tips, empty secondary sample containers, etc.). If the rack is determined to carry samples, the pre-analytical system computing device queries its memory to determine if the user interface has indicated that the rack is a priority rack. If yes, the pre-analytical computing device 1350 places this rack at a place in the processing queue consistent with its priority designation. If no, the pre-analytical device places the rack at the end of the processing queue. The pre-analytical computing device develops a rack processing queue that is typically first in and first out, with rack priority designations received from the user the mechanism by which racks are advanced in the queue.

For racks of consumables, those are typically placed in the back of the queue for racks bringing consumables into the pre-analytical system. Therefore, in this embodiment, the pre-analytical computing device 1350 manages and updates two queues, one being the sample rack queue and the other the consumable rack queue. Once a rack is assigned a place in its queue, the queue is updated in the pre-analytical computing device 1330, which then issues instructions to the rack handler robot 320 to move the rack to the storage deck 22.

Pipette Head

Figure 27:
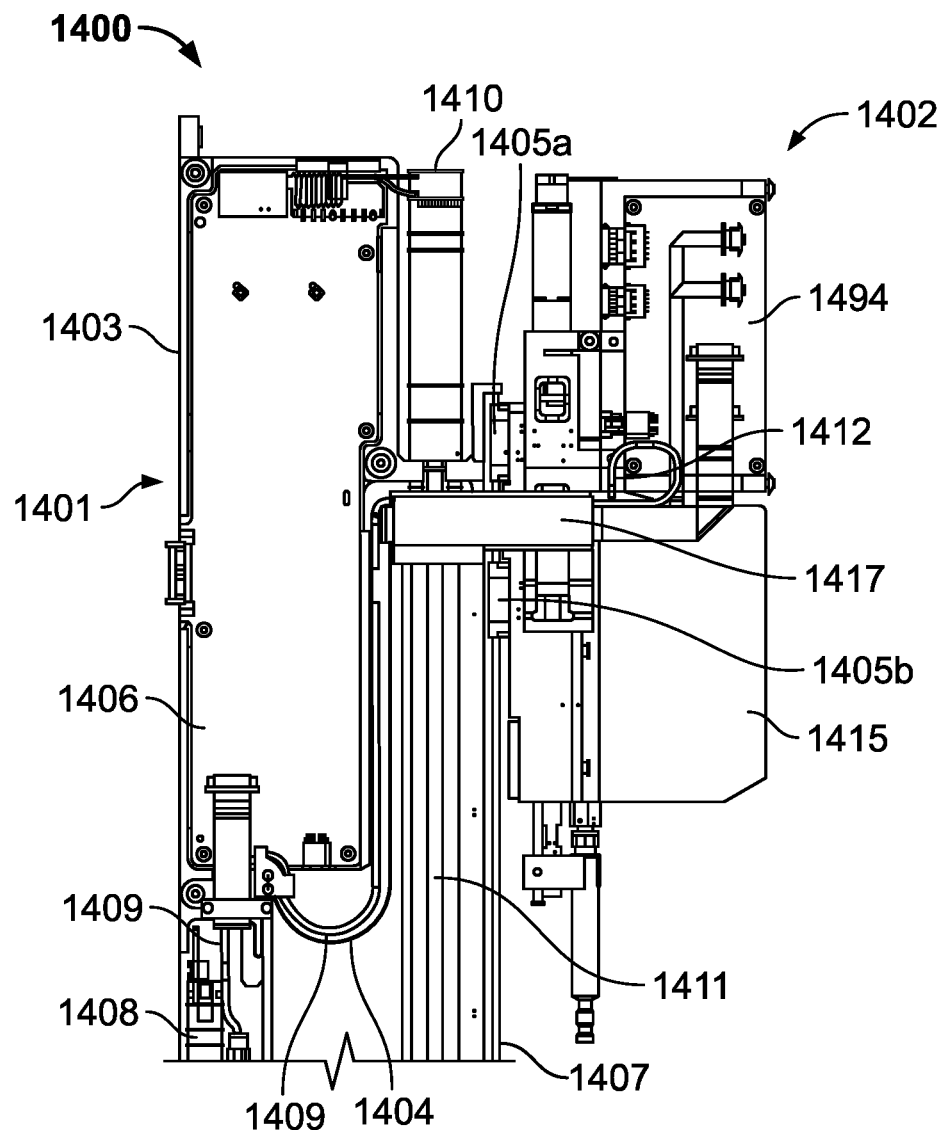
FIG. 27 is a front, partial cutaway view of a pipette head according to a further embodiment of the present disclosure.

FIG. 27 depicts a pipette head 1400 according to another embodiment of the present disclosure. Pipette head 1400 is similar to pipette head 500 in that it includes a main board 1401 and pipette assembly 1402. Pipette assembly 1402 is similar to pipette assembly 502 but differs with regard to the connector arm 1417 which is described below. Additionally, pipette head 1400 differs in that pipette head 1400 has an integrated z-axis drive mechanism. In other words, the z-axis drive mechanism of pipette head 1400 couples main board 1401 to pipette assembly 1402 whereas the z-axis drive mechanism of robot 481 couples pipette head 500, via main board 501, to pipette arm 483. This allows pipette assembly 1402 to be moved vertically relative to main board 1401.

Main board 1401 includes a housing or shell 1403 which includes various components disposed therein that interconnect with pipette assembly 1402. For example, in the depicted embodiment, housing 1403 includes a printed circuit board ("PCB") 1406 and a valve 1408 disposed therein. PCB 1406 provides data and power to pipette assembly 1402 via interconnect cable 1404. Valve 1408 connects to positive and negative pressure inputs (not shown). Valve 1408 combines these inputs and outputs a positive or negative pressure via a single conduit 1409 such that the pressure of a liquid or gas disposed within conduit 1409 can be regulated to control sample aspiration.

In this regard, interconnect cable 1404 and conduit 1409 are connected to pipette assembly 1402 via connector arm 1417 of pipette assembly 1402. This differs from connector arm 517 of assembly 502 in that positive and negative pressure inputs are connected directly to connector arm 517. Instead, conduit 1409 and interconnect cable 1404 are routed through housing 1403 and connector arm 1417 to pipette assembly 1402. At pipette assembly 1402, cable 1404 is connected to control unit 1494 and control unit 1415, and conduit 1409 is connected to the pipette channel via control unit 1412.

The z-axis drive mechanism of head 1400 includes a vertical rail 1407, motor 1410, and drive shaft 1411. Vertical rail 1407 extends along an outer surface of housing 1403 and drive shaft 1411 extends into housing 1403 adjacent to and offset from vertical rail 1407. Motor 1410 is connected to drive shaft 1411 and is mounted to an outer surface of housing 1403 for ease of maintenance. However, motor 1410 may also be disposed within housing 1403. Connector arm 1417 is threadedly connected to drive shaft 1411 so that rotation of drive shaft 1411 drives pipette assembly 1402 vertically or along a z-axis in up or down directions. Cable 1404 and conduit 1409 may be provided with slack so as to allow connector arm 1417 to travel vertically without tensioning and possibly damaging cable 1404 and conduit 1409. Motor 1410 is connected to and is controlled by PCB 1406. In this regard, controller 1494 can detect liquid levels via a disposable pipette tip (not shown) and send a detection signal to PCB 1406 via cable 1404. PCB 1406 can control motor 1410 in response to such signal which can include stopping the vertical travel of pipette assembly 1402 in response to a liquid level detection or moving pipette assembly 1402 a predefined rate in response to such signal so as to aspirate a sample into a disposable pipette tip in a regulated manner.

Pipette assembly 1402 is stabilized during vertical travel by vertical rail 1407 being connected to pipette assembly 1402. In particular, pipette assembly 1402 is hingedly connected to vertical rail 1407 via a first and second hinge mount 1405*a-b*. Hinge mounts 1405*a-b* are slidably connected to vertical rail 1407 and are vertically offset from each other such that connector arm 1417 is disposed therebetween. This allows pipette assembly 1402 to pivot about hinge mounts 1405*a-b* without interference by connector arm 1417.

In this regard, pipette assembly 1402 has a first hinge position and a second hinge position. In the first hinge position, pipette assembly 1402 is generally in planar alignment with or at zero degrees relative to main board 1401 as depicted in FIG. 27. In the second position, pipette assembly 1402 is rotated about hinge mounts 1405*a-b* from the first position about 180 degrees so that pipette assembly 1402 is in planar offset from main board 1401 as depicted in FIGS. 28A-29. However, it should be understood that pipette assembly 1402 can be oriented relative to main board 1401 to any angle between 0 and 180 degrees.

Figure 28B:
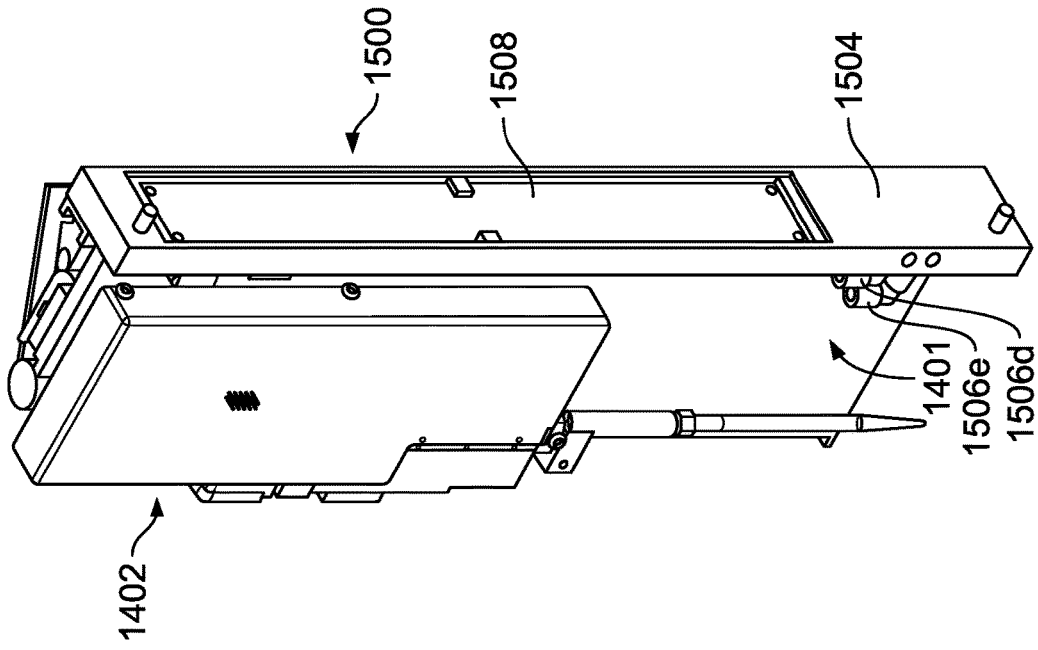
FIGS. 28A and 28B are alternating rear perspective views of a backplane connector connected to the pipette head of FIG. 27.
Figure 28A:
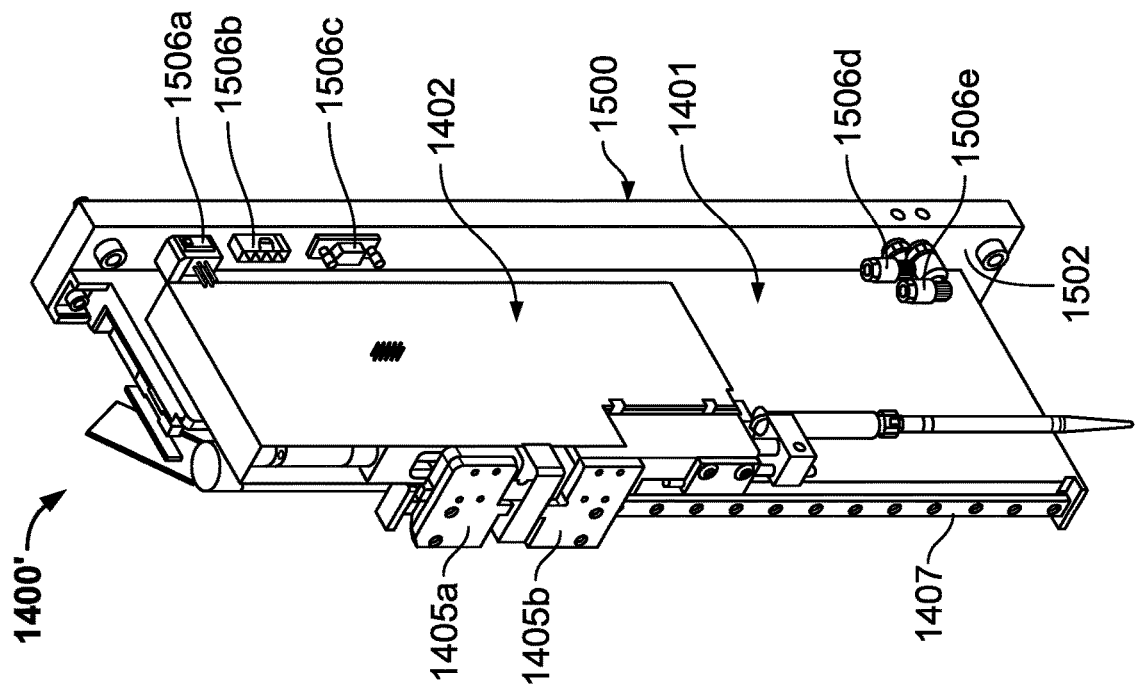
Figure 29:
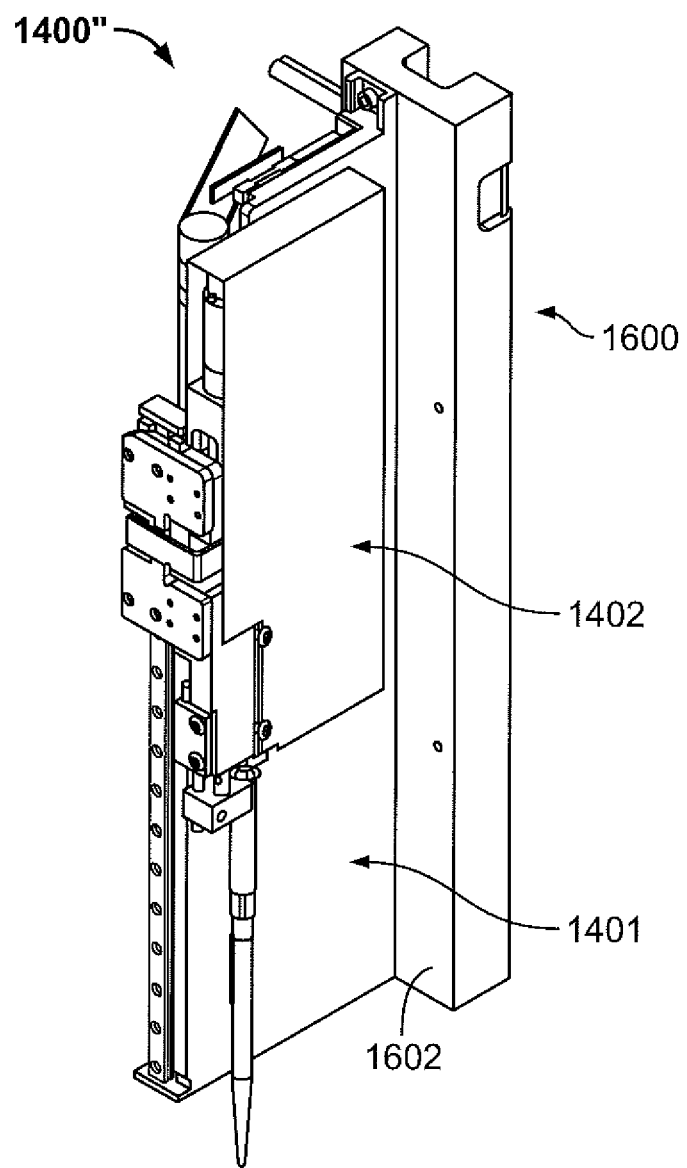
FIG. 29 is a perspective views of a backplane connector connected to the pipette head of FIG. 27.

FIGS. 28A and 28B also depict an alternative pipette head embodiment 1400' in which main board 1401 and pipette assembly 1402 are connected to a backplane connector 1500. Backplane connector 1500 connects main board 1401 and pipette assembly 1402 to a pipette arm, such as arm 483. In addition, backplane connector 1500 includes one or more connectors 1506*a-e*. For example, in the embodiment depicted, backplane connector 1500 has a first surface 1502 and a second surface 1504. First surface 1502 is connected to a surface of housing 1401 at an opposite side from pipette assembly 1402. Second surface 1504 connects to a pipette arm. First surface 1502 includes several connectors including an Ethernet connector 1506*a*, a power connector 1506*b*, a multipin connector 1506*c*, positive pressure input connector 1506*d*, and vacuum pressure input connector 1506*e*. Thus, these connectors 1506*a-e* face a direction toward pipette assembly 1402. More or less connectors may be provided at this surface 1502 as needed. A PCB 1508 is disposed within backplane connector 1500 and connects connectors 1506*a-b* to PCB board 1406 within main board housing 1403.

FIG. 29 depicts another alternative pipette head embodiment 1400" in which main board 1401 and pipette assembly 1402 are connected to a backplane connector 1600. Backplane connector 1600 is similar to backplane connector 1500 in that it is connected to main board 1401 and connects to a pipette arm, such as arm 483. However, backplane connector 1600 differs in that connectors are disposed within a backplane connector housing and face a direction away from pipette assembly 1402.

The system 10 described herein includes a plurality of robotic mechanisms that translate through a plurality of positions. A home position is provided for each mechanism such that, when the system "reboots" after a power outage or reset, the robotic mechanisms are all at their home position at the time of the reboot. In one embodiment, the system 10 has a power recovery module. Before returning to normal processing, an inventory is performed in the conversion/preparation module 710, shuttle processing module 750, and the consumable accumulation module 760. Based upon the inventory, the system 10 compares the last known consumable status before the outage with the post-outage inventory. After the inventory, the system resumes normal processing.

When the system 10, or its components, enters a pause state, the sample processing currently ongoing is completed to the extent possible. For those samples in a warmer 230, the warming cycle times out (if cycle times are equal to or less than a threshold), after which time the samples are transferred to a cooler 290. To the extent that samples are in queue to be sent to a diagnostic module ($A_1, A_2, A_n$), those samples are transferred after a shuttle returns home. From the first pre-analytical processing deck 24, the sample racks 30, 40, 50 are cleared and placed in the rack storage area 22. An instruction is sent prohibiting samples from being transferred from one deck level to another until normal processing resumes. All deck level motors are shut off and the doors to system 10 are unlocked after which a message is sent to an operator that the system 10 has entered a paused state.

When recovering from a pause state, the operator first has the system 10 re-read the barcode on samples or shuttles removed by the operator in response to the pause error. The operator then closes the door and activates the door lock. The system 10 then interrogates the operator to determine the cause of the error and the operator response. The system 10 then runs through a checklist to address possible problems (e.g., if a shuttle is in the penalty box, it is evaluated to determine if it has a stuck pipette tip). The positions of the pick-and-place robots 410*b-c* are inspected to determine if the back of the apparatus was accessed during pause and, in doing so, such robots 410*b-c* were moved. Robots 410*b-c* transition to home positions as noted above. If there are tubes in the vortexer 220, the system 10 reenters the pause state so that they may be removed. If there is a third-type sample container 03 in a tube holder, the system 10 is re-paused so that the third-type sample container can be removed.

Figure 22G:
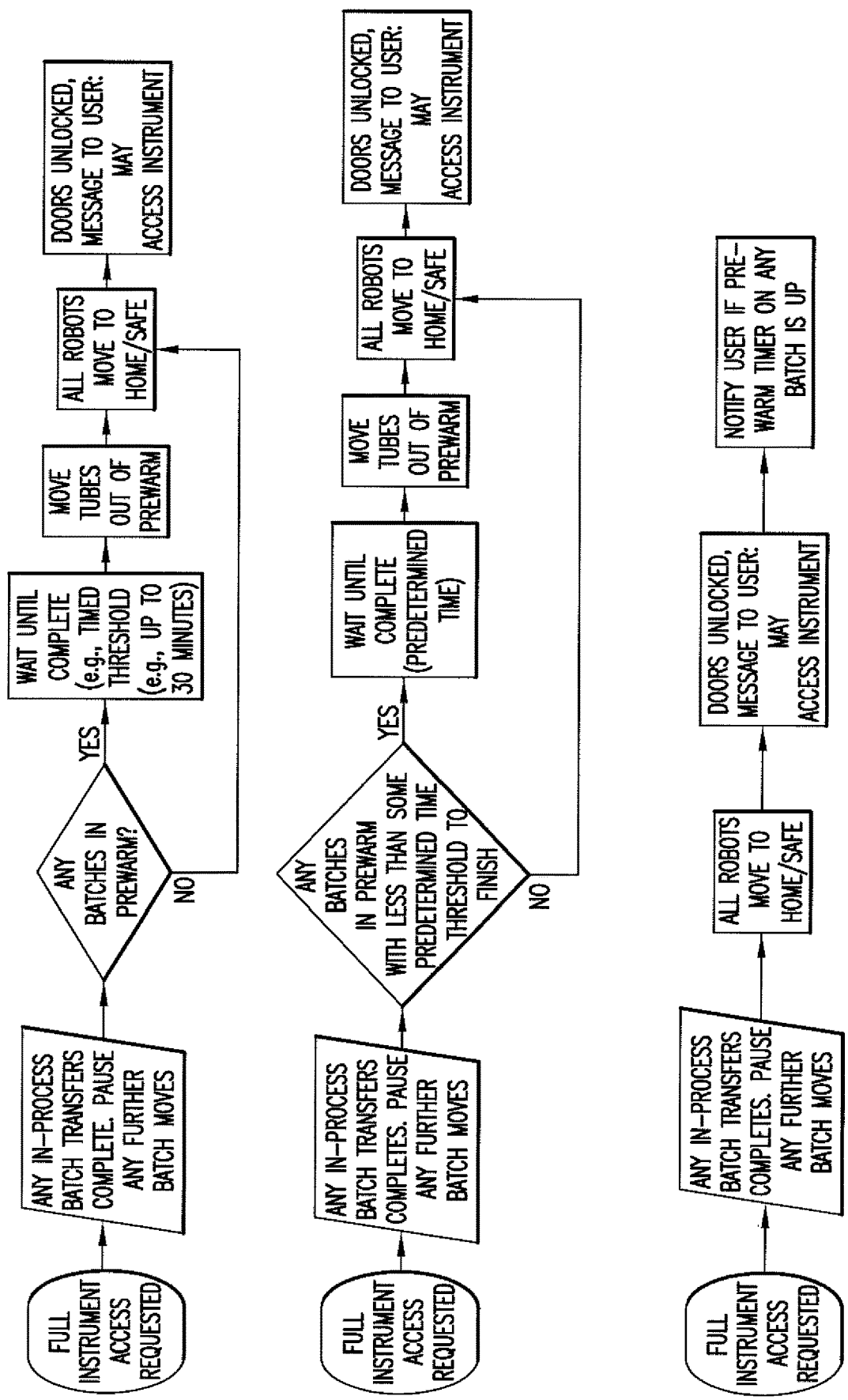

FIG. 22G illustrates embodiments of system responses when an operator requests instrument access. In one example, the pre-analytical system is in the process of performing a batch transfer. Any batch transfers in progress are completed. If there are any samples in prewarm, prewarm is completed and those tubes in prewarm are moved out of the warmer. The robots then move to their home positions. In another embodiment, there is time threshold for allowing samples to complete prewarm. The prewarm completes for those samples where the prewarm time is under the specified threshold. When prewarm is completed, the samples are moved out of prewarm and the robots return to home, after which the access doors are unlocked and the user can access the system. In another embodiment the request for access allows batch transfers to complete, pauses further batch transfers, has the robots return to home and unlocks the system for access. In this embodiment, prewarm is allowed to continue but the user is notified if any prewarm has timed out.

If a shuttle 280 is in the unload spot, such as on platform 260*c*, it is retrieved by the shuttle robot 240, its barcode is read and it is returned to the unload spot 260*c*. If all of the sample containers in the shuttle 280 are processed, then the shuttle 280 is parked by the shuttle robot 240. If all of the samples are not processed, the unprocessed samples are marked as ejected and a shuttle error is processed. Once any and all errors are cleared, the elevator 360 is brought back online and rack handler robot 320 brings the racks 30, 40 or 50 back up to the processing deck.

As noted above, the system 10 proceeds with an inventory when restarting from a pause state. For example, the robots within system 10 are interrogated to determine if they are in their home position. If the robots are not, then the system 10 places them in the home position. If the robots/shuttles/vortexers contain sample containers, the system 10 reenters the pause state until the sample containers are cleared therefrom.

As noted above, the system can either pass-through samples that are already prepared to be processed by the one or more analyzers. Typically, when racks are loaded into the rack, the samples carried by the rack are either samples that require conversion or samples that do not require conversion. The information regarding the pre-processing requirements for the samples carried by the rack is carried by the rack label. Each sample container also has an accession number which is linked to information about the pre-processing requirements for a particular sample. The accession number is associated with the sample by the workflow computing device 1330. When the rack label information and the sample accession number is communicated to the pre-analytical system computing device 1350, the pre-analytical computing device 1350 communicates with the controllers of the various subsystems in the pre-analytical system 10 (e.g. the conversion assembly 130, the rack handler robot 320, the pick and place robot 410, the robotic pipette 481, etc.).

Optional Tray

FIGS. 30A-30D illustrate an optional tray for use with system 10 as described herein. Tray can be utilized for transporting any of containers 01, 02, and 03, which may occur external to the housing of system 10. Such containers are collectively referred to as container 1710 in the following description. In addition to being capable of transporting a plurality of containers 1710, tray 1710 may also be used to help load any of racks 30, 40, and 50, which are collectively referred to as rack 1720, with respective containers 01, 02, 03.

As depicted in FIG. 30A, tray 1700 has receptacles 1705 adapted to receive empty consumable tubes 1710. Such sample consumable tubes 1710 are typically cylindrical. In addition, tray 1700 includes a handle 1704 integrated into an end thereof adjacent receptacles 1705. Tray 1700 has a vertical profile that allows tray 1700 to be used as a carrier tray 1700 for the sample containers and/or as a lid to be placed on top of sample containers 1710 disposed in another tray.

Figure 30B:
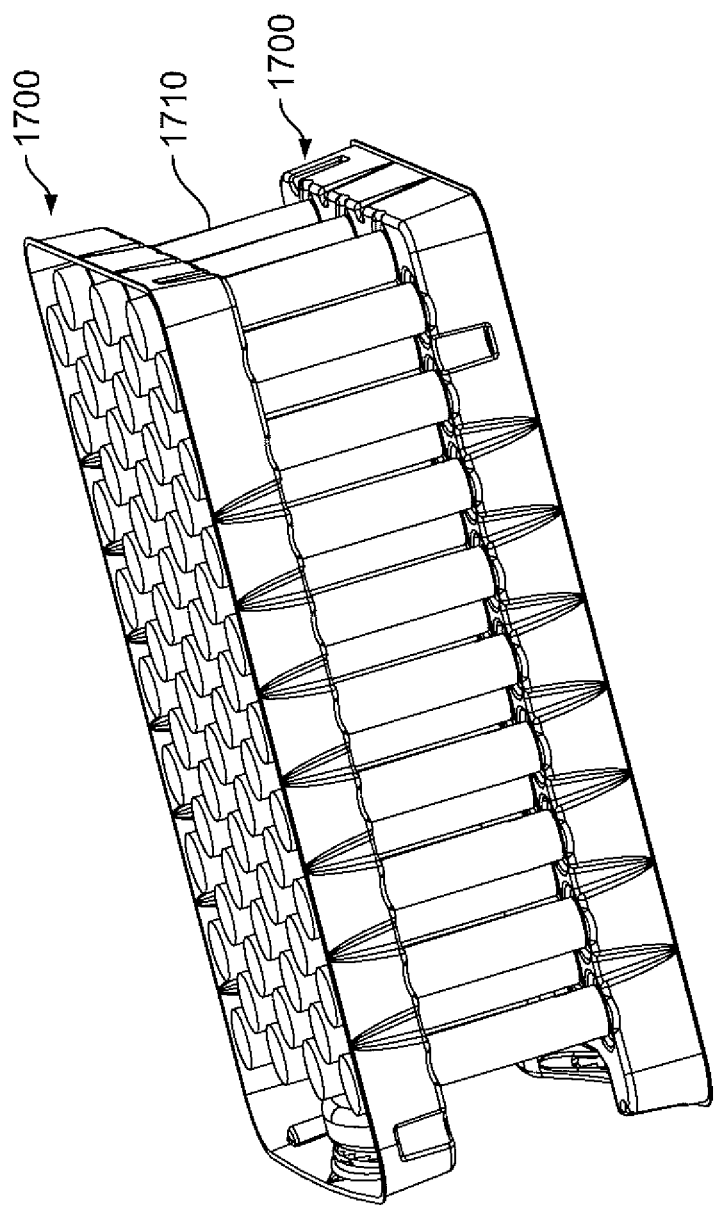

FIG. 30B illustrates the embodiment where the consumables are received with one tray 1700 supporting one end of the consumable tubes 1710 and a second tray 1700 retaining the opposite end of the consumable tubes 1710. In other embodiments, the consumable tubes 1710 are received supported by only one tray 1700.

Figure 30C:
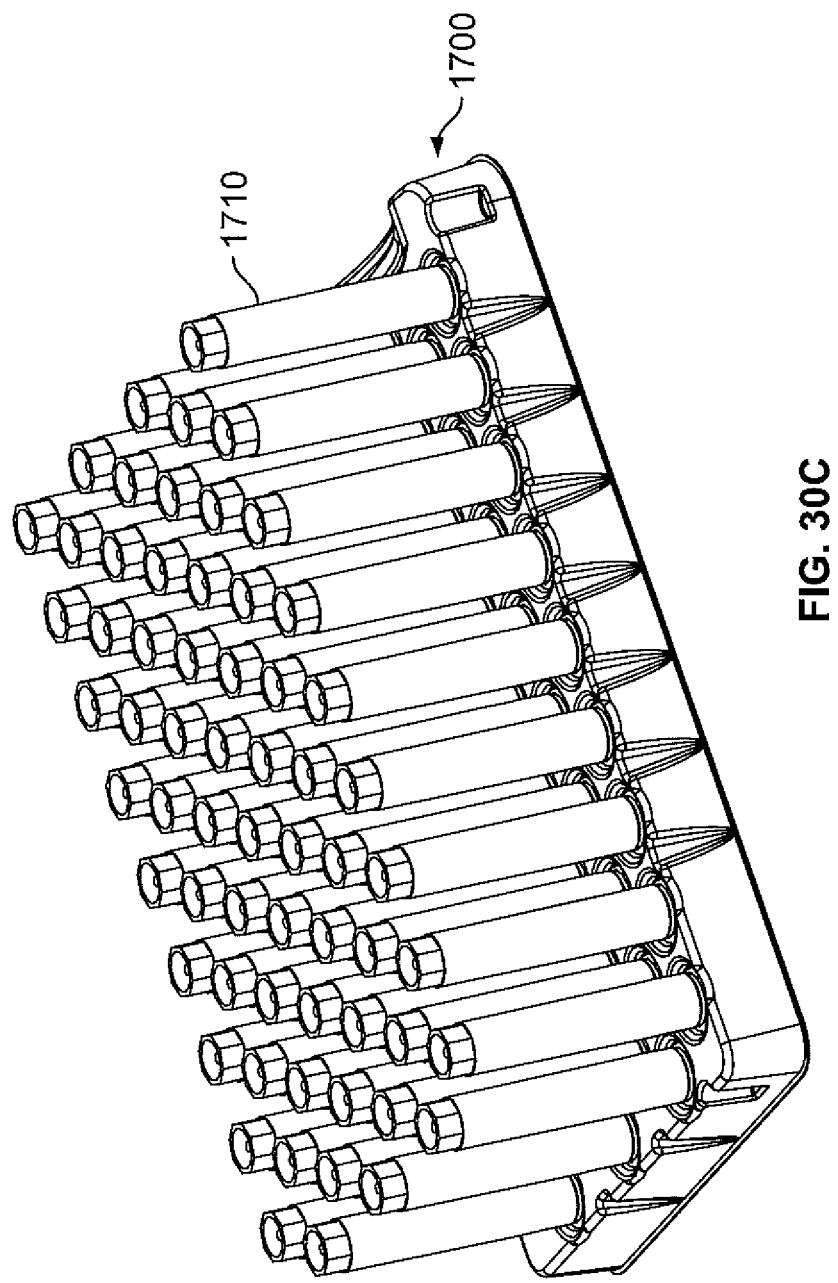

FIG. 30C illustrates the embodiment where the consumable tubes 1710 are received disposed in one tray 1700. Note that, in this embodiment, the consumable tubes are oriented upside down, so that a cap end of the consumable tubes 1710 is supported by the tray 1700. In this orientation relative to tubes 1710, a rack 1720 with receptacles 1725 therein can receive consumable tubes 1710 so that rack 1720 can be used to deliver the consumables tubes 1710 into the automated pre-analytical system 10 described herein. The receptacles 1725 in rack 1720 are sized such that they cannot receive the cap end of the consumable tubes 1710. This ensures that the consumable tubes 1710 are delivered into the rack 1720 in the proper orientation.

Figure 30D:
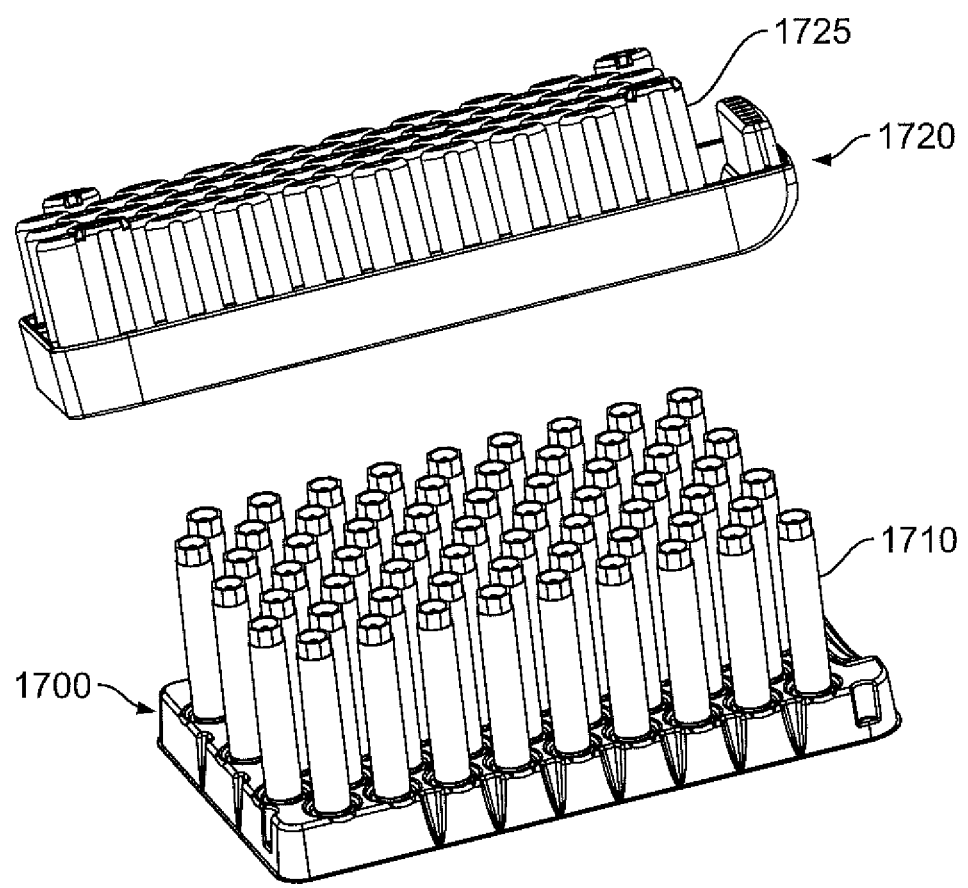

FIG. 30D illustrates the rack 1720 being inverted and brought over the array of consumable tubes 1710 supported by the tray 1700. As noted above, the rack 1720 is brought over the consumable tubes 1710 such that the bottom end (the end opposite the capped end) of the consumable tubes 1710 extends into the receptacles 1725 of the rack 1720. The receptacles 1705, 1725 of the tray 1700 and the rack 1720, respectively, are dimensioned to retain the consumable tubes 1710 in a substantially vertical orientation but not so snugly that force is required to remove the consumable tubes 1710 from the tray 1700 or the rack 1720.

Figure 30E:
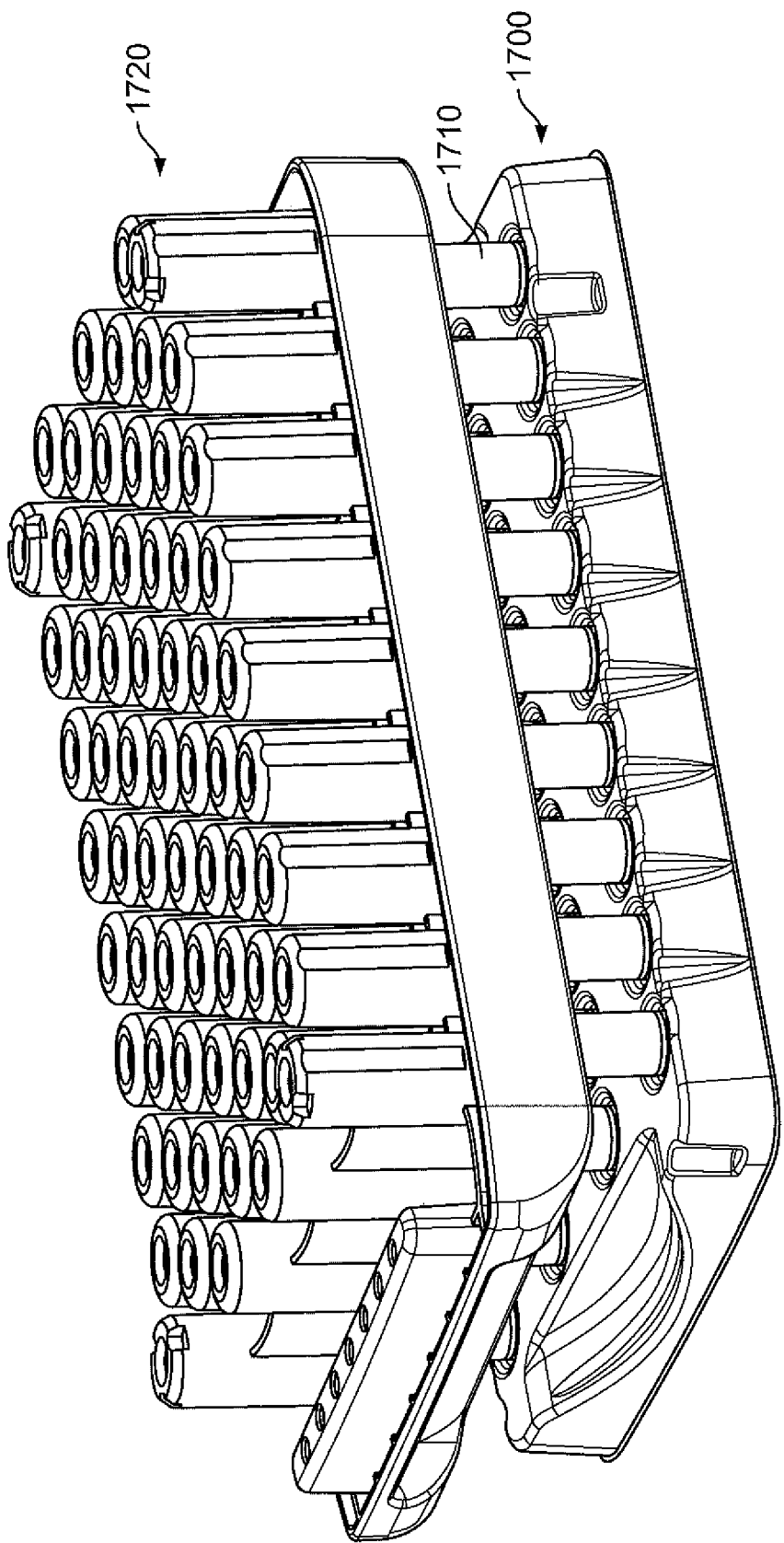

FIG. 30E illustrates the rack 1720 placed over the consumable tubes 1710 supported by the tray 1700. After the rack 1720 is so placed, the assembly illustrated in FIG. 30D is inverted, the tray 1700 removed from the assembly and the rack 1720 carrying the tubes 1710 with the cap ends up is placed in the pre-analytical system 10 described herein. The loading of racks 1720 into the pre-analytical system 10 is described elsewhere herein.

Alternative Decapper Assembly

FIGS. 31A-31L depict an alternative decapper assembly 2000 to that of decapper assembly 470. In this regard, decapper assembly 2000 can be carried by decapper robot 450. As previously mentioned, decapper robot 450 can be utilized to move sample containers 01, 02, and 03 to and from racks 30, 40, and 50, respectively. However, this can be challenging as containers 01, 02, and 03 are located in a dense array of rack receptacles, such as receptacles 32, 42, or 52, so that the distance directly between each container is small which limits the useable space around a target container for grippers to grip such container. This is made even more challenging in that the same decapper that retrieves the target container also decaps the container. Thus, a decapper assembly and its container grippers may be bulkier than might otherwise be needed only for container transport so that the decapper assembly can deliver enough torque to a wide range of container caps. Such torque may be 30 in-lbs (3.4 Nm) or less. In addition, many of the containers utilized in system 10 have a penetrable seal, such as container 03, that should be avoided to prevent incidental and unwanted penetration which could result in contamination.

As illustrated in FIG. 31J, sample containers 03 are arrayed in a rack 50', which is a smaller, exemplary version of rack 50. For a decapper having three gripper fingers, target locations A, B, and C for each gripper finger relative to a target container T and to containers surrounding the target container are specifically located to position container grippers within useable space and to avoid contacting a penetrable seal. Such locations A, B, and C, may each correspond to a space within a triangular formation of three adjacent sample containers, one of which being the target container T, wherein each container defines an apex of the triangle. Decapper assembly, is configured to consistently position gripper fingers in such locations A, B, and C and to reliably handle thousands of containers while being able to deliver enough torque to open a wide variety of container caps.

As shown, decapper assembly 2000 generally includes a gripper motor 2002a, a decapper motor 2002b, a plurality of gears, a plurality of gripper assemblies 2100, a container contact sensor assembly 2060, a rotational home sensor assembly, and a guide plate 2050. Gripper motor 2002a is connected to a gripper pinion 2004a. Decapper motor 2002b is connected to a decapper pinion 2004b. The plurality of gears includes first and second gripper gears 2010, 2032 and a decapper gear 2020. Second gripper gear 2032 is connected to a main shaft 2034 which extends from second griper gear 2032 in a direction parallel to a rotational axis thereof, as best shown in FIG. 31K. Main shaft 2034 has a longitudinal opening that is configured to receive a plunger shaft 2062 which is described further below. Such gears 2010, 2032, 2020 can be made from several different types of materials including brass, stainless steel, and plastic.

A gripper assembly 2100 is shown in detail in FIGS. 31G-31I. Decapper assembly 2000 preferably includes three gripper assemblies, such as a first, second and third gripper assembly 2100a-c. However, more or less gripper assemblies 2100 are contemplated. Each gripper assembly 2100 includes a gripper arm 2120, gripper finger 2130, and a planetary gear 2110. A torsion spring 2140, as shown in FIG. 31F, is optionally provided in the gripper assembly. As shown in FIG. 31H, gripper arm 2120 includes an upper arm portion 2122 and a lower arm portion 2124. Upper arm portion 2122 includes a cylindrical projection 2121 extending in an upward direction and an opening 2123 that extends through the entirety of upper arm portion 2122 including the cylindrical projection 2121. Bearings 2128 are press-fit within opening 2123 of upper arm portion 2122. Planetary gear 2110 is positioned over cylindrical projection 2123 and is fixed to upper arm 2122 via a plurality of fasteners 2104. Gripper arm 2120 may be made from a metallic material, such as aluminum, while planetary gear 2110 may be made from a polymer material. Connecting bearings 2128 to upper portion of gripper arm 2122, rather than to planetary gear 2110, helps provide robustness and reduces play.

Lower arm portion 2124 has an axis offset from an axis of upper arm portion 2122. An opening extends through lower arm portion 2124 which is configured to receive a gripper finger 2130 and a fastener 2102, as best shown in FIG. 31I. A notch 2126 extends into lower arm portion 2124 from an exterior thereof for engagement with torsion spring 2140. Gripper finger 2130 includes a connection post 2132, a collar 2134 and a gripper portion 2136. Connection post 2132 includes a threaded opening. Gripper portion 2136 is separated from connection post 2132 by collar 2134 and includes a fully-rounded end 2138 and straight knurling. Fully-rounded end 2138 helps reduce incidence of container pick-up failure by providing tolerance to misalignment of finger 2130 to the target container T. When connected to lower arm portion 2124, post 2132 of gripper finger 2130 is received within the opening of lower arm portion 2124 so that collar 2134 contacts a bottom end of lower arm portion 2124 and fastener 2102 fixes gripper finger 2130 in position. This configuration allows gripper finger 2130 to be easily replaced without the need for disassembly of other components.

Container contact sensor assembly 2060 is shown in detail in FIGS. 31K and 31L. Container contact sensor assembly 2060 includes a sensor 2064a-b, a plunger 2061 and a keyed plunger cap 2065. Plunger 2061 includes a plunger shaft 2062 and an end portion 2063 that has a larger cross-sectional dimension than shaft 2062. Keyed plunger cap 2065 includes a plurality of fins 2066 extending from a central body 2067. In the particular embodiment depicted, there are three fins 2066 circumferentially distributed in a proximately symmetric pattern around central body 2067. These fins 2066 are keyed to slots 2054 in guide plate 2050. In addition, plunger cap 2065 includes extension members 2068 that extend radially outwardly from a bottom end of each fin 2066. Central body 2067 includes a threaded opening at one end thereof which is threadedly connected to shaft 2061. At another end of central body 2067, fins 2066 and central body 2067 define a tapering recess 2069. This tapering recess 2069 allows for a cylindrical cap 091 of a sample container 03 to contact fins 2066 at a radial edge of the cap 091 without disturbing a penetrable seal disposed inwardly of the radial edge of cap 091, as is illustrated in FIG. 31K. Such tapering recess 2069 allows caps of various sizes to contact fins 2066 in this manner. The sensor 2064 may be a Hall effect sensor, optical sensor, or the like. In the particular embodiment depicted, sensor 2064 is an optical sensor and includes first and second sensor elements 2064a-b that are so positioned as to form a gap therebetween. First sensor 2064a may be an emitter and second sensor 2064b may be a detector. As described below, end portion 2063 of shaft 2062 may be utilized in conjunction with sensor 2064 so that end portion 2063 extends through the gap to interfere with emissions between first and second sensor elements 2064a-b so as to produce a signal indicating the presence of a cap 091 between gripper fingers 20130 which initiates a grip sequence.

The rotational home sensor assembly includes a slotted disc 2040 and a sensor 2044. Sensor 2040 may be an optical sensor and may include first and second sensor elements 2044a-b similar to that of sensor 2064. In this regard, first and second sensor elements 2064a-b are so positioned as to form a gap therebetween. As described below, slotted disc 2040 may be utilized in conjunction with sensor 2044 so that disc 2040 interferes with emissions between first and second sensor 2044a-b except when sensors 2044a-b are aligned with slot 242 thereby generating a signal that rotational home of decapper assembly 2000 has been achieved.

When decapper assembly 2000 is fully assembled, the gripper motor 2002a and decapper motor 2002b may be face-mounted to a mounting plate 2072. Mounting plate 2072 is connected to a support arm 2070 which may be suspended from robot 450. The mounting plate 2072 includes notches 2074 extending through and edge 2074 thereof which allows motors 2002*a* and 2002*b* to be slid into such notches and fixed to the mount 2072 via fasteners. This allows for easy removal and replacement of motors 2002*a-b* without extensive disassembly of other components. A first sensor support arm 2076 is also connected to mounting plate 2072 and is suspended therefrom. Sensor elements 2044*a-b* are connected to first support arm 2076 and are vertically arranged so as to form a gap therebetween. Sensor elements 2064*a-b* are also supported by mounting plate 2072 via a second sensor support arm 2077 that extends above mounting plate 2072. Sensor elements 2044*a-b* are horizontally arranged so as to form a gap therebetween.

Figures 31A, 31B:
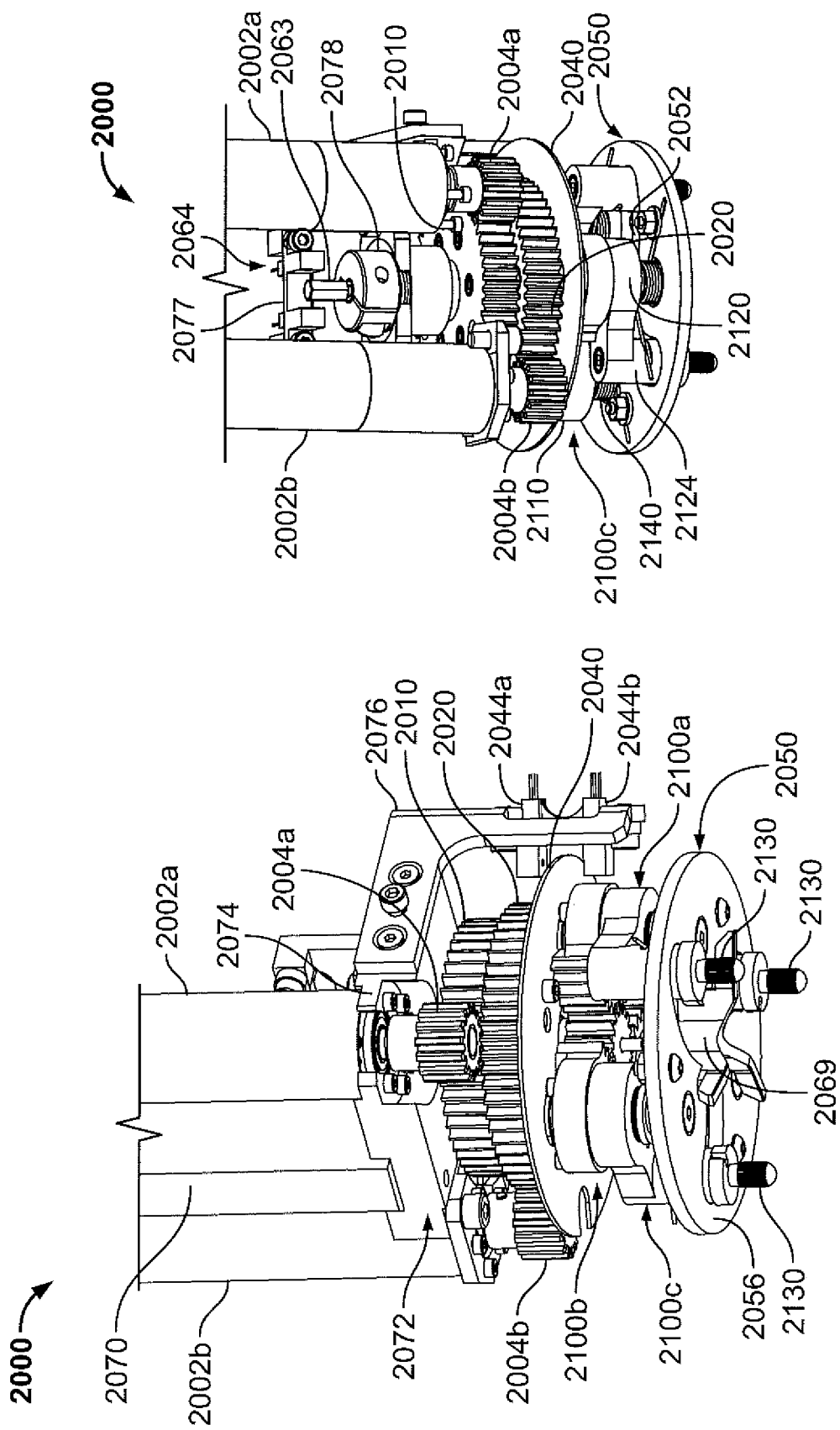
FIGS. 31A-31C are perspective views of a decapper assembly according to another embodiment of the present disclosure.
Figure 31D:
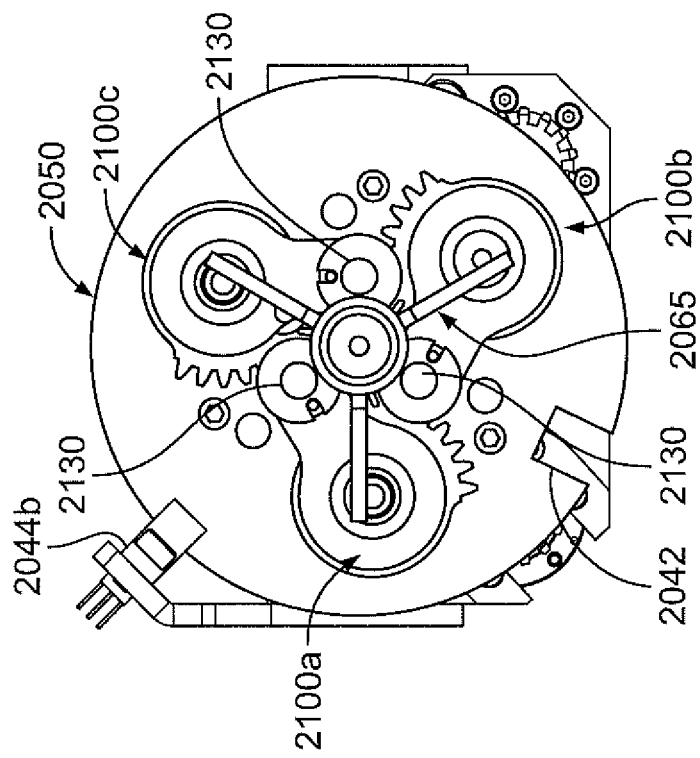
FIG. 31D is a bottom view of the decapper assembly of FIG. 31A.
Figure 31C:
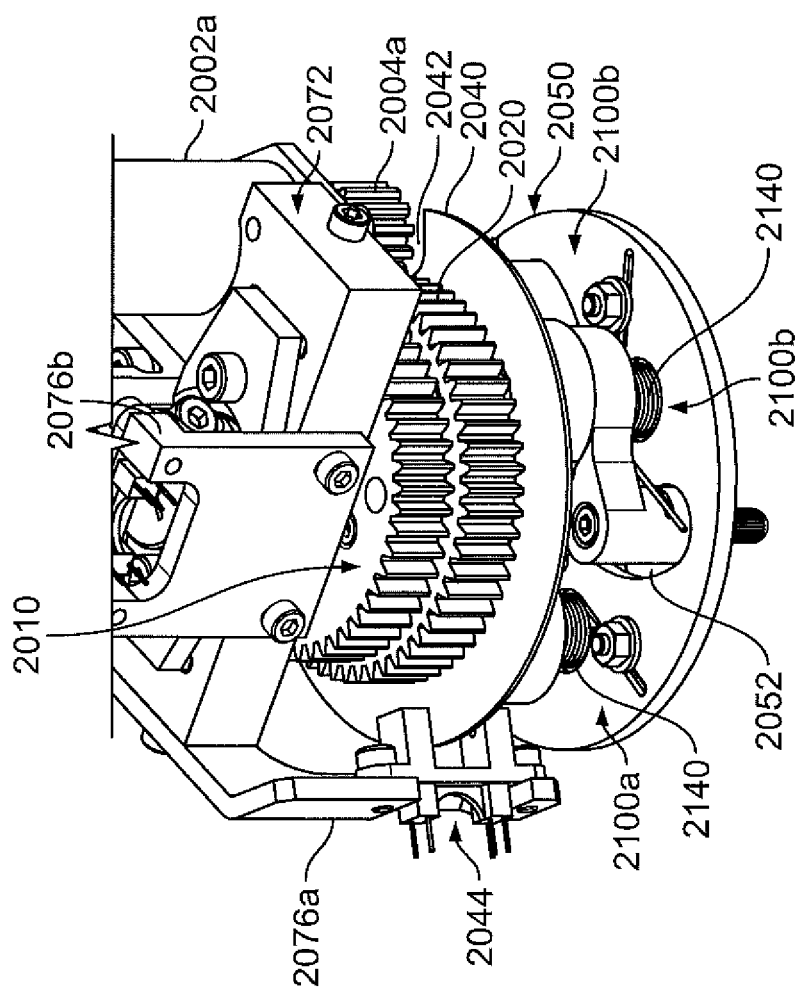
Figure 31E:
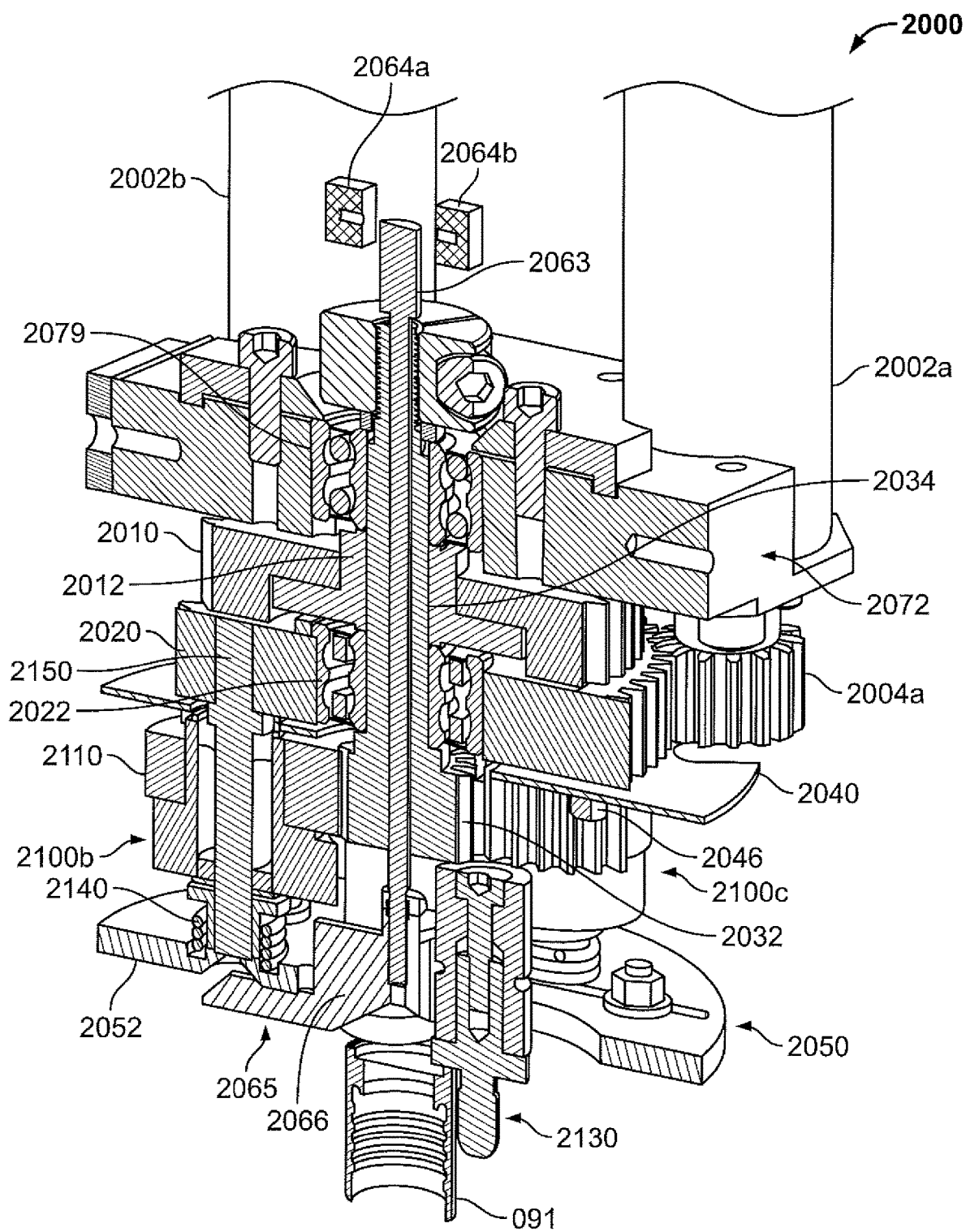
FIG. 31E is a sectional view of the decapper assembly of FIG. 31A taken along a midline thereof.
Figure 31F:
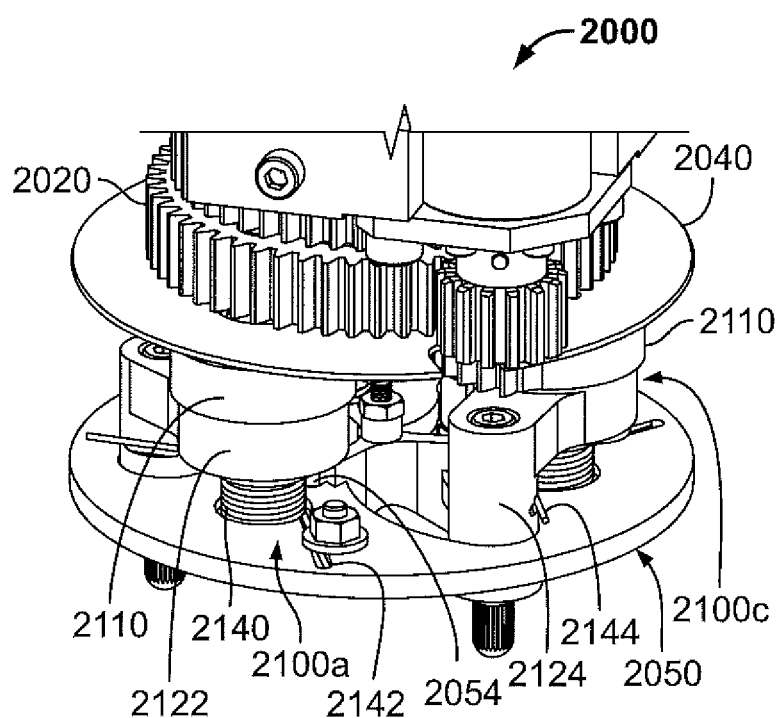
FIG. 31F is another perspective view of the decapper assembly of FIG. 31A.

As shown in FIG. 31E, main shaft 2034 of gripper drive assembly 2030 extends downwardly through a first angular contact bearing 2079 which is press-fit into mounting plate 2072. A threaded end cap 2078 is threaded to an end of main shaft 2034 and is positioned above mounting plate 2072. First gripper gear 2010 is stacked above decapper gear 2020 which are both disposed about main shaft 2034. First gripper gear 2010 is fixed to main shaft 2034 via a gripper drive hub 2012 so that rotation of first gripper gear 2010 causes gripper drive assembly 2030 to rotate. Decapper gear 2020 is rotatably connected to main shaft 2034 via an angular contact bearing 2022 press-fit to decapper gear 2020. The slotted disc 2040 is also arranged about the main shaft 2034 and is positioned beneath decapper gear 2020. Slotted disc 2040 in this position projects radially outwardly beyond decapper gear 2020 so as to partially extend into the gap formed between sensor elements 2044*a-b*. Slotted disc 2040 is connected to a bottom side of decapper gear 2020 via fasteners 2046 (best shown in FIG. 31E).

In addition, gripper assemblies 2100*a-c* and guide plate 2050 are connected to and suspended from decapper gear 2020 via a plurality of connection shafts 2150. In this regard, a connection shaft 2150 extends through slotted disc 2040 and through opening 2123 of upper arm portion 2122 of each gripper assembly 2100*a-c* and interfaces with bearings 2128 so that upper arm 2122 can rotate about connection shaft 2150. A bottom end of each connection shaft 2150 is connected to guide plate 2050. A torsion spring 2140 is disposed about each connection shaft 2150 between guide plate 2050 and gripper assembly 2100. A first arm 2142 of the torsion spring 2140 is embedded in guide plate 2050, and a second arm 2144 of spring 2140 is disposed within groove 2126 of gripper arm 2124 (see FIG. 31F). Each torsion spring 2140 has a spring stiffness sufficient to keep respective gripper fingers 2130 compressed against container cap 091 so as to maintain control of cap and container in the event of a power failure. In this regard, torsion springs 2140 provide a power loss fail-safe to prevent decapper assembly 2000 from dropping a container and potentially contaminating system 10. Lower arm portions 2124 and gripper fingers 2130 project through curvilinear slots 2052 in guide plate 2050 offset from the connection shaft 2150. When each gripper assembly 2100 is rotated about a respective connection shaft 2150, gripper fingers 2130 translate along curvilinear slot 2052.

Plunger 2062 is slidably disposed within the longitudinal opening of gripper drive member 2050 and extends through main shaft 2034 and second gripper gear 2032. Plunger shaft 2062 also extends through end cap 2078 so that end portion 2063 is disposed above end cap 2078. Keyed plunger cap 2065 is slidably connected to guide plate 2050 via fins 2066 which are positioned within slots 2054 in guide plate 2050.

Extension members 2068 extend along a bottom surface 2056 of guide plate and act as an axial stop by abutting the bottom surface 2056 when plunger 2061 moves axially upwardly a predetermined distance. Gripper motor pinion 2004*a* is meshed with first gripper gear 2010. Second gripper gear 2032, which is positioned beneath decapper gear 2020, is meshed with the planetary gears 2110 of each of gripper assemblies 2100*a-c*. Decapper motor 2002*b* is meshed with decapper gear 2020. In this regard, gripper motor 2020 operates to move gripper fingers 2130 so as to grip and ungrip cap 091, and decapper motor 2002*b* operates to rotate assembly 2000 to decap and recap cap 091. In a method of operation, gripper robot 450 is moved to a position above a plurality of containers 03 arranged in a dense array within rack 50. Robot 450 moves decapper assembly 2000 downward over a target container T so that gripper fingers 2130 are positioned about target container in locations A, B, and C. Robot 450 continues to lower decapper assembly so that a cap 901 of target container 03 is positioned partially within tapered recess 2069 and abuts fins 2066 of keyed plunger cap 2065. As robot 405 is continued to be lowered, cap 091 pushes plunger 2061 upward so that end portion 2063 of plunger 2061 moves into the gap between sensor elements 2064*a-b* causing an emission from the sensor 2064*a* to be disrupted. Such disruption generates an electrical signal that communicates with computing device 1350 which in turn initiates a gripping sequence.

In the gripping sequence, gripper motor 2002*a* is operated so as to rotate gripper pinion 2004*a* in a first direction. Gripper pinion 2004*a* then drives first gripper gear 2010 which in turn rotates second gripper gear 2032. Second gripper gear 2032 drives the planetary gears 2110, which causes gripper assemblies 2100*a-c* to rotate about respective connections shafts 2150. As gripper assemblies 2100*a-c* are rotated about connections shafts 2150, gripper fingers translate along curvilinear slots 2052 in guide plate 2050 until cap 091 is securely gripped by gripper fingers 2130. Robot 450 then lifts container 03 out of rack 50 and transports it to another location, such as between clamping jaws at station 160. Should power to motor 2002*a* cease at any point during such transport operation, torsion springs 2140 will hold container 03 by pushing against lower arm portion 2124 so as to maintain a grip on container 03.

Once container 03 is positioned in station 160 and a bottom end of container 03 meshes with an engagement feature therein, a decapping sequence is initiated. In this regard, decapper motor 2002*b* is operated so as to rotate decapper pinion 2004*b* in a first direction. Decapper pinion 2002*b* drives decapper gear 2020. As mentioned above, decapper gear 2020 is fixedly connected to slotted disc 2040 and is also connected to gripper assemblies 2100*a-c* and guide plate 2050. Thus, as decapper gear 2020 is rotated by decapper pinion 2004*b*, slotted disc 2040, guide plate 2050, and gripper assemblies 2100*a-c* are correspondingly rotated so that gripper fingers 2130 decap container 03. Gripper assembles 2100*a-c* hold onto cap until the container is ready to be recapped. Should the cap fall away from the gripper assemblies, plunger 2061 automatically drops which activates sensor elements 2064*a-b* indicating to system 10 that cap 091 has been dropped.

When container 03 is ready, decapper robot 450 places cap 091 back onto container 03 and a capping sequence is initiated in which motor 2002*b* is operated so that decapper pinion 2004*b* is rotated in a second direction causing decapper gear 2020 and fingers 2130 to rotate in an opposite direction as in the decapping sequence. Once container 03 is recapped, robot 450 moves container 03 back to rack 50.

A home sequence may be operated in which decapper motor 2002b is again operated so that decapper gear 2020, slotted disc 2040, and gripper assemblies 2100a-c are rotated. Such rotation occurs until slot 2042 is aligned with sensors 2044a-b allowing an emission from sensor 2044a to pass through to the sensor 2002b. This indicates that gripper fingers 2130 are in the home position. In this position, gripper fingers 2130 are angularly located about a rotational axis extending through second gripper gear 2032 so that when decapper assembly 2000 is lowered over rack 50, gripper fingers 2030 will be positioned at locations A, B, and C. Thus, once rotational home is indicated, motor 2002b stops operating and container 03 is lowered back into rack 50. Fingers 2030 being positioned at home prevents fingers 2030 from disturbing adjacent containers.

Once container 03 is back in its rack 50, an ungrip sequence is initiated in which gripper motor 2002a is operated to rotate gripper pinion 2004a in a second direction which causes first and second gripper gears 2010, 2032 to rotate in an opposite direction to that of the grip sequence. This causes gripper assemblies 2100a-c to be rotated about connection shaft 2150 so that gripper fingers 2130 are moved away from cap 091. The number of pinion rotations to ungrip cap 091 without bumping into adjacent containers can be preprogramed and verified during operation by an encoder of motor 2002a. With fingers 2130 still in the rotational home position, decapper assembly 450 can be moved to another container to perform the same method. In this regard, fingers 2130 will be located in positions A, B, and C relative to the next target container so that fingers 2130 can be located in respective spaces adjacent the target container sufficient for gripping the container without disrupting adjacent containers.

Alternative Warmer FIGS. 32A-32C depict a batch warmer array 2200 according to another embodiment of the present disclosure. Batch warmer array 2200 may be utilized as a substitute for warmer 230. Batch warmer array 2200 includes a plurality of batch warmers 2210a-c arranged adjacent one another. As shown, the array 2200 may include a first, second and third batch warmers 2210a-c. Referring to the cross-section of FIG. 32A in FIG. 32B, each warmer 2210 includes a cover 2220, upper insulation layer 2232, lower insulation layer 2242, upper conduction block 2234, lower conduction block 2244 and heater 2250. Heater 2250 in this particular embodiment is a thin sheet heating element, such as a Kapton® heater, which is sandwiched between an upper layer 2230 comprised of the upper insulation layer 2232 and conduction block 2234 and a lower layer 2240 comprised of the lower insulation layer 2242 and conduction block 2244. In this particular arrangement heating is from the middle out which helps generate a uniform distribution of heat within the conduction blocks 2234, 2244 between the insulation layers 2232, 2242 as the heat tend to flow outwardly toward the cooler exterior. Conduction blocks 2234 and 2244 may be made from any heat conductive material, such as aluminum, and define, along with upper insulation layer 2232 and cover 2220, a plurality of sample container receptacles 2212. The number of receptacles 2212 may be selected based on the number of containers 03 typically processed in a batch. Thus, each batch warmer 2210 is configured to warm an entire batch of samples or less. Conduction blocks 2234 and 2244 have a combined height so that when a sample container 03 is disposed within a receptacle 2212, a sample 03' contained within the container 03 is disposed substantially between ends 2236 and 2246 of the conduction blocks 2234, 2244 so that heat emanating therefrom uniformly encompasses the sample 03'. A temperature detector 2252, such as a pair of resistance temperature detectors, are located at the middle of a receptacle array 2214 and adjacent heater 2250. A thermal cut-off 2254 is provided to prevent overheating of batch warmer 2200. The cover 2220, which is preferably made from a polymer material, such as a Kydex®, surrounds and contains the insulation layers 2232, 2242 and conduction blocks 2234, 2244. Thus, each warmer 2210 of the array 2200 is thermally isolated from one another.

Batch warmer array 2200 has many advantages one of which is its suitability to batch processing. As previously described, system 10 can process batches of samples to be distributed to an analyzer which may include pre-warming the batch. In this regard, a first batch may be loaded into first warmer 2210a. At some time later, a second batch may be loaded into second warmer 2210b. The isolation of first warmer 2210a from second warmer 2210b prevents the second batch, which may be cooler than the first batch when loaded into second warmer 2210b, from impacting the warming cycle of the first batch.

Cooler

Figure 33A:
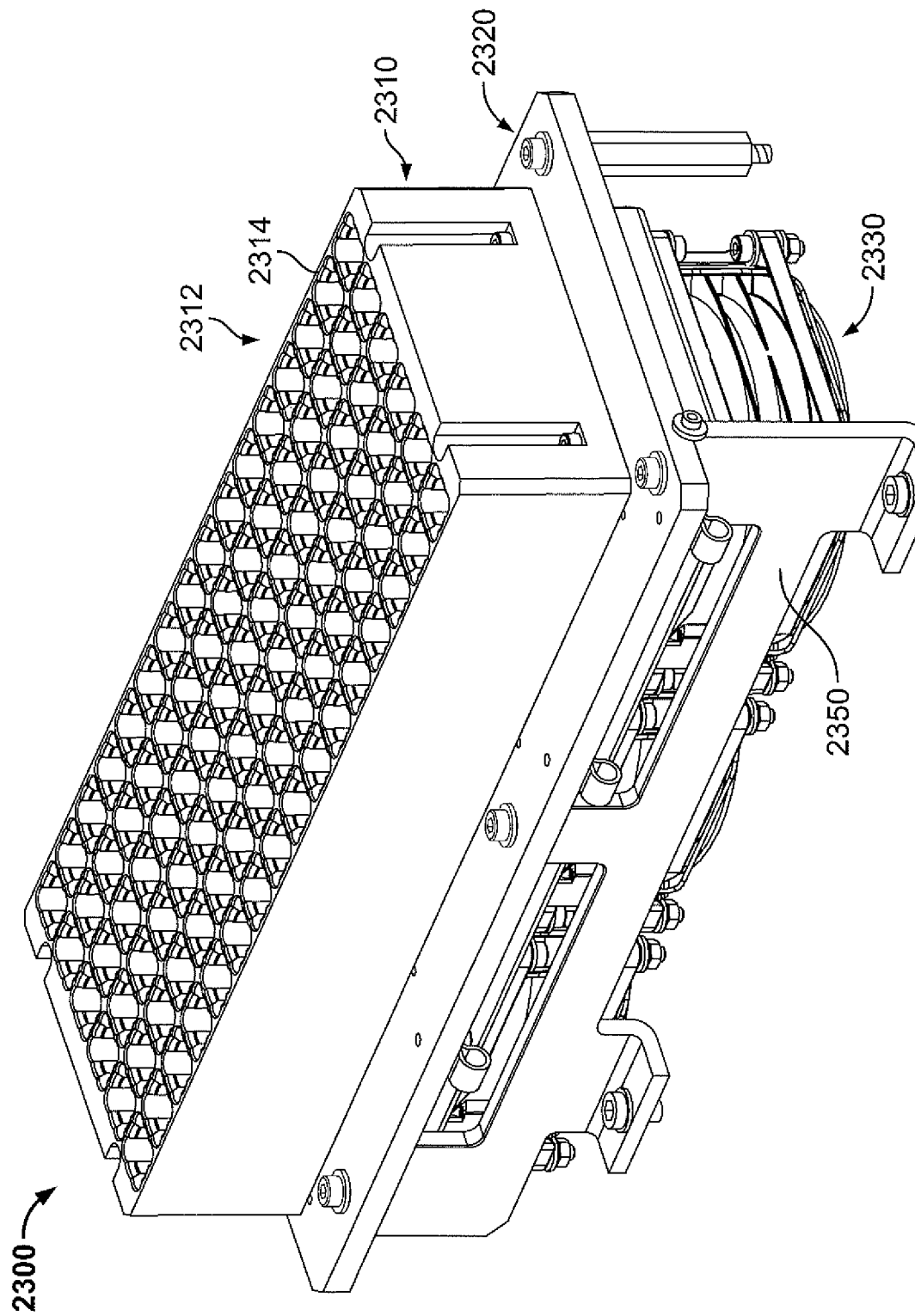
FIGS. 33A and 33B are perspective views of a cooler according to a further embodiment of the present disclosure.
Figure 33B:
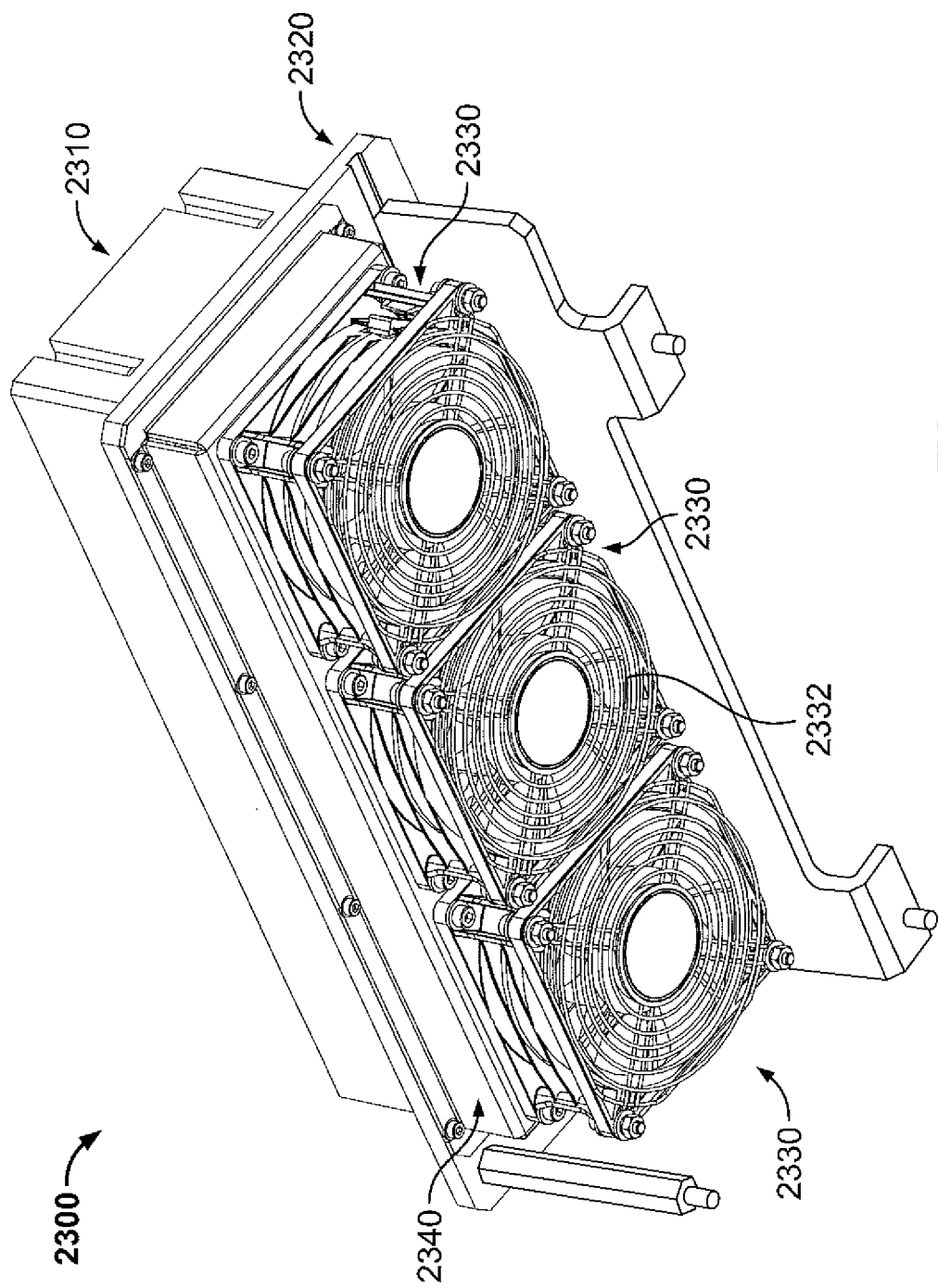

FIGS. 33A-33B depict a cooler 2300 according to a further embodiment of the present disclosure. Cooler 2300 is similar to cooler 290 in that it includes a plurality of fan units 2330, a plenum 2340, a mounting plate 2320, and a container rack/block 2310. In this regard, block 2310 is mounted to one side of plate 2320, and plenum 2340 and fans 2330 are connected to another side of mounting plate 2320. However, cooler 2300 differs in that it includes a mounting bracket 2350 for mounting cooler 2300 to second pre-analytical processing deck 26 so that fans 2330 are positioned at a predetermined height above second deck 26 to allow fans 2330 to draw a sufficient volume of air into their respective inlets 2332 to cool containers 03 disposed in block 2310. In addition, block 2310 is a single block rather than a plurality of blocks as is the case with cooler 290. Also, block 2310 defines a plurality of sample container receptacles 2312 that each have a square shaped opening and include ribs 2314, such as four ribs, extending along interior surfaces thereof. These ribs 2314 form air flow channels therebetween for air to flow over and around each sample container 03 disposed within receptacles 2312 for even cooling.

One illustration described herein is a method for pre-analytical processing of a biological sample for analysis. The method includes the steps of: i) providing to an automated system for pre-processing a primary biological sample for analysis, a rack carrying a plurality of sample containers wherein each of the sample containers in the rack is one of at least a first type of container or a second type of container; ii) interrogating a label on the rack for information about at least one of the rack type, the one or more types of sample containers carried by the rack or both; and iii) communicating the rack label information to a processor that, based on the rack label information type or the type of sample containers carried by the rack, assigns an order for the pre-analytical to the rack for the samples in the containers disposed in the rack.

Another illustration described herein is a method for pre-analytical processing of biological sample for analysis. The method includes: i) in a pre-analytical module, accumulating sample containers with a biological sample disposed in a batching area; ii) associating a plurality of the sample containers as a batch based on a requested analysis for the sample in the containers, wherein the requested analysis for each sample in the batch causes the batch to be transported to an analyzer associated with the pre-analytical module; iii) removing individual sample containers from the receptacle array; iv) reading the label information on the sample containers; v) placing each unloaded sample container into a receptacle in an array of receptacles in the batching area; vi) communicating the location of the sample container in the receptacle array to a processor in the pre-analytical module; vii) based on a communication between the automated system for pre-processing and the automated analyzer, determining when the batch of sample containers can be received by the automated analyzer for analysis; viii) removing the sample containers from the array of receptacles and placing sample containers in a common shuttle according to their assigned batch; and ix) transporting the shuttle carrying the batch of sample containers from the automated system for pre-analytical processing to the automated analyzer. This method can include the following steps for preparing the samples prior to accumulation. The steps include: i) providing to the automated system for pre-analytical processing a primary biological sample for analysis, a rack carrying a plurality of sample containers wherein each of the sample containers in the rack of sample containers is one of at least a first type of container or a second type of container; ii) interrogating a label on the rack for information about at least one of the rack type, the one or more types of sample containers carried by the rack or both; iii) communicating the rack label information to a processor that, based on the rack label information, assigns an order for pre-analytical processing to the rack for the samples in the containers disposed in the rack; and iv) based on the assigned order of processing, delivering the rack of samples to an automated station that is capable of automatically preparing the primary biological sample for analysis, wherein the first type of sample container cannot be passed through the automated station for further processing by the automated system and the second type of sample container can be passed through the automated station and further processed by the automated system.

Another illustration described herein is a method for pre-analytical processing of biological sample for analysis. The method includes, providing an assigned processing order to a rack received by a pre-analytical processing system, the rack having a plurality of containers each having a biological sample disposed therein, and based on that assigned processing order, delivering the rack of samples to an automated station that is capable of automatically preparing the primary biological sample for analysis wherein the first type of sample container cannot be passed through the automated station for handling by the automated system and the second type of sample container can be passed through the automated station and directly handled by the automated system. The method proceeds according the following logic. If the rack of samples contains a first type of container that cannot be directly handled by the pre-analytical processing system, then a) each first type of container in the rack is removed; b) identifying information on the first type container is read; c) the identifying information is communicated to a processor that, based on the identifying information, determines pre-ordered analytical assay information for the primary sample which determines at least the pre-analytical processing for the sample in the container; d) an empty secondary container of a third type is provided that can be handled by the pre-analytical processing system, wherein the third type container can be the same as or different from the second type container; e) identifying information on the first type container having primary sample disposed therein is associated with identifying information on the empty third type secondary container; f) a predetermined aliquot of primary sample from the first type of container is obtained and the predetermined aliquot of the obtained primary sample is dispensed into the obtained third type secondary container; g) a predetermined aliquot of diluent is dispensed into the obtained third type sample container thereby preparing a secondary sample; and h) the third type secondary sample container carrying the secondary sample is placed into a rack at a destination location for sample handling. If the contains a second type of container that can be directly handled by the pre-analytical processing system, then a) each second type container in the rack is removed; b) identifying information on the second type container is read; c) the identifying information is communicated to a processor that, from the identifying information, determines pre-ordered analytical assay information for the primary sample that determines at least the pre-analytical processing for the second type container; and d) the second type container is placed into a rack at the destination location.

Another illustration described herein is a method for pre-analytical processing of a biological sample for analysis. The method includes: i) providing to an automated system for pre-processing a primary biological sample for analysis, a rack carrying a plurality of sample containers wherein each of the sample containers in the rack is one of at least a first type of container or a second type of container; ii) interrogating a label on the rack for information about at least one of the rack type, the one or more types of sample containers carried by the rack or both; iii) communicating the rack label information to a processor that, based on the rack label information, assigns a processing order to the rack for the samples in the containers disposed in the rack; and iv) based on the processing order, delivering the rack of samples to an automated station that is capable of automatically preparing the primary biological sample for analysis wherein the first type of sample container cannot be passed through the automated station for handling by the pre-analytical processing system and the second type of sample container can be passed through the automated station and directly handled by the pre-analytical processing system according to the following considerations. If the rack of samples contains the first type of container that cannot be directly handled by the automated system for pre-processing, then: a) each first type of container in the rack is removed; b) identifying information on the first type container is read; c) the identifying information is communicated to a processor that, based on the identifying information, determines pre-ordered analytical assay information for the primary sample which determines at least the pre-analytical processing for the sample in the container; d) an empty secondary container of a third type is provided that can be handled by the automated system, wherein the third type container can be the same as or different from the second type container; e) identifying information on the first type container having primary sample disposed therein is associated with identifying information on the empty third type secondary container; f) a predetermined aliquot of primary sample is obtained from the first type of container and dispensed into the obtained third type secondary container; g) a predetermined aliquot of diluent is dispensed into the obtained third type sample container thereby preparing a secondary sample; h) the third type secondary sample container carrying the secondary sample is placed into a rack at a destination location for sample handling. However, if the rack of samples contains the second type of container that can be directly handled by the pre-analytical processing system, then: a) each second type container in the rack is removed; b) identifying information on the second type container is read; c) the identifying information is communicated to a processor that, from the identifying information, determines pre-ordered analytical assay information for the primary sample that determines at least the pre-analytical processing for the second type container; and d) the second type container is placed into a rack at the destination location.

After the samples have been prepared the methods further include: i) transporting a rack of sample containers from the destination location to a batching area; ii) associating a plurality of sample containers into a batch; iii) removing individual sample containers from the rack; iv) reading the label information on the sample containers; v) placing each unloaded sample container into a receptacle in an array of receptacles in the batching area; vi) communicating the location of the sample container in the receptacle array to the processor; vii) based on a communication between the automated system for pre-analytical processing and an automated analyzer, determining when the batch of sample containers can be received by the automated analyzer for analysis; viii) removing the sample containers from the array of receptacles and placing sample containers in a common shuttle according to their assigned batch; and ix) transporting the shuttle carrying the batch of sample containers from the automated system for pre-analytical processing to the automated analyzer.

In the methods above, the step of dispensing a predetermined aliquot of sample into the obtained primary sample into the obtained secondary sample container is performed using one of a diluent dispenser or an automated pipettor. In the automated systems a rack robot delivers the rack of samples to an automated station is performed by a rack robot. The steps of: i) providing an empty secondary container of a third type; ii) placing the secondary sample container carrying the secondary sample into a rack, iii) removing each second type container in the rack; iv) placing the second type container into a rack at the destination location; and v) moving, removing and placing can all be performed by a robot.

In the methods, the rack of samples is delivered to an automated station based on the assigned order for pre-analytical processing. The automated station is capable of automatically preparing the primary biological sample for analysis. The first type of sample container cannot be passed through the automated station for further processing by the automated system and the second type of sample container can be passed through the automated station and further processed by the automated system. In such methods, if the rack of samples contains the first type of container that cannot be directly handled by the automated system for pre-analytical processing, then: a) each first type of container in the rack is removed; b) identifying information on the first type container is read; c) the identifying information is communicated to a processor that, based on the identifying information, determines pre-ordered analytical assay information for the primary sample which determines at least the pre-analytical processing for the sample in the container; d) an empty secondary container of a third type is provided that can be further handled by the automated system, wherein the third type container can be the same as or different from the second type container; e) identifying information on the first type container having primary sample disposed therein is associated with identifying information on the empty third type secondary container; f) a predetermined aliquot of primary sample is obtained from the first type of container and dispensing the predetermined aliquot of the obtained primary sample into the obtained third type secondary sample container; g) a predetermined aliquot of diluent is dispensed into the obtained third type secondary container thereby preparing providing a secondary sample; and h) the third type secondary container carrying the secondary sample is placed into a rack at a destination location for sample handling. If the rack of samples contains the second type of container that can be directly handled by the pre-processing system, then: a) each second type container in the rack is removed; b) identifying information on the second type container is read; c) the identifying information is communicated to a processor that, from the identifying information, determines pre-ordered analytical assay information for the primary sample that determines at least the pre-analytical processing for the second type container; and d) the second type container is placed into a rack at the destination location.

In the methods, each sample container in the same batch is transported to the same analyzer either simultaneously or sequentially.

In one example the automated pre-analytical sample processing module includes: i) an enclosure; ii) a port in the enclosure, the port configured to receive a rack; iii) a reader configured to read a rack label, the rack label information about rack contents being received by a processor in the automated pre-analytical sample preparation module; iv) a rack elevator robot system comprising a rack elevator robot configured to move the rack received by the port to one of a plurality of locations in the enclosure of the automated preparation module; v) the rack elevator robot system configured to deliver racks to and carry racks from first and second processing decks wherein the first and second processing decks are separated to allow the rack elevator robot system to access first and second decks; vi) a rack storage unit having a plurality of compartments wherein the rack elevator robot is configured to place racks into and remove racks from the compartments in the rack storage unit. The first processing deck has: i) a plurality of rack receiving areas wherein the plurality of rack receiving areas are located adjacent an automated secondary sample preparation station the secondary sample preparation station comprising: ii) a first rack receiving area for receiving racks carrying containers of a first type; iii) a second rack receiving area for receiving racks carrying containers of a second type; iv) a primary container receiving station for receiving containers of a plurality of sizes; v) a secondary container receiving station for receiving containers of a type that is the same or different from the type of container received by the primary container receiving station; vi) a diluent dispenser; vii) a plurality of readers for reading a label on a sample container, the reader in communication with a processor that assigns at least pre-analytical processing instructions for the sample in the container based on the container label information and associates the at least pre-analytical processing instructions with the label information for that sample; and vii) optionally a destination location. The second preparation processing deck includes: i) a plurality of rack receiving areas; ii) a batch accumulation area; and iii) a shuttle handling assembly. The shuttle handling assembly includes: i) one or more shuttle racks for supporting a plurality of shuttles, wherein shuttles are adapted to receive a plurality of containers therein; ii) a transfer arm that engages a shuttle disposed on the shuttle racks and places the shuttle onto a conveyor; iii) a suspended robot assembly that has the following features: a) at least one pick and place robot; b) at least one pipettor robot; and c) at least one decapper robot. In this example the robots are suspended above the first and second processing decks and travel laterally along a support beam proximately parallel to the processing decks and wherein the pick and place robot can retrieve containers from and place containers into racks placed on the first and second processing decks, the primary and secondary container receiving stations, the batch accumulation area and the shuttles. In these examples the conveyer can be adapted to convey a shuttle to at least one adjacent analyzer or a plurality of analyzers. In operation the assigned pre-analytical processing instructions can cause the samples prepared by the system to be grouped into a batch. The batch of prepared samples is populated into a shuttle by the robot.

In another example the automated pre-analytical processing module has: i) an enclosure; ii) a port in the enclosure, the port having a means to receive a rack; iii) a reader configured to read a rack label, the rack label information providing information about the rack contents and the reader communicates the rack label contents to a processor in the automated pre-analytical processing module; iii) a rack elevator robot means adapted to move the rack received by the port to one of a plurality of locations in the enclosure of the automated pre-analytical processing module; iv) first and second sample processing decks, and the rack elevator robot mean is configured to deliver racks to and carry racks from first and second processing decks wherein the first and second processing decks are separated to allow the rack elevator robot means to access first and second decks; and v) a rack storage unit having a plurality of compartments wherein the rack elevator robot means is configured to place racks into and remove racks from the compartments in the rack storage unit. The first processing deck has: a plurality of rack receiving areas wherein the plurality of rack receiving areas are located adjacent an automated sample preparation station the sample preparation station that has: a) a first rack receiving means for receiving racks carrying containers of a first type; b) a second rack receiving means for receiving racks carrying containers of a second type; c) a primary container receiving means for receiving containers of a plurality of sizes; d) a secondary container receiving means for receiving containers of a type that is the same or different from the type of container received by the primary container receiving station; and e) a diluent dispenser means; f) a reader for reading a label on a sample container, the reader in communication with a processor that assigns at least pre-analytical processing instructions for the sample in the container based on the container label information and associates the assigned at least pre-analytical processing instructions with the label information for that sample. The second preparation processing deck has: a) at least one rack receiving area; b) a batch accumulation area; and c) a shuttle handling means, the shuttle handling means having: i) one or more shuttle racks for supporting a plurality of shuttles, wherein shuttles are adapted to receive a plurality of containers therein; and ii) a transfer arm that engages a shuttle disposed on the shuttle racks and places the shuttle onto a conveyor. The system also has a suspended robot means including: i) at least one pick and place robot; ii) at least one pipettor robot; and iii) at least one decapper robot; in which the robots are suspended above the first and second processing decks and travel laterally along a support beam means proximately parallel to the processing decks and wherein the pick and place robot can retrieve containers from and place containers into racks placed on the first and second processing decks, the primary and secondary container receiving means, the batch accumulation area and the shuttles. The pre-analytical processing module can be integrated with at least one analyzer wherein the conveyer transports the shuttle from the pre-analytical processing module to the analyzer.

In another example the automated pre-analytical processing module has: i) a rack elevator robot system comprising a rack elevator robot configured to move a rack received through a port in the automated pre-analytical processing module to one of a plurality of locations in an enclosure of the automated pre-analytical processing module; ii) the rack elevator robot system configured to deliver racks to and carry racks from first and second processing decks wherein the first and second processing decks are separated to allow the rack elevator robot system to access first and second decks; and iii) a rack storage unit having a plurality of compartments wherein the rack elevator robot is configured to place racks into and remove racks from the compartments in the rack storage unit. The processing module can also include: a plurality of rack receiving areas wherein the plurality of rack receiving areas are located adjacent an automated secondary sample preparation station. Such secondary sample preparation station can include: i) a first rack receiving area for receiving racks carrying containers of a first type; ii) a second rack receiving area for receiving racks carrying containers of a second type; iii) a primary container receiving station for receiving containers of a plurality of sizes; iv) a secondary container receiving station for receiving containers of a type that is the same or different from the type of container received by the primary container receiving station; v) a diluent dispenser; and vi) a plurality of readers for reading a label on a sample container the reader in communication with a processor that assigns at least pre-analytical processing instructions for the sample in the container based on the container label information and associates the at least pre-analytical processing instructions with the label information for that sample.

The second preparation processing deck can include: i) a plurality of rack receiving areas; ii) a batch accumulation area; and iii) a shuttle handling assembly, the shuttle handling assembly having: i) one or more shuttle racks for supporting a plurality of shuttles, wherein shuttles are adapted to receive a plurality of containers therein; and ii) a transfer arm that engages a shuttle disposed on the shuttle racks and places the shuttle onto a conveyor. The module above can include: i) at least one pick and place robot; ii) at least one pipettor robot; and iii) at least one decapper robot. In the above example, the robots are suspended above the first and second processing decks and travel laterally along a support beam proximately parallel to the processing decks and wherein the pick and place robot can retrieve containers from and place containers into racks placed on the first and second processing decks, the primary and secondary container receiving stations, the batch accumulation area and the shuttles. The module can further include: i) an enclosure wherein the rack elevator robot system is disposed in the enclosure; ii) a port in the enclosure; iii) a rack receiving location adjacent the port; iv) a rack label reader at the rack receiving location; v) a processor in communication with the rack label reader, the processor configured to assign a location in the rack storage unit to a rack received at the rack receiving location; in which, in response to instructions from the processor, the rack elevator robot system retrieves the rack from the rack receiving location adjacent the port and transports the rack to the rack storage unit. In this example the rack elevator robot system can include: i) a horizontal track member; ii) a vertical track member; and iii) a rack carriage. In this example the horizontal track member includes an elongate base and one or more rails extending along the length of the horizontal track member. The vertical track member includes an elongate base and one or more rails extending along the length of the vertical track member and wherein the vertical track member is slidingly connected to the rails of the horizontal track member such that vertical member slides along the horizontal member. The rack carriage can include: i) a base; ii) a rail mount; iii) a plurality of rack support members; and iv) a rack mover arm positioned between the plurality of rack supports. The rack mover arm further includes: i) first and second elongate members, the proximate end of the first elongate member rotatably coupled to the base and a proximate end of the second elongate member is pivotally coupled to a distal end of the first elongate member, wherein the second elongate member has a rack engagement feature on a distal end thereof. The rack mover arms have at least first second and third positions, so that the rack mover arm may move racks on or off the rack carriage in one of two directions, wherein the rack engagement feature is configured to removably engage a corresponding engagement feature on a rack, such that the rack mover arm conveys the rack onto or off of the rack carriage.

Another example is a container shuttle transport assembly that includes: i) a base; ii) a plurality of docking stations extending from the base; iii) a transfer arm rotatably supported from a carriage by first and second flanges; and iv) at least two drive shafts supported by the base and rotatably coupled thereto wherein the first drive shaft passes through and freely rotates in a first opening in first and second flanges and the second drive shaft is threadedly engaged with at least one of the first and second flanges to drive carriage along first and second shafts by the rotation of the second drive shaft.

The container shuttle transport assembly transfer arm has: i) at least two transfer arm linkages wherein the first transfer arm linkage is an elongate linkage, ii) the first transfer arm linkage is coupled to the first drive shaft. The first transfer arm moves in response to the rotation of the first drive shaft. The first transfer arm linkage is disposed between the first and second flanges. The second transfer arm linkage is pivotally coupled to the distal end of the first transfer arm linkage and further has an engagement feature to engage the bottom end of a shuttle conveyed by the shuttle transport assembly. In this example, the drive shafts are approximately parallel to each other. The docking stations have a plurality of fingers extending toward the drive shafts, the fingers configured to support shuttles placed thereon but spaced to allow the transfer arm to pass therethrough. In a further example the shuttle transport assembly has a barcode scanner. The docking stations may have projections adapted to at least partially fit with notches in the lower portion of shuttles placed on the docking stations.

In the example above the first drive shaft is one of a square shaft, a hexagonal shaft or a splined shaft and the second shaft is a threaded shaft. The shuttle transported by the assembly may have a plurality of receptacles for receiving containers and openings in the bottom that engage with projections to anchor the shuttle to a support platform.

In another example the analytical processing module includes: i) a first rack receiving location for receiving racks carrying containers with samples disposed therein; ii) a second rack receiving location for receiving racks carrying containers with no samples disposed therein; iii) at least one fluid dispenser selected from the group consisting of a diluent dispenser and a robotic pipettor; iv) a label reader; v) a plurality of receptacles for receiving sample containers and empty containers having different sizes wherein at least one of the receptacles is a vortexer; and v) a capper/decapper robot that removes the caps from and places the caps on the sample containers. In this example the fluid dispenser is a diluent dispenser comprising a diluent dispensing head and a plurality of diluent transfer channels fluidically coupled to the diluent dispensing head. Each diluent transfer channel is a tube fluidically coupled to a fluid reservoir and further comprises a pump and wherein the diluent dispensing head is a multichannel dispensing head for dispensing fluid from each channel. The plurality of receptacles comprise an engagement feature that prevents containers from rotating when place in the receptacles. In the above examples the diluent dispenser includes an ultrasonic sensor to verify the diluent dispense into the container. In one example the automated system includes: i) a pipette arm comprising a transport linkage movable affixed to and support by a support beam, a sliding plate for vertical movement and a motor; ii) a pipette head comprising a pipette assembly comprising a pipette channel assembly and pipette tip ejector assembly, wherein the pipette channel assembly comprising a channel housing, a pipette tip adaptor a control unit and a connector arm and wherein the pipette tip ejector assembly comprises upper and lower ejector housings, a tip ejector and a tip ejector driver comprising a lead screw and a pusher nut.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An automated pre-analytical sample preparation module comprising:
    an enclosure;
    a port in the enclosure, the port configured to receive a rack;
    a rack label reader configured to read a rack label, wherein information obtained from the rack label about rack contents is received by a processor in the automated pre-analytical sample preparation module;
    a rack elevator robot system comprising a rack elevator robot configured to move the rack received by the port to one of a plurality of locations in the enclosure of the automated pre-analytical sample preparation module;
    the rack elevator robot system configured to deliver racks to and carry racks from first and second processing decks, wherein the first and second processing decks are separated to allow the rack elevator robot system to access first and second decks;
    a rack storage unit having a plurality of compartments, wherein the rack elevator robot is configured to place racks into and remove racks from the compartments in the rack storage unit;
    the first processing deck comprising:
        a plurality of rack receiving areas, wherein the plurality of rack receiving areas are located adjacent an automated secondary sample preparation station, the secondary sample preparation station comprising:
            a first rack receiving area for receiving racks carrying containers of a first type;
            a second rack receiving area for receiving racks carrying containers of a second type;

a primary container receiving station for receiving containers of a plurality of sizes;
a secondary container receiving station for receiving containers of a type that is the same or different from the type of container received by the primary container receiving station;
a diluent dispenser; and
a container label reader for reading a label on a sample container, the container label reader in communication with a processor that assigns at least pre-analytical processing instructions for the sample in the container based on information obtained from the container label and associates the at least pre-analytical processing instructions with the information obtained from the container label;

the second processing deck comprising:
a plurality of rack receiving areas;
a batch accumulation area; and
a shuttle handling assembly, the shuttle handling assembly comprising:
one or more shuttle racks for supporting a plurality of shuttles, wherein shuttles are adapted to receive a plurality of containers therein; and
a transfer arm that engages a shuttle disposed on the one or more shuttle racks and places the shuttle onto a conveyor;

the system further comprising a suspended robot assembly comprising:
at least one pick and place robot;
at least one pipettor robot; and
at least one decapper robot;
wherein the robots of the suspended robot assembly are suspended above the first and second processing decks and travel laterally along a support beam proximately parallel to the first and second processing decks, and wherein the pick and place robot can retrieve the containers from and place the containers into racks placed on the first and second processing decks, the primary and secondary container receiving stations, the batch accumulation area and the shuttles.

2. The automated pre-analytical sample preparation module of claim 1, wherein a conveyer is adapted to convey a shuttle to at least one adjacent analyzer.

3. The automated pre-analytical sample preparation module of claim 2, wherein the assigned pre-analytical processing instructions causes the samples prepared by the system to be grouped into a batch.

4. The automated pre-analytical sample preparation module of claim 3, wherein a batch of prepared samples is populated into a shuttle by the at least one pick and place robot.

5. The automated pre-analytical sample preparation module of claim 3, wherein the conveyer is adapted to convey a shuttle to one of a plurality of analyzers.

6. An automated pre-analytical processing module comprising:
a rack elevator robot system comprising a rack elevator robot configured to move a rack received through a port in the automated pre-analytical processing module to one of a plurality of locations in an enclosure of the automated pre-analytical processing module;
the rack elevator robot system configured to deliver racks to and carry racks from first and second processing decks, wherein the first and second processing decks are separated to allow the rack elevator robot system to access first and second decks;
a rack storage unit having a plurality of compartments, wherein the rack elevator robot is configured to place racks into and remove racks from the compartments in the rack storage unit;
the second processing deck comprising:
a plurality of rack receiving areas;
a batch accumulation area; and
a shuttle handling assembly, the shuttle handling assembly comprising:
one or more shuttle racks for supporting a plurality of shuttles, wherein shuttles are adapted to receive a plurality of containers therein; and
a transfer arm that engages a shuttle disposed on the one or more shuttle racks and places the shuttle onto a conveyor.

7. The automated pre-analytical processing module of claim 6, wherein the first processing deck comprises:
a plurality of rack receiving areas, wherein the plurality of rack receiving areas are located adjacent an automated secondary sample preparation station, the secondary sample preparation station comprising:
a first rack receiving area for receiving racks carrying containers of a first type;
a second rack receiving area for receiving racks carrying containers of a second type;
a primary container receiving station for receiving containers of a plurality of sizes;
a secondary container receiving station for receiving containers of a type that is the same or different from the type of container received by the primary container receiving station;
a diluent dispenser; and
a reader for reading a label on a sample container, the reader being in communication with a processor that assigns at least pre-analytical processing instructions for the sample in the container based on information obtained from the container label and associates the at least pre-analytical processing instructions with the information obtained from the container label.

8. An automated pre-analytical processing module comprising:
a rack elevator robot system comprising a rack elevator robot configured to move a rack received through a port in the automated pre-analytical processing module to one of a plurality of locations in an enclosure of the automated pre-analytical processing module;
the rack elevator robot system configured to deliver racks to and carry racks from first and second processing decks, wherein the first and second processing decks are separated to allow the rack elevator robot system to access first and second decks;
a rack storage unit having a plurality of compartments, wherein the rack elevator robot is configured to place racks into and remove racks from the compartments in the rack storage unit;
a suspended robot assembly, the suspended robot assembly comprising:
at least one pick and place robot;
at least one pipettor robot; and
at least one decapper robot;
wherein the robots of the suspended robot assembly are suspended above the first and second processing decks and travel laterally along a support beam proximately parallel to the first and second processing decks, and wherein the pick and place robot can retrieve containers from and place containers into racks placed on the first and second processing decks, primary and secondary container receiving stations, a batch accumulation area and shuttles.

9. The automated pre-analytical processing module of claim 8, further comprising:
   a rack receiving location adjacent the port;
   a rack label reader at the rack receiving location; and
   a processor in communication with the rack label reader, the processor configured to assign a location in the rack storage unit to a rack received at the rack receiving location;
   wherein the enclosure comprises the port;
   wherein the rack elevator robot system is disposed in the enclosure; and
   wherein, in response to instructions from the processor, the rack elevator robot system retrieves the rack from the rack receiving location adjacent the port and transports the rack to the rack storage unit.

10. The automated pre-analytical processing module of claim 8, wherein the rack elevator robot system comprises:
   a horizontal track member;
   a vertical track member; and
   a rack carriage;
   wherein the horizontal track member includes an elongate base and one or more rails extending along the length of the horizontal track member;
   wherein the vertical track member includes an elongate base and one or more rails extending along the length of the vertical track member, and wherein the vertical track member is slidingly connected to the one or more rails of the horizontal track member slides along the horizontal track member.

11. The automated pre-analytical processing module of claim 10, wherein the rack carriage comprises:
   a base;
   a rail mount;
   a plurality of rack support members; and
   a rack mover arm positioned between the plurality of rack supports, the rack mover arm comprising:
      first and second elongate members, wherein a proximate end of the first elongate member is rotatably coupled to the base and a proximate end of the second elongate member is pivotally coupled to a distal end of the first elongate member, wherein the second elongate member has a rack engagement feature on a distal end thereof;
      wherein the rack mover arm has at least first, second, and third positions, so that the rack mover arm may move racks on or off the rack carriage in one of two directions, wherein the rack engagement feature is configured to removably engage a corresponding engagement feature on a rack, such that the rack mover arm conveys the rack onto or off of the rack carriage.

12. The automated pre-analytical processing module of claim 6, wherein the shuttle engaged by the transfer arm has a plurality of receptacles for receiving containers and openings in a bottom end that engage with projections to anchor the shuttle to a support platform.

* * * * *